US011034768B2

(12) United States Patent
Amin et al.

(10) Patent No.: US 11,034,768 B2
(45) Date of Patent: Jun. 15, 2021

(54) METHODS FOR TREATING OR PREVENTING ASTHMA BY ADMINISTERING AN IL-4R ANTAGONIST

(71) Applicants: SANOFI BIOTECHNOLOGY, Paris (FR); REGENERON PHARMACEUTICALS, INC., Tarrytown, NY (US)

(72) Inventors: Nikhil Amin, Chappaqua, NY (US); Neil Graham, Croton-on-Hudson, NY (US); Gianluca Pirozzi, Berkeley Heights, NJ (US); Ariel Teper, Bridgewater, NJ (US)

(73) Assignees: SANOFI BIOTECHNOLOGY; REGENERON PHARMACEUTICALS, INC., Tarrytown, NY (US)

( * ) Notice: Subject to any disclaimer, the term of this patent is extended or adjusted under 35 U.S.C. 154(b) by 145 days.

(21) Appl. No.: 16/173,848

(22) Filed: Oct. 29, 2018

(65) Prior Publication Data

US 2019/0169299 A1 Jun. 6, 2019

Related U.S. Application Data

(60) Provisional application No. 62/742,736, filed on Oct. 8, 2018, provisional application No. 62/647,368, filed on Mar. 23, 2018, provisional application No. 62/710,381, filed on Feb. 16, 2018, provisional application No. 62/579,120, filed on Oct. 30, 2017.

(30) Foreign Application Priority Data

May 4, 2018 (EP) .................................... 18305566

(51) Int. Cl.
| | | |
|---|---|---|
| C07K 16/28 | (2006.01) | |
| A61K 39/395 | (2006.01) | |
| A61K 39/00 | (2006.01) | |
| A61P 11/06 | (2006.01) | |
| A61K 31/573 | (2006.01) | |

(52) U.S. Cl.
CPC ........ *C07K 16/2866* (2013.01); *A61K 31/573* (2013.01); *A61K 39/3955* (2013.01); *A61P 11/06* (2018.01); *A61K 2039/505* (2013.01); *A61K 2039/54* (2013.01); *A61K 2039/545* (2013.01); *C07K 2317/21* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,599,905 A | 2/1997 | Mosley et al. |
| 5,714,146 A | 2/1998 | Lewis et al. |
| 5,717,072 A | 2/1998 | Mosley et al. |
| 5,856,296 A | 1/1999 | Mosley et al. |
| 5,985,280 A | 11/1999 | Ritter et al. |
| 6,156,877 A | 12/2000 | Ritter et al. |
| 6,391,581 B1 | 5/2002 | Mosley et al. |
| 6,548,655 B1 | 4/2003 | Mosley et al. |
| 6,596,541 B2 | 7/2003 | Murphy et al. |
| 6,716,587 B2 | 4/2004 | Mosley et al. |
| 6,927,044 B2 | 8/2005 | Stahl et al. |
| 7,141,653 B2 | 11/2006 | Greenfeder et al. |
| 7,186,809 B2 | 3/2007 | Pluenneke |
| 7,317,090 B2 | 1/2008 | Mosley et al. |
| 7,422,742 B2 | 9/2008 | Greenfeder et al. |
| 7,465,450 B2 | 12/2008 | Pluenneke |
| 7,531,169 B2 | 5/2009 | Singh et al. |
| 7,582,298 B2 | 9/2009 | Stevens et al. |
| 7,605,237 B2 | 10/2009 | Stevens et al. |
| 7,608,693 B2 | 10/2009 | Martin et al. |
| 7,794,717 B2 | 9/2010 | Stevens et al. |
| 8,030,003 B2 | 10/2011 | Rothenberg |
| 8,075,887 B2 | 12/2011 | Martin et al. |
| 8,075,897 B2 | 12/2011 | Spertini et al. |
| 8,092,802 B2 | 1/2012 | Stevens et al. |
| 8,092,804 B2 | 1/2012 | Eriksson et al. |
| 8,178,098 B2 | 5/2012 | Lahn et al. |
| 8,252,284 B2 | 8/2012 | Singh et al. |
| 8,324,192 B2 | 12/2012 | Dohil et al. |
| 8,337,839 B2 | 12/2012 | Martin et al. |

(Continued)

FOREIGN PATENT DOCUMENTS

| | | |
|---|---|---|
| CA | 2737044 A1 | 5/2010 |
| CN | 102197052 A | 9/2011 |

(Continued)

OTHER PUBLICATIONS

Regeneron: "Highlights of Prescribing Information," https://www.regeneron.com/sites/default/files/Dupixent_FPI.pdf (Apr. 7, 2017), XP055534130.

(Continued)

*Primary Examiner* — Elizabeth C. Kemmerer
*Assistant Examiner* — Fozia Hamud
(74) *Attorney, Agent, or Firm* — Lathrop GPM LLP; James H. Velema, Esq.; Judith L. Stone-Hulslander

(57) ABSTRACT

The invention provides methods for treating or preventing asthma and associated conditions in a patient. The methods featured in the invention comprise administering to a subject in need thereof a therapeutic composition comprising an interleukin-4 receptor (IL-4R) antagonist, such as an anti-IL-4R antibody.

40 Claims, 36 Drawing Sheets
Specification includes a Sequence Listing.

(56) References Cited

U.S. PATENT DOCUMENTS

| | | | |
|---|---|---|---|
| 8,338,135 | B2 | 12/2012 | Stevens et al. |
| 8,497,528 | B2 | 7/2013 | Lee et al. |
| 8,604,171 | B2 | 12/2013 | Singh et al. |
| 8,637,239 | B2 | 1/2014 | Furuta et al. |
| 8,735,095 | B2 | 5/2014 | Martin et al. |
| 8,945,559 | B2 | 2/2015 | Dix et al. |
| 9,238,692 | B2 | 1/2016 | Dix et al. |
| 9,415,015 | B2 | 8/2016 | Jacobi et al. |
| 9,574,004 | B2 | 2/2017 | Ardeleanu et al. |
| 10,059,771 | B2 | 8/2018 | Mannent et al. |
| 10,066,017 | B2 | 9/2018 | Mannent et al. |
| 10,137,193 | B2 | 11/2018 | Pirozzi et al. |
| 10,485,844 | B2 | 11/2019 | Radin |
| 2003/0103938 | A1 | 6/2003 | Jinquan et al. |
| 2003/0113387 | A1 | 6/2003 | Tsuchida et al. |
| 2003/0124121 | A1 | 7/2003 | Pluenneke |
| 2005/0031609 | A1 | 2/2005 | Hultsch et al. |
| 2005/0074462 | A1 | 4/2005 | Holmgren et al. |
| 2005/0118176 | A1 | 6/2005 | Mosley et al. |
| 2005/0255532 | A1 | 11/2005 | Ruben et al. |
| 2005/0282181 | A1 | 12/2005 | Yan et al. |
| 2006/0013811 | A1 | 1/2006 | Dina |
| 2007/0041976 | A1 | 2/2007 | Pluenneke et al. |
| 2007/0274996 | A1 | 11/2007 | Carter et al. |
| 2008/0054606 | A1 | 3/2008 | Mitsuo et al. |
| 2008/0160035 | A1 | 7/2008 | Stevens et al. |
| 2009/0062168 | A1 | 3/2009 | Timar et al. |
| 2009/0074793 | A1 | 3/2009 | Martin et al. |
| 2009/0098142 | A1 | 4/2009 | Kassalan et al. |
| 2009/0264392 | A1 | 10/2009 | Warndahl et al. |
| 2010/0021476 | A1 | 1/2010 | Stevens et al. |
| 2010/0047254 | A1 | 2/2010 | Martin et al. |
| 2010/0144646 | A1 | 6/2010 | Paterson |
| 2010/0291107 | A1 | 11/2010 | Stevens et al. |
| 2011/0195500 | A1 | 8/2011 | Rothenberg |
| 2012/0004205 | A1 | 1/2012 | Rothenberg |
| 2012/0052072 | A1 | 3/2012 | Martin et al. |
| 2012/0088814 | A1 | 4/2012 | Gregory |
| 2012/0097565 | A1 | 4/2012 | Dix et al. |
| 2012/0135010 | A1 | 5/2012 | Stevens et al. |
| 2012/0164080 | A1 | 6/2012 | Hill et al. |
| 2012/0207815 | A1 | 8/2012 | Benhamou et al. |
| 2012/0240930 | A1 | 9/2012 | Kristensson et al. |
| 2013/0052190 | A1 | 2/2013 | Collins et al. |
| 2013/0078675 | A1 | 3/2013 | Martin et al. |
| 2013/0324435 | A1 | 12/2013 | Rothenberg et al. |
| 2014/0056920 | A1 | 2/2014 | Ardeleanu et al. |
| 2014/0072583 | A1 | 3/2014 | Ardeleanu et al. |
| 2014/0187523 | A1 | 7/2014 | Dohil et al. |
| 2014/0271681 | A1 | 9/2014 | Martin et al. |
| 2015/0017182 | A1 | 1/2015 | Mannent et al. |
| 2015/0185228 | A1 | 7/2015 | Reisacher et al. |
| 2015/0246119 | A1 | 9/2015 | Pirozzi et al. |
| 2016/0102147 | A1 | 4/2016 | Dix et al. |
| 2016/0185866 | A1 | 6/2016 | Mannent et al. |
| 2018/0016343 | A1* | 1/2018 | Ardeleanu ............ A61P 37/00 |
| 2019/0040146 | A1 | 2/2019 | Mannent et al. |
| 2019/0040147 | A1 | 2/2019 | Mannent et al. |
| 2019/0125865 | A1* | 5/2019 | Pirozzi .................. A61K 31/56 |
| 2019/0364622 | A1 | 11/2019 | Carlsson et al. |
| 2019/0367622 | A1 | 12/2019 | Graham |

FOREIGN PATENT DOCUMENTS

| | | |
|---|---|---|
| CN | 105517570 A | 4/2016 |
| EP | 0 367 566 A1 | 5/1990 |
| EP | 0 604 693 A1 | 7/1994 |
| EP | 1 229 034 B1 | 4/2005 |
| EP | 1 113 818 B1 | 5/2006 |
| EP | 2 022 507 A1 | 2/2009 |
| EP | 1 527 100 B1 | 7/2009 |
| EP | 1 283 851 B1 | 3/2012 |
| EP | 2 888 281 A1 | 7/2015 |
| EP | 3 010 539 A1 | 4/2016 |
| EP | 3 107 575 A1 | 12/2016 |
| EP | 3 218 412 A1 | 9/2017 |
| EP | 3 470 432 A1 | 4/2019 |
| EP | 3 613 432 A1 | 2/2020 |
| JP | H05-246874 A | 9/1993 |
| JP | 2006-131623 A | 5/2006 |
| JP | 2012-507294 A | 3/2012 |
| JP | 2015-527364 A | 9/2015 |
| JP | 2016-521713 A | 7/2016 |
| JP | 64-63351 B2 | 1/2019 |
| RU | 2162711 C2 | 2/2001 |
| RU | 2488595 C2 | 7/2013 |
| RU | 2674680 C2 | 12/2018 |
| TW | 201029664 A | 8/2010 |
| TW | 201221141 A | 6/2012 |
| WO | WO 1992/019259 A1 | 11/1992 |
| WO | WO 1994/014975 A1 | 7/1994 |
| WO | WO 2000/016804 A1 | 3/2000 |
| WO | 2001/092340 A2 | 12/2001 |
| WO | 2002/007745 A1 | 1/2002 |
| WO | WO 2003/048083 A2 | 6/2003 |
| WO | WO 2003/085089 A2 | 10/2003 |
| WO | 2005/047331 A2 | 5/2005 |
| WO | 2005/085284 A1 | 9/2005 |
| WO | WO 2006/003407 A2 | 1/2006 |
| WO | 2006/072564 A1 | 7/2006 |
| WO | WO 2006/083390 A2 | 8/2006 |
| WO | WO 2007/085815 A2 | 8/2007 |
| WO | 2008/054606 A2 | 5/2008 |
| WO | WO 2008/116165 A2 | 9/2008 |
| WO | WO 2009/081201 A2 | 7/2009 |
| WO | WO 2009/124954 A1 | 10/2009 |
| WO | 2010/053751 A1 | 5/2010 |
| WO | WO 2010/065557 A2 | 6/2010 |
| WO | 2010/120524 A1 | 10/2010 |
| WO | WO 2011/026966 A2 | 3/2011 |
| WO | 2012/047954 A1 | 4/2012 |
| WO | WO 2012/094643 A2 | 7/2012 |
| WO | WO 2012/177945 A2 | 12/2012 |
| WO | WO 2013/051928 A1 | 4/2013 |
| WO | WO 2013/066780 A2 | 5/2013 |
| WO | 2013/088109 A1 | 6/2013 |
| WO | WO 2013/155010 A1 | 10/2013 |
| WO | 2014/031610 A1 | 2/2014 |
| WO | 2014/039461 A1 | 3/2014 |
| WO | WO 2014/059178 A1 | 4/2014 |
| WO | WO 2014/031610 A8 | 11/2014 |
| WO | 2014/197470 A1 | 12/2014 |
| WO | 2014/205365 A1 | 12/2014 |
| WO | 2015/006571 A1 | 1/2015 |
| WO | 2015/127229 A1 | 8/2015 |
| WO | 2016/077675 A1 | 5/2016 |
| WO | 2017143270 A1 | 8/2017 |
| WO | 2018/045130 A1 | 3/2018 |
| WO | 2018/057776 A1 | 3/2018 |
| WO | WO 2019/089473 A1 | 5/2019 |

OTHER PUBLICATIONS

Huang et al., " Severe Atopic Dermatitis in Children", Current Allergy and Asthma Reports, Current Science, US, vol. 18, No. 6, (May 10, 2018) pp. 1-8, XP036511794.

Akinlade et al., "Conjunctivitis in dupilumab clinical trials", British Journal of Dermatology, (Mar. 9, 2019) pp. 1-5, XP55610279.

Regeneron: "Dupixent: Highlights of Prescribing Information", https://d1egnxy4x1q3f.cloudfront.net/Regeneron/Dupixent_FPI.pdf (Mar. 1, 2019) pp. 1-8, XP55610296.

Paller et al., " Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4, XP55610351.

Paller et al., "621 Dupilumab in adolescents with moderate-to-severe atopic dermatitis and a history of inadequate response, or intolerance to cyclosporine: subgroup analysis from a pivotal 16-week trial", XP002793332, 2019.

Cork, M.J., "605 Efficacy and safety of dupilumab in adolescent patients with moderate-to-severe atopic dermatitis", (May 1, 2019) XP002793331.

(56) References Cited

OTHER PUBLICATIONS

International Search Report dated Aug. 20, 2019 in related PCT Application No. PCT/US2019/031801 (19 pages).
Molfino et al. (Sep. 23, 2011) "Molecular and clinical rationale for therapeutic targeting of interleukin-5 and its receptor," Clinical and Experimental Allergy. 42(5):712-737.
Mordenti et al. (1991) "Interspecies scaling of clearance and volume of distribution data for five therapeutic proteins," Pharma. Res. 8:1351.
Morioka et al. (2009) "IL-4/IL-13 antagonist DNA vaccination successfully suppresses Th2 type chronic dermatitis," British Journal of Dermatology. 160(6):1172-1179.
National Heart, Lung, and Blood Institute (NHLBI) (2007) "Quick Refernece Charts for the Classification and Stepwise Treatment of Asthma," 2 pgs.
Newton et al. (2008) "A review of nasal polyposis," Ther. Clin. Risk Manag. 4(2):507-512.
Niranjan et al. (May 21, 2013) "Pathogenesis of allergen-induced eosinophilic esophagitis is independent of Interleukin (IL)-13," Immunology and Cell Biology. 91(6):408-415.
Oh et al. (2010) "Investigational therapeutics targeting the IL-4/IL-13/STAT-6 pathway for the treatment of asthma," European Respiratory Review. 19(115):46-54.
Otulana et al. (2011) "A Phase 2b Study of Inhaled Pitrakinra, an IL-4R/IL-13 Antagonist, Successfully Identified Responder Subpopulations of Patients with Uncontrolled Asthma," American Journal of Respiratory and Critical Care Medicine. 183:A6179.
Portolano et al. (1993) "Lack of promiscuity in autoantigen-specific H and L chain combinations as revealed by human H and L chain roulette," J. Immunol. 150(3):880-887.
PUBCHEM Database [online] (Feb. 2, 2014) "CAS Registry No. 1190264-60-8," PubChem SID No. 172232447. National Center for Biotechnology Information. Accessible on the Internet at URL: http://pubchem.ncbi.nlm.nih.gov/substance/172232447#section=Top. [Mar. 14, 2016].
Regeneron Pharmaceuticals, Inc. (Sep. 30, 2014) "Regeneron and Sanofi Announce Positive Phase 2 Top-Line Dupilumab Results in Patients with Chronic Sinusitis with Nasal Polyps," Acquire Media.
Sanofi With Regeneron Pharmaceuticals (Jun. 2014) "An Evaluation of Dupilumab in Patients with Nasal Polyposis and Chronic Symptoms of Sinusitis," ClinicalTrials.gov. Identifier: NCT01920893.
Sato et al. (1993) "Recombinant soluble murine IL-4 receptor can inhibit or enhance IgE responses in vivo," The Journal of Immunology. 150(7):2717-2723.
Scavuzzo et al. (2005) "Inflammatory mediators and eosinophilia in atopic and non-atopic patients with nasal polyposis," Biomedicine and Pharmacotherapy. 59(6):323-329.
Schmidt-Weber (Mar. 13, 2012) "Anti-IL-4 as a New Strategy in Allergy," Chem. Immunol. Allergy. 96:120-125.
Schubert et al. (1998) "Evaluation and treatment of allergic fungal sinusitis. I. Demographics and diagnosis," J. Allergy Clin. Immunol. 102(3):387-394.
Schubert et al. (1998) "Evaluation and treatment of allergic fungal sinusitis. II. Treatment and follow-up," J. Allergy Clin. Immunol. 102(3):395-402.
Sekiya et al. (2002) "Increased levels of a TH2-type CC chemokine thymus and activation-regulated chemokine (TARC) in serum and induced sputum of asthmatics," Allergy. 57(2):173-177.
Sheahan et al. (Feb. 2010) "Local IgE production in nonatopic nasal polyposis," Journal of Otolaryngology-Head and Neck Surgery. 39(1):45-51.
Slager et al. (Apr. 26, 2012) "IL-4 Receptor Polymorphisms Predict Reduction in Asthma Exacerbations During Response to an Anti-IL-4 Receptor Alpha Antagonist," Journal of Allergy and Clinical Immunology. 130(2):516-522.
Small et al. (2005) "Efficacy and safety of mometasone furoate nasal spray in nasal polyposis," J. Allergy Clin. Immunol. 116:1275-1281.
Taylor et al. (1992) "A transgenic mouse that expresses a diversity of human sequence heavy and light chain immunoglobulins," Nucl. Acids Res. 20:6287-6295.

Tazawa et al. (2004) "Relative importance of IL-4 and IL-13 in lesional skin of atopic dermatitis," Arch. Dermatol. Res. 295:459-464.
Tomkinson et al. (2001) "A murine IL-4 receptor antagonist that inhibits IL-4-and IL-13-induced responses prevents antigen-induced airway eosinophilia and airway hyperresponsiveness," The Journal of Immunology. 166(9):5792-5800.
Trangsrud et al. (2002) "Intranasal Corticosteroids for Allergic Rhinitis," Pharmacotherapy. 22(11):1458-1467.—Abstract only.
Van Zele et al. (2006) "Differentiation of chronic sinus diseases by measurement of inflammatory mediators," Allergy. 61:1280-1289.
Van Zele et al. (2010) "Oral steroids and doxycycline: two different approaches to treat nasal polyps," J. Allergy Clin. Immunol. 125(5):1069-1076.
Virchow et al. (1994) "Cellular and immunological markers of allergic and intrinsic bronchial asthma," Lung. 172(6):313-334.
Vlaminck et al. (May 2014) "The importance of local eosinophilia in the surgical outcome of chronic rhinosinusitis: a 3-year prospective observational study," Am. J. Rhinol. Allergy. 28(3):260-264.
Walker et al. (1993) "Atopic dermatitis: correlation of peripheral blood T cell activation, eosinophilia and serum factors with clinical severity," Clinical and Experimental Allergy. 23:145-153.
Walker et al. (2008) "Use of Biologics as Immunotherapy in Asthma and Related Diseases," Expert Review of Clinical Immunology. 4(6):743-756.
Wenzel et al. (2007) "Effect of an interleukin-4 variant on late phase asthmatic response to allergen challenge in asthmatic patients: results of two phase 2a studies," The Lancet. 370(9596):1422-1431.
Wenzel et al. (2010) "ERS—Programme," European Respiratory Society, Annual Congress 2010. pp. 3980.
Wenzel et al. (Apr. 27, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
Wenzel et al. (May 21, 2013) "Dupilumab in Persistent Asthma with Elevated Eosinophil Levels," The New England Journal of Medicine. 368(26):2455-2466.
Wils-Karp et al. (2008) "Untangling the Complex Web of IL-4 and IL-13 Mediated Signaling Pathways," Science Signaling. 1(51):1-5.
Woodruff et al. (2009) "T-helper type 2-driven inflammation defines major subphenotypes of asthma," American Journal of Respiratory and Critical Care Medicine. 180(5):388-395.
World Health Organization (Jan. 1, 2012) "International Nonproprietary Names for Pharmaceutical Substances (INN)," WHO Drug Information. 26(4):401-471.
Wu et al. (1987) "Receptor-mediated in vitro gene transformation by a soluble DNA carrier system," J. Biol. Chem. 262:4429-4432.
Yamanaka et al. (2011) "The Role of Cytokines/Chemokines in the Pathogenesis of Atopic Dermatitis," Curr. Probl. Dermatol. 41:80-92.
Zuo et al. (2010) "IL-13 Induced Esophageal Remodeling and Gene Expression by an Eosinophil-Independent, Il-13R {alpha}2-Inhibited Pathway," Journal of Immunology. 185:660-669.
Zurawski et al. (1995) "The primary binding subunit of the human interleukin-4 receptor is also a component of the interleukin-13 receptor," Journal of Biological Chemistry. 270(23):13869-13878.
Ivashkin et al. (2013) [Eosinophilic Esophagitis: A Training Manual for Doctors]. Moscow, Russia. pp. 13-21, 57-62.—provided with an English machine translation.
Saeki (2009) "Guidelines for management of atopic dermatitis," Advances in Medicine. Special Issue. 228(1):75-79.—English translation of the abstract only.
Simpson et al. (Jun. 4, 2016) "Dupilumab therapy provides clinically meaningful improvement in patient-reported outcomes (PROs): A phase IIB, randomized, placebo-controlled, clinical trial in adult patients with moderate to severe atopic dermatitis (AD)," J. Am. Acad. Dermatol. 75(3):506-515.
Simpson et al. (Jan. 14, 2016) "Patient burden of moderate to severe atopic dermatitis (AD): Insights from a phase 2b clinical trial of dupilumab in adults," J. Am. Acad. Dermatol. 74(3):491-498.
Thaçi et al. (Oct. 8, 2015) "Efficacy and safety of dupilumab in adults with moderate-to-severe atopic dermatitis inadequately con-

(56) References Cited

OTHER PUBLICATIONS trolled by topical treatments: a randomised, placebo-controlled, dose-ranging phase 2b trial," Lancet. 387(10013):40-52.
Tsianakas et al. (Oct. 8, 2015) "Dupilumab: a milestone in the treatment of atopic dermatitis," Lancet. 387(10013):4-5.
Akiyama et al. (1997) "[a study on indoor allergens measured in home environments of adult-asthmatic patients]," Housing Research Foundation. No. 24. Study No. 9620.—English Synopsis Only.
Bieber et al. (2012) "Atopic dermatitis: a candidate for disease-modifying strategy," Allergy. 67:969-975.
Blanchard et al., (2006) "Eosinophilic esophagitis: Pathogenesis, genetics, and therapy," J. Allergy Clin. Immunol., 118:10549-9.
Clinicaltrials.gov (Nov. 4, 2019) "Efficacy, Safety, and Tolerability of Dupilumab in Patients With Persisten Moderate to Severe Eosinophilic Asthma," [accessible on the internet at: https://clinicaltrials.gov/ct2/show/NCT01312961].
Clinical Trials, "History of Changes for Study: NCT01548404 Study of Dupilumab in Adult Patients With Extrinsic Moderate-to-Severe Atopic Dermatitis", U.S. National Library of Medicine, Retrieved at URL: https://clinicaltrials.gov/ct2/history/NCT01548404?V2=view#StudyPageTop, 2017.
Clinical Trials, History of Changes for Study: NCT01259323 Sequential Ascending Dose Study to Assess the Safety and Tolerability of REGN668 (SAR231893) in Patients With Atopic Dermatitis, U.S. National Library of Medicine, Retrieved at URL: https://clinicaltrials.gov/ct2/history/NCT01259323?V_5=View#StudyPageTop, Oct. 2012.
Regeneron Apr. 2011 Annual Report (12 pages).
Al-Lazikani et al. (1997) "Standard conformations for the canonical structures of immunoglobulins," J. Mol. Biol. 273:927-948.
American Academy of Allergy, Asthma & Immunology. "Rhinitis (Hay Fever)" American Academy of Allergy, Asthma & Immunology. Accessible on the Internet at URL: http://www.aaaai.org/conditions-and-treatments/allergies/rhinitis. [Last Accessed May 7, 2016].
Angal et al. (1993) "A single amino acid substitution abolishes the heterogeneity of chimeric mouse/human (IgG4) antibody," Molecular Immunology. 30:105.
Arron et al. (2009) "Peripheral biomarkers of an IL-13 induced bronchial epithelial gene signature in asthma," Journal of Allergy and Clinical Immunology. 179(2):A2536.
Bachert et al.(2005) "Pharmacological management of nasal polyposis," Drugs. 65(11):1537-1552.
Basic Local Alignment Search Tool. Search Results: "Alignment Heavy Chain Dupilumab with SEQ ID No. 10," National Center for Biotechnology Information. [Retrieved on Jan. 12, 2016].
Basic Local Alignment Search Tool. Search Results: "Alignment Heavy Chain Dupilumab with SEQ ID No. 9," National Center for Biotechnology Information. [Retrieved on Jan. 12, 2016].
Bateman et al. (2004) "Can guideline-defined asthma control be achieved? The Gaining Optimal Asthma Control study," Am. J. Respir. Crit. Care Med. 170(8):836-844.
Borish et al. (2001) "Efficacy of soluble IL-4 receptor for the treatment of adults with asthma," J. Clin. Allergy Clin. Immunol. 107:963-970.
Brorson et al. (1999) "Mutational analysis of avidity and fine specificity of anti-levan antibodies," J. Immunol. 163:6694-6701.
Brummell et al. (1993) "Probing the combining site of an anti-carbohydrate antibody by saturation-mutagenesis: role of the heavy-chain CDR3 residues," Biochemistry. 32:1180-1187.
Burmeister-Getz et al. (2009) "Human Pharmacokinetics/Pharmacodynamics of an Interleukin-4 and Interleukin-13 Dual Antagonist in Asthma," J. Clin. Pharmacol. 49:1025-1036.
Cho et al. (Apr. 11, 2012) "Spontaneous Eosinophilic Nasal Inflammation in a Genetically-Mutant Mouse: Comparative Study with an Allergic Inflammation Model," PLoS One. 7(4):e35114. pp. 1-8.
Clackson et al. (1991) "Making antibody fragments using phage display libraries," Nature. 352:624-628.
Colman (1994) "Effects of amino acid sequence changes on antibody-antigen interactions," Research in Immunology. 145:33-36.

Corren et al. (2010) "A Randomized, Controlled, Phase 2 Study of AMG 317, an IL-4R Antagonist, in Patients with Asthma," Am. J. Respir. Crit. Care Med. 181(8):788-796.
Davies et al. (1996) "Affinity improvement of single antibody VH domains: residues in all three hypervariable regions affect antigen binding," Immunotechnology. 2(3):169-179.
Figueiredo et al. (2008) "Inflammatory genes in nasal polyposis," Curr. Opin. Otolaryngol. Head Neck Surg. 16:18-21.
Frois et al. (2009) "Inhaled corticosteroids or long-acting beta-agonists alone or in fixed-dose combinations in asthma treatment: a systematic review of fluticasone/budesonide and formoterol/salmeterol," Clinical Therapeutics. 31(12):2779-2802.
Gavett et al. (1997) "Interleukin-4 receptor blockade prevents airway responses induced by antigen challenge in mice," American Journal of Physiology—Lung Cellular and Molecular Physiology. 16(2):L253-L261.
Getz et al. (2009) "Human Pharmacokinetics|Pharmacodynamics of an Interleukin-4 and Interleukin-13 Dual Antagonist in Asthma," The Journal of Clinical Pharmacology. 49(9):1025-1036.
Gevaert et al. (2006) "Nasal Il-5 levels determine the response to anti-IL-5 treatment in patients with nasal polyps," Journal of Allergy and Clinical Immunology. 118(5):1133-1141.
Gevaert et al. (Nov. 2011) "Mepolizumab, a humanized anti-IL-5 mAb, as a treatment option for severe nasal polyposis," J. Allergy Clin. Immunol. 128(5):989-995.
Giembycz et al. (2008) "A Holy Grail of asthma management: toward understanding how long-acting beta(2)-adrenoceptor agonists enhance the clinical efficacy of inhaled corticosteroids," British Journal of Pharmacology.153:1090-1104.
Glare et al. (1999) "Asthmatic airway biopsy specimens are more likely to express the IL-4 alternative splice variant IL-4δ2," J. Allergy Clin. Immunol. 104:978-982.
Groves et al. (2007) "Inhibition of IL-4 and IL-13 with an IL-4 mutein (Aeroderm) protects against flares in atopic eczema," AERODERM in AD. Poster at St. John's Institute of Dermatology.
Grunewald et al. (1998) "An antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo," The Journal of Immunology. 160(8):4004-4009.
Gu et al. (Feb. 2011) "Expression and role of acidic mammalian chitinase and eotaxin-3 in chronic rhinosinusitis with nasal polyps," Journal of Otolaryngology—Head and Neck Surgery. 40(1):64-69.
Holt et al. (2003) "Domain antibodies: proteins for therapy," Trends in Biotechnology. 21(11):484-490.
Hopkins et al. (2007) "The Lund-Mackay staging system for chronic rhinosinusitis: How is it used and what does it predict?" Otolaryngology—Head and Neck Surgery. 137(4):555-561.
Hopkins et al. (2009) "Psychometric validity of the 22-item Sinonasal Outcome Test," Clinical Otolaryngology. 34(5):447-454.
International Search Report with Written Opinion corresponding to International Patent Application No. PCT/US2014/043440, dated Oct. 6, 2014.
International Search Report with Written Opinion corresponding to International Patent Application No. PCT/US2013/055747, dated Feb. 13, 2014.
International Search Report with Written Opinion corresponding to International Patent Application No. PCT/US2015/016852, dated May 11, 2015.
International Search Report with Written Opinion corresponding to International Patent Application No. PCT/US2015/060540, dated Feb. 17, 2016.
Jia et al. (Aug. 1, 2012) "Periostin is a systemic biomarker of eosinophilic airway inflammation in asthmatic patients," J. Allergy Clin. Immunol. 130:647-654.
Junitlla et al. (2008) "Tuning sensitivity to IL-4 and IL-13: differential expression of IL-4Ra, IL-13Ral, and Yc regulates relative cytokine sensitivity," J. Exp. Med. 205(11):2595-2608.
Kakkar et al. (2011) "Population Pk and IgE Pharmacodynamic Analysis of a Fully Human Monoclonal Antibody Against IL4 Receptor," Pharmaceutical Research. 28(10):2530-2542.
KEGG: Kyoto Encyclopedia of Genes and Genomes. "Drug: D10354," KEGG Drug Entry No. D10354. Kanehisa Laboratories. Accessible

(56) References Cited

OTHER PUBLICATIONS on the Internet at URL: http://www.genomajp/dbget-bin/www_bget?dr:D10354. [Last Accessed on Jan. 12, 2016].
Kimura et al. (Jul. 2011) "Increased expression and role of thymic stromal lymphopoietin in nasal polyposis," Allergy Asthma Immunol. Res. 3(3):186-193.
Knappik et al. (2000) "Fully synthetic human combinatorial antibody libraries (HuCAL) based on modular consensus frameworks and CDRs randomized with trinucleotides," J. Mol. Biol. 296(1):57-86.
Kobayashi et al. (1999) "Tryptophan H33 plays an important role in pyrimidine (6-4) pyrimidone photoproduct binding by a high-affinity antibody," Protein Engineering. 12:879-844.
Kopf et al. (1993) "Disruption of the murine IL-4 gene blocks Th2 cytokine responses," Letters to Nature. 362:245-248.
Kostic et al. (2010) "A Fully Human IL4Ra Antibody for Inhibition of IL-4/IL-13-driven TH2 Responses in Allergic Disease," Clinical Immunology. 135:S105-S106.
Langer (1990) "New methods of drug delivery," Science. 249:1527-1533.
Lezcano-Meza et al. (2003) "Interleukin (IL)-4 and to a lesser extent either IL-13 or interferon-gamma regulate the production of eotaxin-2/CCL24 in nasal polyps," Allergy. 58(10):1011-1017.
Lilly et al. (1999) "Elevated plasma eotaxin levels in patients with acute asthma," J. Allergy Clin. Immunol. 104:786-790.
Ludmila et al. (Feb. 3, 2014) "Poster 1013: IL-4R alpha antibody inhibits IgE production and airway remodeling in the mouse model of house dust mite-induced eosinophilic asthma," World Allergy Organization Journal. 7(1):P8.
Maliszewski et al. (1994) "In Vivo Biological Effects of Recombinant Soluble Interleukin-4 Receptor," Experimental Biology and Medicine. 206(3):233-237.
Martin et al. (1989) "Modeling antibody hypervariable loops: a combined algorithm," Proc. Natl. Acad. Sci. USA. 86:9268-9272.
Burton et al. (2012) "Direct effects of IL-4 on mast cells drive their intestinal expansion and increase susceptibility to anaphylaxis in a murine model of food allergy," Mucosal Immunol. 6(4):740-50.
Dupixent Food and Drug Administration Label (Issued Mar. 2017) "Highlights of Prescribing Information (Dupixent)," Regeneron Pharmaceuticals, Inc.
Mathias et al. (2011) "IgE-mediated systemic anaphylaxis and impaired tolerance to food antigens in mice with enhanced IL-4 receptor signaling," J. Allergy Clin. Immunol. 127(3):795-805.
Nadeau et al. (2012) "Oral Immunotherapy and Anti-IgE Antibody-Adjunctive Treatment for Food Allergy," Immunol Allergy Clin. North Am. 32(1):111-33.
Regeneron Pharmaceuticals, Inc. (May 21, 2013) "Sanofi and Regeneron Announce Publication of Positive Phase 2a Results of Dupilumab in Asthma in the New England Journal of Medicine," Press Release. Acquire Media, 3 pgs.
Terui et al. (2000) "[Learning from Fungus Allergy in Atopic Dermatitis Patients]," Jpn. J. Med. Mycol. 41(3):157-160.—English Abstract Only.
Wang et al. (2010) "Peanut-induced intestinal allergy is mediated through a mast cell-IgE-FcepsilonRI-IL-13 pathway," J. Allergy Clin. Immunol. 126(2):306-316.
Wong et al. (Sep. 2017) "Guidelines for the management of atopic dermatitis (eczema) for pharmacists," Can. Pharm. J. (Ott). 150(5):285-297.
Hong et al. (2011) "Management of Itch in Atopic Dermatitis," Semin. Cutan. Med. Surg. 30(2):71-86.
Paton (Sep. 2017) "Dupilimab: human monoclonal antibody against IL-4Ralpha for moderate to server atopic dermatitis," Drugs Today (Barc). 53(9):477-487.
Cortes (Sep. 13, 2009) "Proton pump inhibitors inhibit IL-4 and IL-13 signaling stat6 activation." Journal of Immunology, vol. 39, pp. 5204.
Assa'ad (2011) "What is new in the treatment of eosinophilic eosophag it is?" From Food Allergy and Anaphylaxis Meeting 2011, Venice, Italy. Feb. 17-19, 2011, 1 pg.

Bagnasco et al. (2016) "A Critical Evaluation of Anti-IL-13 and Anti-IL-4 Strategies in Severe Asthma," Int Arch Allergy Immunol;170; pp. 122-131.
Durham et al. (2016) "Targeted anti-inflammatory therapeutics in asthma and chronic obstructive lung disease," Translational Research, vol. 167, No. 1, pp. 192-203.
Romaniuk, L.I., "Allergan-specific immunotherapy: mechanisms, methods and efficacy", Clinical Immunology, Allergology and Infectology, 2012, special issue, pp. 44-47. (with English translation of the cited portion).
Regeneron Press Release, Nov. 22, 2013 "Sanofi and Regeneron Report Positive Results with Sarilumab in First Phase 3 Rheumatoid Arthritis Registration Trial," 3 pp.
Almagro et al. (2008) "Humanization of antibodies." Frontiers in Bioscience, 13, pp. 1619-1633.
Blauvelt et al. (2016) "Long-term management of moderate-to-severe atopic dermatitis with dupilumab and concomitant topical corticosteroids (LIBERTY AD CHRONOS): a 1-year, randomised, double-blinded, placebo-controlled, phase 3 trial." The Lancet, Published online May 4, 2016 at www.thelancet.com (http://dx.doi.org/10.1016/S0140-6736(17)31191-1), 65 pp.
Hamilton et al. (2015) "Drug evaluation review: dupilumab in atopic dermatitis." Immunotherapy, 7 (10), 16 pp.
Martel et al. (2017) "Translational Animal Models of Atopic Dermatitis for Preclinical Studies." Yale Journal of Thology and Medicine, 90, 14 pp.
Oetjen et al. (2017) "Sensory Neurons Co-opt Classical Immune Signaling Pathways to Mediate Chronic Itch." Cell, 171, 26 pp.
Silverberg et al. (2017) "Dupilumab Treatment Rapidly Improves Itch in Patients With Moderate-to-Severe Atopic Dermatitis." Presented at the 75th Annual Scientific Meeting of the American College of Asthma, Silverberg et al. (2017) "Dupilumab Treatment Rapidly Improves Itch in Patients With Moderate-to-Severe Atopic Dermatitis." Presented at the 75th Annual Scientific Meeting of the American College of Asthma, Allergy, and Immunology (ACAAI) 2017; Boston, MA, USA; Oct. 26-30, 2017, 1 pg.
Silverberg et al. (2017) "Dupilumab Treatment Induces Rapid Clinical Improvement of Itch in Patients With Moderate-to-Severe Atopic Dermatitis." Presented at the 76th American Academy of Dermatology Annual Meeting; San Diego, CA, USA; Feb. 16-20, 2018, 1 pg.
Simpson et al. (2016) "Two Phase 3 Trials of Dupilumab versus Placebo in Atopic Dermatitis." The New England Journal of Medicine, Downloaded from nejm.org on Sep. 30, 2016, 14 pp.
Mueller et al. (2002) "Structure, binding, and antagonists in the IL-4/IL-13 receptor system," Biochimica et Biophysica Acta 1592, 237-250.
Ul-Haq et al. (2016) "Interleukin-4 receptor signaling and its binding mechanism: A therapeutic insight from inhibitors tool box," Cytokine and Growth Factor Reviews, 32:3-15.
Vakharia et al. (2017) "Monoclonal Antibodies for Atopic Dermatitis: Progress and Potential," BioDrugs, 31:409-422.
International Preliminary Report on Patentability corresponding to International Patent Application No. PCT/US2013/055747, dated Feb. 24, 2015.
Collins et al. "Baseline Characteristics and Correlation Between Dysphagia and Disease Activity in Patients with Eosinophilic Esophagitis in a Randomized, Placebo-Controlled, Phase 2 Dupilumab Trial," Sa115 Abstract, AGA Abstract, May 2018.
Ikuo Hirano et al. "Correlation between esophageal distensibility and objectivity measures of disease in patients with active eosinophilic esopagitis a post hoc analysis of a randomized, placebo-controlled, phase 2 dupilumab trial," Sa1113 Asbtract, AGA Abstract, p. S-244, May 2018.
Dellon Evan S. (2016) "19—A randomized, Double-Blind, Placebo-Controlled Trail of a Novel Recombinant, Humanized, Anti-Interleukin-13 Monoclonal Antibody (RPC4046) in Patients with Active Eosinophilic Esophagitis: Results of the HEROES Study," ACG 2016 Annual Scientific Meeting and PostGraduate Course, The Venetian LAs Vegas NV, Oct. 14-19, 2016, 3 pages.
Ikuo Hirano et al. (2017) "Dupilumab Efficacy and Safety in Adult Patients With Active Eosinophilic Espophagitis: a Randomized

(56) References Cited

OTHER PUBLICATIONS

Double-Blind Placebo-Controlled Phase 2 Trial," World Congress of Gastroenterology ACG 2017, Orlando Florida, Oct. 13-18, 2017, 20 pages.
Pesek et al. (2018) "Emerging drugs for eosinophilic esophagitis," Expert Opinion on Emerging Drugs, 23(2):173-183.
Rothenberg et al. (2015) "Intravenous anti-IL-13 mAb QAX576 for the treatment of eosinophilic esophagitis," J. Allergy Clin. Immunol., 135(2):500-507.
Barranco et al., (2017) "Dupilumab in the management of moderate-to-severe asthma: the data so far," Therapeutics and Clinical Risk Management, 13:1139-1149.
Anonymous: "Archive History for NCT02528214," Oct. 24, 2017, Retrieved from the Internet: https://clinicaltrials.gov/ct2/history/NCT025282147V_38=View#StudyPageTop, retrieved on Feb. 13, 2019.
Darveaux et al., (2015) "Biologics in Asthma—The Next Step Towards Personalized Treatment," J. Allergy Clin. Immunol. Pract., 3(2):152-161.
Extended European Search Report for European Patent Application No. 18194745.8, dated Jan. 16, 2019.
Meteran et al., (2017) "Novel monoclonal treatments in severe asthma," Journal of Asthma, 54(10):991-1011.
Shannon et al., (2008) "Differences in Airway Cytokine Profile in Severe Asthma Compared to Moderate Asthma," Chest, 133(2):420-426.
"Expert Panel Report 3: Guidelines for the Diagnosis and Management of Asthma", National Heart, Blood and Lung Institute, NIH, Aug. 28, 2007, 440 Pages.
"Section 3, The Four Components of Asthma Management", Guidelines for the Diagnosis and Management of Asthma, Aug. 28, 2007, 1 Page.
"WHO Drug Information", 2012, vol. 26, No. 4, Proposed INN: List 108, p. 412.
"Annual Report 2013", Receptos Inc., Apr. 2013, 411 Pages.
"International Nonproprietary Names for Pharmaceutical Substances (INN)", WHO Drug Information records—World Health Organization, Jan. 1, 2014, pp. 379-422.
Abonia, et al. (Apr. 2013) "High Prevalence of Eosinophilic Esophagitis in Patients with Inherited Connective Tissue Disorders", Journal of Allergy and Clinical Immunology, vol. 132, No. 2, pp. 378-386.
Aceves, et al. (Feb. 29, 2009) "Relationships Between Eosinophilic Inflammation, Tissue Remodeling and Fibrosis in Eosinophilic Esophagitis", Immunology and Allergy Clinics of North America, vol. 29, No. 1, pp. 197-211.
Akinlade et al. (2019) "Conjunctivities in dupilmab clinical trials," British Journal of Dermatology, Mar. 9, 2019, pp. 1-15.
Alving, et al. (1993) "Increased amount of nitric oxide in exhaled air of asthmatics", European Respiratory Journal, vol. 6, pp. 1368-1370.
Assa'ad, et al. (Aug. 10, 2011) "An Antibody Against IL-5 Reduces Numbers of Esophageal Intraepithelial Eosinophils in Children with Eosinophilic Esophagitis", Gastroenterology, vol. 141, No. 5, pp. 1593-1604.
Avdeeva, et al. (Apr. 2018) "Precision Medicine in Chronic Rhinosinusitis with Nasal Polyps", Current Allergy and Asthma Reports, vol. 18, No. 4, p. 25.
Bachert, et al. (Sep. 19, 2019) "Efficacy and Safety of Dupilumab in Patients with Severe Chronic Rhinosinusitis with Nasal Polyps (LIBERTY NP SINUS-24 and LIBERTY NP SINUS-52): Results from Two Multicentre, Randomised, Double-Blind, Placebo-Controlled, Parallel-Group Phase 3 Trials", The Lancet, vol. 394, pp. 1638-1650.
Balint, et al. (Dec. 27, 1993) "Antibody Engineering by Parsimonious Mutagenesis", Gene, vol. 137, Issue 1, pp. 109-118.
Barnes, et al. (Nov. 3, 2008) "The Cytokine Network in Asthma and Chronic Obstructive Pulmonary Disease", The Journal of Clinical Investigation, vol. 118, No. 11, pp. 3546-3556.
Beyer, et al. (Apr. 2, 2002) "Human Milk-Specific Mucosal Lymphocytes of the Gastrointestinal Tract Display a Th2 Cytokine Profile", Journal of Allergy and Clinical Immunology, vol. 109, Issue 4, pp. 707-713.
Bhardwaj, et al. (Sep. 2012) "Biomarkers for Eosinophilic Esophagitis: A Review", Annals of Allergy, Asthma & Immunology, vol. 109, Issue 3, pp. 155-159.
Blanchard, et al. (Feb. 2009) "Chemotactic Factors Associated with Eosinophilic Gastrointestinal Diseases", Immunology and allergy clinics of North America, vol. 29, No. 1, pp. 141-148.
Blanchard, et al. (Feb. 2005) "Eotaxin-3 and a Uniquely Conserved Gene-Expression Profile in Eosinophilic Esophagitis", The Journal of Clinical Investigation, vol. 116, No. 2, pp. 536-547.
Blanchard, et al. (Jan. 1, 2011) "A Striking Local Esophageal Cytokine Expression Profile in Eosinophilic Esophagitis", Journal of Allergy and Clinical Immunology, vol. 127, No. 1, pp. 208-217.
Blanchard, et al. (Apr. 2010) "Coordinate Interaction Between IL-13 and Epithelial Differentiation Cluster Genes in Eosinophilic Esophagitis", The Journal of Immunology, vol. 184, No. 7 (2010), pp. 4033-4041.
Blanchard, et al. (Dec. 2, 2007) "IL-13 Involvement in Eosinophilic Esophagitis: Transcriptome Analysis and Reversibility with Glucocorticoids", Journal of Allergy and Clinical Immunology, vol. 120, No. 6, pp. 1292-1300.
Blanchard, et al. (Aug. 24, 2005) "Inhibition of Human Interleukin-13-Induced Respiratory and Oesophageal Inflammation by Anti-Human-Interleukin-13 Antibody (CAT-354)", Clinical & Experimental Allergy, vol. 35, No. 8, pp. 1096-1103.
Carter, Paul J. (May 2006) "Potent Antibody Therapeutics by Design", Nature Reviews Immunology, vol. 6, No. 5, pp. 343-357.
Chan, et al. (Oct. 1, 2001) "Expression of Interleukin-4 in the Epidermis of Transgenic Mice Results in a Pruritic Inflammatory Skin Disease: An Experimental Animal Model to Study Atopic Dermatitis", Journal of Investigative Dermatology, vol. 117, No. 4, pp. 977-983.
Chehade, et al. (Feb. 2009) "The Role of Lymphocytes in Eosinophilic Gastrointestinal Disorders", Immunology and Allergy Clinics of North America, vol. 29, Issue 1, pp. 149-158.
Colice, et al.(Aug. 2004) "Categorizing Asthma Severity: An Overview of National Guidelines", Clinical Medicine & Research, vol. 2, No. 3, pp. 155-163.
Davis, et al. (Aug. 2004) "The Evolutionary and Structural 'Logic' of Antigen Receptor Diversity", Seminars in Immunology, vol. 16, Issue 4, pp. 239-243.
Dellon, Evan S. (Apr. 27, 2013) "The Pathogenesis of Eosinophilic Esophagitis: Beyond the Eosinophil", Digestive Diseases and Sciences, vol. 58, pp. 1445-1448.
Desreumaux, et al. (Mar. 1, 1996) "Interleukin 3, Granulocyte-Macrophage Colony-Stimulating Factor, and Interleukin 5 in Eosinophilic Gastroenteritis", Gastroenterology, vol. 110, No. 3, pp. 768-774.
Djukanovic, et al. (2002) "Standardised Methodology of Sputum Induction and Processing", European Respiratory Journal, pp. 1S-2S.
Extended European Search Report received for European Application No. 19187112.8, dated Jan. 23, 2020, 13 Pages.
Fillon, et al. (2009) "Epithelial Function in Eosinophilic Gastrointestinal Diseases", Immunology and Allergy Clinics of North America, vol. 29, No. 1, pp. 171-178.
Foroughi, et al. (Sep. 1, 2007) "Anti-IgE Treatment of Eosinophil-Associated Gastrointestinal Disorders", Journal of Allergy and Clinical Immunology, vol. 120, Issue 3, pp. 594-601.
Franciosi, et al. (Feb. 2009) "Eosinophilic Esophagitis", Immunology and Allergy Clinics of North America, vol. 29, Issue 1, pp. 19-27.
Frieri, (Mar. 28, 2014) "Asthma Linked with Rhinosinusitis: An Extensive Review", Allergy & Rhinology (Providence), vol. 5, No. 1, pp. e41-e49.
Goodson, et al. (1984) "Dental Applications", Medical Applications of Controlled Release, vol. 2, pp. 115-138.
Green, et al. (2012) "Molecular Cloning: A Laboratory Manual", Cold Spring Harbor Laboratory Press, Fourth Edition, 34 Pages.
Hijnen, et al. (Feb. 2004) "Serum Thymus and Activation-Regulated Chemokine (TARC) and Cutaneous T Cell-Attracting Chemokine

(56) References Cited

OTHER PUBLICATIONS (CTACK) Levels in Allergic Diseases", Journal of Allergy and Clinical Immunology, vol. 113, No. 2, pp. 334-340.
Ivashkin, et al. (2012) "Eosinophilic Esophagitis: A Review of the Literature and a Description of its Own Observation", Fughc, vol. 22, No. 1, Available at: <<RZHGGK online—www.gastro-j.ru>>, pp. 71-81.
Jahnz-Rozyk, et al. (Apr. 6, 2005) "Serum Thymus and Activation-Regulated Chemokine, Macrophage-Derived Chemokine and Eotaxin as Markers of Severity of Atopic Dermatitis", Allergy, vol. 60, No. 5, pp. 685-688.
Jakubke, et al. (1985) "Amino Acids, Peptides, Proteins", M: Mir, pp. 92-94.
Jakubke et al., "Amino acids, peptides and proteins", Martin-Luther-Universitat Halle-Wittenberg, 1977 The Macmillan Press Ltd. doi 10.1007/978-1-349-02503.
Jyonouchi, et al. (2013) "Invariant Natural Killer T cells in children with Eosinophilic Esophagitis", Basic Mechanisms in Allergic Disease, Clinical & Experimental Allergy, vol. 44, No. 1, pp. 58-68.
Kagami, et al. (2003) "Significant Elevation of Serum Levels of Eotaxin-3/CCL26, but not of Eotaxin-2/CCL24, in Patients with Atopic Dermatitis: Serum Eotaxin-3/CCL26 Levels Reflect the Disease Activity of Atopic Dermatitis", Clinical & Experimental Immunology, vol. 134, No. 2, pp. 309-313.
Kakinuma, et al. (2002) "Serum Macrophage-Derived Chemokine (MDC) Levels are Closely Related with the Disease Activity of Atopic Dermatitis", Clinical & Experimental Immunology, vol. 127, No. 2, pp. 270-273.
Kakinuma, et al. (Mar. 1, 2001) "Thymus and Activation-Regulated Chemokine in Atopic Dermatitis: Serum Thymus and Activation-Regulated Chemokine Level is Closely Related with Disease Activity", Journal of Allergy and Clinical Immunology, vol. 107, No. 3, pp. 535-541.
Katial, Rohit (Feb. 2009) "Biomarkers for Nononcologic Gastrointestinal Diseases", Immunology and Allergy Clinics of North America, vol. 29, Issue 1, pp. 119-127.
Kim, et al. (Dec. 1, 2004) "Rebound Eosinophilia after Treatment of Hypereosinophilic Syndrome and Eosinophilic Gastroenteritis with Monoclonal Anti-IL-5 Antibody SCH55700", Journal of Allergy and Clinical Immunology, vol. 114, No. 6, pp. 1449-1455.
Klementina, et al. (Mar. 24, 2018) "Precision Medicine in Chronic Rhinosinusitis with Nasal Polyps", Allergy and Asthma Reports, vol. 18, No. 4, 8 Pages.
Konikoff, et al. (Nov. 1, 2006) "A Randomized, Double-Blind, Placebo-Controlled Trial of Fluticasone Propionate for Pediatric Eosinophilic Esophagitis", Gastroenterology, vol. 131, No. 5, pp. 1381-1391.
Kopp et al., (2009) "Combination of omalizumab and specific immunotherapy is superior to immunotherapy in patients with seasonal allergic rhinoconjunctivitis and co-morbid seasonal allergic asthma," Clinical and Experimental Allergy, 39:271-279.
Kottyan, et al. (Aug. 2014) "Genome-Wide Association Analysis of Eosinophilic Esophagitis Provides Insight into the Tissue Specificity of this Allergic Disease", Nature Genetics, vol. 46, No. 8, pp. 895-900.
Kroegel, et al. (May 2009) "Global Initiative for Asthma (GINA) guidelines: 15 Years of Application", Expert Review of Clinical Immunology, vol. 5, No. 3, pp. 239-249.
Kulis, et al. (Nov. 19, 2010) "Single-Tree Nut Immunotherapy Attenuates Allergic Reactions in Mice with Hypersensitivity to Multiple Tree Nuts", Journal of Allergy and Clinical Immunology, vol. 127, No. 1, pp. 81-88.
Leung, et al. (Mar. 13, 2003) "Effect of Anti-IgE Therapy in Patients with Peanut Allergy", New England Journal of Medicine, vol. 348, No. 11, pp. 986-993.
Leung, et al. (Apr. 2004) "New Insights into Atopic Dermatitis", The Journal of Clinical Investigation, vol. 113, No. 5, pp. 651-657.
Liacouras, et al. (Apr. 8, 2011) "Eosinophilic Esophagitis: Updated Consensus Recommendations for Children and Adults", Journal of Allergy and Clinical Immunology, vol. 128, No. 1, pp. 3-20.
Liu, et al. (Aug. 9, 1999) "Hydrodynamics-Based Transfection in Animals by Systemic Administration of Plasmid DNA", Gene Therapy, vol. 6, No. 7, pp. 1258-1266.
Lucendo, et al. (Nov. 1, 2012) "Adult Versus Pediatric Eosinophilic Esophagitis: Important Differences and Similarities for the Clinician to Understand", Expert Review of Clinical Immunology, vol. 8, No. 8, pp. 733-745.
Lwin, et al. (Apr. 2011) "Eosinophilic Gastritis: Histopathological Characterization and Quantification of the Normal Gastric Eosinophil Content", Modern Pathology, vol. 24, No. 4, pp. 556-563.
Mannon, et al. (2012) "Interleukin 13 and its Role in Gut Defence and Inflammation", Gut, vol. 61, No. 12, pp. 1765-1773.
Marone, et al. (Dec. 6, 2013) "The Intriguing Role of Interleukin 13 in the Pathophysiology of Asthma", Frontiers in Pharmacology, vol. 10, pp. 1-13.
Masterson, et al. (Oct. 2011) "Update on Clinical and Immunological Features of Eosinophilic Gastrointestinal Diseases", Current Opinion in Gastroenterology, vol. 27, No. 6, pp. 515-522.
Mishra, et al. (Nov. 1, 2003) "Intratracheal IL-13 Induces Eosinophilic Esophagitis by an IL-5, Eotaxin-1, and STAT6-Dependent Mechanism", Gastroenterology, vol. 125, No. 5, pp. 1419-1427.
Mishra, et al. (Jan. 1, 2001) "An Etiological Role for Aeroallergens and Eosinophils in Experimental Esophagitis", The Journal of Clinical Investigation, vol. 107, No. 1, pp. 83-90.
Mishra, et al. (Mar. 1, 2002) "IL-5 Promotes Eosinophil Trafficking to the Esophagus", The Journal of Immunology, vol. 168, No. 5, pp. 2464-2469.
Naclerio, et al. (Feb. 1, 2017) "Dupilumab Improves Sense of Smell and Reduces Anosmia Among Patients with Nasal Polyposis and Chronic Sinusitis: Results from a Phase 2a Trial", Journal of Allergy and Clinical Immunology, vol. 139, No. 2, AB90, 1 Page.
Nadeau, et al. (Jun. 2011) "Rapid Oral Desensitization in Combination with Omalizumab Therapy in Patients with Cow's Milk Allergy", The Journal of Allergy and Clinical Immunology, vol. 127, No. 6, pp. 1622-1624.
Nguyen, et al. (Jul. 2011) "Immune Modulation for Treatment of Allergic Disease", Immunological Reviews, vol. 242, No. 1, pp. 258-271.
Nicodeme, et al. (Sep. 2013) "Esophageal Distensibility as a Measure of Disease Severity in Patients with Eosinophilic Esophagitis", Clinical Gastroenterology and Hepatology, vol. 11, No. 9, pp. 1101-1107.
Niederberger, Verena (Feb. 2009) "Allergen Specific Immunotherapy", Immunology Letters, vol. 122, Issue 2, pp. 131-133.
Noel, et al. (Aug. 24, 2006) "Eosinophilic Esophagitis", The New England Journal of Medicine, vol. 351, pp. 940-941.
Novartis Pharmaceuticals (2013) "A Double Blinded, Randomized, Placebo-Controlled Trial of Intravenous QAX576 in the treatment of Eosinophilic Esophagitis", QAX576.
Ohno, et al. (May 1, 1985) "Antigen-Binding Specificities of Antibodies are Primarily Determined by Seven Residues of VH", Proceedings of the National Academy of Sciences, vol. 82, No. 9, pp. 2945-2949.
Ong, Peck Y. (2012) "Editorial Update on Emerging Treatments of Atopic Dermatitis", Expert Opinion on Emerging Drugs, vol. 17, No. 2, pp. 129-133.
Otani, et al. (Apr. 29, 2013) "Anti-IL-5 Therapy Reduces Mast Cell and IL-9 Cell Numbers in Pediatric Patients with Eosinophilic Esophagitis", Journal of Allergy and Clinical Immunology, vol. 131, No. 6, pp. 1576-1582.
Oyoshi, et al. (Jan. 1, 2009) "Cellular and Molecular Mechanisms in Atopic Dermatitis", Advances in Immunology, vol. 102, pp. 135-226.
Peserico, et al. (2008) "Reduction of Relapses of Atopic Dermatitis with Methylprednisolone Aceptonate Cream Twice Weekly in Addition to Maintenance Treatment with Enrollment: A Multicentre, Randomized, Double-Blind, Controlled Study", British Journal of Dermatology, vol. 158, No. 04, pp. 801-807.
Phan, et al. (2012) "Assessment of Pruritus Intensity: Prospective Study on Validity and Reliability of the Visual Analogue Scale, Numerical Rating Scale and Verbal Rating Scale in 471 Patients with Chronic Pruritus", Acta Dermato-Venereologica, vol. 92, pp. 449-581.

(56) References Cited

OTHER PUBLICATIONS

Powell, et al. (Sep.-Oct. 1998) "Compendium of Excipients for Parenteral Formulations", PDA Journal of Pharmaceutical Science and Technology, vol. 52, No. 5, pp. 238-311.
Prieto, et al. (May 24, 2013) "Eosinophilic Esophagitis in Adults: An Update on Medical Management", Current Gastroenterology Reports, vol. 15, No. 6, p. 324.
Prussin, et al. (Dec. 1, 2009) "Eosinophilic Gastrointestinal Disease and Peanut Allergy are Alternatively Associated with IL-51 and IL-5-TH2 Responses", Journal of Allergy and Clinical Immunology, vol. 124, No. 6, pp. 1326-1332.
Rafi, et al. (Jan. 1, 2010) "Effects of Omalizumab in Patients with Food Allergy", In Allergy & Asthma Proceedings, vol. 31, No. 1, pp. 76-83.
Rayapudi (Aug. 2010) "Indoor insect Allergens are Potent Inducers of Experimental Eosinophilic Esophagitis in Mice", Journal of Leukocyte Biology, vol. 88, No. 2, pp. 337-346.
Regeneron Pharmaceuticals (Oct. 16, 2017) Regeneron and Sanofi Announce Positive Phase 2 Study Results for Dupilumab in Patients Active Moderate-to-severe Eosinophilic Esophagitis, Acquire Media, 4 Pages.
Regeneron Pharmaceuticals, Apr. 2011 Annual Report (12 pages).
Ring, et al. (2012) "Guidelines for Treatment of Atopic Eczema Part I", Journal of the European Academy of Dermatology and Venereology, vol. 26, pp. 1045-1060.
Rizk, Habib (2011) "Role of Aspirin Desensitization in the Management of Chronic Rhinosinusitis", Current Opinion in Otolaryngology & Head and Neck Surgery, vol. 19, Issue 3, pp. 210-217.
Roitt, et al. (2001) "Immunology—Sixth Edition", Mosby—Harcourt Publishers Limited, pp. 110-111.
Roll, et al. (Jan. 1, 2006) "Safety of Specific Immunotherapy using a Four-Hour Ultra-Rush Induction Scheme in Bee and Wasp Allergy", Journal of Investigational Allergology and Clinical Immunology, vol. 16, No. 2, pp. 79-85.
Romaniuk, L I. (2012) "Allergan-Specific Immunotherapy Mechanisms Methods and Efficacy", Clinical Immunology, Allergology and Infectology, Special Issue, pp. 44-47.
Rothenberg, Marc E. (Oct. 2009) "Eosinophilic Esophagitis: Biology to Therapy", Gastroenterology, vol. 137, No. 4, pp. 1238-1249.
Rothenberg, Marc E. (Jan. 1, 2004) "Eosinophilic Gastrointestinal Disorders (EGID)", Journal of Allergy and Clinical Immunology, vol. 113, No. 1, pp. 11-28.
Sampson, et al. (May 2011) "A Phase II, Randomized, Double-Blind, Parallel-Group, Placebo0controlled Oral Food Challenge Trial of Xolair (Omalizumab) in Peanut Allergy", The Journal of Allergy and Clinical Immunology, vol. 127, No. 5, pp. 1309-1310. e1.
Sanofi (Oct. 19, 2018) "Evaluation of Dupilumab in Patients with Severe Steroid Dependent Asthma (VENTURE)", Archive History for NCT02528214, Retrieved at URL: <<https://clinicaltrials.gov/ct2/history/NCT02528214?V_38=View#StudyPageTop>>, 15 Pages.
Sanofi (43671) "A Controlled Clinical Study of Dupilumab in Patients with Bilateral Nasal Polyps (SINUS-24)", ClinicalTrials.gov Identifier: NCT02912468, 18 Pages.
Sanofi (Oct. 23, 2019) "Controlled Clinical Study of Dupilumab in Patients with Nasal Polyps (SINUS-52)", ClinicalTrials.gov Identifier: NCT02898454, 18 Pages.
Sanofi (May 18, 2020) "Evaluation of SAR440340 and as Combination Therapy with Dupilumab in Moderate-to-Severe Asthma Participants", Clinical Trials Accession No. NCT03387852, Retrieved from: <<https://clinicaltrials.gov/ct2/show/NCT03387852>>, 10 Pages.
Sanofi, Clinical Trials, "History of Changes for Study: NCT01259323 Sequential Ascending Dose Study to Assess the Safety and Tolerability of REGN668 (SAR231893) in Patients With Atopic Dermatitis,", U.S. National Library of Medicine, Retrieved at URL: https://clinicaltrials.gov/ct2/history/NCT01259323?V_5=View#StudyPageTop.
Sanofi, Clinical Trials, "History of Changes for Study: NCT01548404 Study of Dupilumab in Adult Patients With Extrinsic Moderate-to_ Severe Atopic Dermatitis", U.S. National Library of Medicine, Retrieved at URL: https://clinicaltrials.gov/ct2/history/NCT01548404?V2=view#StudyPageTop.
Sanofi, Clinicaltrials.gov (Nov. 4, 2019) "Efficacy, Safety, and Tolerability of Dupilumab in Patients With Persistent Moderate to Severe Eosinophilic Asthma," [accessible on the internet at: https://clinicaltrials.gov/ct2/show/NCT01312961].
Schmidt, J J. (1985) "DNA Cloning: A Practical Approach Volumes I and II", Edited by D M Glover, IRL Press Oxford, 1 Page.
Schmitt, et al. (Dec. 1, 2007) "What are the Best Outcome Measurements for Atopic Eczema? A Systematic Review", Journal of Allergy and Clinical Immunology, vol. 120, No. 6, pp. 1389-1398.
Schneider, et al. (Dec. 1, 2002) "A Pilot Study of Omalizumab to Facilitate Rapid Oral Desensitization in High-Risk Peanut-Allergic Patients", Journal of Allergy and Clinical Immunology, vol. 132, No. 6, pp. 1368-1374.
Sefton, MV (Jan. 1, 1987) "Implantable Pumps", Critical Reviews in Biomedical Engineering, vol. 14, No. 3, pp. 201-240.
Stein, et al. (Dec. 1, 2006) "Anti-IL-5 (Mepolizumab) Therapy for Eosinophilic Esophagitis", Journal of Allergy and Clinical Immunology, vol. 118, No. 6, pp. 1312-1319.
Stone, et al. (Dec. 2008) "Immunomodulatory Therapy of Eosinophil-Associated Gastrointestinal Diseases", Clinical & Experimental Allergy, vol. 38, No. 12, pp. 1858-1865.
Straumann, et al. (Jan. 1, 2010) "Anti-Interleukin-5 Antibody Treatment (Mepolizumab) in Active Eosinophilic Oesophagitis: A Randomised, Placebo-Controlled, Double-Blind Trial", Gut, vol. 59, No. 1, pp. 21-30.
Straumann, et al. (Feb. 1, 2009) "Clinical Evaluation of the Adult who has Eosinophilic Esophagitis", Immunology and Allergy Clinics of North America, vol. 29, No. 1, pp. 11-18.
Straumann, et al. (Feb. 1, 2005) "Eosinophilic Esophagitis: Escalating Epidemiology?", Journal of Allergy and Clinical Immunology, vol. 115, 2, pp. 418-419.
Straumann, et al. (Dec. 1, 2001) "Idiopathic Eosinophilic Esophagitis is Associated with a TH2-Type Allergic Inflammatory Response", Journal of Allergy and Clinical Immunology, vol. 108, No. 6, pp. 954-961.
Straumman et al. (2008) "Anti-TNF-a (infliximab) therapy for severe adult eosinophilic esophagitis," J. Allergy Clin. Immunol., 122(2):425-427.
Tang, et al.(2010) "YKL-40 in Asthmatic Patients, and its Correlations with Exacerbation, Eosinophils and Immunoglobulin E", European Respiratory Society, vol. 35, pp. 757-760.
Veerappan, et al. (Apr. 1, 2009) "Prevalence of Eosinophilic Esophagitis in an Adult Population Undergoing Upper Endoscopy: A Prospective Study", Clinical Gastroenterology and Hepatology, vol. 7, No. 4, pp. 420-426.
Vestergaard, et al. (Oct. 1, 2000) "A Th2 Chemokine, TARC, Produced by Keratinocytes May Recruit CLA+CCR4+ Lymphocytes into Lesional Atopic Dermatitis Skin", Journal of Investigative Dermatology, vol. 115, No. 4, pp. 640-646.
Wang, et al. (Dec. 1, 2008) "The IIL-17 Cytokine Family and their Role in Allergic Inflammation", Current Opinion in Immunology, vol. 20 Number, pp. 697-702.
Wark, et al. (Aug. 7, 2006) "Latest Technologies for the Enhancement of Antibody Affinity", Advanced Drug Delivery Reviews, vol. 58, No. 5-6, pp. 657-670.
Weber, et al. (Mar. 13, 2012) "Anti-IL-4 as a New Strategy in Allergy", Chemical immunology and Allergy, vol. 96, pp. 120-125.
Wegmann, et al. (2017) "Targeting Cytokines in Asthma Therapy: Could IL-37 be a Solution?", Expert Review of Respiratory Medicine, vol. 11, No. 9, pp. 675-677.
Weihrauch, et al. (Jul. 1, 2005) "Elevated Serum Levels of CC Thymus and Activation-Related Chemokine (Tarc) in Primary Hodgkin's Disease: Potential for a Prognostic Factor", Cancer Research, vol. 65, No. 13, pp. 5516-5519.
Weinbrand-Goichberg, et al. (Jul. 1, 2013) "Eosinophilic Esophagitis: An Immune-Mediated Esophageal Disease", Immunologic Research, vol. 56, No. 2-3, pp. 249-260.
Wershil, (Feb. 1, 2009) "Exploring the Role of Mast Cells in Eosinophilic Esophagitis", Immunology and Allergy Clinics of North America, vol. 29, No. 1, pp. 189-195.

(56) References Cited

OTHER PUBLICATIONS

Whalley, et al. (Feb. 2004) "A New Instrument for Assessing Quality of Life in Atopic Dermatitis: International Development of the Quality of Life Index for Atopic Dermatitis (Qoliad)", British Journal of Dermatology, vol. 150, pp. 274-283.

Wilhelm, et al. (Nov. 28, 2011) "Innate Lymphoid Cells and Type 2 ($T_H2$) Mediated Immune Responses—Pathogenic or Beneficial?", Frontiers in Immunology, vol. 2, Article 68, pp. 1-4.

Yasuhara, et al. (Jul. 2010) "Fundamentals of Clinical Pharmacokinetics", Clinical Pharmacology, vol. 41, Issue 4, pp. 155-158.

\* cited by examiner

Baseline Demographics – ITT

| Category | Data | N=116 V PBO | N=94 V 300 | N=210 V ALL | N=1902 QUEST ALL |
|---|---|---|---|---|---|
| Age (y) | Mean (SD) | 50.7 (12.8) | 51.9 (12.5) | 51.3 (12.6) | 47.9 (15.3) |
| Sex [n (%)] | Female | 65 (60.7%) | 62 (60.2%) | 127 (60.5%) | 1197 (62.9%) |
| BMI group (kg/m2) [n (%)] | >=30 | 49 (45.8%) | 38 (36.9%) | 87 (41.4%) | 751 (39.5%) |
| ICS at BL | High | High | High | High | 979 (51.5%) |
| Age at onset of asthma (y) | Mean (SD) | 31.6 (16.4) | 31.2 (18.9) | 31.4 (17.6) | 27.0 (19.1) |
| Age at onset of asthma (y) | <18 | 24 (22.4%) | 26 (25.2%) | 50 (23.8%) | 704 (37.0%) |
| Age at onset of asthma (y) | 18 - 40 | 51 (47.7%) | 43 (41.7%) | 94 (44.8%) | 665 (35.0%) |
| Age at onset of asthma (y) | >40 | 32 (29.9%) | 34 (33.0%) | 66 (31.4%) | 533 (28.0%) |
| # of severe asthma exac exp. past year | Mean (SD) | 2.17 (2.24) | 2.01 (2.08) | 2.09 (2.16) | 2.09 (2.15) |
| Daily OCS @ V1 | Mean (SD) | 11.83 (6.02) | 11.79 (6.40) | 11.81 (6.20) | n/a |
| Daily OCS @ BL | Mean (SD) | 11.75 (6.31) | 10.75 (5.90) | 11.26 (6.12) | n/a |
| BL pre-BD FEV1 (L) | Mean (SD) | 1.63 (0.61) | 1.53 (0.53) | 1.58 (0.57) | 1.78 (0.60) |
| BL pre-BD FEV1 percent predicted (%) | Mean (SD) | 52.69 (15.14) | 51.64 (15.28) | 52.18 (15.18) | 58.43 (13.52) |
| BL post-BD FEV1 (L) | Mean (SD) | 1.89 (0.73) | 1.83 (0.60) | 1.86 (0.67) | 2.16 (0.72) |
| BL FEV1 reversibility (%) | Mean (SD) | 18.39 (22.97) | 20.58 (23.59) | 19.47 (23.25) | 26.29 (21.73) |
| BL ACQ-5 score | Mean (SD) | 2.58 (1.09) | 2.42 (1.24) | 2.50 (1.16) | 2.76 (0.77) |
| BL ACQ-7 score | Mean (SD) | 2.81 (1.00) | 2.70 (0.98) | 2.75 (0.99) | 2.86 (0.69) |
| BL Global AQLQ score | Mean (SD) | 4.31 (1.12) | 4.38 (1.24) | 4.35 (1.17) | 4.29 (1.05) |
| BL Blood Eosinophil (GIGA/L) | Mean (SD) | 0.33 (0.30) | 0.37 (0.32) | 0.35 (0.31) | 0.36 (0.37) |
| BL Blood Eosinophil (GIGA/L) | Median | 0.24 | 0.28 | 0.26 | 0.26 |
| BL Total IgE (IU/ML) | Mean (SD) | 426.62 (881.22) | 434.65 (654.54) | 430.58 (775.96) | 432.40 (746.66) |
| BL FeNO (ppb) | Mean (SD) | 39.62 (34.12) | 35.55 (28.34) | 37.61 (31.38) | 34.97 (32.85) |
| BL FeNO (ppb) | Median | 29 | 28 | 28.5 | 25 |

Fig. 3

***P<0.001 versus placebo

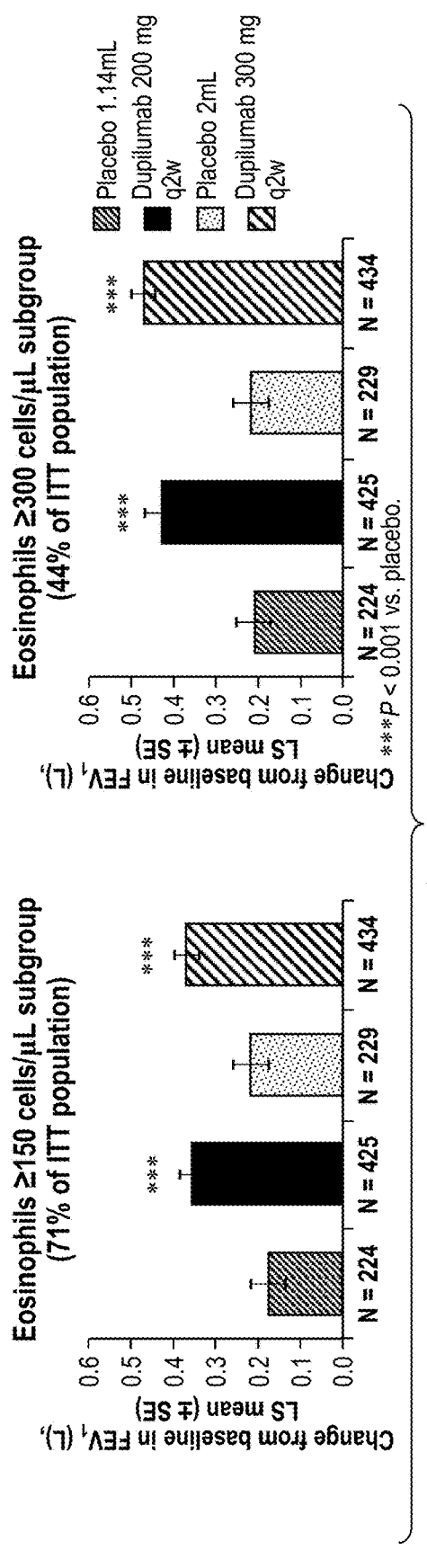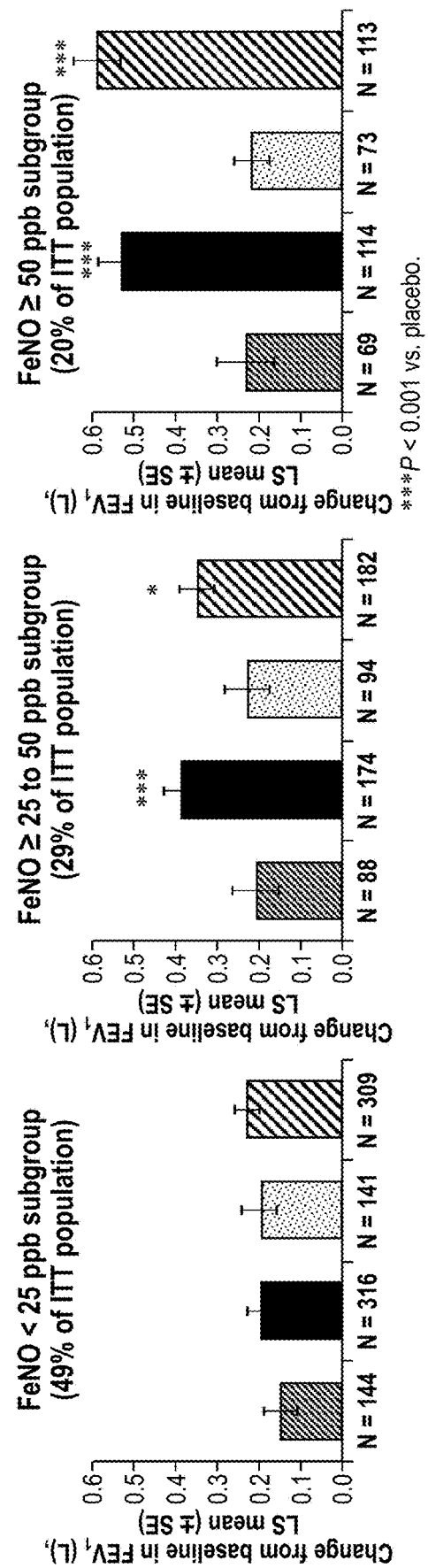
Fig. 10B
Fig. 10C

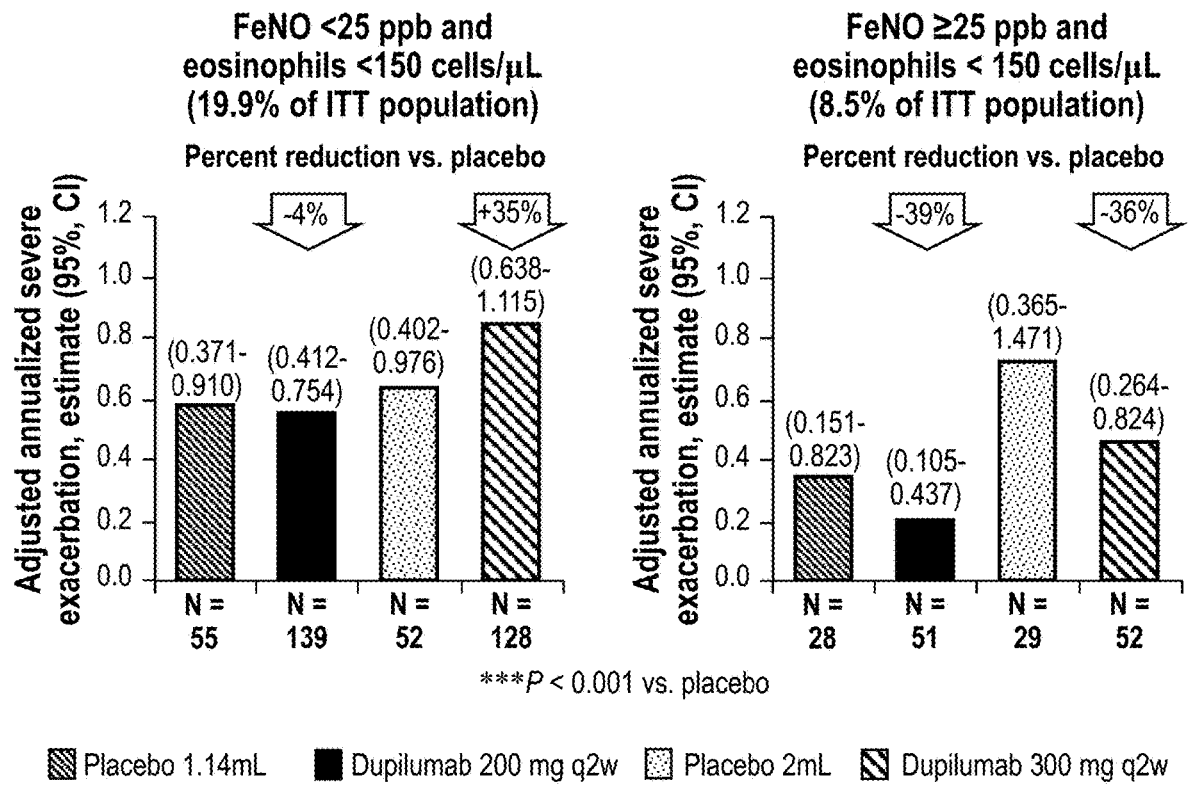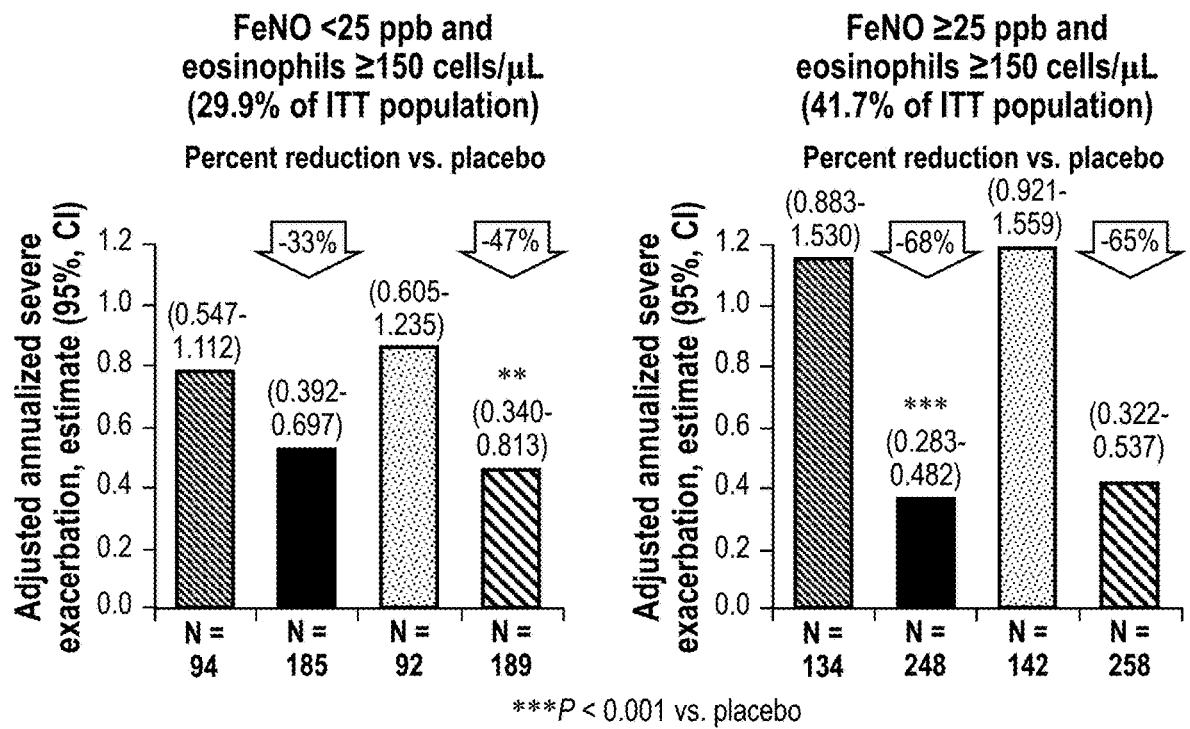
Fig. 11A

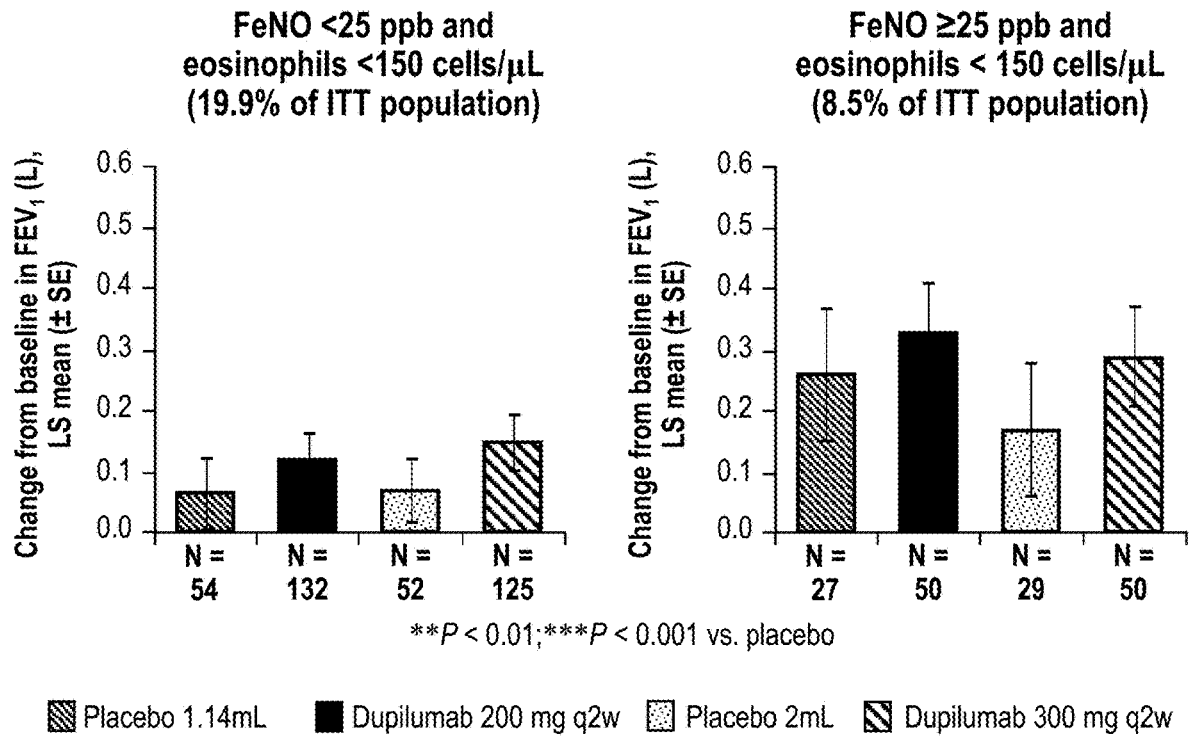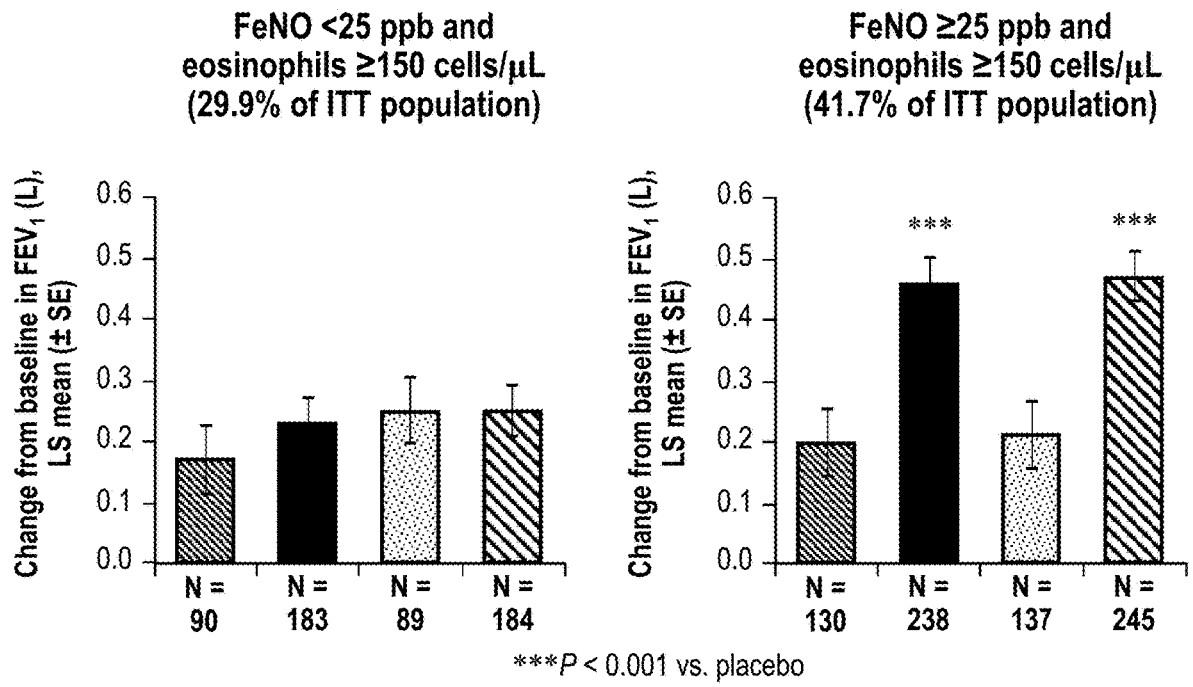
Fig. 11B

|  | Adolescents (n = 107) | | Adults (n = 1795) | |
| --- | --- | --- | --- | --- |
|  | Placebo q2w pooled (n = 39) | Dupilumab 200+300 mg q2w (n = 68) | Placebo q2w pooled (n = 599) | Dupilumab 200+300 mg q2w (n = 1196) |
| Age, mean (SD), years | 14.4 (1.6) | 14.1 (1.9) | 50.4 (12.9) | 49.7 (13.5) |
| Female sex, n (%) | 13 (33.3) | 25 (36.8) | 403 (67.3) | 756 (63.2) |
| Age at asthma onset, mean (SD), years | 4.7 (3.8) | 5.1 (3.9) | 28.8 (18.5) | 28.1 (19.1) |
| Pre-bronchodilator FEV$_1$, mean (SD), L | 2.47 (0.65) | 2.25 (0.51) | 1.71 (0.55) | 1.76 (0.61) |
| Pre-bronchodilator FEV$_1$, mean (SD), % predicted | 72.13 (10.35) | 69.49 (11.70) | 57.50 (13.24) | 57.82 (13.34) |
| FEV$_1$ reversibility %, mean (SD) | 22.86 (12.99) | 24.94 (17.11) | 25.94 (18.49) | 26.65 (23.61) |
| Exacerbations in previous year, mean (SD), n | 2.18 (1.93) | 1.75 (1.30) | 2.19 (1.84) | 2.06 (2.34) |
| High-dose ICS use, n (%) | 9 (23.1) | 17 (25.0) | 330 (55.1) | 623 (52.1) |
| ACQ-5 score, mean (SD) | 2.52 (0.66) | 2.49 (0.62) | 2.75 (0.76) | 2.78 (0.78) |
| Blood eosinophil count, median (IQR), GIGA/L | 0.29 (0.12–0.69) | 0.21 (0.13–0.57) | 0.27 (0.14–0.47) | 0.25 (0.13–0.46) |
| FeNO, median (IQR), ppb | 41.00 (21.00–73.00) | 24.00 (13.00–48.00) | 26.00 (15.00–44.00) | 24.00 (14.00–42.00) |
| Any comorbid medical history, n (%) | 38 (97.4) | 63 (92.6) | 474 (79.1) | 926 (77.4) |
| Atopic dermatitis | 15 (38.5) | 14 (20.6) | 68 (11.4) | 125 (10.5) |
| Allergic rhinitis | 38 (97.4) | 62 (91.2) | 411 (68.6) | 808 (67.6) |
| Nasal polyposis | 0 | 0 | 106 (17.7) | 204 (17.1) |
| Nasal polyposis | 0 | 0 | 106 (17.7) | 204 (17.1) |

*Fig. 12*

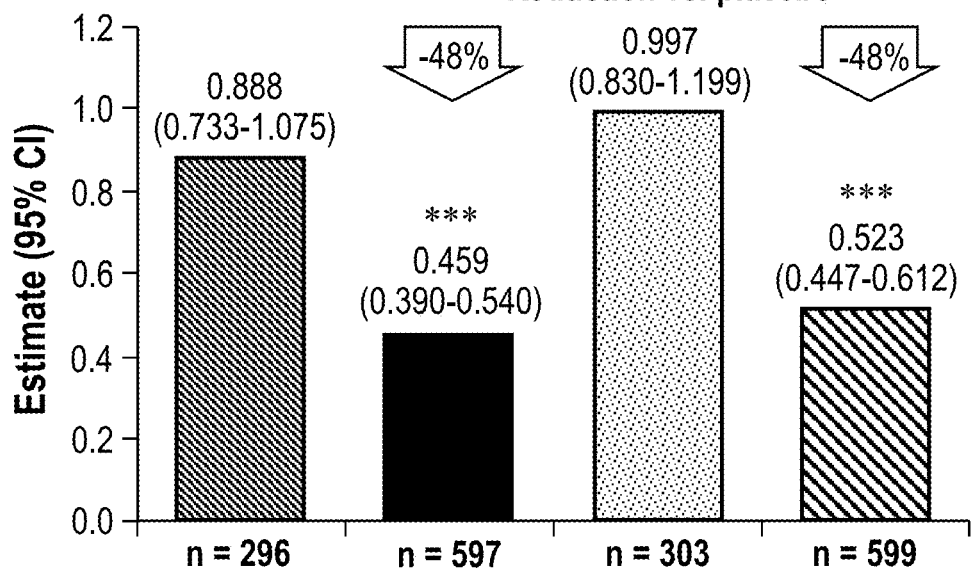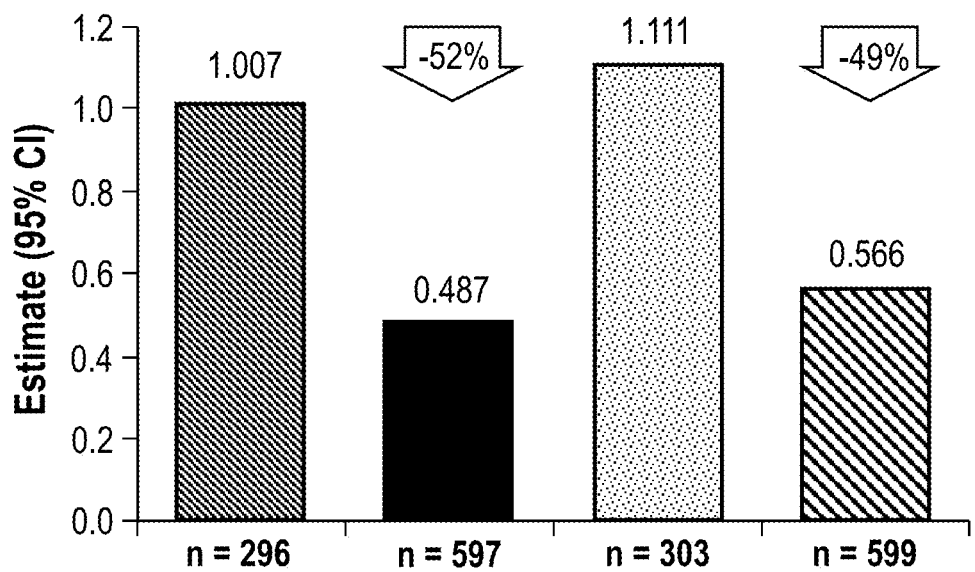
Fig. 14B

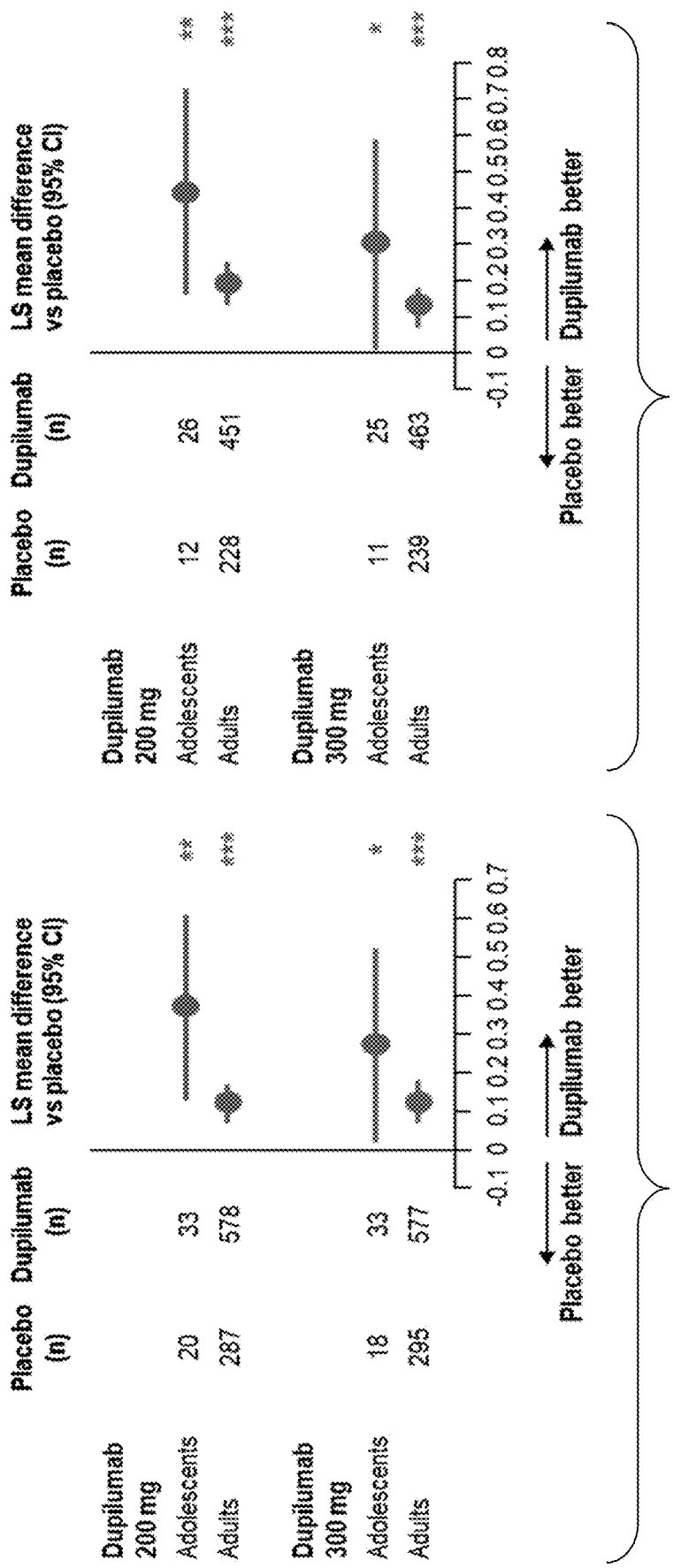

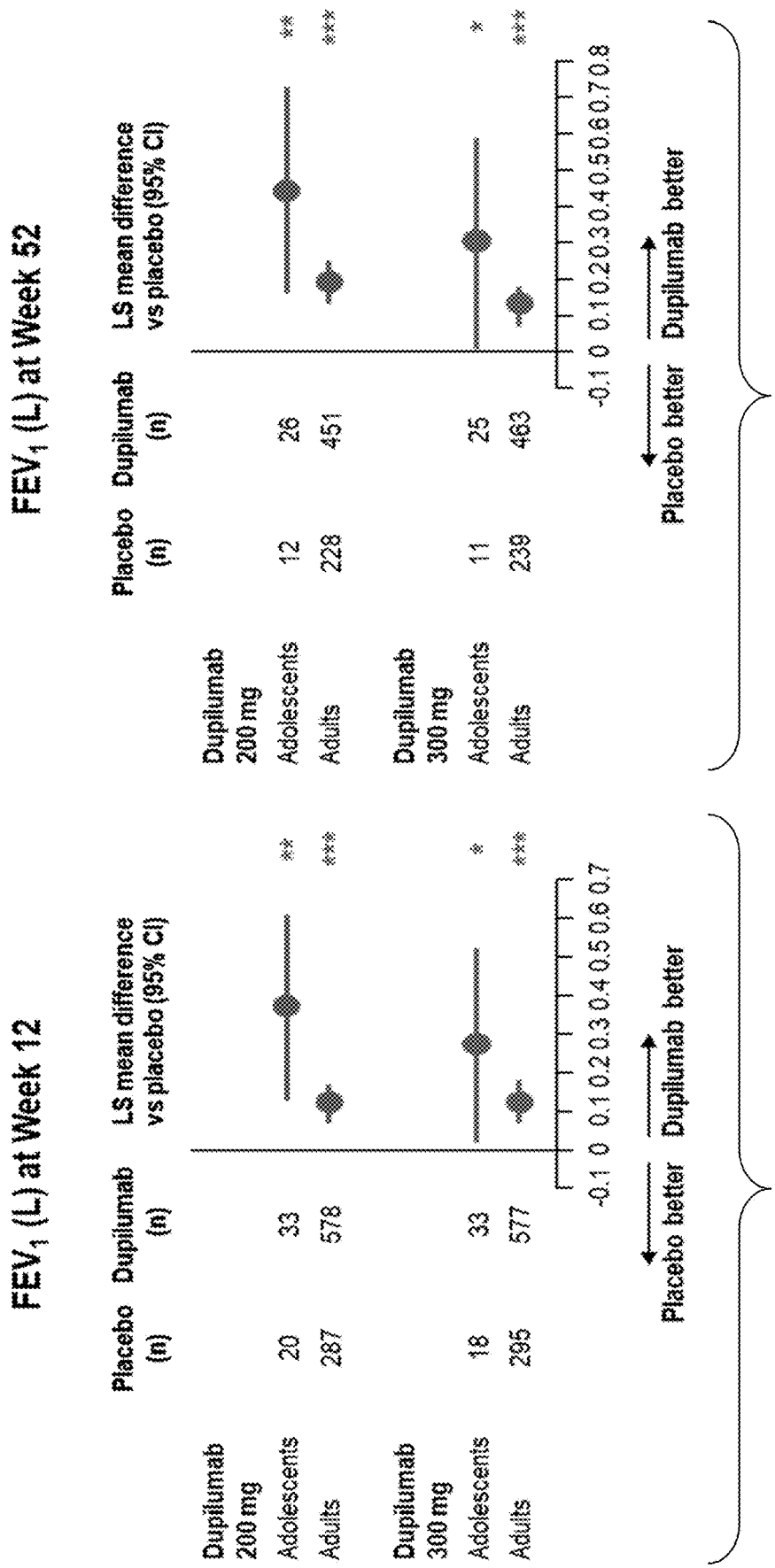

| n (%) | Adolescents (N = 107) | | | | Adults (N = 1,795) | | | | |
|---|---|---|---|---|---|---|---|---|---|
| | Placebo 1.14mL (n = 21) | Dupilumab 200mg q2w (n = 34) | Placebo 2mL (n = 18) | Dupilumab 300mg q2w (n = 34) | Placebo 1.14mL (n = 21) | Dupilumab 200mg q2w (n = 34) | Placebo 2mL (n = 18) | Dupilumab 300mg q2w (n = 34) | |
| Any TEAE | 16 (76.2) | 24 (70.6) | 16 (88.9) | 26 (76.5) | 241 (82.5) | 484 (81.1) | 254 (83.8) | 489 (81.8) | |
| Treatment emergent SAE | 0 | 3 (8.8) | 2 (11.1) | 1 (2.9) | 26 (8.9) | 46 (7.7) | 25 (8.3) | 54 (9.0) | |
| Any TEAE leading to death | 0 | 0 | 0 | 0 | 3 (1.0) | 1 (0.2) | 0 | 4 (0.7) | |
| Any TEAE leading to treatment discontinuation | 0 | 1 (2.9) | 1 (5.6) | 2 (5.9) | 19 (6.5) | 18 (3.0) | 9 (3.0) | 42 (7.0) | |
| Conjunctivitis (PT) | 0 | 0 | 1 (5.6) | 0 | 1 (0.3) | 2 (0.3) | 3 (1.0) | 4 (0.7) | |
| Eosinophilia* | 0 | 0 | 0 | 0 | 3 (1.0) | 28 (4.7) | 1 (0.3) | 24 (4.0) | |
| Injection-site reactions (HLT) | 0 | 3 (8.8) | 1 (5.6) | 4 (11.8) | 17 (5.8) | 93 (15.6) | 32 (10.6) | 112 (18.7) | |

Fig. 17

| n (%) | Placebo 1.14 mL 2qw | Dupilumab 200 mg q2w | Placebo 2 mL q2w | Dupilumab 300 mg q2w |
|---|---|---|---|---|
| Adolescents (12–17 years) | (n = 21) | (n = 34) | (n = 18) | (n = 34) |
| Viral upper respiratory tract infection | 6 (28.6) | 2 (5.9) | 7 (38.9) | 10 (29.4) |
| Upper respiratory tract infection | 0 | 4 (11.8) | 1 (5.6) | 2 (5.9) |
| Respiratory tract infection viral | 0 | 3 (8.8) | 2 (11.1) | 4 (11.8) |
| Respiratory tract infection | 1 (4.8) | 0 | 2 (11.1) | 0 |
| Bronchitis | 1 (4.8) | 4 (11.8) | 0 | 2 (5.9) |
| Injection-site erythema | 0 | 2 (5.9) | 1 (5.6) | 4 (11.8) |
| Injection-site oedema | 0 | 2 (5.9) | 1 (5.6) | 4 (11.8) |
| Pharyngitis | 4 (19.1) | 1 (2.9) | 1 (5.6) | 0 |
| Viral pharyngitis | 0 | 1 (2.9) | 2 (11.1) | 0 |
| Influenza | 3 (14.3) | 1 (2.9) | 3 (16.7) | 1 (2.9) |
| Rhinitis (allergic) | 1 (4.8) | 0 | 3 (16.7) | 1 (2.9) |
| Adults (≥ 18 years) | (n = 292) | (n = 597) | (n = 303) | (n = 598) |
| Viral upper respiratory tract infection | 54 (18.5) | 117 (19.6) | 57 (18.8) | 101 (16.9%) |
| Upper respiratory tract infection | 37 (12.7) | 65 (10.9) | 48 (15.8) | 75 (12.5%) |
| Bronchitis | 46 (15.8) | 69 (11.6) | 42 (13.9%) | 69 (11.5%) |
| Injection-site erythema | 13 (4.5) | 74 (12.4) | 21 (6.9%) | 94 (15.7%) |

*Fig. 22*

| Conjunctivitis (narrow), n (%) | Adolescent patients (aged 12-17 years) | | | | Adults (aged ≥ 18 years) | | | |
|---|---|---|---|---|---|---|---|---|
| | Placebo 1.14 mL q2w (n = 21) | Dupilumab 200 mg q2w (n = 34) | Placebo 2 mL q2w (n = 18) | Dupilumab 300 mg q2w (n = 34) | Placebo 1.14 mL q2w (n = 292) | Dupilumab 200 mg q2w (n = 597) | Placebo 1.14 mL q2w (n = 303) | Dupilumab 300 mg q2w (n = 598) |
| Any TEAE | 0 | 2 (5.9) | 1 (5.6) | 0 | 6 (2.1) | 6 (1.0) | 8 (2.6) | 14 (2.3) |
| Any SAE | 0 | 0 | 0 | 0 | 0 | 0 | 0 | 0 |
| Any treatment-emergent SAE | 0 | 0 | 0 | 0 | 0 | 0 | 0 | 0 |
| Any TEAE leading to permanent treatment discontinuation | 0 | 0 | 0 | 0 | 0 | 0 | 0 | 0 |
| Conjunctivitis (broad) | | | | | | | | |
| Any TEAE | 0 | 2 (5.9) | 1 (5.6) | 0 | 10 (3.4) | 8 (1.3) | 10 (3.3) | 19 (3.2) |
| Any SAE | 0 | 0 | 0 | 0 | 0 | 0 | 0 | 0 |
| Any treatment-emergent SAE | 0 | 0 | 0 | 0 | 0 | 0 | 0 | 0 |
| Any TEAE leading to permanent treatment discontinuation | 0 | 0 | 0 | 0 | 0 | 0 | 0 | 0 |

*Fig. 23*

| Eosinophilia, n (%) | Adolescent patients (aged 12-17 years) | | | | Adults (aged ≥ 18 years) | | | |
|---|---|---|---|---|---|---|---|---|
| | Placebo 1.14 mL q2w (n = 21) | Dupilumab 200 mg q2w (n = 34) | Placebo 2 mL q2w (n = 18) | Dupilumab 300 mg q2w (n = 34) | Placebo 1.14 mL q2w (n = 292) | Dupilumab 200 mg q2w (n = 597) | Placebo 2 mL q2w (n = 303) | Dupilumab 300 mg q2w (n = 598) |
| Any TEAE | 0 | 0 | 0 | 0 | 3 (1.0) | 28 (4.7) | 1 (0.3) | 24 (4.0) |
| Any SAE | 0 | 0 | 0 | 0 | 0 | 0 | 0 | 2 (0.3) |
| Any treatment-emergent SAE | 0 | 0 | 0 | 0 | 0 | 0 | 0 | 2 (0.3) |
| Any TEAE leading to permanent treatment discontinuation | 0 | 0 | 0 | 0 | 0 | 0 | 0 | 0 |
| Eosinophilic disorders (HLT), n (%) | | | | | | | | |
| Any TEAE | 0 | 0 | 0 | 0 | 2 (0.7) | 21 (3.5) | 0 | 17 (2.8) |
| Any SAE | 0 | 0 | 0 | 0 | 0 | 0 | 0 | 1 (0.2) |
| Any treatment-emergent SAE | 0 | 0 | 0 | 0 | 0 | 0 | 0 | 1 (0.2) |
| Any TEAE leading to permanent treatment discontinuation | 0 | 0 | 0 | 0 | 1 (0.3) | 1 (0.2) | 0 | 2 (0.3) |
| Eosinophil count increased (PT), n (%) | | | | | | | | |
| Any TEAE | 0 | 0 | 0 | 0 | 1 (0.3) | 8 (1.3) | 1 (0.3) | 7 (1.2) |
| Any SAE | 0 | 0 | 0 | 0 | 0 | 0 | 0 | 0 |
| Any treatment-emergent SAE | 0 | 0 | 0 | 0 | 0 | 0 | 0 | 0 |
| Any TEAE leading to permanent treatment discontinuation | 0 | 0 | 0 | 0 | 0 | 0 | 0 | 3 (0.5) |

*Fig. 24*

| | Age of onset of asthma >40 years and baseline post-bronchodilator FEV₁/FVC <0.7 | | | | Age of onset of asthma >40 years and baseline post-bronchodilator FEV₁/FVC ≥0.7 | | | |
|---|---|---|---|---|---|---|---|---|
| | 1.14mL/200mg q2w | | 2mL/300mg q2w | | 1.14mL/200mg q2w | | 2mL/300mg q2w | |
| | Placebo (n=56) | Dupilumab (n=104) | Placebo (n=53) | Dupilumab (n=95) | Placebo (n=38) | Dupilumab (n=74) | Placebo (n=41) | Dupilumab (n=72) |
| Estimate (95% CI) | 1.53 (1.02–2.30) | 0.48 (0.33–0.70) | 1.34 (0.90–2.00) | 0.33 (0.21–0.51) | 0.82 (0.49–1.39) | 0.37 (0.23–0.59) | 0.75 (0.47–1.22) | 0.37 (0.23–0.60) |
| Relative risk vs placebo (95% CI), % | | −68.8 (−45.6 to −82.1) | | −75.7 (−56.0 to −86.6) | | −55.1 (−7.9 to −78.1) | | −50.7 (−4.3 to −74.6) |
| P value vs placebo | | <0.0001 | | <0.0001 | | 0.03 | | 0.04 |
| Baseline, mean (SD) | 1.42 (0.48) | 1.45 (0.48) | 1.36 (0.50) | 1.37 (0.44) | 1.66 (0.42) | 1.67 (0.52) | 1.65 (0.38) | 1.68 (0.47) |
| Change from baseline at Week 12, n | 52 | 101 | 52 | 91 | 36 | 72 | 41 | 70 |
| LS mean (SE) | 0.19 (0.05) | 0.34 (0.04) | 0.14 (0.05) | 0.34 (0.04) | 0.12 (0.06) | 0.23 (0.04) | 0.18 (0.05) | 0.30 (0.04) |
| P value vs placebo | | 0.01 | | 0.003 | | 0.12 | | 0.05 |
| Change from baseline at Week 52, n | 44 | 80 | 43 | 71 | 24 | 51 | 32 | 59 |
| LS mean (SE) | 0.16 (0.06) | 0.36 (0.04) | 0.20 (0.06) | 0.33 (0.04) | 0.10 (0.07) | 0.25 (0.05) | 0.19 (0.06) | 0.30 (0.05) |
| P value vs placebo | | 0.004 | | 0.09 | | 0.06 | | 0.12 |

Fig. 27A

| | | | | | | | | |
|---|---|---|---|---|---|---|---|---|
| Post-bronchodilator FEV₁, L | | | | | | | | |
| Baseline, mean (SD) | 1.74 (0.56) | 1.77 (0.57) | 1.62 (0.56) | 1.64 (0.48) | 2.08 (0.54) | 2.06 (0.62) | 2.07 (0.54) | 2.12 (0.52) |
| Change from baseline at Week 12, n | 52 | 101 | 51 | 91 | 36 | 72 | 40 | 69 |
| LS mean (SE) | 0.12 (0.05) | 0.22 (0.04) | 0.04 (0.05) | 0.24 (0.04) | −0.09 (0.06) | 0.00 (0.04) | −0.05 (0.05) | 0.03 (0.04) |
| P value vs placebo | | 0.09 | | 0.003 | | 0.18 | | 0.16 |
| Change from baseline at Week 52, n | 43 | 85 | 44 | 71 | 24 | 53 | 32 | 60 |
| LS mean (SE) | 0.05 (0.06) | 0.23 (0.04) | 0.07 (0.06) | 0.21 (0.04) | −0.15 (0.07) | −0.01 (0.05) | −0.07 (0.06) | 0.00 (0.04) |
| P value vs placebo | | 0.01 | | 0.06 | | 0.06 | | 0.30 |
| Pre-bronchodilator FEV₁/FVC ratio, % | | | | | | | | |
| Baseline, mean (SD) | 55.13 (8.07) | 55.06 (8.89) | 56.42 (9.71) | 56.00 (9.03) | 70.53 (6.60) | 70.66 (7.92) | 69.88 (7.15) | 70.57 (5.63) |
| Change from baseline at Week 12, n | 52 | 101 | 52 | 91 | 36 | 72 | 41 | 70 |
| LS mean (SE) | 2.02 (0.84) | 4.45 (0.62) | 1.10 (0.86) | 4.78 (0.65) | 0.67 (1.02) | 0.31 (0.74) | 0.84 (0.95) | 2.43 (0.72) |
| P value vs placebo | | 0.02 | | 0.0006 | | 0.77 | | 0.17 |
| Change from baseline at Week 52, n | 44 | 80 | 43 | 71 | 24 | 51 | 32 | 59 |
| LS mean (SE) | 2.16 (0.99) | 5.59 (0.74) | 3.02 (1.03) | 4.96 (0.77) | 0.10 (1.10) | 2.05 (0.79) | 1.64 (1.00) | 2.31 (0.75) |
| P value vs placebo | | 0.005 | | 0.13 | | 0.14 | | 0.58 |

Fig. 27B

SEQUENCE LISTING

```
<160> NUMBER OF SEQ ID NOS: 8

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      HCVR polypeptide

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      LCVR polypeptide

<400> SEQUENCE: 2
```

-continued

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR1 peptide

<400> SEQUENCE: 3

```
Gly Phe Thr Phe Arg Asp Tyr Ala
1               5
```

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR2 peptide

<400> SEQUENCE: 4

```
Ile Ser Gly Ser Gly Gly Asn Thr
1               5
```

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      HCDR3 peptide

<400> SEQUENCE: 5

```
Ala Lys Asp Arg Leu Ser Ile Thr Ile Arg Pro Arg Tyr Tyr Gly Leu
1               5                   10                  15

Asp Val
```

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR1 peptide

<400> SEQUENCE: 6

```
Gln Ser Leu Leu Tyr Ser Ile Gly Tyr Asn Tyr
1               5                   10
```

```
<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      LCDR2 peptide

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      LCDR3 peptide

<400> SEQUENCE: 8

Met Gln Ala Leu Gln Thr Pro Tyr Thr
1               5
```

METHODS FOR TREATING OR PREVENTING ASTHMA BY ADMINISTERING AN IL-4R ANTAGONIST

RELATED APPLICATIONS

This application claims the benefit of U.S. Provisional Application Nos. 62/579,120, filed Oct. 30, 2017; 62/710,381, filed Feb. 16, 2018; 62/647,368, filed Mar. 23, 2018; and 62/742,736, filed Oct. 8, 2018, and EP Application No. EP18305566.4, filed May 4, 2018, each of which is incorporated herein by reference in its entirety.

FIELD OF THE INVENTION

The invention relates to the treatment and/or prevention of asthma and related conditions. More specifically, the invention relates to the administration of an interleukin-4 receptor (IL-4R) antagonist to treat or prevent asthma in a patient in need thereof.

BACKGROUND

Asthma is a chronic inflammatory disease of the airways characterized by airway hyper responsiveness, acute and chronic bronchoconstriction, airway edema, and mucus plugging. The inflammation component of asthma is thought to involve many cell types, including mast cells, eosinophils, T lymphocytes, neutrophils, and epithelial cells, and their biological products. Patients with asthma most often present with symptoms of wheezing, shortness of breath, cough, and chest tightness. For most asthma patients, a regimen of controller therapy and bronchodilator therapy provides adequate long-term control. Inhaled corticosteroids (ICS) are considered the "gold standard" in controlling asthma symptoms, and inhaled beta2-agonists are the most effective bronchodilators currently available. Studies have shown that combination therapy of an ICS with an inhaled long-acting beta2-agonist (LABA) provides better asthma control than high doses of ICS alone. Consequently, combination therapy has been the recommended treatment for subjects who are not controlled on low doses of ICS alone.

Nonetheless, it is estimated that 5% to 10% of the population with asthma has symptomatic disease despite maximum recommended treatment with combinations of anti-inflammatory and bronchodilator drugs. Furthermore, this severe asthma population accounts for up to 50% of the total health cost through hospital admissions, use of emergency services, and unscheduled physician visits. There is an unmet need for a new therapy in this severe asthma population as many of these patients are poorly responsive to ICS due to a number of cellular and molecular mechanisms. In addition, the long term adverse effects of systemic and inhaled corticosteroids on bone metabolism, adrenal function, and growth in children lead to attempts to minimize the amount of corticosteroid usage. Although a large portion of asthma patients are managed reasonably well with current treatments, patients with severe uncontrolled asthma (e.g., severe corticosteroid-refractory asthma or steroid-intolerant asthma) have few therapeutic treatment options that can adequately control the disease. The consequence of unresponsiveness to therapy or lack of compliance with therapy is loss of asthma control and ultimately asthma exacerbation.

An estimated 45% of patients with severe asthma require systemic glucocorticoids to control their disease, and to prevent life-threatening exacerbations associated with increased risk of permanent damage to lung tissue, progressive fixed airway obstruction, and accelerated decline in lung function. However, systemic glucocorticoids act non-selectively and are associated with significant multi-organ toxicities and broad immunosuppression. There is a need for safer and more effective targeted therapies that prevent exacerbations and lung function impairment, improve asthma symptoms and control, and reduce or obviate the need for oral glucocorticoids.

Approximately 20% of patients with asthma have uncontrolled, moderate-to-severe disease with recurrent exacerbations and persistent symptoms despite maximized standard-of-care controller therapy. This population is at an increased risk of morbidity (especially exacerbations) and accounts for significant healthcare resources. These patients have substantially reduced lung function, despite maximum treatment, and are destined to inexorably further lose lung function. No currently approved treatments have been shown to slow this inexorable decline in these patients, or to consistently and meaningfully increase lung function.

Accordingly, a need exists in the art for novel targeted therapies for the treatment and/or prevention of asthma.

BRIEF SUMMARY OF THE INVENTION

According to one aspect, a method for treating a subject having severe uncontrolled asthma (e.g., severe steroid-dependent asthma) comprising administering to the subject a loading dose of an antibody or an antigen-binding fragment thereof that specifically binds to interleukin-4 receptor (IL-4R), and administering to the subject a plurality of maintenance doses of the antibody or the antigen-binding fragment thereof, wherein the plurality of maintenance doses are administered during a treatment phase comprising an induction phase, an oral corticosteroid (OCS) reduction phase, and an OCS maintenance phase is provided.

In certain exemplary embodiments, a maintenance dose of antibody or antigen-binding fragment thereof is administered once every other week (q2w). In certain exemplary embodiments, a maintenance dose of antibody or antigen-binding fragment thereof is administered every fourth week (q4w).

In certain embodiments, the subject is administered a loading dose, and the subject is administered a maintenance dose having a dose regimen of 500 mg q4w or 750 mg q4w.

In certain embodiments, the loading dose is eliminated. In certain embodiments, the subject is administered a dose regimen of 500 mg q4w or 750 mg q4w.

In certain exemplary embodiments, the loading dose is about 600 mg of the antibody or the antigen-binding fragment thereof, and/or each maintenance dose of antibody or antigen-binding fragment thereof is about 300 mg of the antibody or the antigen-binding fragment thereof.

In certain exemplary embodiments, the maintenance doses of antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, the OCS reduction phase is about 16 weeks in length.

In certain exemplary embodiments, OCS use by the subject is reduced during the OCS reduction phase. In certain exemplary embodiments, the subject uses 50% or less, 75% or less or 90% or less OCS in the maintenance phase compared to the induction phase. In certain exemplary embodiments, OCS use by the subject is reduced to about 5 mg/day or less in the maintenance phase. In other exemplary embodiments, the OCS is reduced and/or eliminated, for example the subject is weaned off of the previous OCS dose. In certain exemplary embodiments, the administration of the OCS is completely eliminated from a treatment regimen.

In certain exemplary embodiments, the subject has a blood eosinophil count of less than or equal to about 150 cells/µl. In certain exemplary embodiments, the subject has a blood eosinophil count of greater than about 150 cells/µl. In certain exemplary embodiments, the subject has a blood eosinophil count of greater than about 300 cells/µl.

In certain exemplary embodiments, the subject experiences a reduction in annualized severe asthma exacerbations. In certain exemplary embodiments, the subject experiences an improvement in lung function as measured by forced expiratory volume ($FEV_1$). In other embodiments, the subject exhibits an improvement in small airway lung function and/or a reduction in small airway inflammation. In certain embodiments, the improvement in lung function and reduction in inflammation is measured by forced expiratory flow at 25-75% of the pulmonary volume (FEF25-75).

In certain exemplary embodiments, OCS use by the subject is optimized prior to treatment with the antibody or antigen-binding fragment thereof. In certain exemplary embodiments, the OCS is prednisone or prednisolone.

In certain exemplary embodiments, the antibody or antigen-binding fragment thereof comprises heavy and light chain complementary determining region (CDR) sequences from the heavy chain variable region (HCVR)/light chain variable region (LCVR) sequence pair comprising SEQ ID NOs: 1 and 2. In certain exemplary embodiments, the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively. In certain exemplary embodiments, the antibody or antigen-binding fragment thereof comprises a HCVR comprising the amino acid sequence of SEQ ID NO: 1 and a LCVR comprising the amino acid sequence of SEQ ID NO: 2.

In certain exemplary embodiments, the subject is an adult. In certain exemplary embodiments, the subject is an adolescent. In certain exemplary embodiments, the subject is an adult or an adolescent, e.g., is 12 years or older.

In another aspect, a method for treating a subject having severe uncontrolled asthma (e.g., severe steroid-dependent asthma) comprising administering to the subject a loading dose of an antibody or an antigen-binding fragment thereof that specifically binds to interleukin-4 receptor (IL-4R), and administering to the subject a plurality of maintenance doses of the antibody or the antigen-binding fragment thereof, wherein the plurality of maintenance doses are administered during a treatment phase comprising an induction phase, an oral corticosteroid (OCS) reduction phase, and a maintenance phase, and wherein the antibody or antigen-binding fragment thereof comprises heavy and light chain CDR sequences from the HCVR/LCVR sequence pair comprising SEQ ID NOs: 1 and 2, is provided.

In another aspect, a method for treating a subject having severe uncontrolled asthma, e.g., severe steroid-dependent asthma, comprising administering to the subject a loading dose of about 600 mg of an antibody or an antigen-binding fragment thereof that specifically binds to interleukin-4 receptor (IL-4R), and administering to the subject a plurality of maintenance doses of the antibody or the antigen-binding fragment thereof, wherein each maintenance dose is about 300 mg of the antibody or antigen-binding fragment thereof, wherein the plurality of maintenance doses are administered during a treatment phase comprising an induction phase, an oral corticosteroid (OCS) reduction phase, and a maintenance phase, and wherein the antibody or antigen-binding fragment thereof comprises heavy and light chain CDR sequences from the HCVR/LCVR sequence pair comprising SEQ ID NOs: 1 and 2, is provided.

In another aspect, a method for reducing an annualized severe exacerbation rate in a subject having moderate-to-severe uncontrolled asthma, comprising administering to the subject q2w or q4w an antibody or an antigen-binding fragment thereof that specifically binds to IL-4R, is provided.

In certain exemplary embodiments, the dosage is 200 mg q2w, or 300 mg q2w.

In certain exemplary embodiments, a maintenance dose of antibody or antigen-binding fragment thereof is administered every fourth week (q4w).

In certain embodiments, the subject is administered a loading dose and maintenance doses, and the subject is administered a dose regimen of 500 mg q4w or750 mg q4w.

In certain embodiments, the loading dose is eliminated. In certain embodiments, the subject is administered a dose regimen of 500 mg q4w or 750 mg q4w.

In certain exemplary embodiments, the subject has a blood eosinophil count of less than about 150 cell/µl, of greater than or equal to about 150 cells/µl, or of greater than about 300 cells/µl.

In certain exemplary embodiments, the subject has a fractional exhaled nitric oxide (FeNO) level of greater than or equal to about 25 parts per billion (ppb), has an FeNO level of greater than or equal to about 50 ppb, or has an FeNO level of between greater than or equal to about 25 ppb and about 50 ppb.

In another aspect, a method for improving an $FEV_1$ score in a subject having uncontrolled moderate-to-severe asthma, comprising administering to the subject q2w or q4w an antibody or an antigen-binding fragment thereof that specifically binds to IL-4R, is provided.

In certain exemplary embodiments, the dosage is administered at 200 mg q2w or 300 mg q2w. In certain exemplary embodiments, the dosage is administered at 500 mg q4w or 750 mg q4w.

In certain exemplary embodiments, the subject has a blood eosinophil count of less than about 150 cells/µl, of greater than or equal to about 150 cells/µl, or of greater than about 300 cells/µl.

In certain exemplary embodiments, the subject has a fractional exhaled nitric oxide (FeNO) level of greater than or equal to about 25 parts per billion (ppb), has an FeNO level of greater than or equal to about 50 ppb, or has an FeNO level of between greater than or equal to about 25 ppb and about 50 ppb.

In another embodiment, the subject exhibits at least a 10%, 15%, 20% or 25% reduction in a biomarker selected from the group consisting of FeNO, eotaxin-3, total IgE, periostin and thymus and activation regulated chemokine (TARC) at week 4, week 12 or week 24 following administration of the IL-4R antibody or fragment thereof.

In certain exemplary embodiments, the subject is an adult. In certain exemplary embodiments, the subject is an adolescent. In certain exemplary embodiments, the subject is an adult or an adolescent, e.g., is 12 years or older.

In other aspects, the disclosure provides a method for improving a forced expiratory flow at 25-75% of the pulmonary volume (FEF25-75) score in a subject having uncontrolled moderate-to-severe asthma, comprising administering to the subject q2w or q4w an antibody or an antigen-binding fragment thereof that specifically binds to IL-4R.

In one embodiment, the dosage is 200 mg q2w or 300 mg q2w. In one embodiment, the dosage is 500 mg q4w or 750 mg q4w.

In one embodiment, the subject has a blood eosinophil count of less than about 150 cells/µl. In one embodiment, the subject has a blood eosinophil count of greater than or equal to about 150 cells/µl. In one embodiment, the subject has a blood eosinophil count of greater than about 300 cells/µl.

In another embodiment, the subject has an FeNO level of greater than or equal to about 25 ppb. In another embodiment, the subject has an FeNO level of greater than or equal to about 50 ppb. In another embodiment, the subject has an FeNO level of between greater than or equal to about 25 ppb and about 50 ppb.

In another embodiment, the subject exhibits at least a 10%, at least a 15%, at least a 20%, or at least a 25% reduction in a biomarker selected from the group consisting of FeNO, eotaxin-3, total periostin and thymus and activation regulated chemokine (TARC) at week 4, week 12 or 24 following administration of the IL4R antibody or fragment thereof.

In certain exemplary embodiments, the subject is an adult. In certain exemplary embodiments, the subject is an adolescent. In certain exemplary embodiments, the subject is an adult or an adolescent, e.g., is 12 years or older.

In another aspect, the disclosure provides a method of reducing or eliminating OCS use in a subject suffering from steroid dependent severe asthma, the method comprising administering to the subject a loading dose of an antibody or an antigen-binding fragment thereof that specifically binds to an IL-4R; and administering to the subject a plurality of maintenance doses of the antibody or the antigen-binding fragment thereof, wherein a reduction of at least 50% or greater, of at least 75% or greater, or of at least 90% or greater in OCS use is achieved at week 24 following administration of the loading dose.

In one embodiment, the OCS use is reduced to less than 5 mg per day at week 24 following administration of the loading dose. In another embodiment, the OCC is substantially eliminated after a period of time 1 year) following administration of the loading dose. In certain embodiments, the OCS is substantially eliminated after 40 weeks, 45 weeks, 50 weeks, 52 weeks or greater after first dose following administration of the loading dose.

In one embodiment, the maintenance dose of antibody or antigen-binding fragment thereof is administered once every other week (q2w). In one embodiment, the loading dose is about 600 mg of the antibody or the antigen-binding fragment thereof. In one embodiment, each maintenance dose of antibody or antigen-binding fragment thereof is about 300 mg of the antibody or the antigen-binding fragment thereof. In another embodiment, the maintenance doses of antibody or antigen-binding fragment thereof are administered for at least 24 weeks. In one embodiment, a first maintenance dose of antibody or antigen-binding fragment thereof is administered two weeks after the loading dose of antibody or antigen-binding fragment thereof. In one embodiment, the OCS is prednisone or predni solone.

In one embodiment, the antibody or antigen-binding fragment thereof comprises heavy and light chain complementary determining region (CDR) sequences from the heavy chain variable region (HCVR)/light chain variable region (LCVR) sequence pair comprising SEQ ID NOs: 1 and 2. In one embodiment, the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively. In one embodiment, the antibody or antigen-binding fragment thereof comprises a HCVR comprising the amino acid sequence of SEQ ID NO: 1 and a LCVR comprising the amino acid sequence of SEQ ID NO: 2.

In certain exemplary embodiments, a maintenance dose of antibody or antigen-binding fragment thereof is administered every fourth week (q4w).

In certain embodiments, the subject is administered a loading dose is administered, and the subject is administered a dose regimen of 500 mg q4w, and 750 mg q4w.

In certain embodiments, the loading dose is eliminated. In certain embodiments, the subject is administered a dose regimen of 500 mg q4w, and 750 mg q4w.

In certain exemplary embodiments, the subject is an adult. In certain exemplary embodiments, the subject is an adolescent. In certain exemplary embodiments, the subject is an adult or an adolescent, e.g., is 12 years or older.

In another aspect, a method for treating a subject having oral corticosteroid (OCS)-dependent, moderate-to-severe asthma is provided, comprising administering to the subject a loading dose of an antibody or an antigen-binding fragment thereof that specifically binds to interleukin-4 receptor (IL 4R), and administering to the subject a plurality of maintenance doses of the antibody or the antigen-binding fragment thereof, wherein the loading dose and the plurality of maintenance doses are administered as an add-on maintenance asthma therapy.

In certain exemplary embodiments, the antibody or antigen-binding fragment thereof comprises heavy and light chain complementary determining region (CDR) sequences from the heavy chain variable region (HCVR)/light chain variable region (LCVR) sequence pair comprising SEQ ID NOs: 1 and 2, In certain exemplary embodiments, the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively. In certain exemplary embodiments, the antibody or antigen-binding fragment thereof comprises a HCVR comprising the amino acid sequence of SEQ ID NO: 1 and a LCVR comprising the amino acid sequence of SEQ ID NO: 2.

In certain exemplary embodiments, the loading dose is about 600 mg of the antibody or the antigen-binding fragment thereof. In certain exemplary embodiments, each maintenance dose of antibody or antigen-binding fragment thereof is about 300 mg of the antibody or the antigen-binding fragment thereof.

In certain exemplary embodiments, the loading dose is about 400 mg of the antibody or the antigen-binding fragment thereof. In certain exemplary embodiments, each maintenance dose of antibody or antigen-binding fragment thereof is about 200 mg of the antibody or the antigen-binding fragment thereof.

In certain exemplary embodiments, the subject is 12 years of age or older.

In certain exemplary embodiments, the OCS is prednisone or prednisolone.

In another aspect, a method for treating a subject having moderate-to-severe asthma and co-morbid moderate-to-severe atopic dermatitis is provided, comprising administering to the subject a loading dose of an antibody or an antigen-binding fragment thereof that specifically binds to interleukin-4 receptor (IL-4R), and administering to the subject a plurality of maintenance doses of the antibody or the antigen-binding fragment thereof, wherein the loading dose and the plurality of maintenance doses are administered as an add-on maintenance asthma therapy.

In another aspect, a method for treating a subject having moderate-to-severe uncontrolled asthma wherein onset of asthma occurred when the subject was greater than 40 years of age is provided, comprising administering to the subject a loading dose of an antibody or an antigen-binding fragment thereof that specifically binds to interleukin-4 receptor (IL-4R), and administering to the subject a plurality of maintenance doses of the antibody or the antigen-binding fragment thereof, wherein the loading dose and the plurality of maintenance doses are administered as an add-on maintenance asthma therapy.

In another aspect, a method for treating a subject having moderate-to-severe uncontrolled asthma and one or both of co-morbid chronic rhinosinusitis and nasal polyposis is provided, comprising administering to the subject a loading dose of an antibody or an antigen-binding fragment thereof that specifically binds to interleukin-4 receptor (IL-4R), and administering to the subject a plurality of maintenance doses of the antibody or the antigen-binding fragment thereof, wherein the loading dose and the plurality of maintenance doses are administered as an add-on maintenance asthma therapy.

In another aspect, a method for treating a subject having moderate-to-severe uncontrolled asthma and co-morbid allergic rhinitis is provided, comprising administering to the subject a loading dose of an antibody or an antigen-binding fragment thereof that specifically binds to interleukin-4 receptor (IL-4R), and administering to the subject a plurality of maintenance doses of the antibody or the antigen-binding fragment thereof, wherein the loading dose and the plurality of maintenance doses are administered as an add-on maintenance asthma therapy.

In another aspect, a method for improving allergic rhinitis-related quality of life of a subject having moderate-to-severe uncontrolled asthma and co-morbid allergic rhinitis is provided, comprising administering to the subject a loading dose of an antibody or an antigen-binding fragment thereof that specifically binds to interleukin-4 receptor (IL-4R), and administering to the subject a plurality of maintenance doses of the antibody or the antigen-binding fragment thereof, wherein the loading dose and the plurality of maintenance doses are administered as an add-on maintenance asthma therapy.

In another aspect, a method for improving allergic rhinitis-related quality of life in a subject having oral corticosteroid-dependent asthma is provided, comprising administering to the subject a loading dose of an antibody or an antigen-binding fragment thereof that specifically binds to interleukin-4 receptor (IL-4R), and administering to the subject a plurality of maintenance doses of the antibody or the antigen-binding fragment thereof, wherein the loading dose and the plurality of maintenance doses are administered as an add-on maintenance asthma therapy.

In certain exemplary embodiments, morning and evening daily asthma symptoms are improved.

In certain exemplary embodiments, the oral corticosteroid-dependent asthma is oral corticosteroid-dependent severe asthma.

In another aspect, a method for improving asthma control in a subject having oral corticosteroid-dependent asthma is provided, comprising administering to the subject a loading dose of an antibody or an antigen-binding fragment thereof that specifically binds to interleukin-4 receptor (IL-4R), and administering to the subject a plurality of maintenance doses of the antibody or the antigen-binding fragment thereof, wherein the loading dose and the plurality of maintenance doses are administered as an add-on maintenance asthma therapy.

In certain exemplary embodiments, health related quality of life is improved.

In certain exemplary embodiments, the oral corticosteroid-dependent asthma is oral corticosteroid-dependent severe asthma.

Other embodiments will become apparent from a review of the ensuing detailed description, drawings, tables and accompanying claims.

BRIEF DESCRIPTION OF THE FIGURES

The foregoing and other features and advantages of the present invention will be more fully understood from the following detailed description of illustrative embodiments taken in conjunction with the accompanying drawings. The file of this patent contains at least one drawing/photograph executed in color. Copies of this patent with color drawing(s)/photograph(s) will be provided by the Office upon request and payment of the necessary fee.

FIG. 3 is a chart showing the baseline demographics for the patient population.

FIG. 4A depicts primary and secondary oral glucocorticoid endpoints at week 24. FIG. 4B depicts the annualized rate of severe exacerbations. FIG. 4C depicts change in pre-bronchodilator $FEV_1$ (in L). FIG. 4D depicts and change in FeNO (in ppb).

FIG. 5A depicts primary endpoint data. FIG. 5B depicts secondary oral glucocorticoid endpoint data.

FIG. 10A FIG. 10C depict change from baseline in $FEV_1$ over time in the ITT population (FIG. 10 A), at week 12 in subgroups defined by baseline blood eosinophils ≥150 and ≥300 cells/µl (FIG. 10 B), and subgroups defined by baseline FeNO Levels <25 ppb, ≥25 to 50 ppb, and ≥50 ppb (FIG. 10 C).

FIG. 11A-FIG. 11B graphically depict post hoc analysis of severe asthma exacerbations (FIG. 11 A) and change from baseline in $FEV_1$ (FIG. 11 B) in patients with high (≥25 ppb) or low (<25 ppb) baseline FeNO levels and high (≥150 cells/µl) or low (<150 cells/µl) baseline blood eosinophils.

FIG. 12 depicts baseline demographics and clinical characteristics of adolescents (n=107) and adults (n=1795). Bold text highlights key differences between subgroups. FeNO, fractionated exhaled nitric oxide; LABA, long-acting β-agonist; SD, standard deviation.

FIG. 14A-FIG. 14B graphically depict a reduction in severe exacerbation rates in adolescents and adults. Light grey circles, 1.14 mL placebo; dark grey circles, 2 mL placebo; orange, 200 mg q2w dupilumab; blue, 300 mg q2w dupilumab. ***P<0.001 vs. placebo; NS, non-significant.

FIG. 15A-FIG. 15B graphically depict improved $FEV_1$ at week 12 and at week 52 in adolescents and adults. Despite higher baseline levels, adolescents had a greater increase in $FEV_1$. <0.05, P<0.01, *P<0.001 vs. placebo.

FIG. 16A-FIG. 16B graphically depict improved $FEV_1$ during the 52-week treatment period in adolescents and adults. *P<0.05, **P<0.01 vs. placebo.

FIG. 17 depicts that the adverse event profiled was comparable between subgroups (safety population). Eosinophilia is identified as AE with HLT as eosinophilic disorders, or PT as eosinophil count increased. HLT, high-level term; PT, preferred term; SAE, severe adverse event; TEAE, treatment-emergent adverse event.

FIG. 22 depicts TEAEs (PT) occurring in ≥10% of patients according to adolescent and adult subgroups (safety population).

FIG. 23 depicts conjunctivitis TEAE information (safety population).

FIG. 24 depicts eosinophilia TEAE information (safety population). Eosinophilia is identified as AE with HLT as eosinophilic disorders, or PT as eosinophil count increased.

FIG. 27A-FIG. 27B depict the effect of dupilumab on severe exacerbation rate, FEV1 and FEV1/FVC ratio in patients with uncontrolled, moderate-severe-asthma who were >40 years old at the onset of asthma, and had baseline post-bronchodilator FEV1/FVC <0.7 or ≥0.7.

DETAILED DESCRIPTION

Figure 1:
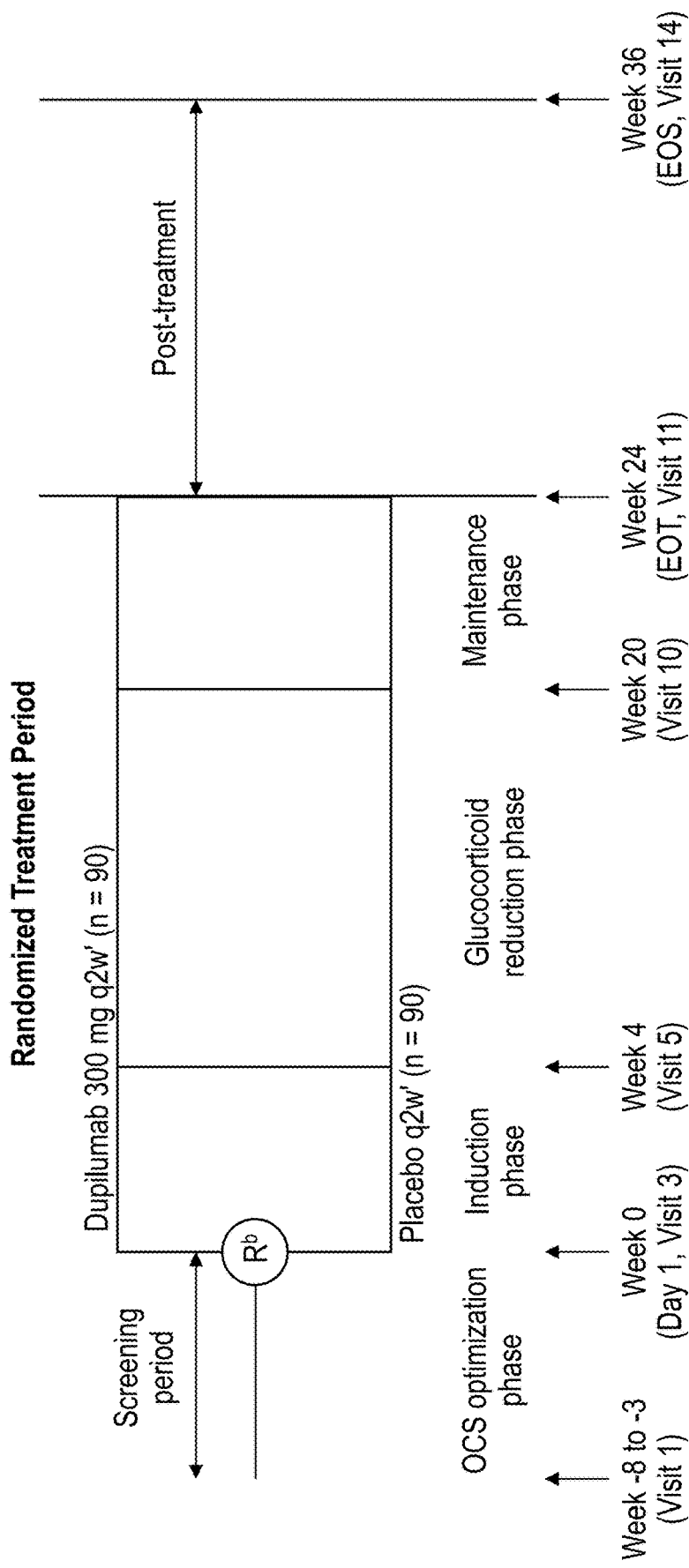
FIG. 1 depicts the Venture (EFC13691) study design for the phase 3 trial. EOS denotes end of study, EOT end of treatment, OCS oral glucocorticoid, q2w every 2 weeks, R Randomization visit. $^a$600 mg (or matching placebo) loading dose on day 1; $^b$randomization and first investigational medicinal product administration occurred at this visit; $^c$the screening period could be increased to 10 weeks for patients experiencing an asthma exacerbation that required a change in glucocorticoid dose to allow for 2 weeks of stabilization prior to randomization.

Before the invention is described, it is to be understood that this invention is not limited to particular methods and experimental conditions described, as such methods and conditions may vary. It is also to be understood that the terminology used herein is for the purpose of describing particular embodiments only, and is not intended to be limiting, because the scope of the invention will be limited only by the appended claims.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "treat," "treating," or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the invention, the typical methods and materials are now described. All publications mentioned herein are incorporated herein by reference in their entirety.

Methods for Reducing the Incidence of Asthma Exacerbations

The invention includes methods for reducing the incidence of asthma exacerbations in a subject in need thereof comprising administering a pharmaceutical composition comprising an IL-4R antagonist to the subject. According to certain embodiments, the IL-4R antagonist is an antibody or antigen-binding fragment thereof that specifically binds IL-4R. Exemplary anti-IL-4R antibodies that can be used in the context of the methods featured in the invention are described elsewhere herein. As used herein, the expression "asthma exacerbation" means an increase in the severity and/or frequency and/or duration of one or more symptoms or indicia of asthma. An "asthma exacerbation" also includes any deterioration in the respiratory health of a subject that requires and or is treatable by a therapeutic intervention for asthma (such as, e.g., steroid treatment, inhaled corticosteroid treatment, hospitalization, etc.). There are two types of asthma exacerbation events: a loss of asthma control (LOAC) event and a severe exacerbation event.

According to certain embodiments, a loss of asthma control (LOAC) event is defined as one or more of the following: (a) greater than or equal to 6 additional reliever puffs of salbutamol/albuterol or levosalbutamol/levalbuterol in a 24 hour period (compared to baseline) on 2 consecutive days; (b) an increase in ICS greater than or equal to 4 times the dose at visit 2; and (c) use of systemic corticosteroids for greater than or equal to 3 days; or (d) hospitalization or emergency room visit because of asthma, requiring systemic corticosteroids.

In certain instances, an asthma exacerbation may be categorized as a "severe asthma exacerbation event." A severe asthma exacerbation event means an incident requiring immediate intervention in the form of treatment with either systemic corticosteroids or with inhaled corticosteroids at four or more times the dose taken prior to the incident. According to certain embodiments, a severe asthma exacerbation event is defined as a deterioration of asthma requiring: use of systemic corticosteroids for greater than or equal to 3 days; or hospitalization or emergency room visit because of asthma, requiring systemic corticosteroids. The general expression "asthma exacerbation" therefore includes and encompasses the more specific subcategory of "severe asthma exacerbations," Accordingly, methods for reducing the incidence of severe asthma exacerbations in a patient in need thereof are included.

A "reduction in the incidence" of an asthma exacerbation means that a subject has received a pharmaceutical composition comprising an IL-4R antagonist experiences fewer asthma exacerbations (i.e., at least one fewer exacerbation) after treatment than before treatment, or experiences no asthma exacerbations for at least 4 weeks (e.g., 4, 6, 8, 12, 14, or more weeks) following initiation of treatment with the pharmaceutical composition. A "reduction in the incidence" of an asthma exacerbation alternatively means that, following administration of the pharmaceutical composition, the likelihood that a subject experiences an asthma exacerbation is decreased by at least 10% (e.g., 10%, 15%, 20%, 25%, 30%, 35%, 40%, 45%, 50%, or more) as compared to a subject who has not received the pharmaceutical composition.

The invention includes methods for reducing the incidence of asthma exacerbations in a subject in need thereof comprising administering a pharmaceutical composition comprising an IL-4R antagonist to the subject as well as administering to the subject one or more maintenance doses of an inhaled corticosteroid (ICS) and/or one or more maintenance doses of a second controller, e.g., a long-acting beta-agonist (LABA) or a leukotriene receptor antagonist (LTA). Suitable ICSs include, but are not limited to, fluticasone (e.g., fluticasone propionate, e.g., Flovent™), budesonide, mometasone (e.g., mometasone furoate, e.g., Asmanex™), flunisolide (e.g., Aerohid™), dexamethasone acetate/phenobarbital/theophylline (e.g., Azmacort™), beclomethasone dipropionate HFA (Qvar™), and the like. Suitable LABAs include, but are not limited to, salmeterol (e.g., Serevent™), formoterol (e.g., Foradil™), and the like.

Suitable LTAs include, but are not limited to, montelukast (e.g., Singulaire™), zafirlukast (e.g., Accolate™), and the like.

The invention includes methods for reducing the incidence of asthma exacerbations in a subject in need thereof comprising administering a pharmaceutical composition comprising an IL-4R antagonist to the subject as well as administering to the subject one or more reliever medications to eliminate or reduce one or more asthma-associated symptoms. Suitable reliever medications include, but are not limited to, quick-acting beta2-adrenergic receptor agonists such as, e.g., albuterol (i.e., salbutamol, e.g., Proventil™, Ventolin™, Xopenex™ and the like), pirbuterol (e.g., Maxair™), metaproterenol (e.g., Alupent™) and the like.

Methods for Improving Asthma-Associated Parameters

The invention also includes methods for improving one or more asthma-associated parameters in a subject in need thereof, wherein the methods comprise administering a pharmaceutical composition comprising an IL-4R antagonist to the subject. A reduction in the incidence of an asthma exacerbation (as described above) may correlate with an improvement in one or more asthma-associated parameters; however, such a correlation is not necessarily observed in all cases.

Examples of "asthma-associated parameters" include: (1) relative percent change from baseline (e.g., at week 12) in forced expiratory volume in 1 second ($FEV_1$); (2) a relative percent change from baseline (e.g., at week 12) as measured by forced expiratory flow at 25-75% of the pulmonary volume (FM5-75); (3) annualized rate of loss of asthma control events during the treatment period; (4) annualized rate of severe exacerbation events during the treatment period; (5) time to loss of asthma control events during the treatment period; (6) time to severe exacerbation events during the treatment period; (7) time to loss of asthma control events during overall study period; (8) time to severe exacerbation events during overall study period; (9) health care resource utilization; (10) change from baseline at week 12 in: i) morning and evening asthma symptom scores, ii) ACQ-5 score, iii) AQLQ score, iv) morning and evening PEF, v) number of inhalations/day of salbutamol/albuterol or levosalbutamol/levalbuterol for symptom relief, vi) nocturnal awakenings; (11) change from baseline at week 12 and week 24 in: i) 22-item Sino Nasal Outcome Test (SNOT-22), ii) Hospital Anxiety and Depression Score (BADS), iii) EuroQual questionnaire (EQ-5D-3L or EQ-5D-5L). An "improvement in an asthma-associated parameter" means an increase from baseline of one or more of $FEV_1$, AM PEF or PM PEF, and/or a decrease from baseline of one or more of daily albuterol/levalbuterol use, ACQ5 score, average nighttime awakenings or SNOT-22 score. As used herein, the term "baseline," with regard to an asthma-associated parameter, means the numerical value of the asthma-associated parameter for a patient prior to or at the time of administration of a pharmaceutical composition comprising an IL-4R antagonist.

To determine whether an asthma-associated parameter has "improved," the parameter is quantified at baseline and at a time point after administration of the pharmaceutical composition described herein. For example, an asthma-associated parameter may be measured at day 1, day 2, day 3, day 4, day 5, day 6, day 7, day 8, day 9, day 10, day 11, day 12, day 14, or at week 3, week 4, week 5, week 6, week 7, week 8, week 9, week 10, week 11, week 12, week 13, week 14, week 15, week 16, week 17, week 18, week 19, week 20, week 21, week 2.2, week 23, week 24, or longer, after the initial treatment with the pharmaceutical composition. The difference between the value of the parameter at a particular time point following initiation of treatment and the value of the parameter at baseline is used to establish whether there has been an "improvement" in the asthma associated parameter (e g , an increase or decrease, as the case may be, depending on the specific parameter being measured).

The terms "acquire" or "acquiring" as used herein, refer to obtaining possession of a physical entity, or a value, e.g., a numerical value, by "directly acquiring" or "indirectly acquiring" the physical entity or value, such as an asthma-associated parameter. "Directly acquiring" means performing a process (e.g., performing a synthetic or analytical method) to obtain the physical entity or value. "Indirectly acquiring" refers to receiving the physical entity or value from another party or source (e.g., a third-party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis").

Information that is acquired indirectly can be provided in the form of a report, e.g., supplied in paper or electronic form, such as from an online database or application (an "App"). The report or information can be provided by, for example, a healthcare institution, such as a hospital or clinic; or a healthcare provider, such as a doctor or nurse.

Forced Expiratory Volume in 1 Second ($FEV_1$). According to certain embodiments, administration of an IL-4R antagonist to a patient results in an increase from baseline of forced expiratory volume in 1 second ($FEV_1$). Methods for measuring $FEV_1$ are known in the art. For example, a spirometer that meets the 2005 American Thoracic Society (ATS)/European Respiratory Society (ERS) recommendations can be used to measure $FEV_1$ in a patient. The ATS/ERS Standardization of Spirometry may be used as a guideline. Spirometry is generally performed between 6 and 10 AM after an albuterol withhold of at least 6 hours. Pulmonary function tests are generally measured in the sitting position, and the highest measure is recorded for $FEV_1$ (in liters).

The invention includes therapeutic methods that result in an increase of $FEV_1$ from baseline of at least 0.05 L at week 12 following initiation of treatment with a pharmaceutical composition comprising an anti-IL-4R antagonist. For example, administration of an IL-4R antagonist to a subject in need thereof causes an increase of $FEV_1$ from baseline of about 0.05 L, 0.10 L, 0.12 L, 0.14 L, 0.16 L, 0.18 L, 0.20 L, 0.22 L, 0.24 L, 0.26 L, 0.28 L, 0.30 L, 0.32 L, 0.34 L, 0.36 L, 0.38 L, 0.40 L, 0.42 L, 0.44 L, 0.46 L, 0.48 L, 0.50 L, or more at week 12.

FEF25-75%. According to certain embodiments, administration of an IL-4R antagonist to a patient results in an increase from baseline of FEF25-75%. Methods for measuring FEF are known in the art. For example, a spirometer that meets the 2005 American Thoracic Society (ATS)/European Respiratory Society (ERS) recommendations can be used to measure FEVs in a patient. The FE 25-75 (forced expiratory flow between 25% and 75%) is the speed (in liters per second) at which a person can empty the middle half of his or her air during a maximum expiration (i.e., Forced Vital Capacity or FVC). The parameter relates to the average flow from the point at which 25 percent of the FVC has been exhaled to the point at which 75 percent of the FVC has been exhaled. The FEF25-75% of a subject provides information regarding small airway function, such that the extent of mall airway disease and/or inflammation. A change in FEF25-75 is an early indicator of obstructive lung disease. In certain embodiments, an improvement and/or increase in the FM5-75% parameter is an improvement of at least 10%, 25%, 50% or more as compared to baseline. In certain embodiments, the methods of the invention result in normal FEF25-75% values in a subject (e.g., values ranging from 50-60% and up to 130% of the average).

Morning and Evening Peak Expiratory Flow (AM PEF and PM PEF). According to certain embodiments, administration of an IL-4R antagonist to a patient results in an increase from baseline of morning (AM) and/or evening (PM) peak expiratory flow (AM PEF and/or PM PEF). Methods for measuring PEF are known in the art. For example, according to one method for measuring PEF, patients are issued an electronic PEF meter for recording morning (AM) and evening (PM) PEF (as well as daily albuterol use, morning and evening asthma symptom scores, and number of nighttime awakenings due to asthma symptoms that require rescue medications). Patients are instructed on the use of the device, and written instructions on the use of the electronic PEF meter are provided to the patients. In addition, a medical professional may instruct the patients on how to record pertinent variables in the electronic PEF meter, AM PEF is generally performed within 15 minutes after arising (between 6 am and 10 am) prior to taking any albuterol. PM PEF is generally performed in the evening (between 6 pm and 10 pm) prior to taking any albuterol. Subjects should try to withhold albuterol for at least 6 hours prior to measuring their PEF. Three PEI efforts are performed by the patient and all 3 values are recorded by the electronic PEF meter. Usually the highest value is used for evaluation, Baseline AM PEF may be calculated as the mean AM measurement recorded for the 7 days prior to administration of the first dose of pharmaceutical composition comprising the IL-4R antagonist, and baseline PM PEF may be calculated as the mean PM measurement recorded for the 7 days prior to administration of the first dose of pharmaceutical composition comprising the IL-4R antagonist.

The invention includes therapeutic methods that result in an increase in AM PEF and/or PM PEF from baseline of at least 1.0 L/min at week 12 following initiation of treatment with a pharmaceutical composition comprising an anti-IL-4R antagonist. For example, according to the invention, administration of an IL-4R antagonist to a subject in need thereof causes an increase in PEF from baseline of about 0.5 L/min, 1.0 L/min, 1.5 L/min, 2.0 L/min, 2.5 L/min, 3.0 L/min, 3.5 L/min, 4.0 L/min, 4.5 L/min, 5.0 L/min, 5.5 L/min, 6.0 L/min, 6.5 L/min, 7.0 L/min, 7.5 L/min, 8.0 L/min, 8.5 L/min, 9.0 L/min, 9.5 L/min, 10.0 L/min, 10.5 L/min, 11.0 L/min, 12.0 L/min, 15 L/min, 20 L/min, or more at week 12.

Albuterol/Levalbuterol Use. According to certain embodiments, administration of an IL-4R antagonist to a patient results in a decrease from baseline of daily albuterol or levalbuterol use. The number of albuterol/levalbuterol inhalations can be recorded daily by the patients in a diary, PEF meter, or other recording device. During treatment with the pharmaceutical composition described herein, use of albuterol/levalbuterol typically may be on an as-needed basis for symptoms, not on a regular basis or prophylactically. The baseline number of albuterol/levalbuterol inhalations/day may be calculated based on the mean for the 7 days prior to administration of the first dose of pharmaceutical composition comprising the IL-4R antagonist.

The invention includes therapeutic methods that result in a decrease in albuterol/levalbuterol use from baseline of at least 0.25 puffs per day at week 12 following initiation of treatment with a pharmaceutical composition comprising an anti-IL-4R antagonist. For example, administration of an IL-4R antagonist to a subject in need thereof causes a decrease in albuterol/levalbuterol use from baseline of about 0.25 puffs per day, 0.50 puffs per day, 0.75 puffs per day, 1.00 puff per day, 1.25 puffs per day, 1.5 puffs per day, 1.75 puffs per day, 2.00 puffs per day, 2.25 puffs per day, 2.5 puffs per day, 2.75 puffs per day, 3.00 puffs per day, or more at week 12.

OCS Use. According to certain embodiments, administration of an IL-4R antagonist to a patient can be used in conjunction with an OCS such as oral prednisone. The number of OCS administrations can be recorded daily by the patients in a diary, PEF meter, or other recording device. During treatment with the pharmaceutical composition described herein, occasional short-term use of prednisone typically can be used to control acute asthmatic episodes, e.g., episodes in which bronchodilators and other anti-inflammatory agents fail to control symptoms. In other aspects, prednisone is used concurrent with or as a substitution for ICS. Oral prednisone may be administered in dosages of about 5 mg, 10 mg, 15 mg, 20 mg, 25 mg, 30 mg, 35 mg or 40 mg. OCS can optionally be administered once a day or multiple times a day (e.g., twice a day, three times a day, four times a day, etc.)

In certain exemplary embodiments, the invention provides methods for reducing or eliminating the dependency of the subject on OCS use. The reduction or elimination of steroid dependency is highly advantageous and desirable. In certain embodiments, a reduction of 50% or greater (e.g., 50%, 60%, 70%, 80%, 90% or more) in the OCS dose is achieved after administration of IL-4R antibody therapy at a period of time (e.g., at week 24 In certain embodiments, the OCS is substantially eliminated after 40 weeks, 45 weeks, 50 weeks, 52 weeks, or greater after first dose following administration of the loading dose. In other embodiments, the level of OCS use is reduced to less than 5 mg per day (e.g., less than 5 mg, 4 mg, 3 mg, 2 mg or less per day). In other embodiments, the dependency on OCS use is substantially eliminated after 3 months, 6 months, 9 months or 1 year following treatment with IL4R antibody or fragment thereof.

5-Item Asthma. Control Questionnaire (ACQ) Score. According to certain embodiments, administration of an IL-4R antagonist to a patient results in a decrease from baseline of five-item Asthma Control Questionnaire (ACQ5) score. The ACQ5 is a validated questionnaire to evaluate asthma control.

The invention includes therapeutic methods that result in a decrease in ACQ5 score from baseline of at least 0.10 points at week 12 following initiation of treatment with a pharmaceutical composition comprising an anti-IL-4R antagonist. For example, administration of an IL-4R antagonist to a subject in need thereof causes a decrease in ACQ score from baseline of about 0.10 points, 0.15 points, 0.20 points, 0.25 points, 0.30 points, 0.35 points, 0.40 points, 0.45 points, 0.50 points, 0.55 points, 0.60 points, 0.65 points, 0.70 points, 0.75 points, 0.80 points, 0.85 points, or more at week 12.

Night-Time Awakenings. According to certain embodiments, administration of an IL-4R antagonist to a patient results in a decrease from baseline of average number of nighttime awakenings.

In certain embodiments, the methods decrease the average number of nighttime awakenings from baseline by at least about 0.10 times per night at week 12 following initiation of treatment. For example, administration of an IL-4R antagonist to a subject in need thereof can cause a decrease in average number of nighttime awakenings from baseline of about 0.10 times per night, 0.15 times per night, 0.20 times per night, 0.25 times per night, 0.30 times per night, 0.35 times per night, 0.40 times per night, 0.45 times per night, 0.50 times per night, 0.55 times per night, 0.60 times per night, 0.65 times per night, 0.70 times per night, 0.75 times per night, 0.80 times per night, 0.85 times per night, 0.90 times per night, 0.95 times per night, 1.0 times per night, 2.0 times per night, or more at week 12.

22-Item Sinonasal Outcome Test (SNOT-22) Score. According to certain embodiments, administration of an IL-4R antagonist to a patient results in a decrease from baseline of 22-item Sinonasal Outcome Test (SNOT-22). The SNOT-22 is a validated questionnaire to assess the impact of chronic rhinosinusitis on quality of life (Hopkins et al 2009. Clin. Otolaryngol. 34: 447-454).

The invention includes therapeutic methods that result in a decrease in SNOT-22 score from baseline of at least 1 point at week 12 following initiation of treatment with a pharmaceutical composition comprising an anti-IL-4R antagonist. For example, administration of an IL-4R antagonist to a subject in need thereof can cause a decrease in SNOT-22 score from baseline of about 1, 2, 3, 4, 5, 6, 7, 8, 9, 10, 11, 12, 13 points, or more at week 12.

Biomarkers. In certain embodiments, the subject experiences an improvement in lung function as measured by a biomarker, e.g., a biomarker associated with severe steroid-dependent asthma or severe uncontrolled asthma. For example, the biomarker may be fractional exhaled nitric oxide (FeNO), Eotaxin-3, total IgE, Periostin, or thymus and activation-regulated chemokine (TARC). In certain embodiments, an improvement in lung function is indicated by a reduction or increase (as appropriate) at week 4, week 12 or week 24 following treatment.

Methods for Treating Asthma

In some embodiments, the invention provides methods for treating asthma, including, e.g., moderate-to-severe uncontrolled asthma or inadequately controlled asthma, in a subject in need thereof, wherein the methods comprise administering a pharmaceutical composition comprising an IL-4R antagonist to the subject. In certain embodiments, the methods are useful for treating moderate-to-severe uncontrolled asthma in a subject.

As used herein, the term "asthma" can be used interchangeably with "intermittent asthma," or "bronchial asthma." "Asthma," "bronchial asthma" and "intermittent asthma" refer to asthma in which one or any combination of the following are true: symptoms occur 2 or fewer days per week; symptoms do not interfere with normal activities; nighttime symptoms occur fewer than 2 days per month; or one or more lung function tests (e.g., forced expiratory volume in one second ($FEV_1$) and/or peak expiratory flow (PEF) of greater than 80%) are normal when the subject is not suffering from an asthma attack.

As used herein, the term "persistent asthma" or "persistent bronchial asthma" refers to asthma that is more severe than (bronchial) asthmatintermittent (bronchial) asthma. A subject suffering from persistent asthma or persistent bronchial asthma experiences one or more of the following: symptoms more than 2 days per week; symptoms that interfere with normal activities; nighttime symptoms that occur more than 2 days per month; or one or more lung function tests (e.g., forced expiratory volume in one second ($FEV_1$) and/or peak expiratory flow (PEF) of less than 80%) that are not normal when the subject is not suffering from an asthma attack; the subject relies on daily asthma control medication; the subject has taken a systemic steroid more than once in the last year after a severe asthma flare-up; or use of a short-acting beta-2 agonist more than two days per week for relief of asthma symptoms.

Asthma/intermittent asthma, bronchial asthma/intermittent bronchial asthma, and persistent asthma/persistent bronchial asthma can be categorized as "mild," "moderate," "severe" or "moderate-to-severe." "Mild intermittent asthma" or "mild intermittent bronchial asthma" is defined as having symptoms less than once a week, and having forced expiratory volume in one second ($FEV_1$) or peak expiratory flow (PEF)≥80%. "Mild persistent asthma" or "mild persistent bronchial asthma" differs in that symptoms frequency is greater than once per week but less than once per day, and variability in $FEV_1$ or PEF is <20%-30%. "Moderate intermittent asthma" or "moderate intermittent bronchial asthma" is defined as having symptoms less than once a week, and having forced expiratory volume in one second ($FEV_1$) or peak expiratory flow (PEF) of 60-80%. "Moderate persistent asthma" or "moderate persistent bronchial asthma" is defined as having daily symptoms, exacerbations that may affect activity and/or sleep, nocturnal symptoms more than once a week, daily use of inhaled short-acting beta-2 agonist and having forced expiratory volume in one second ($FEV_1$) or peak expiratory flow (PEF) of 60-80%. "Severe intermittent asthma" or "severe intermittent bronchial asthma" is defined as having symptoms less than once a week, and having forced expiratory volume in one second ($FEV_1$) or peak expiratory flow (PEE) of 60%. "Severe persistent asthma" or "severe persistent bronchial asthma" is defined as having daily symptoms, frequent exacerbations that may affect activity and/or sleep, frequent nocturnal symptoms, limitation of physical activities, daily use of inhaled short-acting beta-2 agonist, and having forced expiratory volume in one second ($FEV_1$) or peak expiratory flow (PEF) of 60%. "Moderate-to-severe intermittent asthma" or "moderate-to-severe intermittent bronchial asthma" is defined as having symptoms between those of moderate intermittent asthma/moderate intermittent bronchial asthma and severe intermittent asthma/severe intermittent bronchial asthma. "Moderate-to-severe persistent asthma" or "moderate-to-severe persistent bronchial asthma" is defined as having symptoms between those of moderate persistent asthma/moderate persistent bronchial asthma and severe persistent asthma/severe persistent bronchial asthma.

As used herein, the term "inadequately controlled asthma" refers to patients whose asthma is either "not well controlled" or "very poorly controlled" as defined by the "Expert Panel Report 3: Guidelines for the Diagnosis and Management of Asthma," National Heart, Blood and Lung Institute, NIH, Aug. 28, 2007. "Not well controlled asthma" is defined as having symptoms greater than two days per week, nighttime awakenings one to three times per week, some limitations on normal activity, short-acting beta2-agonist use for symptom control greater than two days per week, $FEV_1$ of 60-80% of predicted and/or personal best, an ATAQ score of 1-2, an ACQ score of 1.5 or greater, and an ACT score of 16-19. "Very poorly controlled asthma" is defined as having symptoms throughout the day, nighttime awakenings four times or more per week, extreme limitations on normal activity, short-acting beta?-agonist use for symptom control several times per day, $FEV_1$ of less than 60% of predicted and/or personal best, an ATAQ score of 3-4, an ACQ score of N/A, and an ACT score of less than or equal to 15.

In some embodiments, a subject is identified as having "moderate-to-severe uncontrolled" asthma if the subject receives such a diagnosis from a physician, based on the Global Initiative for Asthma (GINA) 2009 Guidelines, and one or more of the following criteria: i) Existing treatment with moderate- or high-dose ICS/LABA (2 fluticasone propionate 250 µg twice daily or equipotent daily dosage) with a stable dose of ICS/LAB; for greater than or equal to 1 month prior to administration of the loading dose of IL-4R antagonist; ii) $FEV_1$ 40 to 80% predicted normal prior to administration of the loading dose of IL-4R antagonist; iii) ACQ-5 score greater than or equal to 1.5 prior to administration of the loading dose of IL-4R antagonist; iv) reversibility of at least 12% and 200 mL in $FEV_1$ after 200 µg to 400 µg (2 to 4 inhalations) of salbutamol/albuterol prior to administration of the loading dose of IL-4R antagonist; or v) has experienced, within 1 year prior to administration of the loading dose of IL-4R antagonist, any of the following events: (a) treatment with greater than or equal to 1 systemic (oral or parenteral) steroid burst for worsening asthma, (b) hospitalization or an emergency/urgent medical care visit for worsening asthma.

"Severe asthma" refers to asthma in which adequate control cannot be achieved by high-dose treatment with inhaled corticosteroids and additional controllers (e.g., long-acting inhaled beta 2 agonists, montelukast, and/or theophylline) or by oral corticosteroid treatment (e.g., for at least six months per year), or is lost when the treatment is reduced. In certain embodiments, severe asthma includes asthma that is treated with high-dose ICS and at least one additional controller (e.g., LABA, montelukast, or theophylline) or oral corticosteroids >6 months/year, wherein at least one of the following occurs or would occur if treatment is reduced: ACT<20 or ACQ>1.5; at least 2 exacerbations in the last 12 months; at least 1 exacerbation treated in hospital or requiring mechanical ventilation in the last 12 months; or FEV1<80% (if FEV1/FVC below the lower limit of normal).

"Steroid-dependent asthma" refers to asthma which requires one or more of the following treatments: frequent, short term oral corticosteroid treatment bursts in the past 12 months; regular use of high dose inhaled corticosteroids in the past 12 months; regular use of injected long acting corticosteroids; daily use of oral corticosteroids; alternate-day oral corticosteroids; or prolonged use of oral corticosteroids in the past year.

"Oral corticosteroid-dependent asthma" refers to a subject having ≥3 30-day oral corticosteroid (OCS) fills over a 12-month period and a primary asthma diagnosis within 12 months of the first OCS fill. Subjects with OCS-dependent asthma may also experience one or any combination of the following: have received physician prescribed LABA and high dose ICS (total daily dose >500 µg fluticasone propionate dry powder formulation equivalent) for at least 3 months (the ICS and LABA can be parts of a combination product, or given by separate inhalers); have received additional maintenance asthma controller medications according to standard practice of care e.g., leukotriene receptor antagonists (LTRAs), theophylline, long-acting muscarinic antagonists (LAMAS), secondary ICS and cromones; received OCS for the treatment of asthma at a dose of between ≥7.5 to ≤30 mg (prednisone or prednisolone equivalent); have received an OCS dose administered every other day (or different doses every other day); morning pre-bronchodilator (BD) FEV1 of <80% predicted normal; have evidence of asthma as documented by post-BD (albuterol/salbutatomol) reversibility of FEV1≥12% and ≥200 mL (15-30 min after administration of 4 puffs of albuterol/salbutamol); or have a history of at least one asthma exacerbation event within 12 months.

In one aspect, methods for treating asthma are provided comprising: (a) selecting a patient that exhibits a blood eosinophil level of at least 300 cells per microliter; and (b) administering to the patient a pharmaceutical composition comprising an IL-4R antagonist.

In another aspect, methods for treating asthma are provided comprising: (a) selecting a patient that exhibits a blood eosinophil level of 200-299 cells per microliter; and (b) administering to the patient a pharmaceutical composition comprising an IL-4R antagonist.

In another aspect, methods for treating asthma are provided comprising: (a) selecting a patient that exhibits a blood eosinophil level of less than 200 cells per microliter; and (b) administering to the patient a pharmaceutical composition comprising an IL-4R antagonist.

In a related aspect, methods for treating asthma comprising an add-on therapy to background therapy are provided. In certain embodiments, an IL-4R antagonist is administered as an add-on therapy to an asthma patient who is on background therapy for a certain period of time (e.g., 1 week, 2 weeks, 3 weeks, 1 month, 2 months, 5 months, 12 months, 18 months, 24 months, or longer) (also called the "stable phase"). In some embodiments, the background therapy comprises a ICS and/or a LABA.

In some embodiments, the invention includes a method for reducing an asthma patient's dependence on ICS and/or LABA for the treatment of one or more asthma exacerbations comprising: (a) selecting a patient who has moderate-to-severe asthma that is uncontrolled with a background asthma therapy comprising an ICS, a LABA, or a combination thereof; and administering to the patient a pharmaceutical composition comprising an IL-4R antagonist.

In some embodiments, the invention encompasses methods to treat or alleviate conditions or complications associated with asthma, such as chronic rhino sinusitis, allergic rhinitis, allergic fungal rhino sinusitis, allergic bronchopulmonary aspergillosis, unified airway disease, Churg-Strauss syndrome, vasculitis, chronic obstructive pulmonary disease (COPD), and exercise induced bronchospasm.

The invention also includes methods for treating persistent asthma. As used herein, the term "persistent asthma" means that the subject has symptoms at least once a week at day and/or at night, with the symptoms lasting a few hours to a few days. In certain alternative embodiments, the persistent asthma is "mildly persistent" (e.g., more than twice a week but less than daily with symptoms severe enough to interfere with daily activities or sleep and/or where pulmonary function is normal or reversible with inhalation of a bronchodilator), "moderately persistent" (e.g., symptoms occurring daily with sleep interrupted at least weekly and/or with pulmonary function moderately abnormal), or "severely persistent" (e.g., continuous symptoms despite the correct use of approved medications and/or where pulmonary function is severely affected).

Interleukin-4 Receptor Antagonists

The methods featured in the invention comprise administering to a subject in need thereof a therapeutic composition comprising an IL-4R antagonist. As used herein, an "IL-4R antagonist" is any agent that binds to or interacts with IL-4R and inhibits the normal biological signaling function of IL-4R when IL-4R is expressed on a cell in vitro or in vivo. Non-limiting examples of categories of IL-4R antagonists include small molecule IL-4R antagonists, anti-IL-4R aptamers, peptide-based IL-4R antagonists (e.g., "peptibody" molecules), and antibodies or antigen-binding fragments of antibodies that specifically bind human IL-4R. According to certain embodiments, the IL-4R antagonist comprises an anti-IL-4R antibody that can be used in the context of the methods featured in the invention are described elsewhere herein. For example, in one embodiment, the IL-4R antagonist is an antibody or antigen-binding fragment thereof that specifically binds to an IL-4R, and comprises the heavy chain and light chain (Complementarity Determining Region) CDR sequences from the Heavy Chain Variable Region (HCVR) and Light Chain Variable Region (LCVR) of SEQ ID NOs:1 and 2, respectively.

The term "human IL4R" (hIL-4R) refers to a human cytokine receptor that specifically binds to interleukin-4 (IL-4), such as IL-4Rα.

The term "antibody" refers to immunoglobulin molecules comprising four polypeptide chains, two heavy (H) chains and two light (L) chains inter-connected by disulfide bonds, as well as multimers thereof (e.g., IgM), Each heavy chain comprises a heavy chain variable region (abbreviated herein as HCVR or $V_H$) and a heavy chain constant region. The heavy chain constant region comprises three domains, $C_H1$, $C_H2$, and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody" also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds to an antigen to form a complex. Antigen-binding fragments of an antibody may be derived, e.g., from full antibody molecules using any suitable standard techniques, such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies monovalent nanobodies, bivalent nanobodies, etc.), small modular immunopharmaceuticals (SMIPs), and shark variable IgNAR domains, are also encompassed within the expression "antigen-binding fragment."

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody described herein include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$ (ix) $V_L$-$C_H2$; (x) $V_L$-$C_H3$; (xi) $V_L$-$C_H1$-$C_H2$; (xii) $V_L$-$C_H1$-$C_H2$-$C_H3$; $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids that result in a flexible or semi-flexible linkage between adjacent variable and/or constant domains in a single polypeptide molecule, typically the hinge region may consist of between 2 to 60 amino acids, typically between 5 to 50, or typically between 10 to 40 amino acids. Moreover, an antigen-binding fragment of an antibody described herein may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific bispecific). A multi specific antigen-binding fragment of an anti body will typically comprise at least two different variable domains, wherein each variable domain is capable of specifically binding to a separate antigen or to a different epitope on the same antigen. Any multispecific antibody format, may be adapted for use in the context of an antigen-binding fragment of an antibody described herein using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody" includes antibodies having variable and constant regions derived from human germline immunoglobulin sequences. The human antibodies featured in the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The invention encompasses antibodies having one or more mutations in the hinge, $C_H2$, or $C_H3$ region, which may be desirable, for example, in production, to improve the yield of the desired antibody form.

An "isolated antibody" means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody". An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4R, as featured in the invention, includes antibodies that bind IL-4R or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM, or less than about 0.5 nM, as measured in a surface plasmon resonance assay. An isolated antibody that specifically binds human IL-4R may, however, have cross-reactivity to other antigens, such as IL-4R molecules from other (non-human) species.

The anti-IL-4R antibodies useful for the methods may comprise one or more amino acid substitutions, insertions, and/or deletions (e.g. 1, 2, 3, 4, 5, 6, 7, 8, 9, or 10 substitutions and/or 1, 2, 3, 4, 5, 6, 7, 8, 9, or 10 insertions and/or 1, 2, 3, 4, 5, 6, 7, 8, 9, or 10 deletions) in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The invention includes methods involving the use of antibodies, and antigen-binding fragments thereof, that are derived from any of the amino acid sequences disclosed herein, wherein one or more amino acids (e.g. 1, 2, 3, 4, 5, 6, 7, 8, 9, or 10 amino acids) within one or more framework and/or one or more (e.g. 1, 2, 3, 4, 5, 6, 7, 8, 9, 10, 11 or 12 with respect to the tetrameric antibody or 1, 2, 3, 4, 5 or 6 with respect to the HCVR and LCVR of an antibody) CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the invention.

The invention also includes methods involving the use of anti-IL-4R antibodies comprising variants of any of the HCVR, LCVR, and/or CDR amino acid sequences disclosed herein having one or more conservative substitutions. For example, the invention includes the use of anti-IL-4R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance" refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$" refers to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Preparation of Human Antibodies

Methods for generating human antibodies in transgenic mice are known in the art. Any such known methods can be used to make human antibodies that specifically bind to human IL-4R.

Using VELOCIMMUNE® technology (see, for example, U.S. Pat. No. 6,596,541, Regeneron Pharmaceuticals) or any other known method for generating monoclonal antibodies, high affinity chimeric antibodies to IL4R are initially isolated having a human variable region and a mouse constant region. The VELOCLMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate a fully human antibody featured in the invention, for example wild-type or modified IgG1 or IgG4. While the constant region selected may vary according to specific use, high affinity antigen-binding and target specificity characteristics reside in the variable region.

In general, the antibodies that can be used in the methods possess high affinities, as described above, when measured by binding to antigen either immobilized on solid phase or in solution phase. The mouse constant regions are replaced with desired human constant regions to generate the fully human antibodies featured in the invention. While the constant region selected may vary according to specific use, high affinity antigen-binding and target specificity characteristics reside in the variable region.

In one embodiment, human antibody or antigen-binding fragment thereof that specifically binds IL-4R that can be used in the context of the methods featured in the invention comprises the three heavy chain CDRs (HCDR1, HCDR2 and HCDR3) contained within a heavy chain variable region (HCVR) having an amino acid sequence of SEQ ID NO: 1. The antibody or antigen-binding fragment may comprise the three light chain CDRs (LCVR1, LCVR2, LCVR3) contained within a light chain variable region (LCVR) having an amino acid sequence of SEQ ID NO: 2. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AhM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) of SEQ ID NOs: 1 and 2.

In certain embodiments, the antibody or antigen-binding fragment thereof comprises six CDRs (HCDR1/HCDR2/HCDR3/LCDR/1/LCDR2/LCDR3) having the amino acid sequences of SEQ ID NOs: 3/4/5/6/7/8.

In certain embodiments, the antibody or antigen-binding fragment thereof comprises HCVR/LCVR amino acid sequence pairs of SEQ ID NOs: 1 and 2.

In one embodiment, the antibody is dupilumab, which comprises the HCVR/LCVR amino acid sequence pairs of SEQ ID NOs: 1 and 2.

Pharmaceutical Compositions

The invention includes methods that comprise administering an IL-4R antagonist to a patient, wherein the IL-4R antagonist is contained within a pharmaceutical composition. The pharmaceutical compositions featured in the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical compositions featured in the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, intra-tracheal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition featured in the invention can be delivered subcutaneously or intravenously with a standard needle and syringe. In addition, with respect to subcutaneous delivery, a pen delivery device (e.g., an auto-injector pen) readily has applications in delivering a pharmaceutical composition featured in the invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition. Examples include, but are not limited to AUTOPEN™ (Owen Mumford, Inc., Woodstock, UK), DISETRONIC™ pen (Disetronic Medical Systems, Bergdorf, Switzerland), HUMALO MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition featured in the invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few. Examples of large-volume delivery devices (e.g., large-volume injectors) include, but are not limited to, bolus injectors such as, e.g., BD Libertas West SmartDose, Enable Injections, SteadyMed PatchPump, Sensile SenseTrial, YPsomed YpsoDose, Bespak Lapas, and the like.

For direct administration to the sinuses, the pharmaceutical compositions featured in the invention may be administered using, e.g., a microcatheter (e.g., an endoscope and microcatheter), an aerosolizer, a powder dispenser, a nebulizer or an inhaler. The methods include administration of an IL-4R antagonist to a subject in need thereof, in an aerosolized formulation. For example, aerosolized antibodies to IL-4R may be administered to treat asthma in a patient. Aerosolized antibodies can be prepared as described in, for example, U.S. Pat. No. 8,178,098, incorporated herein by reference in its entirety.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant (e.g., polysorbate 80, HCO-50 (polyoxyethylene (50 mol) adduct of hydrogenated castor oil)), etc. As the oily medium, there are employed, e.g., sesame oil, soybean oil, etc., which may be used in combination with a solubilizing agent such as benzyl benzoate, benzyl alcohol, etc. The injection thus prepared is typically filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the invention are disclosed, e.g., in US Patent Application Publication No. 2012/0097565.

Dosage

The amount of IL-4R antagonist (e.g., anti-IL-4R antibody) administered to a subject according to the methods featured in the invention is, generally, a therapeutically effective amount. As used herein, the phrase "therapeutically effective amount" means an amount of IL-4R antagonist that results in one or more of: (a) a reduction in the incidence of asthma exacerbations; (b) an improvement in one or more asthma-associated parameters (as defined elsewhere herein); and/or (c) a detectable improvement in one or more symptoms or indicia of an upper airway inflammatory condition. A "therapeutically effective amount" also includes an amount of IL-4R antagonist that inhibits, prevents, lessens, or delays the progression of asthma in a subject.

In the case of an anti-IL-4R antibody, a therapeutically effective amount can be from about 0.05 mg to about 700 mg, e.g., about 0.05 mg, about 0.1 mg, about 1.0 mg, about 1.5 mg, about 2.0 mg, about 3.0 mg, about 5.0 mg, about 7.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, or about 700 mg of the anti-IL-4R antibody. In certain embodiments, 300 mg of an anti-IL-4R antibody is administered.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight. For example, the IL-4R antagonist can be administered at a dose of 1 mg/kg, 2 mg/kg, 3 mg/kg, or 4 mg/kg.

In some embodiments, the dose of IL-4R antagonist may vary according to eosinophil count. For example, the subject may have a blood eosinophil count (high blood eosinophils) ≥300 cells/μL, or 300-499 cells/μL, or ≥500 cells/pt (HEos); a blood eosinophil count of 200 to 299 cells/μL. (moderate blood eosinophils); or a blood eosinophil count <200 cells/μL (low blood eosinophils).

In certain embodiments, the methods comprise a loading dose of about 400 to about 600 mg of an IL-4R antagonist.

In certain embodiments, the methods comprise one or more maintenance doses of about 200 to about 300 mg of the IL-4R antagonist.

In certain embodiments, the ICS and LABA are administered for the duration of administration of the IL-4R antagonist.

In certain embodiments, the loading dose comprises 600 mg of an anti-IL-4R antibody or antigen-binding fragment thereof, and the one or more maintenance doses comprises 300 mg of the antibody or antigen-binding fragment thereof administered every other week.

IN certain embodiments, the loading dose comprises 400 mg of an anti-IL-4R antibody or antigen-binding fragment thereof, and the one or more maintenance dose comprises 200 mg of the antibody or antigen-binding fragment thereof administered every other week.

In certain embodiments, the loading dose comprises 400 mg of an anti-IL-4R antibody or antigen-binding fragment thereof, and the one or more maintenance dose comprises 200 mg of the antibody or antigen-binding fragment thereof administered every other week, which may be increased to 300 mg of the antibody or antigen-binding fragment thereof administered every other week.

In other embodiments, the loading dose comprises 600 mg of an anti-IL-4R antibody or antigen-binding fragment thereof, and the one or more maintenance doses comprises 300 mg of the antibody or antigen-binding fragment thereof administered every fourth week.

In other embodiments, the loading dose comprises 400 mg of an anti-IL-4R antibody or antigen-binding fragment thereof, and the one or more maintenance doses comprises 200 mg of the antibody or antigen-binding fragment thereof administered every fourth week.

In other embodiments, the loading dose comprises 600 mg of an anti-IL-4R antibody or antigen-binding fragment thereof, and the one or more maintenance doses comprises 300 mg of the antibody or antigen-binding fragment thereof administered once a week.

In other embodiments, the loading dose comprises 400 mg of an anti-IL-4R antibody or antigen-binding fragment thereof, and the one or more maintenance doses comprises 200 mg of the antibody or antigen-binding fragment thereof administered once a week.

In other embodiments, the loading dose comprises 600 mg of an anti-IL-4R antibody or antigen-binding fragment thereof, and the one or more maintenance doses comprises 300 mg of the antibody or antigen-binding fragment thereof administered every third week.

In other embodiments, the loading dose comprises 400 mg of an anti-IL-4R antibody or antigen-binding fragment thereof, and the one or more maintenance doses comprises 200 mg of the antibody or antigen-binding fragment thereof administered every third week.

In one embodiment, the subject is 6 to <18 years old and the IL-4R antibody or antigen binding fragment thereof is administered at 2 mg/kg or 4 mg/kg.

In another embodiment, the subject is 12 to <18 years old and the IL-4R antibody or antigen binding fragment thereof is administered at 2 mg/kg or 4 mg/kg.

In another embodiment, the subject is 6 to <12 years old and the IL-4R antibody or antigen binding fragment thereof is administered at 2 mg/kg or 4 mg/kg.

In another embodiment, the subject is 2 to <6 years old and the IL-4R antibody or antigen binding fragment thereof is administered at 2 mg/kg or 4 mg/kg.

In yet another embodiment, the subject is <2 years old and the IL-4R antibody or antigen binding fragment thereof is administered at 2 mg/kg or 4 mg/kg.

Combination Therapies

Certain embodiments of the methods featured in the invention comprise administering to the subject one or more additional therapeutic agents in combination with the IL-4R antagonist. As used herein, the expression "in combination with" means that the additional therapeutic agents are administered before, after, or concurrent with the pharmaceutical composition comprising the IL-4R antagonist. In some embodiments, the term "in combination with" includes sequential or concomitant administration of an IL-4R antagonist and a second therapeutic agent. The invention includes methods to treat asthma or an associated condition or complication or to reduce at least one exacerbation, comprising administration of an IL-4R antagonist in combination with a second therapeutic agent for additive or synergistic activity.

For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes, or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, or about 72 hours after the administration of the pharmaceutical composition comprising the antagonist. Administration "concurrent" with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

The additional therapeutic agent may be, e.g., another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), a TNF antagonist, an IL-8 antagonist, an IL-9 antagonist, an IL-17 antagonist, an IL-5 antagonist, an IgE antagonist, a CD48 antagonist, a leukotriene inhibitor, an anti-fungal agent, an NSAID, a long-acting beta2 agonist (e.g., salmeterol or formoterol), an inhaled corticosteroid (e.g., fluticasone or budesonide), a systemic corticosteroid (e.g., oral or intravenous), methylxanthine, nedocromil sodium, cromolyn sodium, or combinations thereof. For example, in certain embodiments, the pharmaceutical composition comprising an IL-4R antagonist is administered in combination with a combination comprising a long-acting beta2 agonist and an inhaled corticosteroid (e.g., fluticasone+salmeterol [e.g., Advair® (GlaxoSmithKline)]; or budesonide+formoterol [e.g., SYMBICORT® (Astra Zeneca)]).

Administration Regimens

According to certain embodiments, multiple doses of an IL-4R antagonist may be administered to a subject over a defined time course. Such methods comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks, or months). The invention includes methods that comprise sequentially administering to the patient a single initial dose of an IL-4R antagonist, followed by one or more secondary doses of the IL-4R antagonist, and optionally followed by one or more tertiary doses of the IL-4R antagonist.

The invention includes methods comprising administering to a subject a pharmaceutical composition comprising an IL-4R antagonist at a dosing frequency of about four times a week, twice a week, once a week (qiw), once every two weeks (bi-weekly or q2w), once every three weeks (tri-weekly or q3w), once every four weeks (monthly or q4w), once every five weeks (q5w), once every six weeks (q6w), once every eight weeks (q8w), once every twelve weeks (q12w), or less frequently so long as a therapeutic response is achieved. In certain embodiments involving the administration of a pharmaceutical composition comprising an anti-IL-4R antibody, once a week dosing of an amount of about 75 mg, 100 mg, 150 mg, 200 mg, or 300 mg, can be employed. In other embodiments involving the administration of a pharmaceutical composition comprising an anti-IL-4R antibody, once every two weeks dosing (bi-weekly dosing) of an amount of about 75 mg, 100 mg, 150 mg, 200 mg, or 300 mg, can be employed. In other embodiments involving the administration of a pharmaceutical composition comprising an anti-IL-4R antibody, once every three weeks dosing of an amount of about 75 mg, 100 mg, 150 mg, 200 mg, or 300 mg, can be employed. In other embodiments involving the administration of a pharmaceutical composition comprising an anti-IL-4R antibody, once every four weeks dosing (monthly dosing) of an amount of about 75 mg, 100 mg, 150 mg, 200 mg, or 300 mg, can be employed. In other embodiments involving the administration of a pharmaceutical composition comprising an anti-IL-4R antibody, once every five weeks dosing of an amount of about 75 mg, 100 mg, 150 mg, 200 mg, or 300 mg, can be employed. In other embodiments involving the administration of a pharmaceutical composition comprising an anti-IL-4R antibody, once every six weeks dosing of an amount of about 75 mg, 100 mg, 150 mg, 200 mg, or 300 mg, can be employed. In other embodiments involving the administration of a pharmaceutical composition comprising an anti-IL-4R antibody, once every eight weeks dosing of an amount of about 75 mg, 100 mg, 150 mg, 200 mg, or 300 mg, can be employed. In other embodiments involving the administration of a pharmaceutical composition comprising an anti-IL-4R antibody, once every twelve weeks dosing of an amount of about 75 mg, 100 mg, 150 mg, 200 mg, or 300 mg, can be employed. In one embodiment, the route of administration is subcutaneous.

The term "week" or "weeks" refers to a period of (n×7 days)±2 days, e.g. (n×7 days)±1 day, or (n×7 days), wherein "a" designates the number of weeks, e.g. 1, 2, 3, 4, 5, 6, 8, 12 or more.

The terms "initial dose," "secondary doses," and "tertiary doses," refer to the temporal sequence of administration of the IL-4R antagonist. Thus, the "initial dose" is the dose that is administered at the beginning of the treatment regimen (also referred to as the "baseline dose"); the "secondary doses" are the doses that are administered after the initial dose; and the "tertiary doses" are the doses that are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses"). In one embodiment, the maintenance dose may be lower than the loading dose. For example, one or more loading doses of 600 mg of IL-4R antagonist may be administered followed by maintenance doses of about 75 mg to about 300 mg.

In certain embodiments, the loading dose is about 400 to about 600 mg of the IL-4R antagonist. In one embodiment, the loading dose is 400 mg of the IL-4R antagonist. In another embodiment, the loading dose is 600 mg of the IL-4R antagonist.

In certain embodiments, the maintenance dose is about 200 to about 300 mg of the IL-4R antagonist. In one embodiment, the maintenance dose is 200 mg of the IL-4R antagonist. In another embodiment, the maintenance dose is 300 mg of the IL-4R antagonist.

In certain embodiments, the loading dose is two times the maintenance dose.

In some embodiments, the loading dose comprises 600 mg of the antibody or antigen-binding fragment thereof, and the one or more maintenance doses comprises 300 mg of the antibody or antigen-binding fragment thereof administered every other week.

In some embodiments, a subject has OCS-dependent asthma, and the loading dose comprises 600 mg of the antibody or antigen-binding fragment thereof, and the one or more maintenance doses comprises 300 mg of the antibody or antigen-binding fragment thereof administered every other week.

In some embodiments, a subject has co-morbid moderate-to-severe atopic dermatitis, and the loading dose comprises 600 mg of the antibody or antigen-binding fragment thereof, and the one or more maintenance doses comprises 300 mg of the antibody or antigen-binding fragment thereof administered every other week.

In some embodiments, the loading dose comprises 400 mg of the antibody or antigen-binding fragment thereof, and the one or more maintenance dose comprises 200 mg of the antibody or antigen-binding fragment thereof administered every other week.

In some embodiments, a subject has OCS-dependent asthma, and the loading dose comprises 400 mg of the antibody or antigen-binding fragment thereof, and the one or more maintenance doses comprises 200 mg of the antibody or antigen-binding fragment thereof administered every other week.

In some embodiments, a subject has co-morbid moderate-to-severe atopic dermatitis, and the loading dose comprises 400 mg of the antibody or antigen-binding fragment thereof, and the one or more maintenance doses comprises 200 mg of the antibody or antigen-binding fragment thereof administered every other week.

In some embodiments, the loading dose comprises 600 mg of the antibody or antigen-binding fragment thereof, and the one or more maintenance doses comprises 300 mg of the antibody or antigen-binding fragment thereof administered every fourth week.

In some embodiments, a subject has OCS-dependent asthma, and the loading dose comprises 600 mg of the antibody or antigen-binding fragment thereof, and the one or more maintenance doses comprises 300 mg of the antibody or antigen-binding fragment thereof administered every fourth week.

In some embodiments, a subject has co-morbid moderate-to-severe atopic dermatitis, and the loading dose comprises 600 mg of the antibody or antigen-binding fragment thereof, and the one or more maintenance doses comprises 300 mg of the antibody or antigen-binding fragment thereof administered every fourth week.

In some embodiments, the loading dose comprises 400 mg of the antibody or antigen-binding fragment thereof, and the one or more maintenance doses comprises 200 mg of the antibody or antigen-binding fragment thereof administered every fourth week.

In some embodiments, a subject has OCS-dependent asthma, and the loading dose comprises 400 mg of the antibody or antigen-binding fragment thereof, and the one or more maintenance doses comprises 200 mg of the antibody or antigen-binding fragment thereof administered every fourth week.

In some embodiments, a subject has co-morbid moderate-to-severe atopic dermatitis, and the loading dose comprises 400 mg of the antibody or antigen-binding fragment thereof, and the one or more maintenance doses comprises 200 mg of the antibody or antigen-binding fragment thereof administered every fourth week.

In one exemplary embodiment, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose" means, in a sequence of multiple administrations, the dose of IL-4R antagonist that is administered to a patient prior to the administration of the very next dose in the sequence with no intervening doses.

The methods may include administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The invention includes methods comprising sequential administration of an IL-4R antagonist and a second therapeutic agent, to a patient to treat asthma or an associated condition. In some embodiments, the methods comprise administering one or more doses of an IL-4R antagonist followed by one or more doses (e.g., 2, 3, 4, 5, 6, 7, 8, or more) of a second therapeutic agent. For example, one or more doses of about 75 mg to about 300 mg of the IL-4R antagonist may be administered after which one or more doses (e.g., 2, 3, 4, 5, 6, 7, 8, or more) of a second therapeutic agent (e.g., an inhaled corticosteroid or a beta2-agonist or any other therapeutic agent, as described elsewhere herein) may be administered to treat, alleviate, reduce or ameliorate one or more symptoms of asthma. In some embodiments, the IL-4R antagonist is administered at one or more doses (e.g., 2, 3, 4, 5, 6, 7, 8, or more) resulting in an improvement in one or more asthma-associated parameters followed by the administration of a second therapeutic agent to prevent recurrence of at least one symptom of asthma. Alternative embodiments pertain to concomitant administration of an IL-4R antagonist and a second therapeutic agent. For example, one or more doses (e.g., 2, 3, 4, 5, 6, 7, 8, or more) of an IL-4R antagonist are administered and a second therapeutic agent is administered at a separate dosage at a similar or different frequency relative to the IL-4R antagonist. In some embodiments, the second therapeutic agent is administered before, after or concurrently with the IL-4R antagonist.

In certain embodiments, the IL-4R antagonist is administered every other week for 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks or more. In other embodiments, the IL-4R antagonist is administered every four weeks for 12 weeks, 16 weeks, 20 weeks, 24 weeks, 28 weeks, 32 weeks, 36 weeks, 40 weeks, 44 weeks, 48 weeks or more. In specific embodiments, the IL-4R antagonist is administered for at least 24 weeks.

The invention includes methods for treating a subject having severe uncontrolled asthma (e.g., severe steroid-dependent asthma) comprising administering to the subject a loading dose of an antibody or an antigen-binding fragment thereof that specifically binds to IL-4R. In certain embodiments, the methods comprise administering to the subject a plurality of maintenance doses of the antibody or the antigen-binding fragment thereof, wherein the plurality of maintenance doses are administered during a treatment phase. The treatment phase comprises an induction phase, an OCS reduction phase, and an OCS maintenance phase.

In certain exemplary embodiments, the induction phase comprises a period during which subjects continuously receive their OCS dose(s). In certain exemplary embodiments, the reduction phase comprises a period during which subjects receive a lower OCS dose relative to the dose received during the induction phase. In certain exemplary embodiments, the maintenance phase comprises a period during which a subject receives a certain stable amount or dose(s) of OCS. Alternatively, the maintenance phase comprises a period in which OCS therapy/administration is reduced or eliminated. In certain embodiments, OCS use by the patient is completely eliminated and the patient is steroid free within less than 1 year of treatment with the IL4R antibody or fragment thereof (e.g., within 1 year, 6 months, 3 months or 1 month of initial treatment).

In another aspect, a method for treating a subject having severe steroid-dependent asthma and/or severe uncontrolled asthma comprises administering to the subject a loading dose of about 600 mg of an antibody or an antigen-binding fragment thereof that specifically binds to interleukin-4 receptor (IL-4R), and administering to the subject a plurality of maintenance doses of the antibody or the antigen-binding fragment thereof. Each maintenance dose is about 300 mg of the antibody or antigen-binding fragment thereof, wherein the plurality of maintenance doses are administered during a treatment phase comprising an induction phase, an oral corticosteroid (OCS) reduction phase, and a maintenance phase, and wherein the antibody or antigen-binding fragment thereof comprises heavy and light chain CDR sequences from the HCVR/LCVR sequence pair comprises SEQ ID NOs: 1 and 2.

Treatment Populations

The methods featured in the invention include administering to a subject in need thereof a therapeutic composition comprising an IL-4R antagonist. The expression "a subject in need thereof" means a human or non-human animal that exhibits one or more symptoms or indicia of asthma (e.g., moderate-to-severe uncontrolled asthma), or who has been diagnosed with asthma. For example, "a subject in need thereof" may include, e.g., subjects who, prior to treatment, exhibit (or have exhibited) one or more asthma-associated parameter, such as, e.g., impaired $FEV_1$ (e.g., less than 2.0 L), impaired FEF25-75%; impaired AM PEF (e.g., less than 400 L/min), impaired PM PEF (e.g., less than 400 L/min), an ACQ5 score of at least 2.5, at least 1 nighttime awakenings per night, and/or a SNOT-22 score of at least 20. In various embodiments, the methods may be used to treat mild, moderate-to-severe, and severe asthma in patients in need thereof. In certain embodiments, the methods may be used to treat mild, moderate-to-severe, and severe asthma in patients in need thereof, wherein the patients further exhibit comorbid moderate-to-severe atopic dermatitis.

In a related embodiment, a "subject in need thereof" may be a subject who, prior to receiving an IL-4R antagonist, has been prescribed or is currently taking a combination of ICS/LABA. Examples of ICS include mometasone furoate, budesonide, and fluticasone propionate. Examples of LABA include formoterol and salmeterol. Examples of ICS/LABA therapies include fluticasone/salmeterol combination therapy and budesonide/formoterol combination therapy. For example, the invention includes methods that comprise administering an IL-4R antagonist to a patient who has been taking a regular course of ICS/LABA for two or more weeks immediately preceding the administration of the IL-4R antagonist (such prior treatments are referred to herein as "background treatments"). The invention includes therapeutic methods in which background treatments are continued in combination with administration of the IL-4R antagonist. In yet other embodiments, the amount of the ICS component, the LABA component, or both, is gradually decreased prior to or after the start of IL-4R antagonist administration. In some embodiments, the invention includes methods to treat patients with persistent asthma for at least ≥12 months. In one embodiment, a patient with persistent asthma may be resistant to treatment by a therapeutic agent, such as a corticosteroid, and may be administered an IL-4R antagonist according to the present methods.

In some embodiments, a "subject in need thereof" may be a subject with elevated levels of an asthma-associated biomarker. Examples of asthma-associated biomarkers include, but are not limited to, IgE, thymus and activation regulated chemokine (TARC), eotaxin-3, CEA, YKL-40, and periostin. In some embodiments, a "subject in need thereof" may be a subject with blood eosinophils ≥300 cells/µL, 200-299 cells/µL, or <200 cells/µL. In one embodiment, a "subject in need thereof" may be a subject with elevated level of bronchial or airway inflammation as measured by the fraction of exhaled nitric oxide (FeNO).

In some embodiments, a "subject in need thereof" is selected from the group consisting of: a subject age 18 years old or older, a subject 12 years or older, a subject age 12 to 17 years old (12 to <18 years old), a subject age 6 to 11 years old (6 to <12 years old), and a subject age 2 to 5 years old (2 to <6 years old). In some embodiments, a "subject in need thereof" is selected from the group consisting of: an adult, an adolescent, and a child. In some embodiments, a "subject in need thereof" is selected from the group consisting of: an adult age 18 years of age or older, an adolescent age 12 to 17 years old (12 to <18 years old), a child age 6 to 11 years old (6 to <12 years old), and a child age 2 to 5 years old (2 to <6 years old). The subject can be less than 2 years of age, e.g., 12 to 23 months, or 6 to 11 months.

A normal IgE level in healthy subjects is less than about 100 kU/L (e.g., as measured using the IMMUNOCAP® assay [Phadia, Inc. Portage, Mich.]). Thus, the invention includes methods comprising selecting a subject who exhibits an elevated serum IgE level, which is a serum IgE level greater than about 100 kU/L, greater than about 150 kU/L, greater than about 500 kU/L, greater than about 1000 kU/L, greater than about 1500 kU/L, greater than about 2000 kU/L, greater than about 2500 kU/L, greater than about 3000 kU/L, greater than about 3500 kU/L, greater than about 4000 kU/L, greater than about 4500 kU/L, or greater than about 5000 kU/L, and administering to the subject a pharmaceutical composition comprising a therapeutically effective amount of an IL-4R antagonist.

TARC levels in healthy subjects are in the range of 106 ng/L to 431 ng/L, with a mean of about 239 ng/L. (An exemplary assay system for measuring TARC level is the TARC quantitative ELISA kit offered as Cat. No. DDN00 by R&D Systems, Minneapolis, Minn.) Thus, the invention involves methods comprising selecting a subject who exhibits an elevated TARC level, which is a serum TARC level greater than about 431 ng/L, greater than about 500 ng/L, greater than about 1000 ng/L, greater than about 1500 ng/L, greater than about 2000 ng/L, greater than about 2500 ng/L, greater than about 3000 ng/L, greater than about 3500 ng/L, greater than about 4000 ng/L, greater than about 4500 ng/L, or greater than about 5000 ng/L, and administering to the subject a pharmaceutical composition comprising a therapeutically effective amount of an IL-4R antagonist.

Eotaxin-3 belongs to a group of chemokines released by airway epithelial cells, which is up-regulated by the Th2 cytokines IL-4 and IL-13 (Lilly et al 1999, J. Allergy Clin.

Immunol. 104: 786-790). The invention includes methods comprising administering an IL-4R antagonist to treat patients with elevated levels of eotaxin-3, such as more than about 100 pg/ml, more than about 150 pg/ml, more than about 200 pg/ml, more than about 300 pg/ml, or more than about 350 pg/ml. Serum eotaxin-3 levels may be measured, for example, by ELISA.

Periostin is an extracellular matrix protein involved in the Th2-mediated inflammatory processes. Periostin levels are found to be up-regulated in patients with asthma (Jia et al 2012 J Allergy Clin Immunol. 130:647-654.e10. doi: 10.1016/j.jaci.2012.06.025, Epub 2012 Aug. 1). The invention includes methods comprising administering an IL-4R antagonist to treat patients with elevated levels of periostin.

Fractional exhaled. NO (FeNO) is a biomarker of bronchial or airway inflammation. FeNO is produced by airway epithelial cells in response to inflammatory cytokines including IL-4 and IL-13 (Alwing et al 1993, Eur. Respir. J. 6: 1368-1370). FeNO levels in healthy adults range from 2 to 30 parts per billion (ppb). An exemplary assay for measuring FeNO is by using a NIOX instrument by Aerocrine AB, Solna, Sweden. The assessment may be conducted prior to spirometry and following a fast of at least an hour. The invention includes methods comprising administering an IL-4R antagonist to patients with elevated levels of exhaled NO (FeNO), such as more than about 30 ppb, more than about 31 ppb, more than about 32 ppb, more than about 33 ppb, more than about 34 ppb, or more than about 35 ppb.

Carcinoembryogenic antigen (CEA) (also known as CEA cell adhesion molecule 5 [CEACAM5]) is a tumor marker that is found correlated to non-neoplastic diseases of the lung (Marechal et al 1988, Anticancer Res. 8: 677-680). CEA levels in serum may be measured by ELISA. The invention includes methods comprising administering an IL-4R antagonist to patients with elevated levels of CEA, such as more than about 1.0 ng/ml, more than about 1.5 ng/ml, more than about 2.0 ng/ml, more than about 2.5 ng/ml, more than about 3.0 ng/ml, more than about 4.0 ng/ml, or more than about 5.0 ng/ml.

YKL-40 (named for its N-terminal amino acids tyrosine (Y), lysine (K) and leucine (L) and its molecular mass of 40 kD) is a chitinase-like protein found to be up regulated and correlated to asthma exacerbation, IgE, and eosinophils (Tang et al 2010 Eur. Respir. J. 35: 757-760). Serum YKL-40 levels are measured by, for example, ELISA. The invention includes methods comprising administering an IL-4R antagonist to patients with elevated levels of YKL-40, such as more than about 40 ng/ml, more than about 50 ng/ml, more than about 100 ng/ml, more than about 150 ng/ml, more than about 200 ng/ml, or more than about 250 ng/ml.

Periostin is a secreted matricellular protein associated with fibrosis, and its expression is upregulated by recombinant IL-4 and IL-13 in cultured bronchial epithelial cells and bronchial fibroblasts (Jia et al. (2012) J. Allergy Clin. Immunol. 130:647). In human asthmatic patients periostin expression levels correlate with reticular basement membrane thickness, an indicator of subepithelial fibrosis. Id. The invention includes methods comprising administering an IL-4R antagonist to patients with elevated levels of periostin.

Induced sputum eosinophils and neutrophils are well-established direct markers of airway inflammation (Djukanovic et al 2002, Eur. Respire. J. 37: 1S-2S). Sputum is induced with inhalation of hypertonic saline solution and processed for cell counts according to methods known in the art, for example, the guidelines of European Respiratory Society.

In some embodiments, the subjects are stratified into the following groups: a blood eosinophil count (high blood eosinophils) ≥300 cells/μL (HEos) or 300-499 cells/μL or ≥500 cells/μL, a blood eosinophil count of 200 to 299 cells/μL (moderate blood eosinophils), or a blood eosinophil count <200 cells/μL (low blood eosinophils), and are administered an anti-IL-4R antibody or antigen binding fragment thereof at a dose or dosing regimen based upon the eosinophil level.

In some embodiments, the subjects are stratified into the following groups: a blood eosinophil count of ≥300 cells/μL, of 300-499 cells/μL, or of ≥500 cells/μL (high blood eosinophils); a blood eosinophil count of ≥150 cells/μL (moderate blood eosinophils); or a blood eosinophil count of <150 cells/μL (low blood eosinophils), and are administered an anti-IL-4R antibody or antigen binding fragment thereof at a dose or dosing regimen based upon the eosinophil level.

In some embodiments, a subject has "eosinophilic phenotype" asthma defined by a blood eosinophil count of ≥150 cells/μL, a blood eosinophil count of ≥300 cells/μL, a blood eosinophil count of 300-499 cells/μL, or a blood eosinophil count of ≥500 cells/μL, and are administered an anti-IL-4R antibody or antigen binding fragment thereof.

Methods for Assessing Pharmacodynamic Asthma-Associated Parameters

The invention also includes methods for assessing one or more pharmacodynamic asthma-associated parameters a subject in need thereof, caused by administration of a pharmaceutical composition comprising an IL-4R antagonist. A reduction in the incidence of an asthma exacerbation (as described above) or an improvement in one or more asthma-associated parameters (as described above) may correlate with an improvement in one or more pharmacodynamic asthma-associated parameters; however, such a correlation is not necessarily observed in all cases.

Examples of "pharmacodynamic asthma-associated parameters" include, for example, the following: (a) biomarker expression levels; (b) serum protein and RNA analysis; (c) induced sputum eosinophils and neutrophil levels; (d) exhaled nitric oxide (FeNO); and (e) blood eosinophil count. An "improvement in a pharmacodynamic asthma-associated parameter" means, for example, a decrease from baseline of one or more biomarkers, such as TARC, eotaxin-3 or IgE, a decrease in sputum eosinophils or neutrophils, FeNO, periostin or blood eosinophil count. As used herein, the term "baseline," with regard to a pharmacodynamic asthma-associated parameter, means the numerical value of the pharmacodynamic asthma-associated parameter for a patient prior to or at the time of administration of a pharmaceutical composition described herein.

To assess a pharmacodynamic asthma-associated parameter, the parameter is quantified at baseline and at a time point after administration of the pharmaceutical composition. For example, a pharmacodynamic asthma-associated parameter may be measured at day 1, day 2, day 3, day 4, day 5, day 6, day 7, day 8, day 9, day 10, day 11, day 12, day 14, or at week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the pharmaceutical composition. The difference between the value of the parameter at a particular time point following initiation of treatment and the value of the parameter at baseline is used to establish whether there has been change, such as an "improvement," in the pharmacodynamic asthma-associated parameter (e.g., an increase or decrease, as the case may be, depending on the specific parameter being measured).

In certain embodiments, administration of an IL-4R antagonist to a patient causes a change, such as a decrease or increase, in expression of a particular biomarker. Asthma-associated biomarkers include, but are not limited to, the following: (a) total IgE; (b) thymus and activation-regulated chemokine (IARC); (c) YKL-40; (d) carcinoembryonic antigen in serum; (e) eotaxin-3 in plasma; and (f) periostin in serum. For example, administration of an IL-4R antagonist to an asthma patient can cause one or more of a decrease in IARC or eotaxin-3 levels, or a decrease in total serum IgE levels. The decrease can be detected at week 1, week 2, week 3, week 4, week 5, or longer following administration of the IL-4R antagonist. Biomarker expression can be assayed by methods known in the art. For example, protein levels can be measured by ELISA (Enzyme Linked Immunosorbent Assay). RNA levels can be measured, for example, by reverse transcription coupled to polymerase chain reaction (RT-PCR).

Biomarker expression, as discussed above, can be assayed by detection of protein or RNA in serum. The serum samples can also be used to monitor additional protein or RNA biomarkers related to response to treatment with an IL-4R antagonist, IL-4/IL-13 signaling, asthma, atopy or eosinophilic diseases (e.g., by measuring soluble IL-4Rα, IL-4, IL-13, periostin). In some embodiments, RNA samples are used to determine RNA levels (non-genetic analysis), e.g., RNA levels of biomarkers; and in other embodiments, RNA samples are used for transcriptome sequencing (e.g., genetic analysis).

Formulations

In some embodiments, the antibody or antigen binding fragment thereof is formulated in a composition comprising: i) about 150 mg/mL of antibody or an antigen-binding fragment thereof that specifically binds to IL-4R, ii) about 20 mM histidine, iii) about 12.5 mM acetate, iv) about 5% (w/v) sucrose, v) about 25 mM arginine hydrochloride, vi) about 0.2% (w/v) polysorbate 80, wherein the pH of the formulation is about 5.9, and wherein the viscosity of the formulation is about 8.5 cPoise.

In alternative embodiments, the antibody or antigen binding fragment thereof is formulated in a composition comprising: i) about 175 mg/mL of antibody or an antigen-binding fragment thereof that specifically binds to IL-4R, ii) about 20 mM histidine, iii) about 12.5 mM acetate, iv) about 5% (w/v) sucrose, v) about 50 mM arginine hydrochloride, vi) about 0.2% (w/v) polysorbate 80, wherein the pH of the formulation is about 5.9, and wherein the viscosity of the formulation is about 8.5 cPoise.

In specific embodiments, the antibody or antigen-binding fragment thereof comprises an HCVR comprising the amino acid sequence of SEQ ID NO: 1 and an LCVR comprising the amino acid sequence of SEQ ID NO: 2.

The present invention is further illustrated by the following examples which should not be construed as further limiting. The contents of the figures and all references, patents and published patent applications cited throughout this application are expressly incorporated herein by reference for all purposes.

Furthermore, in accordance with the present invention there may be employed conventional molecular biology, microbiology, and recombinant DNA techniques within the skill of the art. Such techniques are explained fully in the literature. See, e.g., Green & Sambrook, *Molecular Cloning: A Laboratory Manual*, Fourth Edition (2012) Cold Spring Harbor Laboratory Press, Cold Spring Harbor, N.Y.; *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; 13, Perbal, *A Practical Guide To Molecular Cloning* (1984); F. M. Ausubel et al. (eds.), *Current Protocols in Molecular Biology*, John Wiley & Sons, Inc. (1994).

EXAMPLES

The following examples are put forth so as to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The exemplary IL-4R antagonist used in the following Examples is the human anti-IL-4R antibody named dupilumab (also referred to herein as "mAb1").

Example 1. VENTURE Phase III Trial Study (NCT02528214)

Severe uncontrolled asthma can lead to a dependence on oral corticosteroids, with systemic steroid exposure. This can potentially lead to serious short-term and long-term adverse effects, including weight gain, diabetes, osteoporosis, glaucoma, anxiety, depression, cardiovascular disease and immunosuppression. Patients with severe chronic asthma live with a profound decrease in their lung function, approximately 52 percent of predicted normal for those in this study at baseline. The decrease in lung function impacts their ability to breathe normally and may lead to frequent exacerbations that require acute treatment and hospitalization. These problems occur even in patients who are treated with chronic OCS.

Figure 2:
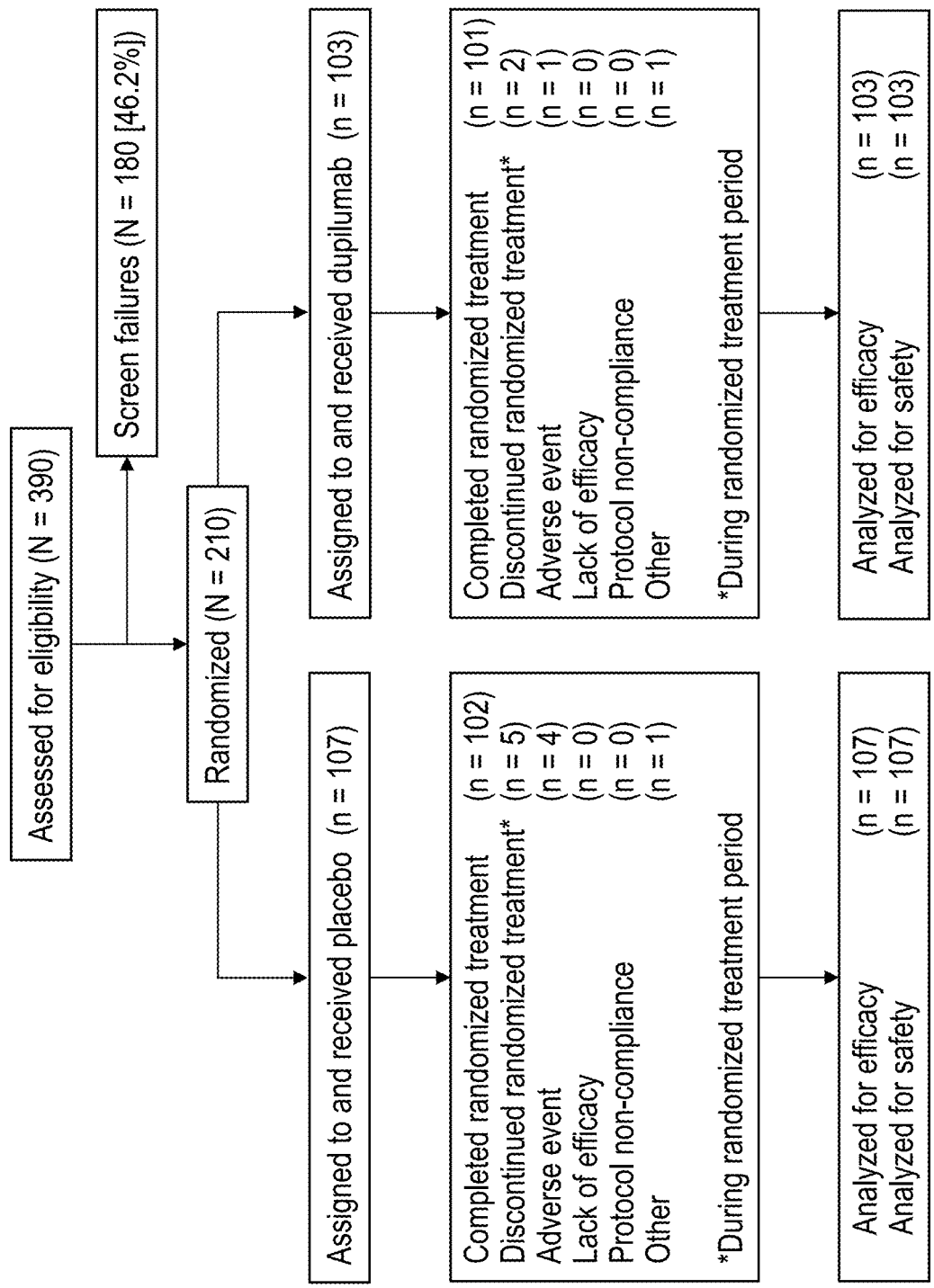
FIG. 2 depicts a CONSORT diagram showing the patient disposition for the Venture (EFC13691) study.

A phase 3 trial/study was performed to evaluate investigational dupilumab in adults and adolescents with severe steroid-dependent asthma, without minimum blood eosinophil requirement, to receive add-on dupilumab 300 mg or placebo every 2 weeks for 24 weeks. The Phase 3 trial (VENTURE) enrolled 210 patients (203 completed the randomized treatment period, with 101 in the dupilumab group and 102 in the placebo group) with severe asthma and regular use of maintenance OCS in the six months prior to the study (FIG. 1). In the study, the prescribed OCS was prednisone or prednisolone. Patients were randomized using a 1:1 randomization ratio and treated with either dupilumab, 300 mg every other week with a loading dose of 600 mg, or placebo (FIG. 2). The median baseline eosinophil count in the study was 260 eosinophils/microliter. Primary endpoint was reduction in glucocorticoid dose at week 24. Key secondary endpoints included proportion of patients achieving ≥50% reduction in glucocorticoid-dose, and reduction to <5 mg/day in glucocorticoid-dose at week 24. Severe exacerbation rates and pre-bronchodilator forced expiratory volume in 1 second (FEV$_1$) were assessed in overall population and in patients with blood eosinophils ≥300 cells/μL. Safety was assessed overall.

Inclusion criteria for the study are shown below in Table 1. Baseline demographics for the study are shown in FIG. 3.

TABLE 1

| Inclusion criteria. | |
|---|---|
| VENTURE study | |
| Age | Adults & adolescents, >=12 years |
| Asthma history | At least 6 m of documented OCS requirement (equivalent to GINA 5 - severe) |
| Existing asthma treatment | High dose ICS<br>OCS daily dose: 5 mg minimum to 35 mg maximum<br>Up to 3 controllers are eligible. |
| Pre-BD FEV$_1$ | <=80% for adults; <=90% for adolescents |
| ACQ-5 | None specified |
| FEV$_1$ Reversibility | Documented history within prior year |
| # severe exacerbations in prior year | None specified |

Exclusion criteria for the Venture study were also used; the criteria for exclusion of patients was EOS <150 restricted to no more than 25% of total population.

The primary endpoint analyzed was the percent reduction of the OCS dose at week 24. Key secondary endpoints analyzed included a reduction of 50% or greater in the OCS dose and a reduction of OCS dose to <5 mg/day. Other secondary endpoints investigated included achieving patient's maximum possible reduction per protocol, and a patient no longer requiring OCS. Disease-specific efficacy measures were used. The measures were a reduction in annualized severe exacerbation and improvement in lung function (FEV$_1$). FIG. 2 shows the overall disposition of the patients in the study.

Primary Outcome

Figure 4A:
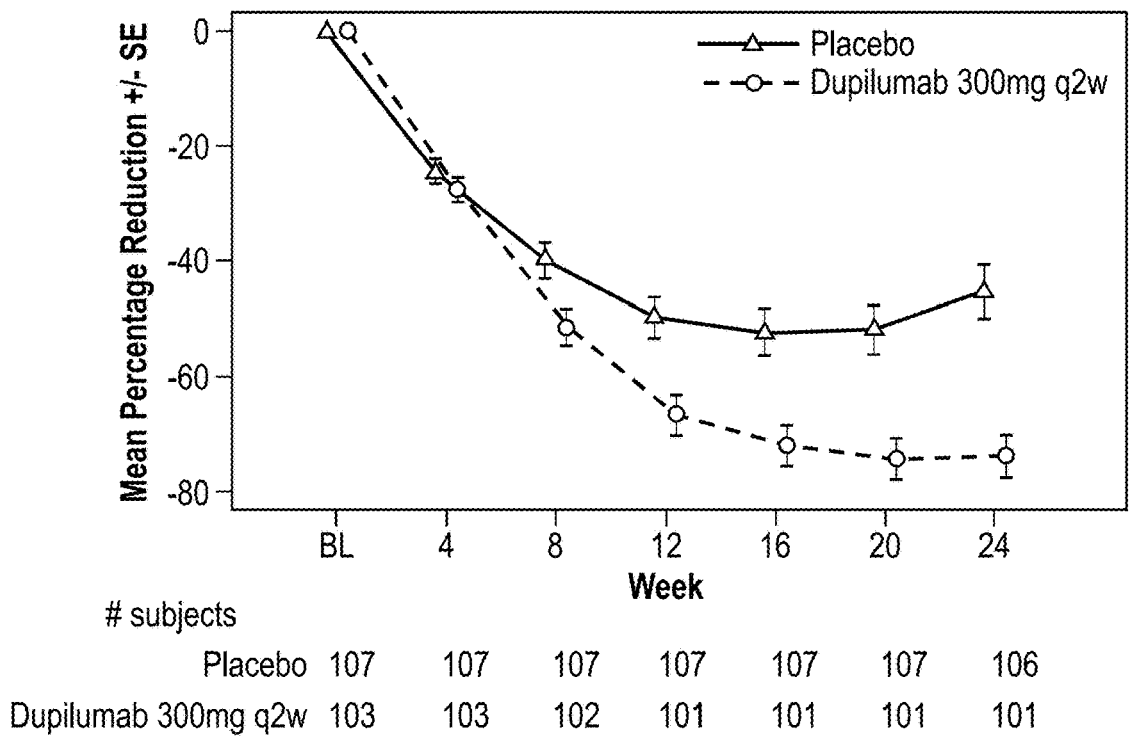
FIG. 4A-FIG. 4D graphically depict primary and secondary endpoints during the 24-week treatment period in an intent to treat (ITT) population.

In the intent to treat (ITT) population, dupilumab treatment significantly reduced oral glucocorticoid dose compared with placebo, while maintaining asthma control: least squares (LS) mean (standard error [SE]) percentage change from baseline to week 24 (−70.1% (4.90) versus −41.9% (4.57) from baseline, respectively (P<0.001; FIG. 4A; Table 2)) The observed median change from baseline to week 24 in dupilumab-treated patients was 100% (interquartile range (IQR), 62.5% to 100%) versus 50% (IQR, 0% to 100%) in the placebo group.

TABLE 2

| Summary of outcomes at week 24 - ITT population. | | |
|---|---|---|
| | Placebo (N = 107) | Dupilumab 300 mg q2w (N = 103) |
| Percentage reduction in oral glucocorticoid dose from baseline at Week 24 | | |
| LS mean change (SE) | −41.85 (4.57) | −70.09 (4.90) |
| LS mean difference versus placebo (95% CI) | | −28.24 (−40.67 to −15.81) |
| P value versus placebo | | <0.001 |
| Median reduction (IQR)$^a$ | −50 (−100 to 0) | −100 (−100 to −62.50) |
| 100% | 29.0 | 52.4 |
| ≥90% | 30.8 | 55.3 |
| ≥75% | 39.3 | 68.9 |
| ≥50% | 53.3 | 79.6 |
| 0% | 68.2 | 86.4 |
| No reduction or increase in glucocorticoid dose, or dropped out of study | 31.8 | 13.6 |
| Reduction in oral glucocorticoid dose from baseline (mg/day) at Week 24 | | |
| LS mean change (SE) | −4.77 (0.54) | −7.58 (0.58) |
| LS mean difference versus placebo (95% CI) | | −2.81 (−4.29 to −1.33) |
| P value versus placebo | | <0.001 |
| Proportion of patients with ≥50% reduction in oral glucocorticoid dose at Week 24 | | |
| Yes - no. (%) | 57 (53.3) | 82 (79.6) |
| Estimate (95% CI) | 0.50 (0.40 to 0.61) | 0.80 (0.70 to 0.87) |
| Odds ratio versus placebo (95% CI) | | 3.98 (2.06 to 7.67) |
| P value versus placebo | | <0.001 |
| Proportion of patients with oral glucocorticoid reduced to <5 mg/day at Week 24 | | |
| Yes - no. (%) | 40 (37.4) | 74 (71.8) |
| Estimate (95% CI) | 0.33 (0.24 to 0.44) | 0.69 (0.58 to 0.79) |
| Odds ratio versus placebo (95% CI) | | 4.48 (2.39 to 8.39) |
| P value versus placebo | | <0.001 |
| Proportion of patients no longer requiring oral glucocorticoid at Week 24 | | |
| Yes - no. (%) | 31 (29.2) | 54 (52.4) |
| Estimate (95% CI) | 0.25 (0.17 to 0.35) | 0.48 (0.36 to 0.59) |
| Odds ratio versus placebo (95% CI) | | 2.74 (1.47 to 5.10) |
| P value versus placebo | | 0.002 |
| Proportion of patients with maximum possible oral glucocorticoid dose at Week 24 | | |
| Yes - no. (%) | 32 (29.9) | 54 (52.4) |
| Estimate (95% CI) | 0.26 (0.18 to 0.36) | 0.48 (0.36 to 0.59) |
| Odds ratio versus placebo (95% CI) | | 2.57 (1.40 to 4.73) |
| P value versus placebo | | 0.002 |

TABLE 2-continued

Summary of outcomes at week 24 - ITT population.

| | Placebo (N = 107) | Dupilumab 300 mg q2w (N = 103) |
|---|---|---|
| Adjusted annualized rate of severe exacerbation events during the 24-week treatment period | | |
| Estimate (95% CI) | 1.597 (1.248 to 2.043) | 0.649 (0.442 to 0.955) |
| Relative risk versus placebo (95% CI) | | 0.407 (0.263 to 0.630) |
| P value versus placebo | | <0.001 |
| Change from baseline in pre-bronchodilator $FEV_1$ (L) at Week 24 | | |
| LS mean change (SE) - L | 0.01 (0.05) | 0.22 (0.05) |
| LS mean difference versus placebo (95% CI) | | 0.22 (0.09 to 0.34) |
| P value versus placebo | | <0.001 |
| Change from baseline in FeNO (ppb) at Week 24 | | |
| Mean change (SE) - ppb | 0.3 (27.9) | −17.3 (27.9) |
| P value versus placebo[b] | | <0.001 |

CI denotes confidence interval, FeNO Fractional exhaled nitric oxide,
$FEV_1$ forced expiratory volume in 1 second,
IQR interquartile range,
LS, least-squares,
ppb parts per billion,
q2w every 2 weeks,
SD standard deviation, and SE standard error.
[a]Calculated from observed data only.
[b]FeNO was tested non-parametrically.

Secondary Outcomes

Glucocorticoid Reduction Outcomes

For the primary endpoint, at 24 weeks in the overall population, dupilumab added to standard therapies significantly reduced the use of maintenance oral corticosteroids (OCS) by 70.1% (median 100 percent) compared to 41.9% with placebo (median 50 percent) (p<0.001).

In pre-specified analyses of patients with baseline eosinophil counts greater than or equal to 300 cells/microliter, adding dupilumab significantly reduced OCS use by 80 percent on average (median 100 percent) compared to 43 percent for placebo (median 50 percent).

The proportion of patients achieving ≥50% reduction in oral glucocorticoid dose relative to baseline at week 24 was significantly greater with dupilumab versus placebo (80% vs. 50%; P<0.001; Observed values: 80% for dupilumab, 53% for placebo) (FIG. 4A; Table 2). Sensitivity analyses also demonstrated greater proportion of patients with 50%, 75%, and 90% reductions in oral glucocorticoids with dupilumab (Table 3). Significantly more patients treated with dupilumab versus placebo achieved a reduction of oral glucocorticoid dose to <5 mg/day (69% vs. 33%; P<0.001; Observed values: 72% for dupilumab, 37% for placebo) (FIG. 4A; Table 2).

TABLE 3

Sensitivity analyses: percentage reduction of oral glucocorticoid dose (mg/day) at week 24 analyzed by proportional odds model - ITT population.

| Percentage reduction in oral glucocorticoid dose from baseline at Week 24 | Placebo (N = 107) | Dupilumab 300 mg q2w (N = 103) |
|---|---|---|
| ≥90% | 33 (30.8) | 57 (55.3) |
| ≥75% | 42 (39.3) | 71 (68.9) |
| ≥50% | 57 (53.3) | 82 (79.6) |
| >0% | 73 (68.2) | 89 (86.4) |

TABLE 3-continued

Sensitivity analyses: percentage reduction of oral glucocorticoid dose (mg/day) at week 24 analyzed by proportional odds model - ITT population.

| Percentage reduction in oral glucocorticoid dose from baseline at Week 24 | Placebo (N = 107) | Dupilumab 300 mg q2w (N = 103) |
|---|---|---|
| No reduction or any increase in oral glucocorticoid dose, or dropped out of study | 34 (31.8) | 14 (13.6) |
| Odds ratio versus placebo (95% CI) | | 3.25 (1.90 to 5.55) |
| P value versus placebo | | <0.001 |

Data are mean (SD), or no. (%).
CI denotes confidence interval,
q2w every 2 weeks, and ITT intent-to-treat.

The percentage reduction of oral glucocorticoid dose at week 24 was classified into five ordinal categories (90% to 100%, 75% to <90%, 50% to <75%, >0% to <50%, no reduction or any increase in oral glucocorticoid dose or dropped out from study). The model used the endpoint category as the response variable, and treatment groups, optimized oral glucocorticoid dose at baseline, regions, and baseline blood eosinophil level subgroups (≥150 cells/μL or <150 cells/μL) as covariates.

Figure 5A:
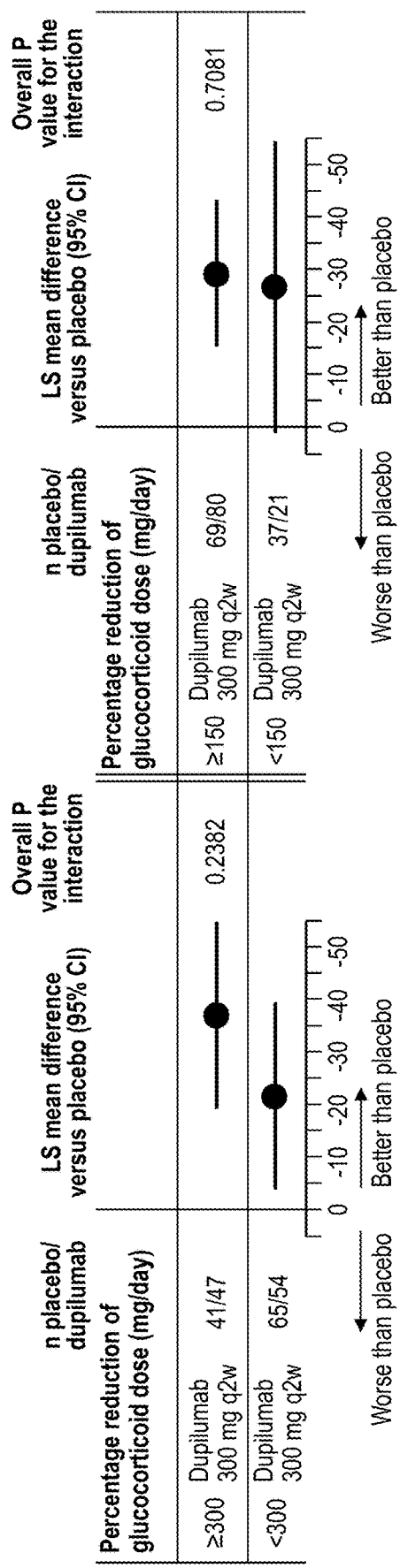
FIG. 5A-FIG. 5B depict week 24 results by baseline blood eosinophil subgroups.
Figure 5B:
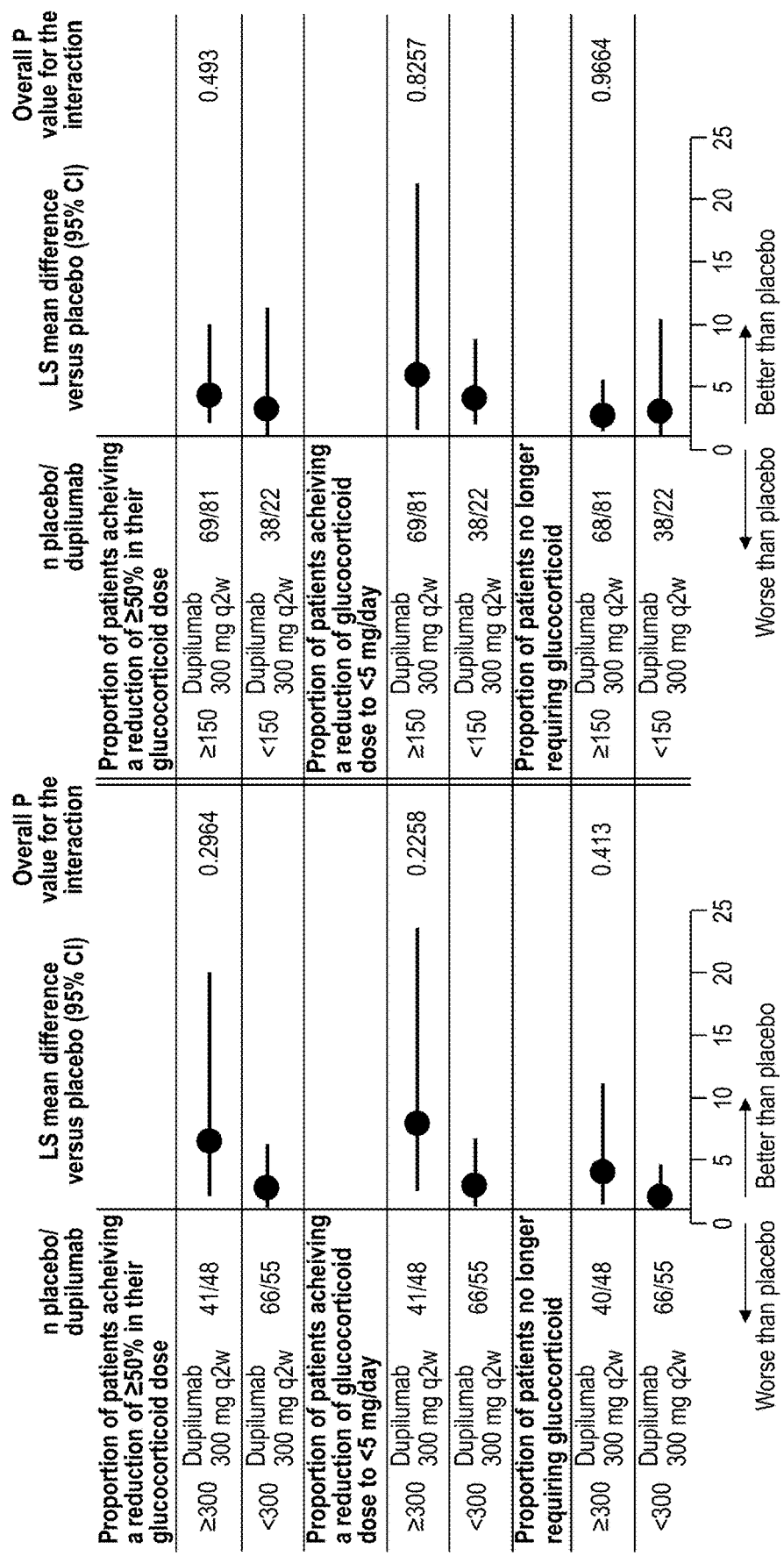

Notably, 48% of the dupilumab-treated patients versus 26% of placebo-treated patients achieved their maximum possible glucocorticoid dose reduction at week 24 (P=0.002; observed values: 52% for dupilumab, 30% for placebo) (FIG. 4A; Table 2). Similarly, 48% of dupilumab-treated patients versus 25% of placebo-treated patients no longer required oral glucocorticoids at week 24 (P=0.002; Observed values: 52% for dupilumab, 29% for placebo) (FIG. 4A; Table 2). Dupilumab consistently reduced oral glucocorticoid outcome measures irrespective of baseline blood eosinophil count (FIG. 5A and FIG. 5B; Table 4).

TABLE 4

Subgroup analyses of oral glucocorticoid endpoints at week 24 by baseline blood eosinophil subgroups.

| | Placebo (N = 107) | Dupilumab 300 mg q2w (N = 103) |
|---|---|---|
| Percentage reduction in oral glucocorticoid dose from baseline (mg/day) | | |
| Baseline blood eosinophils ≥300 cells/µL - no. | 41 | 47 |
| LS mean change (SE) | −42.71 (6.77) | −79.54 (6.36) |
| LS mean difference versus placebo (95% CI) | | −36.83 (−54.71 to −18.94) |
| Baseline blood eosinophils <300 cells/µL - no. | 65 | 54 |
| LS mean change (SE) | −44.98 (6.00) | −66.31 (6.47) |
| LS mean difference versus placebo (95% CI) | | −21.33 (−38.75 to −3.90) |
| Overall P value for interaction | 0.238 | |
| Baseline blood eosinophils ≥150 cells/µL | 69 | 80 |
| LS mean change (SE) | −46.51 (5.21) | −75.91 (4.76) |
| LS mean difference versus placebo (95% CI) | | −29.39 (−43.12 to −15.67) |
| Baseline blood eosinophils <150 cells/µL - no. | 37 | 21 |
| LS mean change (SE) | −36.87 (8.60) | −63.77 (11.14) |
| LS mean difference versus placebo (95% CI) | | −26.89 (−54.52 to 0.73) |
| Overall P value for interaction | 0.708 | |
| Patients with ≥50% reduction in oral glucocorticoid dose | | |
| Baseline blood eosinophils ≥300 cells/µL - no. | 41 | 48 |
| Estimate (95% CI) | 0.52 (0.36 to 0.68) | 0.88 (0.74 to 0.95) |
| Odds ratio versus placebo (95% CI) | | 6.59 (2.13 to 20.42) |
| Baseline blood eosinophils <300 cells/µL - no. | 66 | 55 |
| Estimate (95% CI) | 0.52 (0.40 to 0.65) | 0.76 (0.63 to 0.86) |
| Odds ratio versus placebo (95% CI) | | 2.91 (1.28 to 6.63) |
| Overall P value for interaction | 0.296 | |
| Baseline blood eosinophils ≥150 cells/µL - no. | 69 | 81 |
| Estimate (95% CI) | 0.53 (0.41 to 0.65) | 0.84 (0.74 to 0.90) |
| Odds ratio versus placebo (95% CI) | | 4.49 (2.04 to 9.85) |
| Baseline blood eosinophils <150 cells/µL - no. | 38 | 22 |
| Estimate (95% CI) | 0.47 (0.31 to 0.64) | 0.75 (0.52 to 0.89) |
| Odds ratio versus placebo (95% CI) | | 3.33 (0.97 to 11.48) |
| Overall P value for interaction | 0.493 | |
| Patients with oral glucocorticoid reduced to <5 mg/day | | |
| Baseline blood eosinophils ≥300 cells/µL - no. | 41 | 48 |
| Estimate (95% CI) | 0.40 (0.25 to 0.57) | 0.84 (0.70 to 0.92) |
| Odds ratio versus placebo (95% CI) | | 8.04 (2.71 to 23.82) |
| Baseline blood eosinophils <300 cells/µL - no. | 66 | 55 |
| Estimate (95% CI) | 0.35 (0.24 to 0.48) | 0.63 (0.49 to 0.75) |
| Odds ratio versus placebo (95% CI) | | 3.12 (1.41 to 6.93) |
| Overall P value for interaction | 0.226 | |
| Baseline blood eosinophils ≥150 cells/µL - no. | 69 | 81 |
| Estimate (95% CI) | 0.44 (0.32 to 0.57) | 0.77 (0.66 to 0.85) |
| Odds ratio versus placebo (95% CI) | | 4.29 (2.04 to 9.04) |
| Baseline blood eosinophils <150 cells/µL - no. | 38 | 22 |
| Estimate (95% CI) | 0.21 (0.10 to 0.38) | 0.62 (0.39 to 0.80) |
| Odds ratio versus placebo (95% CI) | | 6.03 (1.70 to 21.44) |
| Overall P value for interaction | 0.826 | |
| Proportion of patients no longer requiring oral glucocorticoid | | |
| Baseline blood eosinophils ≥300 cells/µL - no. | 40 | 48 |
| Estimate (95% CI) | 0.26 (0.13 to 0.44) | 0.59 (0.41 to 0.74) |
| Odds ratio versus placebo (95% CI) | | 4.07 (1.46 to 11.33) |
| Baseline blood eosinophils <300 cells/µL - no. | 66 | 55 |
| Estimate (95% CI) | 0.26 (0.16 to 0.38) | 0.43 (0.30 to 0.57) |
| Odds ratio versus placebo | | 2.15 (0.96 to 4.81) |
| Overall P value for interaction | 0.413 | |
| Baseline blood eosinophils ≥150 cells/µL - no. | 68 | 81 |
| Estimate (95% CI) | 0.30 (0.19 to 0.43) | 0.54 (0.42 to 0.66) |
| Odds ratio versus placebo (95% CI) | | 2.73 (1.31 to 5.70) |
| Baseline blood eosinophils <150 cells/µL - no. | 38 | 22 |
| Estimate (95% CI) | 0.19 (0.09 to 0.35) | 0.42 (0.23 to 0.65) |
| Odds ratio versus placebo (95% CI) | | 3.15 (0.93 to 10.73) |
| Overall P value for interaction | 0.966 | |
| Proportion of patients with maximum possible oral glucocorticoid dose | | |
| Baseline blood eosinophils ≥300 cells/µL - no. | 41 | 48 |
| Estimate (95% CI) | 0.31 (0.18 to 0.48) | 0.59 (0.43 to 0.74) |
| Odds ratio versus placebo (95% CI) | | 3.26 (1.26 to 8.43) |
| Baseline blood eosinophils <300 cells/µL - no. | 66 | 55 |
| Estimate (95% CI) | 0.26 (0.16 to 0.38) | 0.43 (0.30 to 0.57) |
| Odds ratio versus placebo (95% CI) | | 2.15 (0.96 to 4.81) |
| Overall P value for interaction | 0.544 | |
| Baseline blood eosinophils ≥150 cells/µL - no. | 69 | 81 |

TABLE 4-continued

Subgroup analyses of oral glucocorticoid endpoints at week 24 by baseline blood eosinophil subgroups.

| | Placebo (N = 107) | Dupilumab 300 mg q2w (N = 103) |
|---|---|---|
| Estimate (95% CI) | 0.32 (0.21 to 0.45) | 0.54 (0.42 to 0.65) |
| Odds ratio versus placebo (95% CI) | | 2.47 (1.21 to 5.02) |
| Baseline blood eosinophils <150 cells/µL - no. | 38 | 22 |
| Estimate (95% CI) | 0.19 (0.09 to 0.35) | 0.42 (0.23 to 0.65) |
| Odds ratio versus placebo (95% CI) | | 3.15 (0.93 to 10.73) |
| Overall P value for interaction | 0.842 | |

CI denotes confidence interval,
LS least-squares,
SE standard error, and q2w every 2 weeks.

While improvements were observed in all baseline blood eosinophil subgroups, the magnitude of the treatment effect was largest in those with higher baseline eosinophil counts (e.g., odds ratio versus placebo in patients with ≥50% reduction in oral glucocorticoid dose was 6.59 (95% CI, 2.1 to 20.4) for patients with ≥300 cells/µL and 2.91 (95% CI, 1.3 to 6.6) for those with <300 cells/µL at baseline). In the overall population, 69 percent of patients who received dupilumab were able to reduce their OCS dose to less than 5 mg per day while maintaining asthma control compared to 33 percent of patients who received placebo (p less than 0.0001); in the high EOS group, 84 percent of dupilumab patients were able to reduce their OCS dose to less than 5 mg per day compared to 40 percent for placebo. (p equals 0.0002.) Half of the patients completely eliminated oral glucocorticoid use. Despite glucocorticoid reductions, dupilumab versus placebo in the overall population and ≥300 cells/µL Eos subgroup decreased severe exacerbations by 59.3% (P<0.001) and 71.1%, and improved. $FEV_1$ by 0.22 L (P<0.001) and 0.32 L, respectively.

Exacerbations and $FEV_1$

Figure 4B:
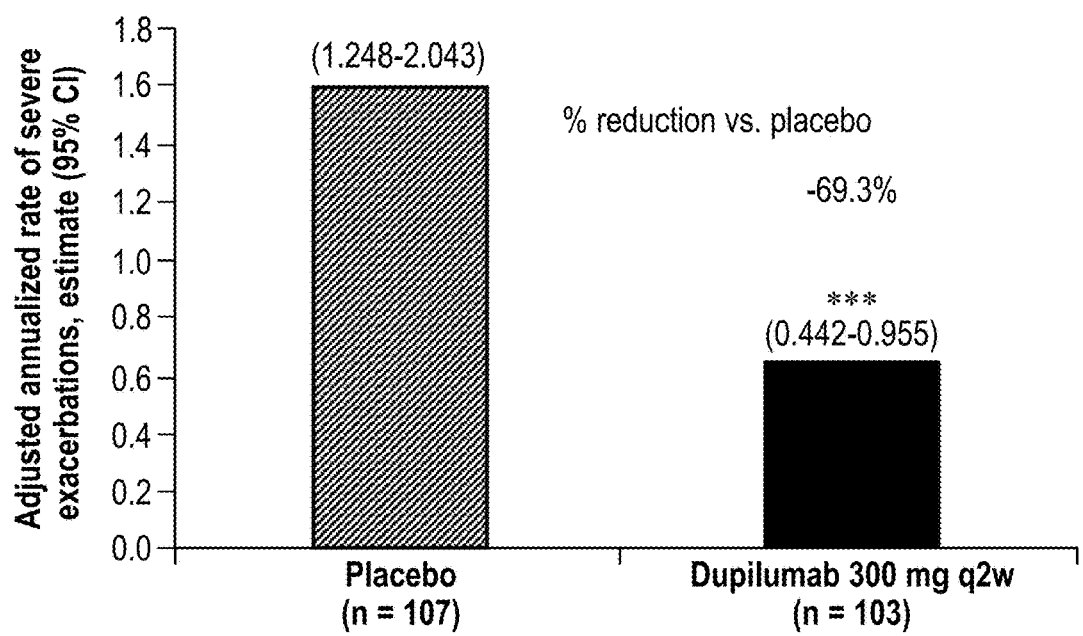
Figure 6A:
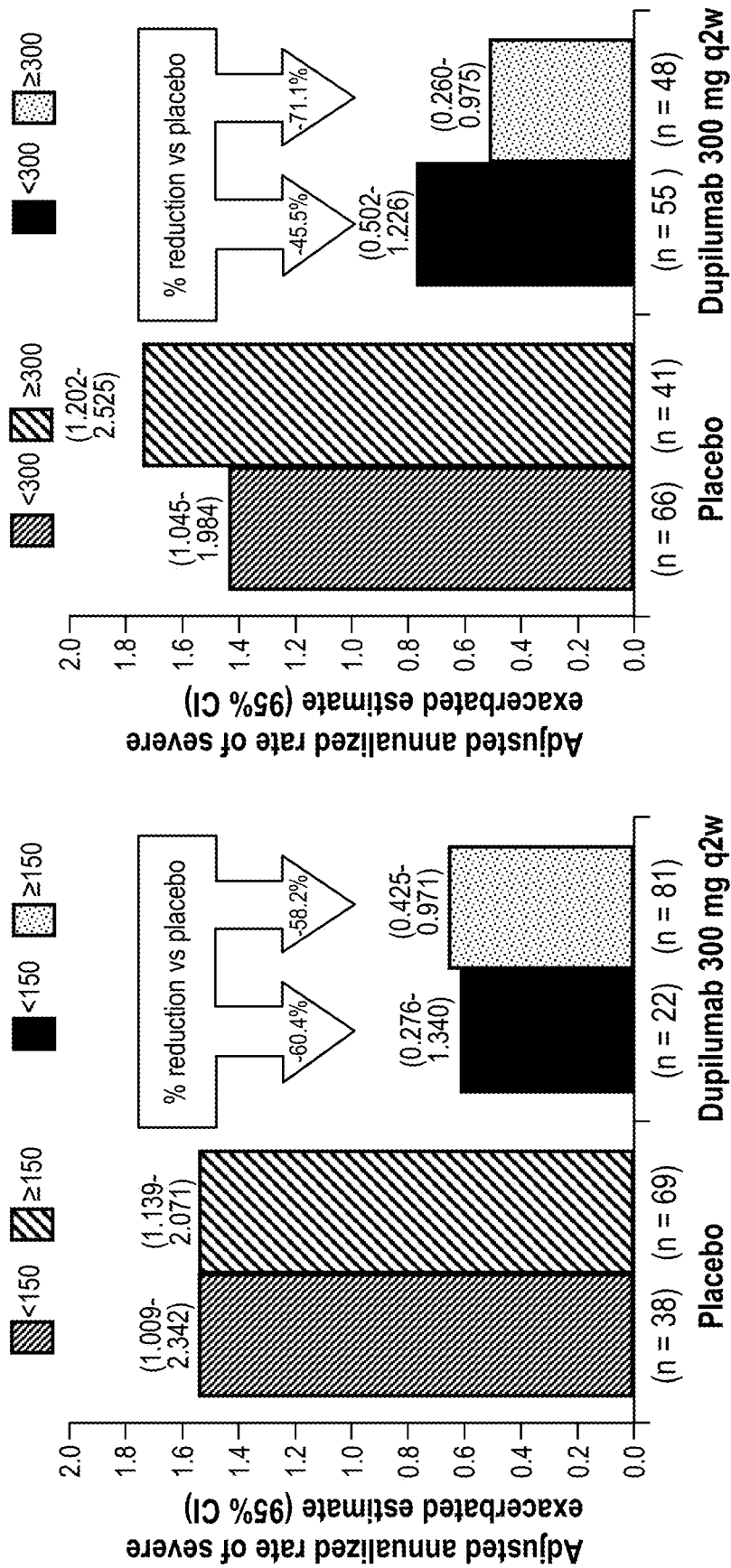
FIG. 6A-FIG. 6B depict severe Asthma Exacerbations (FIG. 6A) and pre-bronchodilator $FEV_1$ (L) (FIG. 6B) during the 24-week treatment period by baseline blood eosinophil subgroups.
Figure 6B:
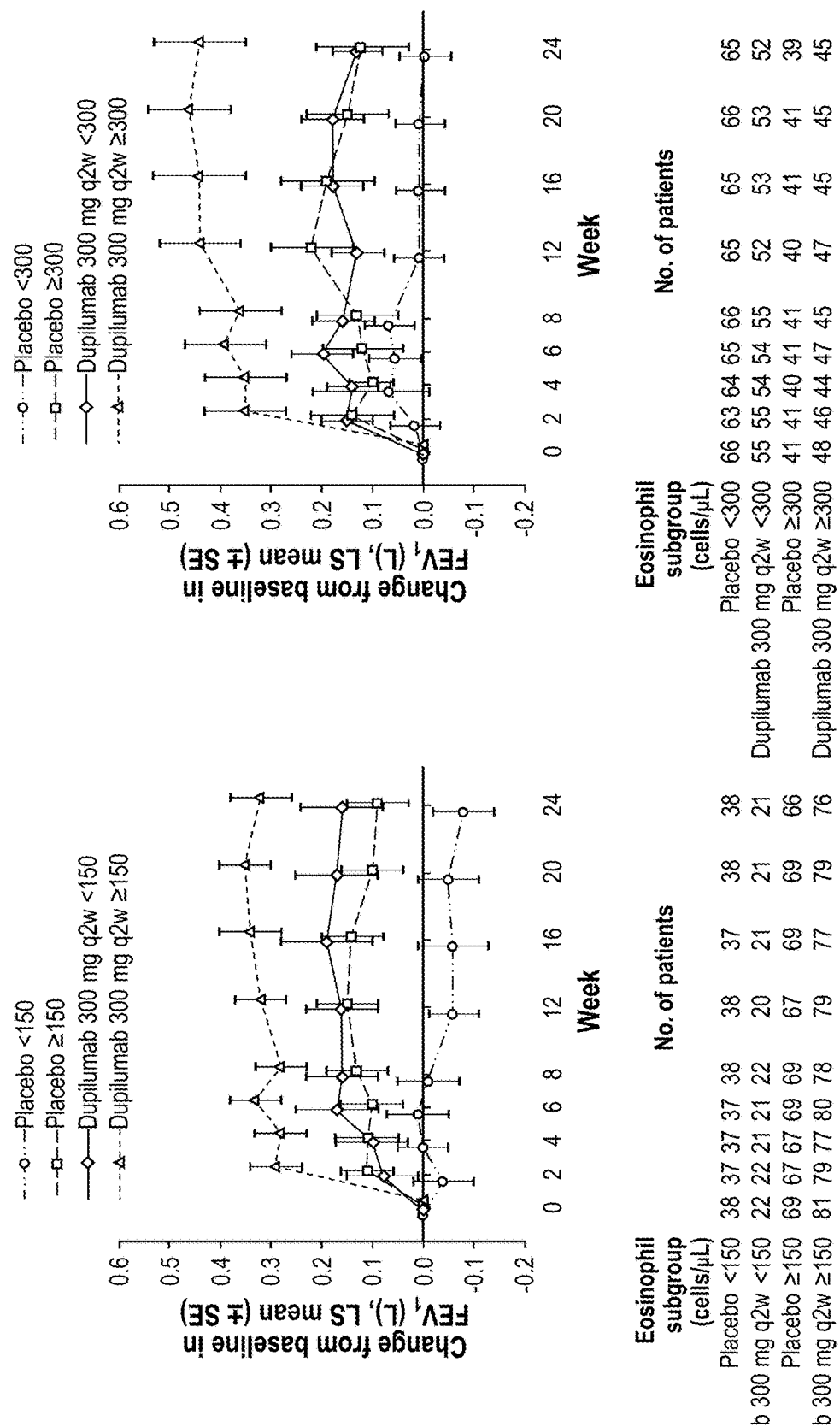

In addition to significant reductions in oral glucocorticoid use during the 24-week treatment period, dupilumab significantly (P<0.001) reduced severe asthma exacerbations versus placebo by 59.3% in the overall population (FIG. 4B and Table 7), and also improved $FEV_1$ by LS mean (SE) 0.22 L (0.05) (vs. 0.01 L [0.05] by placebo, P<0.001) at week 24 in the overall population. Though dupilumab reduced the rate of annualized severe asthma exacerbations and improved $FEV_1$ versus placebo regardless of baseline eosinophil count (FIG. 6A and FIG. 6B, Table 5), these benefits were more pronounced in patients with higher baseline blood eosinophil counts. For example, dupilumab decreased severe exacerbations by 71.1% and improved $FEV_1$ by LS mean (SE) 0.32 L (95% CI 0.10 to 0.54) (both P<0.001 vs. placebo) in patients with baseline blood eosinophils ≥300 cells/µL.

TABLE 5

Subgroup analyses of exacerbations and change in pre-bronchodilator $FEV_1$ at week 24 by baseline blood eosinophil subgroups.

| | Placebo (N = 107) | Dupilumab 300 mg q2w (N = 103) |
|---|---|---|
| Annualized event rate of severe exacerbations | | |
| Baseline blood eosinophils ≥300 cells/µL - no. | 41 | 48 |
| Estimate (95% CI) | 1.742 (1.202 to 2.525) | 0.504 (0.260 to 0.975) |
| Relative risk versus placebo (95% CI) | | 0.289 (0.139 to 0.601) |
| Baseline blood eosinophils <300 cells/µL - no. | 66 | 55 |
| Estimate (95% CI) | 1.440 (1.045 to 1.984) | 0.784 (0.502 to 1.226) |
| Relative risk versus placebo (95% CI) | | 0.545 (0.315 to 0.940) |
| Overall P value for interaction | 0.143 | |
| Baseline blood eosinophils ≥150 cells/µL - no. | 69 | 81 |
| Estimate (95% CI) | 1.536 (1.139 to 2.071) | 0.642 (0.425 to 0.971) |
| Relative risk versus placebo (95% CI) | | 0.418 (0.254 to 0.689) |
| Baseline blood eosinophils <150 cells/µL - no. | 38 | 22 |
| Estimate (95% CI) | 1.537 (1.009 to 2.342) | 0.609 (0.276 to 1.340) |
| Relative risk versus placebo (95% CI) | | 0.396 (0.166 to 0.946) |
| Overall P value for interaction | 0.824 | |
| Pre-bronchodilator $FEV_1$(L) | | |
| Baseline blood eosinophils ≥300 cells/µL | | |
| Baseline - no. | 41 | 48 |
| Mean baseline (SD) - L | 1.57 (0.59) | 1.55 (0.49) |
| Week 24 - no. | 39 | 45 |
| LS mean change (SE) - L | 0.12 (0.09) | 0.44 (0.09) |
| LS mean difference versus placebo (95% CI) | | 0.32 (0.10 to 0.54) |

TABLE 5-continued

Subgroup analyses of exacerbations and change in pre-bronchodilator
$FEV_1$ at week 24 by baseline blood eosinophil subgroups.

|  | Placebo (N = 107) | Dupilumab 300 mg q2w (N = 103) |
|---|---|---|
| Baseline blood eosinophils <300 cells/μL | | |
| Baseline - no. | 66 | 55 |
| Mean baseline (SD) - L | 1.66 (0.62) | 1.52 (0.56) |
| Week 24 - no. | 65 | 52 |
| LS mean change (SE) - L | 0.00 (0.05) | 0.13 (0.05) |
| LS mean difference versus placebo (95% CI) | | 0.13 (−0.02 to 0.28) |
| Overall P value for interaction | | 0.174 |
| Baseline blood eosinophils ≥150 cells/μL | | |
| Baseline - no. | 69 | 81 |
| Mean baseline (SD) - L | 1.68 (0.61) | 1.56 (0.55) |
| Week 24 - no. | 66 | 76 |
| LS mean change (SE) - L | 0.09 (0.06) | 0.32 (0.06) |
| LS mean difference versus placebo (95% CI) | | 0.22 (0.06 to 0.38) |
| Baseline blood eosinophils <150 cells/μL | | |
| Baseline - no. | 38 | 22 |
| Mean baseline (SD) - L | 1.53 (0.61) | 1.45 (0.45) |
| Week 24 - no. | 38 | 21 |
| LS mean change (SE) - L | −0.08 (0.06) | 0.16 (0.08) |
| LS mean difference versus placebo (95% CI) | | 0.24 (0.05 to 0.44) |
| Overall P value for interaction | | 0.949 |

CI denotes confidence interval,
$FEV_1$ forced expiratory volume in 1 second,
LS least-squares,
q2w every 2 weeks,
SD standard deviation and SE standard error.

Figure 4C:
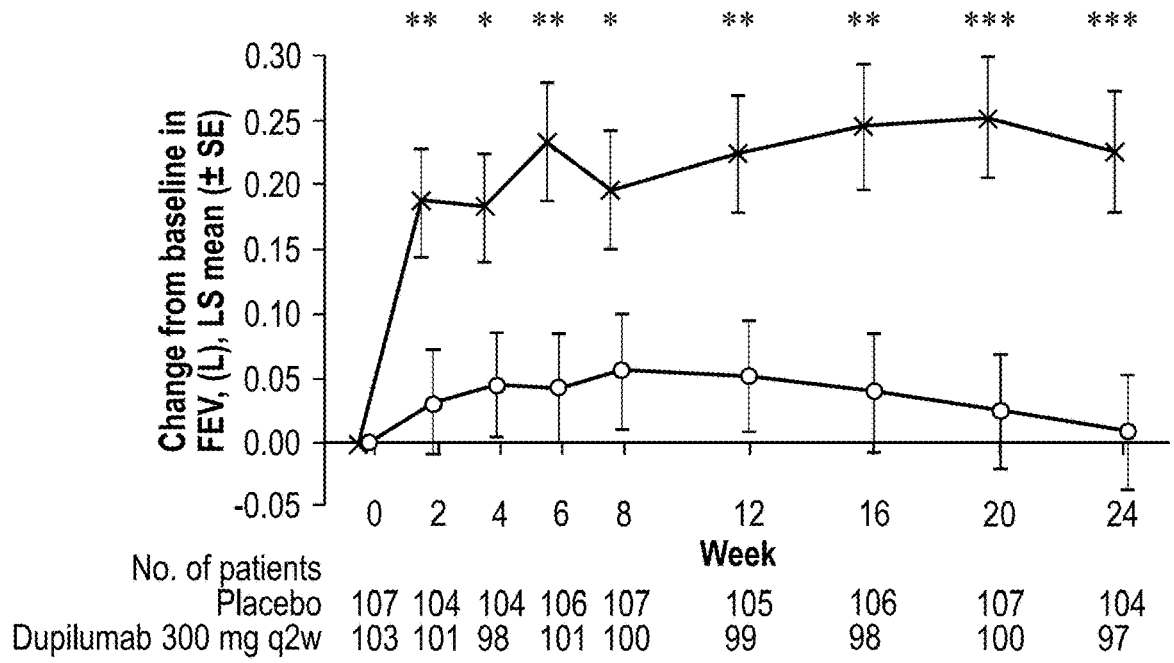

Improvements in $FEV_1$ were rapid and sustained, as early as week two (LS mean change 0.15 L; 95% CI 0.04 to 0.26), and further increased through week 24 (P<0.05 at all time points) (FIG. 4C and Table 2). At 24 weeks, dupilumab improved lung function, as assessed by forced expiratory volume over one second ($FEV_1$) by 220 ml (15 percent) in the overall population (p equals 0.0007) compared with 10 ml for placebo, and by 320 ml (25 percent) compared with 120 ml for placebo in patients with eosinophil counts equal to or greater than 300 cells/microliter (p equals 0.0049).

Other Secondary and Exploratory Outcomes

The Phase 3 study enrolled steroid-dependent severe asthma patients regardless of eosinophil levels or other biomarkers, and the results showed improvements compared to placebo on lung function and exacerbations across patient subgroups: those with baseline eosinophil counts above 300 cells/microliter; above 150 cells/microliter; and below 150 cells/microliter. Dupilumab demonstrated a consistent improvement in lung function across the asthma program for patients with severe asthma struggling with declines in their everyday breathing ability.

ACQ-5 scores at week 24 indicated a significant improvement (P=0.002) in asthma control with dupilumab versus placebo (LS mean difference in change from baseline: −0.47 [95% CI, −0.76 to −0.18]). With dupilumab, the LS mean improvement from baseline (−1.05) at week 24 was twice the minimally clinically important difference of 0.5 for the ACQ-5 instrument.

Figure 4D:
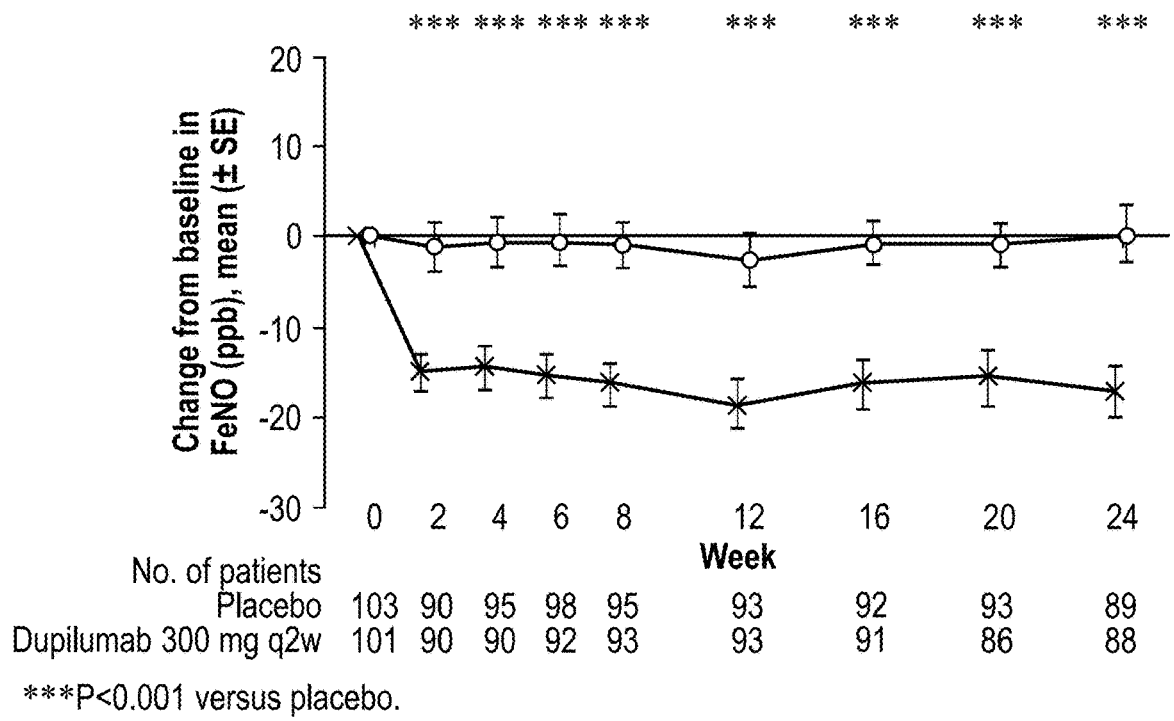

Dupilumab treatment suppressed FeNO by week two and was sustained during the 24-week treatment period (P<0.001 versus placebo at all time points; FIG. 4D). The percentage of patients with FeNO<25 ppb (upper limit of normal) (Table 6) was increased from 43.6% at baseline to 84.4% in dupilumab group, while no change was observed in the placebo group (44.7% to 45.1%).

TABLE 6

Proportion of patients achieving a FeNO suppression of <25 ppb at baseline and week 24.

|  | Placebo (N = 107) | Dupilumab 300 mg q2w (N = 103) |
|---|---|---|
| Baseline, n | 103 | 101 |
| Median (IQR) | 29.0 (17.0 to 56.0) | 28.0 (14.0 to 48.0) |
| <25 ppb - no. (%) | 46 (44.7) | 44 (43.6) |
| Week 24, n | 91 | 90 |
| Median (IQR) | 27.0 (16.0 to 45.0) | 15.0 (11.0 to 21.0) |
| Change from baseline, mean (SD) | 0.3 (27.9) | −17.3 (27.9) |
| <25 ppb - no. (%) | 41 (45.1) | 76 (84.4) |
| P value versus placebo | | <0.001 |

FeNO denotes fractional exhaled nitric oxide,
IQR interquartile range,
ppb parts per billion,
q2w every 2 weeks, and
SD standard deviation.

Morning and Evening Daily Asthma Symptoms in Patients with Oral-Corticosteroid-Dependent Severe Asthma Patients' asthma symptoms were recorded as scores in an e-diary, in the morning for symptoms during the night (AM symptoms), and in the evening (PM symptoms) for symptoms during the day, scoring their severity 0 (mildest) to 4 (most severe). Change from baseline in asthma-symptom scores during 24-week treatment period was analyzed by using mixed-effect models with repeated measures.

Figure 25A:
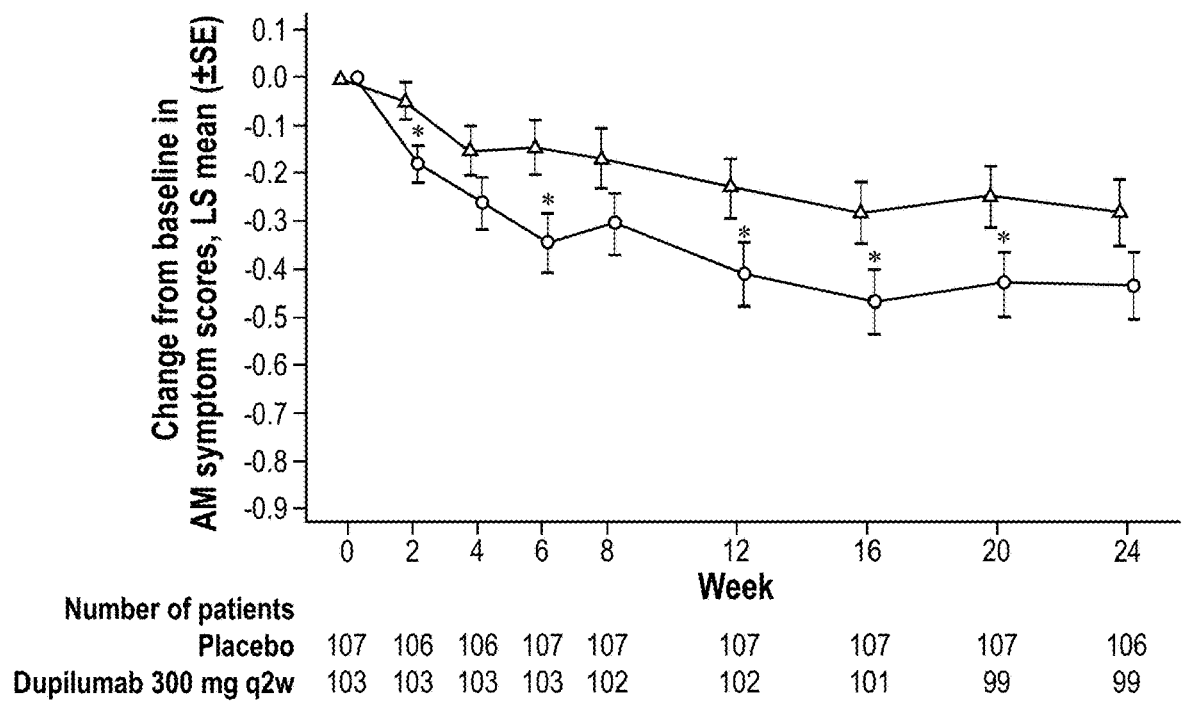
FIG. 25A-FIG. 25D depict the effect of dupilumab during the 24-week treatment period on AM symptom scores in the ITT population (FIG. 25A) and the subgroup of patients who reduced OCS use by 100% by week 24 (FIG. 25B), as well as on PM symptom scores in the ITT population (FIG. 25C) and the subgroup of patients who reduced OCS use by 100% by week 24 (FIG. 25D). *P<0.05, ***P<0.001. SE, standard error. Triangles, placebo; circles, 300 mg q2w dupilumab.
Figure 25B:
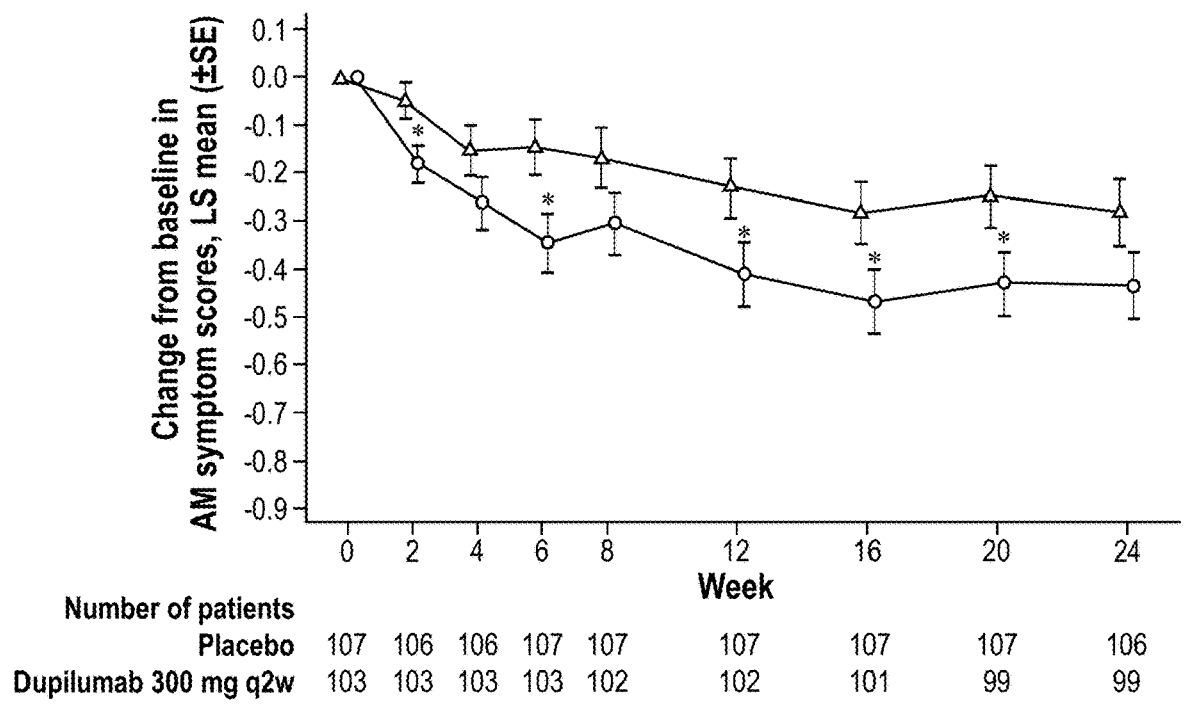
Figure 25C:
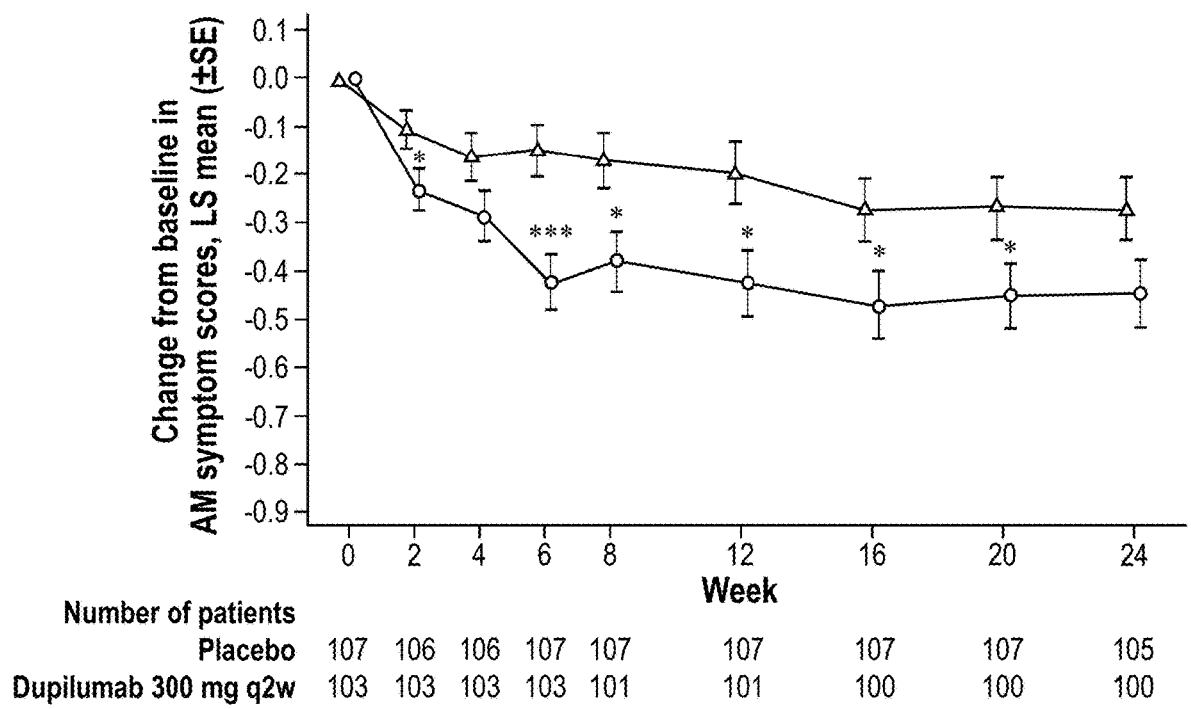
Figure 25D:
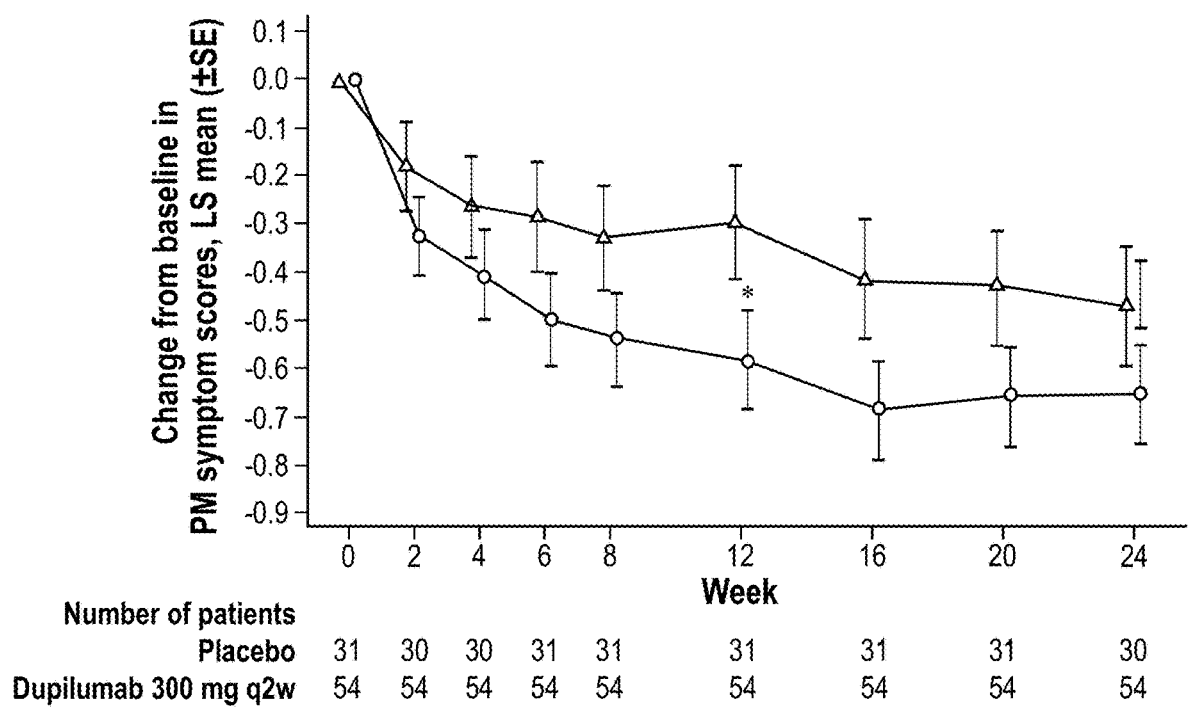

Mean baseline AM/PM symptom scores in the dupilumab and placebo groups, respectively, were 1.37/1.37 and 1.50/1.52 in the ITT population (n=210), and 1.45/1.49 and 1.50/1.52 in patients who reduced OCS use 100% by week 24 (40.5%). In the dupilumab group, symptoms improved rapidly (LS mean change from baseline in AM/PM symptom scores at week 2, −0.18/−0.23; both P<0.05 vs placebo), with continued improvement through week 16 (−0.47/−0.47, both P<0.05 vs placebo), and a maintained positive effect until week 24 (FIG. 25A and FIG. 25C). Patients in the dupilumab group who reduced OCS use 100% by week 24 demonstrated a similar pattern response with a greater magnitude of symptom improvements (FIG. 25B and FIG. 25D). Overall, the most frequent treatment-emergent adverse event occurring in dupilumab- vs. placebo-treated patients was eosinophilia (14% vs 1%), Injection-site reactions occurred in 9% of dupilumab-treated vs. 4% of placebo-treated patients.

Dupilumab improved morning and evening daily asthma symptoms in a rapid and sustained manner, despite OCS withdrawal, in patients with OCS-dependent, severe asthma. Symptom improvements were greatest in patients who reduced OCS use 100% by week 24. Dupilumab was generally well tolerated.

Population: ITT; 100% OCS reduction subgroup. Endpoints: LS mean change from baseline in AM/PM asthma symptoms during the treatment period. Treatment arms: Dupilumab 300 mg q2w; placebo.

Asthma Control and Health-Related Quality of Life

Asthma control was assessed by weekly recording in an e-diary of the validated 5-item Asthma Control Questionnaire (ACQ-5), on which higher scores (range 0-6) indicated less control. Health-related quality of life (HRQoL) was assessed by using the self-administered 7-item asthma quality of life questionnaire (AQLQ), on which higher global scores (range 0-7) indicated better HRQoL. Change from baseline in ACQ-5 and AQLQ scores during the 24-week treatment period were analyzed by using mixed-effect models with repeated measures.

Figure 26A:
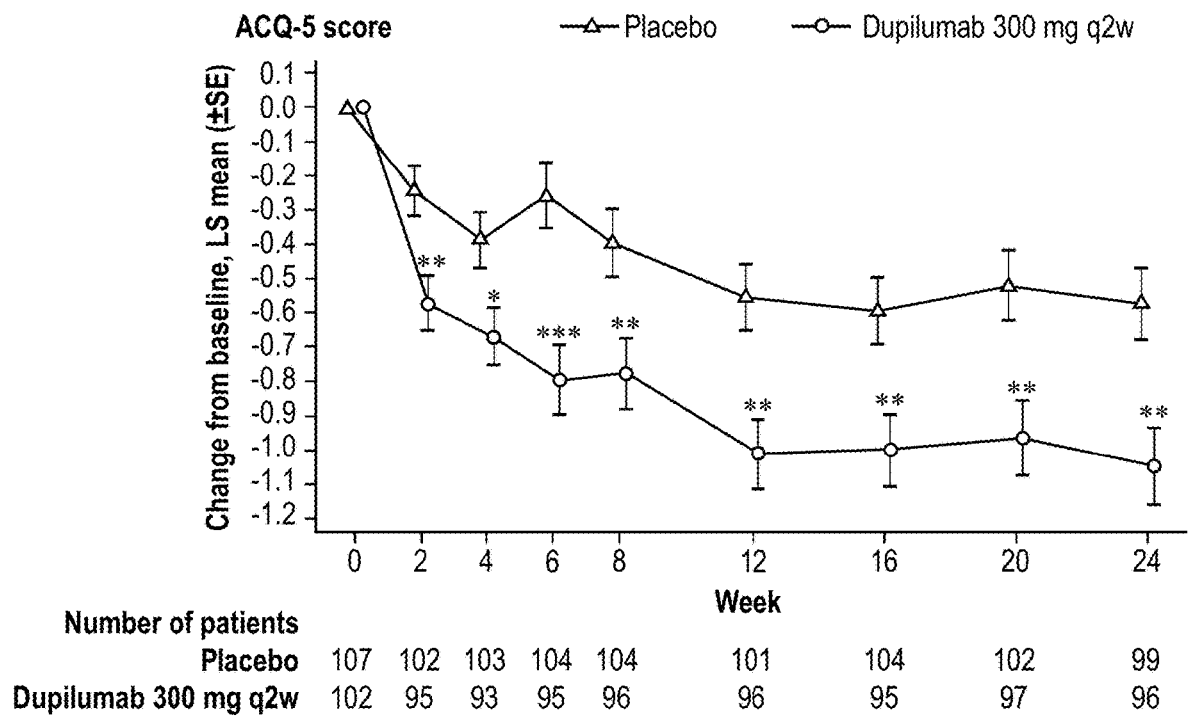
FIG. 26A-FIG. 26B depict the effect of dupilumab on asthma control and HRQoL in patients with OCS-dependent severe asthma, showing ACQ-5 score (FIG. 26A) and AQLQ global score (FIG. 26B). *P<0.05, *P<0.01, ***P<0.001. SE, standard error. The minimum clinically important difference is 0.5 for all scales. Triangles, placebo; circles, 300 mg q2w dupilumab.
Figure 26B:
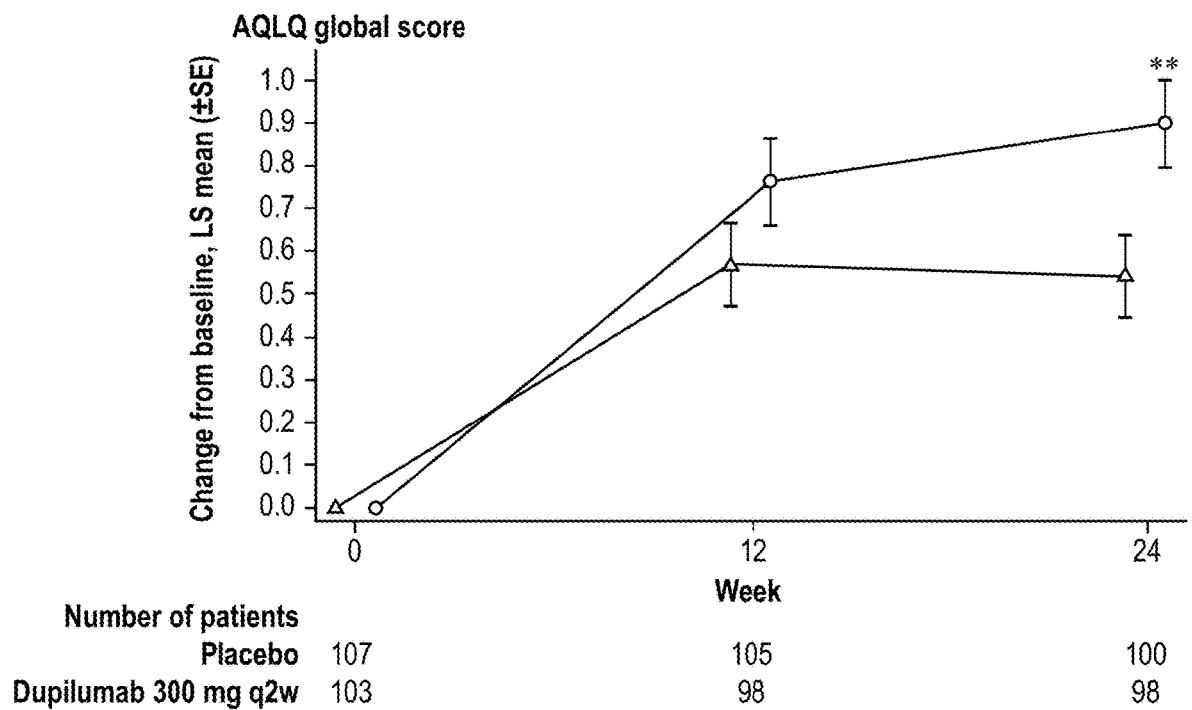

In the dupilumab and placebo groups, respectively, mean baseline ACQ-5 scores were 2.42 and 2.58, and mean baseline AQLQ scores were 4.38 and 4.31. In the dupilumab group, asthma control rapidly improved (week 2, LS mean change from baseline in ACQ-5 score, 0.57; P=0.002 vs. placebo), further improved at week 12 (1.01; P=0.001 vs. placebo), and remained stable through week 24 (1.05; P=0.002 vs. placebo) (FIG. 26A). In patients receiving dupilumab treatment, an LS mean improvement from baseline in AQLQ score of 0.76 was observed at week 12 (P=0.14 vs. placebo), which was further improved to 0.89 at week 24 (P=0.008 vs placebo) (FIG. 26B). Overall, the most frequent treatment-emergent adverse event occurring in dupilumab- vs. placebo-treated patients was eosinophilia (14% vs 1%). Injection-site reactions occurred in 9% of dupilumab-treated vs. 4% of placebo-treated patients.

Add-on dupilumab vs. placebo significantly improved asthma control and improved HRQoL in patients with OCS-dependent, severe asthma. Improvement in asthma control occurred as early as week 2 and was maintained for 24 weeks. Dupilumab was generally well-tolerated.

Population: ITT. Endpoints: LS mean change from baseline in ACQ-5 at weeks 2, 12 and 24; LS mean change from baseline in AQLQ at weeks 12 and 24; safety during treatment period. Treatment arms: Dupilumab 300 mg q2w; placebo.

Safety

The incidence of TEAEs was similar across treatment groups (62.1% vs. 64.5% for dupilumab vs. placebo) in the safety population. The TEAEs by Medical Dictionary for Regulatory Activities (MedDRA) Preferred Term most frequently occurring in ≥5% of patients treated with dupilumab versus placebo were viral upper respiratory tract infection (8.7% vs. 17.8%), bronchitis (6.8% vs. 5.6%), sinusitis (6.8% vs. 3.7%), influenza (2.9% vs. 5.6%), injection-site reactions (8.7% vs. 3.7%) and the laboratory measure of eosinophilia (grouped 'Eosinophil count increase' and 'eosinophilia' Preferred terms) (13.6% vs, 0.9%). Per study protocol, all cases of eosinophil counts >3,000 cells/μL on treatment were to be reported as AEs and occurred in 12.6% of dupilumab-treated patients versus 0.9% in the placebo group. The reported eosinophilia. TEAEs were all exclusively laboratory findings without any clinical consequences or associated AEs.

Serious TEAEs were reported in 9 (8.7%) dupilumab- and 6 (5.6%) placebo-treated patients; serious TEAEs were not related to the investigational medicinal product. There were no deaths in the study. Treatment-emergent anti-drug antibody responses were observed in 5 patients in each group (dupilumab 5.0% placebo 4.7%) and had no meaningful impact on efficacy or safety.

TABLE 7

Changes in $FEV_1$ and inflammatory biomarkers at weeks 4 and 24 in dupilumab vs placebo treated patients.

| | PBO (N = 107) | DPL 300 mg q2w (N = 103) |
|---|---|---|
| Pre-bronchodilator $FEV^1$ | | |
| BL, L, mean (SD) | 1.63 (0.61) | 1.53 (0.53) |
| Change from BL at Week 4, LS mean (SE) | 0.04 (0.04) | 0.18 (0.04)* |
| Change from BL at Week 24, LS mean (SE) | 0.01 (0.05) | 0.22 (0.05)*** |
| FeNO | | |
| BL, ppb, mean (SD) | 39.6 (34.1) | 35.6 (28.3) |
| Change from BL at Week 4, ppb, mean (SD) | −0.7 (25.4) | −14.6 (23.0) |
| Change from BL at Week 24, ppb, mean (SD) | 0.3 (27.9) | −17.3 (27.9) |
| Percentage mean change from BL at Week 4 (SD) | 8.05 (74.96) | −28.19 (38.99)*** |
| Percentage mean change from BL at Week 24 (SD) | 11.07 (51.93) | −30.36 (46.00)*** |
| Eotaxin-3 | | |
| BL, PG/ML, mean (SD) | 50.62 (40.75) | 47.86 (52.18) |
| Percentage mean change from BL at Week 4 (SD) | 64.68 (231.22) | −1.46 (176.66)*** |
| Percentage mean change from BL at Week 24 (SD) | 57.13 (187.87) | 4.90 (181.84)*** |
| Total IgE | | |
| BL, IU/ML, mean (SD) | 426.62 (881.22) | 434.65 (654.54) |
| Percentage mean change from BL at Week 4 (SD) | −0.02 (86.60) | −19.97 (18.01)*** |
| Percentage mean change from BL at Week 24 (SD) | 7.98 (92.76) | −56.21 (19.91)*** |
| Periostin- Shino test | | |
| BL, PG/ML, mean (SD) | 69.10 (24.96) | 78.88 (34.72) |
| Percentage mean change from BL at Week 4 (SD) | 3.50 (20.97) | −14.41 (25.79)*** |
| Percentage mean change from BL at Week 24 (SD) | 8.60 (36.81) | −19.03 (25.35)*** |
| TARC | | |
| BL, PG/ML, mean (SD) | 428.03 (663.07) | 369.81 (298.11) |
| Percentage mean change from BL at Week 4 (SD) | 22.46 (121.05) | −25.03 (54.16)*** |

TABLE 7-continued

Changes in $FEV_1$ and inflammatory biomarkers at weeks 4 and 24 in dupilumab vs placebo treated patients.

|  | PBO (N = 107) | DPL 300 mg q2w (N = 103) |
|---|---|---|
| Percentage mean change from BL at Week 24 (SD) | 12.63 (65.52) | −22.96 (44.94)*** |

*P < 0.05,
**P < 0.01,
***P < 0.001 vs placebo.
CI, confidence interval, SE, standard error, SD, standard deviation, forced expiratory volume in 1 second, $FEV_1$, Fractional exhaled nitric oxide, FeNO, Thymus and Activation Regulated Chemokine, TARC.

Methods

Study Design and Oversight

This Phase 3 multinational, randomized, double-blind, placebo-controlled study assessed efficacy and safety of dupilumab in patients with oral glucocorticoid-dependent severe asthma. Patients completed an 8 to 10-week oral glucocorticoid dose optimization period followed by 1:1 randomization to dupilumab or placebo for a 24-week treatment period. This treatment period consisted of a 4-week induction period, during which optimized oral glucocorticoid dose was continued; a 16-week oral glucocorticoid reduction period (weeks 4 to 20), during which the glucocorticoid dose was down-titrated every 4 weeks according to a protocol pre-specified algorithm; a 4-week maintenance period, during which patients remained on the glucocorticoid dose established at week 20; and a 12-week post-treatment evaluation period. Eligible patients who completed treatment were permitted to enter a long-term, open-label extension study.

The study was conducted in accordance with the Declaration of Helsinki, International Conference on Harmonization Good Clinical Practice guidelines, and applicable regulatory requirements. An independent data and safety monitoring committee conducted blinded monitoring of patient safety data. The local institutional review board or ethics committee at each study center oversaw trial conduct and documentation. All patients provided written informed consent before participating in the trial.

Patients

Patients aged ≥12 years with physician-diagnosed asthma for ≥12 months based on the Global Initiative for Asthma 2014 Guidelines were eligible to participate. Patients were required to be on regular systemic glucocorticoids in the previous 6 months (5 to 35 mg/day of prednisone or prednisolone or equivalent) for 4 weeks prior to screening, and a high-dose inhaled glucocorticoid (fluticasone propionate >500 μg total daily dose or equipotent equivalent) in combination with up to two controllers (e.g. long-acting β2-agonist or leukotriene receptor antagonist) for ≥3 months. Eligible patients had to have pre-bronchodilator forced expiratory volume in 1 second ($FEV_1$) ≤80% of predicted normal (≤90% for adolescents), 17 $FEV_1$ reversibility ≥12% and 200 mL, or airway hyper responsiveness documented in the 12 months prior to screening visit 1. Patients were recruited with no minimum requirement for baseline blood or sputum eosinophil count or any other Type 2 biomarkers (e.g. FeNO or IgE). Key exclusion criteria included lung diseases other than asthma, deterioration of asthma requiring emergency treatment or hospitalization within 4 weeks of Visit 1, and current smokers or smokers who had stopped within 6 months before screening or who had a smoking history of >10 pack-years.

Treatment and Procedures

Patients were randomized (1:1) to receive subcutaneous dupilumab 300 mg (following 600 mg loading dose on Day 1) as add-on therapy or matched placebo every 2 weeks (q2w). Randomization was conducted by interactive voice/web response technology and patients were stratified according to optimized oral glucocorticoid dose (≤10 mg/day or >10 mg/day of prednisone/prednisolone) and country. Patients using other oral glucocorticoids were switched to a clinically comparable dose of prednisone or prednisolone during the screening period.

Optimized oral glucocorticoid dose was defined as the lowest dose a patient could tolerate without experiencing ≥0.5 increase in 5-Item Asthma Control Questionnaire (ACQ-5) score, severe exacerbation or any clinically significant event requiring oral glucocorticoid dose adjustment. During the dose-reduction phase, oral glucocorticoid dose was reduced every 4 weeks to minimize risk of clinically significant events and carryover effects from the previous dose. No dose adjustments were allowed beyond week 20 except for safety reasons. Background asthma controllers were continued at a stable dose and short-acting β2-agonist use was permitted as needed for asthma symptoms.

Endpoints

The primary efficacy endpoint was the percentage reduction in oral glucocorticoid dose from baseline to week 24 while maintaining asthma control. A patient was considered as having maintained asthma control between weeks 20 and 24 if no clinically significant event (based on investigator judgment) required oral glucocorticoid dose adjustment. For patients experiencing an exacerbation, the final oral glucocorticoid dose was considered to be one step higher than the dose they were receiving at the time of the exacerbation.

Key secondary efficacy endpoints assessed in patients maintaining asthma control were proportion of patients achieving ≥50% reduction from baseline in oral glucocorticoid dose and proportion of patients achieving a reduction in oral glucocorticoid dose to <5 mg/day. Other secondary endpoints included absolute reduction in oral glucocorticoid dose, proportion of patients achieving maximum possible oral glucocorticoid dose reduction, and proportion of patients no longer requiring oral glucocorticoids.

Additional efficacy endpoints included annualized rate of severe exacerbation events during the treatment period (defined as requiring hospitalization, emergency room visit, or treatment for ≥3 days with systemic glucocorticoids at least 2 times the current dose); absolute change from baseline in pre-bronchodilator $FEV_1$ at weeks 2, 4, 8, 12, 16, 20, and 24; and change from baseline in ACQ-5 score at week 24.

An exploratory endpoint of absolute change from baseline in FeNO (ppb) was assessed using a NIOX instrument (Aerocrine AB, Solna, Sweden) at weeks 2, 4, 8, 12, 16, 20 and 24.

Statistical Analysis

It was estimated that 90 randomized patients per treatment group would give the study 94% power (2 tailed test at α=0.05) to detect a treatment difference of 27% in daily glucocorticoid dose 18 assuming a common standard deviation of 50%.

The primary endpoint was analyzed using an analysis of covariance (ANCOVA) model. The model included percentage reduction of oral glucocorticoid dose at week 24 as the response variable, and treatment groups, optimized oral glucocorticoid dose at baseline, regions (pooled countries), and baseline eosinophil subgroups (≥150 cells/μL, <150 cells/μL) as covariates. The treatment difference was tested at the 2-sided significance level of α=0.05. For patients who discontinued the study or had missing oral glucocorticoid dose data at week 24 (2 patients in the dupilumab group and 1 in the placebo group), the primary missing data handling approach was a pattern mixture model by multiple imputations (PMM by MI).

The key secondary and other binary secondary endpoints were analyzed using logistic regression models. Annualized rate of severe exacerbation events during the 24-week treatment period was analyzed using a negative binomial regression model. Mixed-effect models with repeated measures approach was used to analyze pre-bronchodilator $FEV_1$ changes from baseline at various time points during the 24-week treatment period and 5-Item Asthma Control Questionnaire (ACQ-5) change from baseline at week 24.

Efficacy analyses were performed on the intent-to-treat (ITT) population, defined as all randomized patients analyzed according to treatment allocated, regardless of treatment received. Primary and key secondary endpoints, $FEV_1$, and severe asthma exacerbation rates were also analyzed in subgroups of patients defined by baseline blood eosinophil levels (≥300 cells/μL, <300 cells/μL, ≥150 cells/μL and <150 cells/μL). The safety population included all patients who received ≥1 dose or a partial dose of investigational treatment, analyzed according to treatment received.

All analyses were conducted using SAS software, version 9.4 (SAS Institute),

Conclusion

This study demonstrated that dupilumab as an add-on therapy significantly reduced oral glucocorticoid use in patients with oral glucocorticoid-dependent severe asthma, reduced severe asthma exacerbations by 59.3% and improved $FEV_1$ by 0.22 L in the overall population, with a 71% reduction in exacerbations and 0.32 L improvement in $FEV_1$ in "eosinophilic" patients with baseline blood eosinophils ≥300 cells/μL. Dupilumab treatment also improved asthma control and reduced FeNO levels, a marker of airway Type 2 inflammation.

Add-on dupilumab 300 mg every 2 weeks (q2w) (vs. placebo) significantly reduced oral corticosteroid (OCS) use at week 24 (least squares [LS] mean 70.1% vs. 41.9%, median 100% vs. 50%), while simultaneously reducing the severe asthma exacerbation rate during the 24-week treatment period (59%) and improving the forced expiratory volume in 1 second (FEV1) at week 24 (LS mean difference 0.22 L), and was generally well tolerated in patients with OCS-dependent, severe asthma.

Dupilumab is the first biologic to show positive efficacy based on multiple asthma outcome measures in the overall study population irrespective of baseline blood eosinophil count (i.e. ≥300, <300, ≥150 and <150 cells/μL). Indeed, 28.6% of the patients enrolled had baseline blood eosinophils of <150 cells/μL. In this subgroup, 75% of dupilumab-treated patients reduced their oral glucocorticoid doses by 50% and 62% of patients reduced their oral glucocorticoid doses to <5 mg/day. These data are in contrast to previous studies with anti-interleukin-5 monoclonal antibodies including mepolizumab and benralizumab that showed a treatment effect exclusively in patients with high baseline blood eosinophils.

In this study, placebo-treated patients also showed a 41.9% reduction in oral glucocorticoid-dependence. Better adherence to drug regimens in a clinical study setting may have contributed to this observation. However, towards the end of the study, these placebo-treated patients demonstrated mild deterioration of lung function ($FEV_1$), further highlighting the need for a treatment that improves lung function in patients with oral glucocorticoid-dependent severe asthma. The ability of dupilumab to increase lung function as markedly as it did in this study, even in the face of glucocorticoid withdrawal, indicates that it appears to be inhibiting key drivers of lung inflammation that lead to reduced lung function.

Dupilumab reduced FeNO levels in the setting of significant withdrawal of oral glucocorticoid in a study population with persistent Type 2 inflammation (determined by elevated FeNO) in spite of chronic glucocorticoid use.

Dupilumab reduced the oral glucocorticoid dose by an observed mean of 74% (observed median of 100%) in a broader population without requiring a minimum baseline blood eosinophils count. Without intending to be bound by scientific theory, these findings indicate that dupilumab, with its dual blockade of the interleukin-4 and interleukin-13 signaling pathways by way of interleukin-4 receptor-alpha blockade, inhibits Type 2 inflammation more broadly than targeting eosinophils alone. While interleukin-4 is central to the differentiation and proliferation of T-helper 2 cells, inducing cytokine production and IgE synthesis, interleukin-13 plays a pivotal role in pathological features of the disease such as goblet cell huperplasia, mucus production, smooth muscle contractility, and airway hyper-responsiveness.

In patients with glucocorticoid-dependent severe asthma, dupilumab was generally well tolerated, with a safety profile consistent with previous studies in asthma and other indications, such as eosinophilic esophagitis, nasal polyposis, and atopic dermatitis. Dupilumab-treated patients showed a greater mean transient increase from baseline in blood eosinophil counts compared with placebo, with increased proportion of patients (12.6%) with eosinophil counts >3,000 cells/μL. Patients with transient elevations in blood eosinophils did not have concomitant clinical AEs or consequences. The increase in blood eosinophil counts is consistent with the hypothesis that dupilumab blocks interleukin-4 and interleukin-13 function in eosinophil survival, activation and recruitment to tissues, but not regress from bone marrow, resulting in transient increase in circulating eosinophil counts. Since glucocorticoids suppress circulating eosinophils, the greater reduction in oral glucocorticoids in the dupilumab group could also be contributing to the eosinophil elevations. No treatment-related conjunctivitis AEs were observed between dupilumab and placebo groups, in contrast to dupilumab atopic dermatitis studies.

In conclusion, add-on therapy with dupilumab significantly reduced the need for oral glucocorticoids, while simultaneously reducing severe exacerbations and improving lung function ($FEV_1$) in glucocorticoid-dependent severe asthma patients regardless of baseline blood eosinophil counts, and was generally well tolerated.

Example 2. QUEST Phase III Trial Study (NCT02414854)

Methods

Asthma patients, ≥12 years with moderate-to-severe asthma, uncontrolled with ICS and one or two controllers, were randomized 2:1 to add-on subcutaneous dupilumab 200 or 300 mg every 2 weeks (q2w), or matched placebos, for 52 weeks in a double-blind, placebo-controlled phase 3 study (NCT02414854). Primary endpoints were annualized rate of severe asthma exacerbations and absolute change from baseline to week 12 in pre-bronchodilator forced expiratory volume in 1 second ($FEV_1$) in the overall study population. Secondary endpoints included exacerbations and $FEV_1$ in patients with ≥300 eosinophils/μL. Asthma control and dupilumab safety were also assessed. Co-primary endpoints were annualized severe exacerbation rate over 52 weeks, and change from baseline to week 12 in $FEV_1$ (L).

Figure 7:
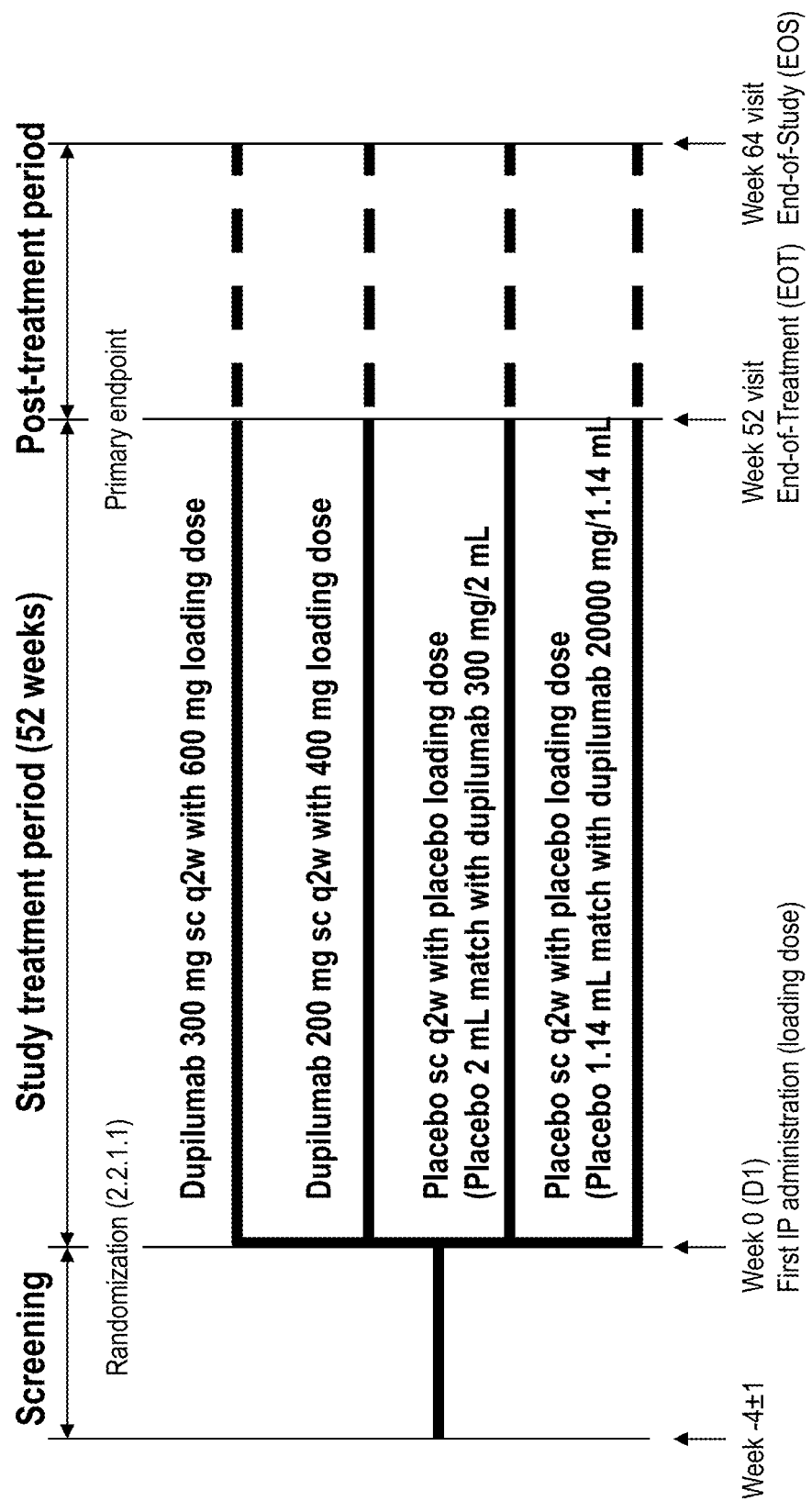
FIG. 7 depicts the Quest study design for the phase 3 trial.

The specific details of the study are described below. This randomized, double-blind, placebo-controlled, parallel-group trial assessed the efficacy of dupilumab in patients with uncontrolled moderate-to-severe asthma. Patients completed a 4±1-week screening period, followed by randomization to dupilumab and matched-volume placebo, a 52-week randomized treatment period, and a 12-week post-treatment follow-up period (see FIG. 7).

Patients

Figure 8:
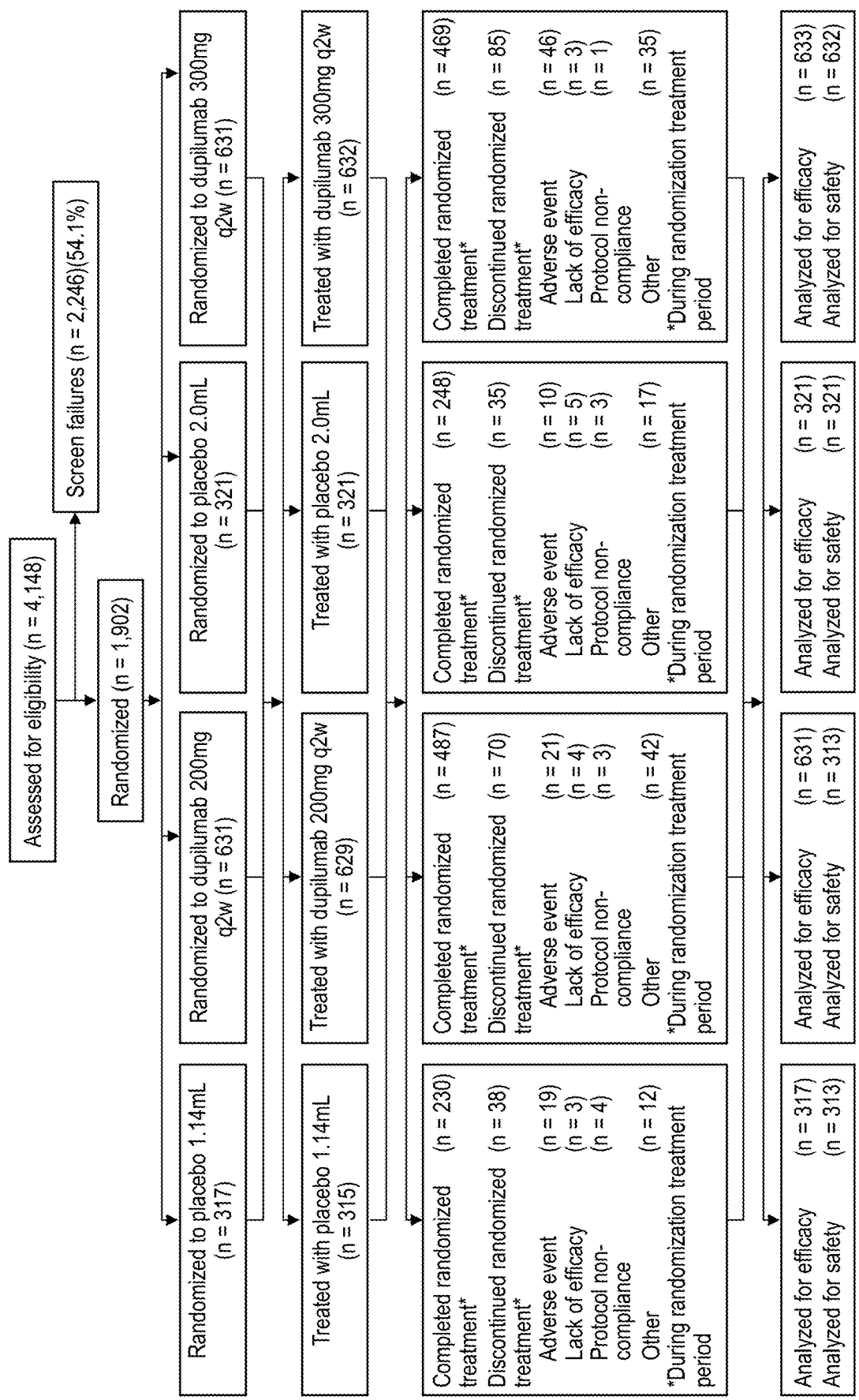
FIG. 8 is the patient disposition for the Quest study.

Patients aged ≥12 years with physician-diagnosed persistent asthma for ≥12 months, based on the Global Initiative for Asthma 2014 Guidelines were eligible to participate, meeting the following key criteria: current treatment with medium-to-high dose inhaled glucocorticoid (fluticasone propionate >500 µg total daily dose or equipotent equivalent) plus up to two additional controllers (e.g., long-acting $\beta_2$ agonist or leukotriene receptor antagonist); pre-bronchodilator (BD) forced expiratory volume in 1 second ($FEV_1$) ≤80% predicted normal ('90% for those aged 12 to 17 years); $FEV_1$ reversibility ≥12% and 200 ml; 5-item asthma control questionnaire (ACQ-5) score ≥1.5; a worsening of asthma in the previous year that required hospitalization, emergency medical care, or treatment with systemic glucocorticoids for ≥3 days. Patients were recruited irrespective of baseline blood eosinophil count or Type 2 biomarkers. (See FIG. 8.)

Treatment and Procedures

Patients were randomized (2:2:1:1) to receive 52 weeks of add-on therapy with subcutaneous dupilumab 200 mg (loading dose 400 mg) or 300 mg (loading dose 600 mg) every 2 weeks (q2w) or a matched-volume placebo for each active dose (supplied in prefilled syringes, 1.14 ml for 200 mg dupilumab and 2.0 ml for 300 mg dupilumab). Randomization was conducted by interactive voice/web response technology and was stratified by age (<18 years, ≥18 years), peripheral blood eosinophil count (<300 cells/µL, ≥300 cells/µL) at screening, inhaled glucocorticoid dose level (medium/high), and country. Background asthma controller medicines were continued at a stable dose throughout the study and recorded daily by patients in an electronic diary. Use of inhaled glucocorticoids, long-acting $\beta_2$ agonists, long-acting muscarinic antagonists, anti-leukotrienes, and methylxanthines was permitted. Throughout the study, patients were permitted to use a short-acting $\beta_2$-adrenergic receptor agonist as necessary for symptom relief. Type 2 biomarkers were measured; the biomarkers included blood eosinophils, FeNO, serum IgE, periostin, TARC, and plasma eotaxin-3.

Endpoints

The primary efficacy endpoints were annualized rate of severe exacerbation events during the 52-week treatment period and absolute change from baseline in pre-BD $FEV_1$ at week 12, in the overall study population. These endpoints were also included as secondary study endpoints for those with blood eosinophil counts ≥300 eosinophils/µL. Additional secondary study endpoints are summarized in Table 8. A severe asthma exacerbation was defined as a deterioration of asthma requiring treatment for ≥3 days with systemic glucocorticoids or hospitalization or an emergency room visit requiring systemic glucocorticoids. Safety and tolerability were reported according to incidence of treatment-emergent adverse events (TEAEs) and serious TEAEs,

TABLE 8

Summary of study outcome measures per hierarchical testing procedure.

| Outcome Measure | Time Frame |
| --- | --- |
| Primary Efficacy Endpoints | |
| Annualized rate of severe asthma exacerbations | 52 weeks |
| Absolute change from baseline in pre-bronchodilator $FEV_1$ | Week 12 |
| Secondary Efficacy Endpoints | |
| Percentage change from baseline in pre-bronchodilator $FEV_1$ | Week 12 |
| Annualized rate of severe asthma exacerbations in patients with ≥150 eosinophils/µl | 52 weeks |
| Absolute change from baseline in pre-bronchodilator $FEV_1$ in pts with ≥150 eosinophils/µl | Week 12 |
| Annualized rate of severe asthma exacerbations in patients with ≥300 eosinophils/µl | 52 weeks |
| Absolute change from baseline in pre-bronchodilator $FEV_1$ in patients with ≥300 eosinophils/µl | Week 12 |
| Annualized rate of severe asthma exacerbations in patients with <300 eosinophils/µl | 52 weeks |
| Annualized rate of severe asthma exacerbations in patients on high-dose inhaled glucocorticoids | 52 weeks |
| Absolute change from baseline in pre-bronchodilator $FEV_1$ in patients on high-dose inhaled glucocorticoids/long-acting $\beta_2$ agonists | Week 12 |
| Change from baseline in AQLQ [S] global score | Week 24 |
| Change from baseline in AQLQ [S] global score in patients with ≥300 eosinophils/µl | Week 24 |
| Change from baseline in ACQ-5 score | Week 24 |
| Annualized rate of severe asthma exacerbations resulting in hospitalization or emergency room visit | 52 weeks |
| Absolute change from baseline in pre-bronchodilator $FEV_1$ in patients with <300 eosinophils/µl | Week 12 |

ACQ-5 denotes Asthma Control Questionnaire 5-item version, and AQLQ (S) asthma quality of life questionnaire (standardized version).

Statistical Analysis

It was estimated that a sample size of approximately 1638 patients would give the study 99% power (2-tailed test at $\alpha=0.05$) to detect a 55% relative risk reduction (i.e., annualized rate of 0.6 and 0.27 for placebo and dupilumab groups, respectively) in the annualized rate of severe exacerbations. This sample size was also expected to provide 98% power to detect a 0.15 L treatment difference in pre-BD FEV$_1$ change from baseline to week 12. Efficacy analyses were performed on the intent-to-treat (ITT) population, defined as all randomized patients by allocated treatment whether or not treatment was received. The annualized rate of severe exacerbations was analyzed using a negative binomial regression model, including the four treatment groups, age, region, baseline eosinophil strata, baseline inhaled glucocorticoid dose level, and 1-year prior exacerbations were included as covariates. Change from baseline in continuous endpoints such as FEV$_1$ and patient-reported outcomes were analyzed using a mixed-effects model with repeated measures (MMRM), including treatment, age, baseline eosinophil strata, baseline inhaled glucocorticoid dose level, visit, treatment-by-visit interaction, baseline value, and baseline-by-visit interaction as covariates. Sex and baseline height were included as covariates only in the models for spirometry parameters.

Results

Figure 9A:
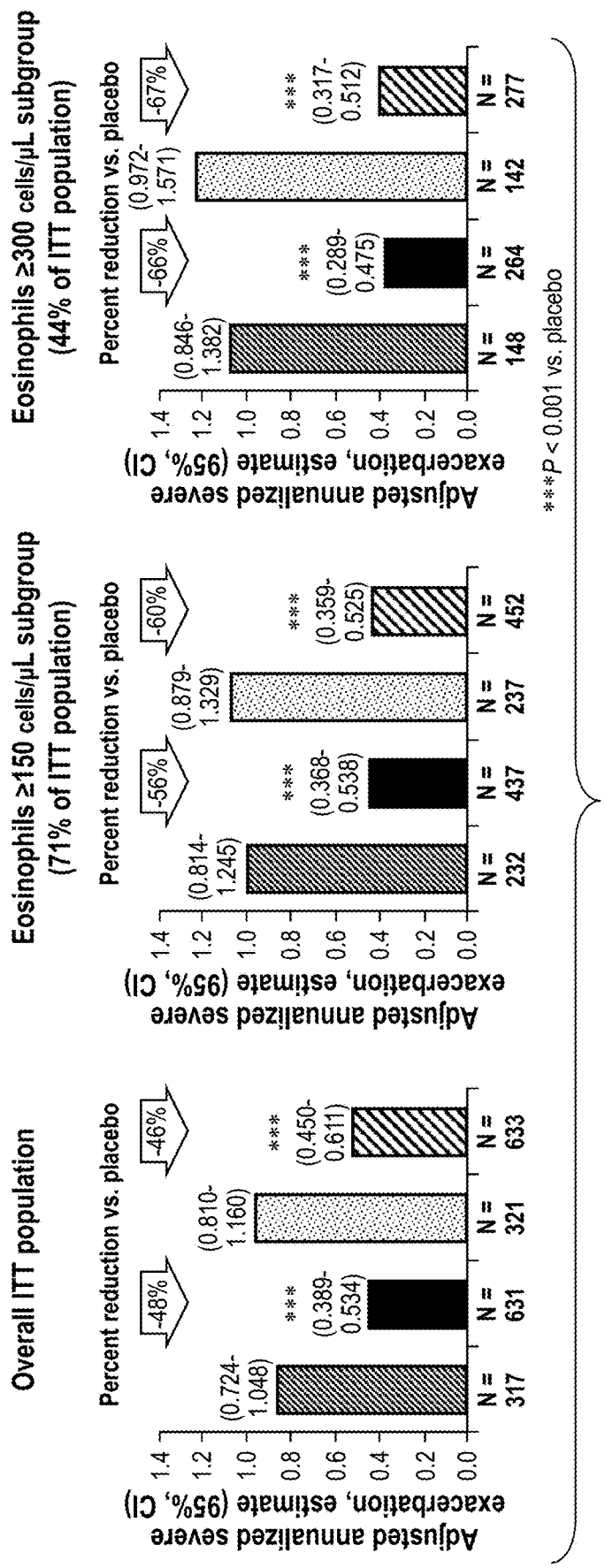
FIG. 9A FIG. 9B graphically depict severe asthma exacerbations in the ITT population and in subgroups defined by baseline blood eosinophils ≥150 and ≥300 cells/µl (FIG. 9A) and subgroups defined by baseline FeNO Levels <25 ppb, ≥25 to 50 ppb and ≥50 ppb (FIG. B).

Baseline demographics and clinical characteristics of the ITT population are shown in Table 4 and were generally similar across the four treatment groups (Table 10). In 1,902 patients, dupilumab 200/300 mg q2w as compared to placebo reduced annualized severe exacerbation rates during the 52-week treatment period by 48%/46%, (both P<0.0001) (FIG. 9A). Improved FEV$_1$ was observed at week 12 (LS mean difference vs placebo 0.14 L/0.13 L; both P<0.0001) in the overall population.

Figure 9B:
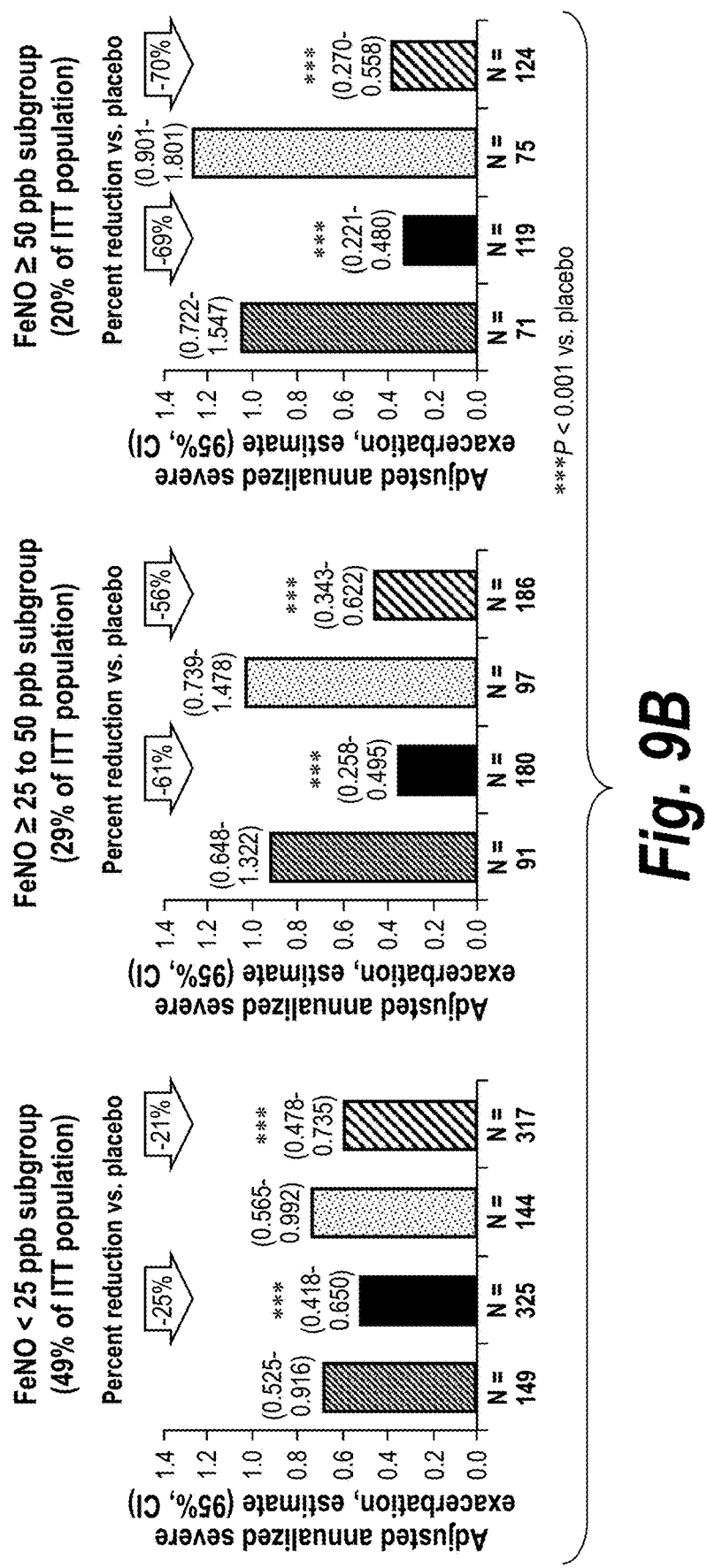

Pre-specified subgroup analyses by baseline blood eosinophil count showed significant reductions in exacerbation rates (P<0.001) with dupilumab 200 and 300 mg compared with matched-volume placebo in patients with ≥300 eosinophils/μL (65.8% and 67.4% reduction vs. placebo), and patients with ≥150 eosinophils/μL (55.8% and 59.8% reduction vs. placebo). There were consistent trends but a lack of signit significance in exacerbations and FEV$_1$ outcomes in patients with <300 eosinophils/μL. Pre-specified subgroup analyses by baseline FeNO levels showed similar effect (P<0.001). (See FIG. 9B and Table 9)

TABLE 9

Summary of primary efficacy and secondary endpoints.

| | Randomized treatment group to overall population | | | |
|---|---|---|---|---|
| | Placebo (N = 317) | Dupilumab 200 mg q2w (N = 631) | Placebo (N = 321) | Dupilumab 300 mg q2w (N = 633) |
| Adjusted annualized rate of severe asthma exacerbations | | | | |
| Estimate (95% CI) | 0.871 (0.724 to 1.048) | 0.456 (0.389 to 0.534) | 0.970 (0.810 to 1.160) | 0.524 (0.450 to 0.611) |
| Relative risk versus matching placebo† (95% CI) | - | 0.523 (0.413 to 0.662) | - | 0.540 (0.430 to 0.680) |
| P value versus matching placebo† | | <0.001 | | <0.001 |
| Mean baseline (SD) pre-bronchodilator FEV$_1$ - L | 1.76 (0.61) | 1.78 (0.62) | 1.75 (0.57) | 1.78 (0.60) |
| Change from baseline in FEV$_1$ at Week 12 | | | | |
| LS mean (SE) change - L | 0.18 (0.02) | 0.32 (0.02) | 0.21 (0.02) | 0.34 (0.02) |
| LS mean difference versus matching placebo (95% CI)‡ | - | 0.14 (0.08 to 0.19) | - | 0.13 (0.08 to 0.18) |
| P value versus matching placebo‡ | | <0.001 | | <0.001 |
| Percent change from baseline in FEV$_1$ at Week 12 | | | | |
| LS mean (SE) | 12.11 (1.56) | 21.34 (1.13) | 13.67 (1.56) | 23.08 (1.13) |
| LS mean difference versus matching placebo (95% CI)‡ | - | 9.23 (5.54 to 12.92) | - | 9.41 (5.74 to 13.07) |
| P value versus matching placebo‡ | | <0.001 | | <0.001 |
| Adjusted annualized rate of severe asthma exacerbations in patients with ≥300 eosinophils/μl | N = 148 | N = 264 | N = 142 | N = 277 |
| Estimate (95% CI) | 1.081 (0.846 to 1.382) | 0.370 (0.289 to 0.475) | 1.236 (0.972 to 1.571) | 0.403 (0.317 to 0.512) |
| Relative risk versus matching placebo† (95% CI) | - | 0.342 (0.244 to 0.480) | - | 0.326 (0.234 to 0.454) |
| P value versus matching placebo† | | <0.001 | | <0.001 |
| Change from baseline in FEV$_1$ in patients with ≥300 eosinophils/μl at Week 12 | N = 144 | N = 256 | N = 139 | N = 266 |
| LS mean (SE) change | 0.21 (0.03) | 0.43 (0.03) | 0.22 (0.03) | 0.47 (0.02) |
| LS mean difference versus matching placebo (95% CI)‡ | - | 0.21 (0.13 to 0.29) | - | 0.24 (0.16 to 0.32) |
| P value versus matching placebo‡ | | <0.001 | | <0.001 |
| Adjusted annualized rate of severe asthma exacerbations in patients with ≥150 eosinophils/μl | N = 232 | N = 437 | N = 237 | N = 452 |
| Estimate (95% CI) | 1.007 (0.814 to 1.245) | 0.445 (0.368 to 0.538) | 1.081 (0.879 to 1.329) | 0.434 (0.359 to 0.525) |
| Relative risk versus matching placebo† | - | 0.442 (0.337 to 0.581) | - | 0.402 (0.307 to 0.526) |
| P value versus matching placebo† | | <0.001 | | <0.001 |
| Change from baseline in FEV$_1$ in patients with ≥150 eosinophils/μl at Week 12 | N = 224 | N = 425 | N = 229 | N = 434 |
| LS mean (SE) change | 0.18 (0.03) | 0.36 (0.02) | 0.22 (0.03) | 0.37 (0.02) |
| LS mean difference versus matching placebo (95% CI)‡ | - | 0.17 (0.11 to 0.23) | - | 0.15 (0.09 to 0.21) |
| P value versus matching placebo‡ | | <0.001 | | <0.001 |

Figure 10A:
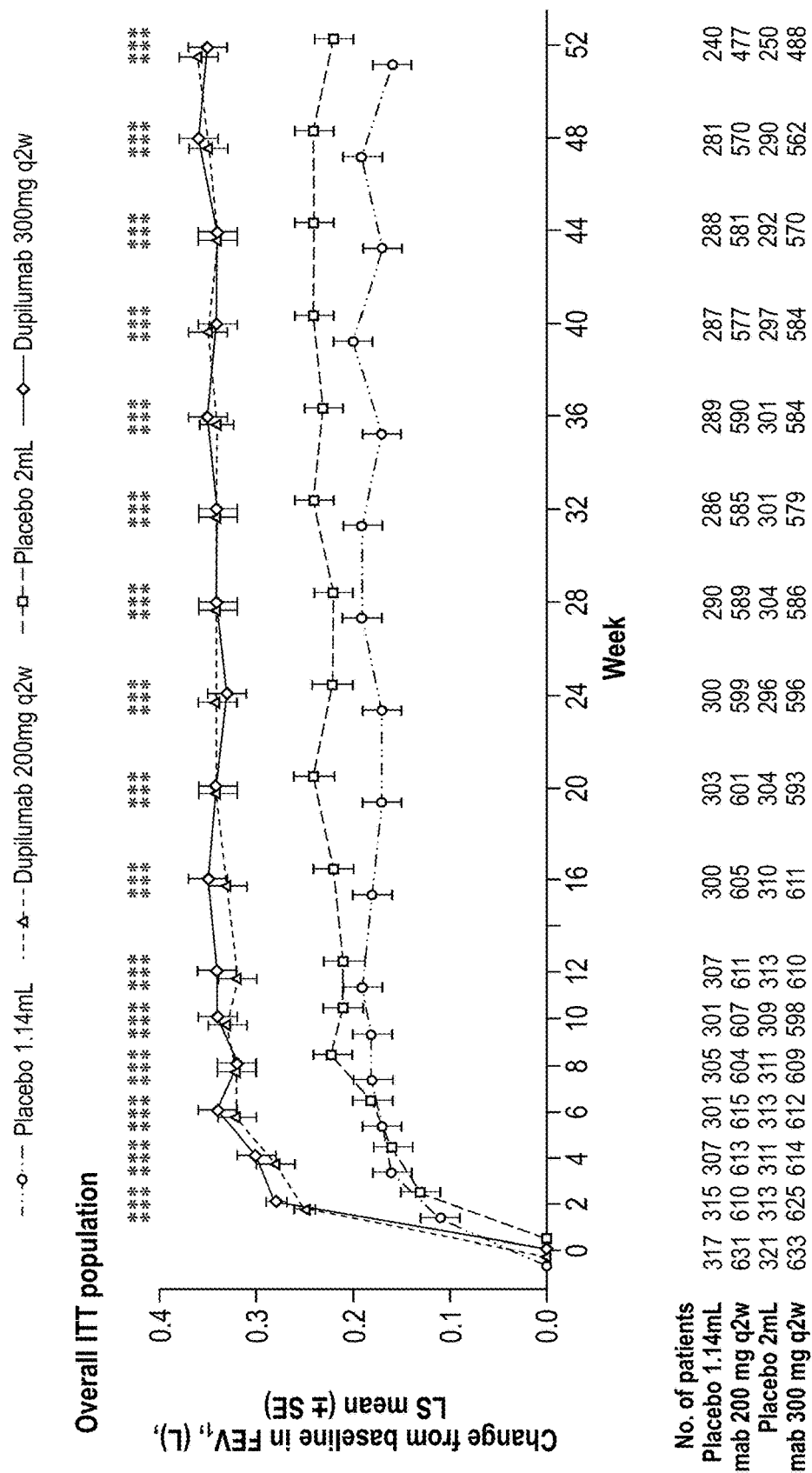

In the overall study population, dupilumab 200 and 300 mg q2w improved pre-BD $FEV_1$ at week 12 by 0.32 L and 0.34 L, respectively (0.14 and 0.13 L difference vs, matched-placebos, P<0.001) (FIG. 10A). In patients with ≥300 eosinophils/µL the FEV improvements were larger, with dupilumab improving $FEV_1$ at week 12 by 0.43 L and 0.47 L, respectively (0.21 to 0.24 L difference as compared to matched-placebos, P<0.001). (See FIG. 10B.) Improvement in $FEV_1$ was rapid (with significant differences as compared to placebo evident by the first evaluation at week 2 for both regimens) and was sustained throughout the 52-week treatment period (P<0.001 for both regimens at week 52). In addition, a post-bronchodilator $FEV_1$ slope analysis between weeks 8 and 52 showed a loss of lung function on placebo of 0.04 L/year, with no loss on either dupilumab dose (P<0.05).

$FEV_1$ improvements at week 12 (P<0.05) with both dose regimens were greater in subgroup of patients with higher baseline FeNO levels (0.19 and 0.12 L for FeNO≥25 to 50; 0.30 and 0.39 L for FeNO≥50 ppb). (See FIG. 10C and Table 8.)

In addition, dupilumab 200 and 300 mg significantly improved percentage change from baseline to week 12 in pre-bronchodilator $FEV_1$ versus placebo: 21.34% versus 12.11% and 23.08% versus 13.67%, respectively (P<0.001). The rate of severe exacerbation events resulting in hospitalization or emergency room visit during the 52-week treatment period was 0.035 versus 0.065 (P=0.004), comparing combined dupilumab-treated with combined placebo-treated patients. This produced a relative risk reduction for dupilumab versus placebo of 46.8%. (See Table 9.)

Dupilumab significantly improved ACQ-5 as early as week 2 and the effect was sustained over the course of treatment (P<0.01). Likewise, Asthma Quality of Life Questionnaire, Standardized Version score, AM and PM asthma symptom scores, and AM and PM peak expiratory flow were improved at week 24 and week 52. (See Table 9.)

Patients treated with dupilumab showed greater reduction from baseline over the course of treatment in FeNO, total IgE, periostin, eotaxin-3, and TARC versus placebo (Table 13). Transient elevations in blood eosinophil counts were observed in both treatment groups that decreased to close to baseline levels by week 52.

In order to better understand the effect of dupilumab on patients with evidence of type 2 inflammation, analyses were conducted to evaluate biomarker efficacy relationships. Each biomarker was tested in an un-penalized spline model for biomarker-by treatment interactions with respect to exacerbations and $FEV_1$. In these analyses, the interactions for eosinophils and FeNO were significant (P<0.05) when exacerbations were the outcome measure, while eosinophils, FeNO, periostin, ECP, IgE, and eotaxin-3 were significant for $FEV_1$ at week 12 (Table 11). Dupilumab effect on exacerbations was similar for IgE levels above and below the median value at baseline (167 IU/mL), and greater for $FEV_1$ improvement for IgE levels above the median.

Dupilumab-treated patients with baseline blood eosinophils ≥150 cells/µL and FeNO≥25 ppb (Type 2-high) experienced greater treatment benefit versus placebo for both severe exacerbation rate reduction and $FEV_1$ improvement. (See FIG. 11A and FIG. 11B.) No treatment effect was observed in patients with baseline eosinophils <150 cells/µL and FeNO<25 ppb (Type 2-low). However, dupilutnab-treated patients with either baseline blood eosinophils <150 cells/µL and FeNO≥25 ppb or ≥150 cells/µL and FeNO 25 ppb experienced numerical reduction in severe exacerbation rates.

The most frequent adverse event in the dupilumab-treated groups vs placebo was injection site reactions (15%/18% vs 5%/10%, respectively). In contrast to dupilumab studies in atopic dermatitis, conjunctivitis rates were similar between dupilumab and placebo.

TABLE 10

Baseline Demographic and Clinical Characteristics (ITT Population).

|  | Placebo N = 317 | Dupilumab 200 mg q2w N = 631 | Placebo N = 321 | Dupilumab 300 mg q2w N = 633 | Overall Population N = 1902 |
|---|---|---|---|---|---|
| Mean (SD) age - yr | 48.2 (15.6) | 47.9 (15.3) | 48.2 (14.7) | 47.7 (15.6) | 47.9 (15.3) |
| <18 yr - no. of patients (%) | 21 (6.6) | 34 (5.4) | 18 (5.6) | 34 (5.4) | 107 (5.6) |
| Female sex - no. of patients (%) | 198 (62.5) | 387 (61.3) | 218 (67.9) | 394 (62.2) | 1197 (62.9) |
| Mean (SD) BMI - kg/m² | 29.76 (7.25) | 29.05 (6.52) | 29.21 (6.95) | 29.07 (6.68) | 29.20 (6.77) |
| Mean (SD) pre-bronchodilator $FEV_1$ - L | 1.76 (0.61) | 1.78 (0.62) | 1.75 (0.57) | 1.78 (0.60) | 1.78 (0.60) |
| Mean (SD) pre-bronchodilator $FEV_1$ - % predicted | 58.43 (13.22) | 58.38 (13.52) | 58.35 (13.87) | 58.51 (13.52) | 58.43 (13.52) |
| Mean (SD) $FEV_1$ reversibility - % | 25.06 (18.76) | 27.39 (22.79) | 26.45 (17.65) | 25.73 (23.79) | 26.29 (21.73) |
| Mean (SD) exacerbations in past year - no. | 2.07 (1.58) | 2.07 (2.66) | 2.31 (2.07) | 2.02 (1.86) | 2.09 (2.15) |
| High-dose inhaled glucocorticoid/LABA use - no. of patients (%) | 172 (54.3) | 317 (50.2) | 167 (52.0) | 323 (51.0) | 979 (51.5) |
| Mean (SD) ACQ-5† score | 2.71 (0.73) | 2.76 (0.80) | 2.77 (0.77) | 2.77 (0.76) | 2.76 (0.77) |
| Mean (SD) AQLQ‡ global score | 4.26 (1.02) | 4.31 (1.08) | 4.30 (1.03) | 4.28 (1.05) | 4.29 (1.05) |
| Mean (SD) AM asthma symptom score§ | 1.16 (0.81) | 1.14 (0.85) | 1.12 (0.84) | 1.12 (0.87) | 1.14 (0.85) |
| Mean (SD) PM asthma symptom score§ | 1.27 (0.82) | 1.26 (0.85) | 1.23 (0.82) | 1.27 (0.84) | 1.26 (0.84) |
| Atopic/allergic ongoing condition - no. of patients (%) | 266 (83.9) | 509 (80.7) | 266 (82.9) | 524 (82.8) | 1565 (82.3) |
| Atopic dermatitis | 35 (11.0) | 61 (9.7) | 38 (11.8) | 62 (9.8) | 196 (10.3) |
| Allergic rhinitis | 221 (69.7) | 421 (66.7) | 225 (70.1) | 438 (69.2) | 1305 (68.6) |
| Nasal polyposis and/or chronic rhinosinusitis | 63 (19.9) | 126 (20.0) | 70 (21.8) | 123 (19.4) | 382 (20.1) |

TABLE 10-continued

Baseline Demographic and Clinical Characteristics (ITT Population).

| | Placebo N = 317 | Dupilumab 200 mg q2w N = 631 | Placebo N = 321 | Dupilumab 300 mg q2w N = 633 | Overall Population N = 1902 |
|---|---|---|---|---|---|
| Former smoker - no. of patients (%) | 59 (18.6) | 126 (20.0) | 67 (20.9) | 116 (18.3) | 368 (19.3) |
| Mean (SD) pack-years - no. | 3.96 (2.81) | 3.89 (2.69) | 4.07 (3.12) | 4.15 (3.04) | 4.02 (2.89) |
| Biomarker levels | | | | | |
| Mean (SD) blood eosinophil count - cells/µl | 370 (338) | 349 (345) | 391 (419) | 351 (369) | 360 (366) |
| Median (min-max) blood eosinophil count - cells/µl | 270 (0-2200) | 250 (0-3610) | 265 (0-3580) | 250 (0-4330) | 255 (0-4330) |
| Mean (SD) FeNO - ppb | 34.47 (28.54) | 34.45 (34.91) | 38.39 (38.00) | 34.01 (29.74) | 34.97 (32.85) |
| Median (min-max) FeNO - ppb | 26.00 (3.0-197.0) | 23.00 (3.0-387.0) | 27.00 (5.0-351.0) | 24.00 (4.0-202.0) | 25.00 (3.0-387.0) |
| Mean (SD) total IgE - IU/ml | 393.90 (624.70) | 460.96 (817.75) | 448.47 (796.66) | 415.08 (701.40) | 432.40 (746.66) |
| Median (min-max) total IgE - IU/ml | 174.50 (1.0-5000.0) | 154.00 (1.0-5000.0) | 178.50 (3.0-5000.0) | 174.00 (1.0-5000.0) | 167.00 (1.0-5000.0) |
| Mean (SD) TARC - pg/ml | 377.88 (288.22) | 394.12 (457.89) | 398.00 (344.16) | 364.35 (295.58) | 382.22 (364.25) |
| Median (min-max) TARC - pg/ml | 296.00 (33.1 to 1970.0) | 314.50 (15.6 to 8600.0) | 300.00 (34.0 to 3210.0) | 295.00 (15.6 to 3170.0) | 302.00 (15.6 to 8600.0) |
| Mean (SD) periostin - ng/ml | 79.62 (36.58) | 79.88 (39.18) | 80.94 (40.73) | 78.49 (37.90) | 79.55 (38.58) |
| Median (min-max) periostin - ng/ml | 71.70 (27.8 to 244.9) | 70.60 (20.5 to 368.2) | 71.00 (25.1 to 312.8) | 69.70 (19.2 to 298.5) | 70.60 (19.2 to 368.2) |
| Mean (SD) eotaxin-3 - pg/ml | 52.11 (86.35) | 78.30 (340.04) | 50.89 (57.85) | 69.53 (481.53) | 66.36 (342.53) |
| Median (min-max) eotaxin-3 - pg/ml | 36.50 (2.0 to 1180.0) | 39.15 (2.0 to 6430.0) | 37.45 (2.0 to 723.0) | 38.30 (2.0 to 12000.0) | 38.20 (2.0 to 12000.0) |

ACQ-5 denotes 5-item Asthma Control Questionnaire,
AQLQ (S) Asthma Quality of Life Questionnaire (Standardized Version),
BMI body mass index,
FeNO fractional exhaled nitric oxide,
$FEV_1$ forced expiratory volume in 1 second,
LABA long-acting $\beta_2$-agonist, min to max minimum to maximum,
ppb parts per billion,
q2w every 2 weeks,
q4w every 4 weeks,
SD standard deviation, and
TARC thymus and activation-regulated chemokine.

[†]ACQ-5 is a patient-reported measure of the adequacy of asthma control and change in asthma control that occurs either spontaneously or as a result of treatment. Higher scores indicate less control; a global score ranging from 0 to 6 is calculated.

[‡]AQLQ (S) is a patient-reported measure of the impact of asthma on quality of life. Higher scores indicate better quality of life; a global score ranging from 1 to 7 is calculated.

[§]Asthma symptom scores are patient-reported measures, taken upon waking and in the evening, of asthma symptoms and their effects on activities (PM) and sleep (AM). Higher scores indicate greater disruption; symptoms are scored on a range from 0 to 4.

TABLE 11

Subgroup Analyses of Primary Endpoints by Baseline Blood Eosinophil Count and FeNO Levels

| | Randomized treatment group - ITT population | | | |
|---|---|---|---|---|
| Subgroup/Endpoint | Placebo (N = 317) | Dupilumab 200 mg q2w (N = 631) | Placebo (N = 321) | Dupilumab 300 mg q2w (N = 633) |
| Baseline EOS ≥300 cells/µl | | | | |
| Annualized rate of severe exacerbations at Week 52 | N = 148 | N = 264 | N = 142 | N = 277 |
| Estimate (95% CI) | 1.081 (0.846 to 1.382) | 0.370 (0.289 to 0.475) | 1.236 (0.972 to 1.571) | 0.403 (0.317 to 0.512) |
| Relative risk versus matching placebo[†] | — | 0.342 (0.244 to 0.480) | — | 0.326 (0.234 to 0.454) |
| P value versus matching placebo[†] | | <0.001 | | <0.001 |
| Change from baseline in $FEV_1$ (l) at Week 12 | N = 144 | N = 256 | N = 139 | N = 266 |
| LS mean (SE) change | 0.21 (0.03) | 0.43 (0.03) | 0.22 (0.03) | 0.47 (0.02) |
| LS mean difference versus matching placebo (95% CI)[‡] | — | 0.21 (0.13 to 0.29) | — | 0.24 (0.16 to 0.32) |
| P value versus matching placebo[‡] | | <0.001 | | <0.001 |
| Baseline EOS ≥150 cells/µl | | | | |
| Annualized rate of severe exacerbations at Week 52 | N = 232 | N = 437 | N = 237 | N = 452 |
| Estimate (95% CI) | 1.007 (0.814 to 1.245) | 0.445 (0.368 to 0.538) | 1.081 (0.879 to 1.329) | 0.434 (0.359 to 0.525) |
| Relative risk versus matching placebo[†] | — | 0.442 (0.337 to 0.581) | — | 0.402 (0.307 to 0.526) |
| P value versus matching placebo[†] | | <0.001 | | <0.001 |
| Change from baseline in $FEV_1$ (l) at Week 12 | N = 224 | N = 425 | N = 229 | N = 434 |

TABLE 11-continued

Subgroup Analyses of Primary Endpoints by Baseline Blood Eosinophil Count and FeNO Levels

| | Randomized treatment group - ITT population | | | |
|---|---|---|---|---|
| Subgroup/Endpoint | Placebo (N = 317) | Dupilumab 200 mg q2w (N = 631) | Placebo (N = 321) | Dupilumab 300 mg q2w (N = 633) |
| LS mean (SE) change | 0.18 (0.03) | 0.36 (0.02) | 0.22 (0.03) | 0.37 (0.02) |
| LS mean difference versus matching placebo (95% CI)‡ | — | 0.17 (0.11 to 0.23) | — | 0.15 (0.09 to 0.21) |
| P value versus matching placebo‡ | | <0.001 | | <0.001 |
| Baseline EOS <300 cells/μl | | | | |
| Annualized rate of severe exacerbations at Week 52† | N = 169 | N = 366 | N = 178 | N = 356 |
| Estimate (95% CI) | 0.675 (0.515 to 0.884) | 0.512 (0.418 to 0.628) | 0.732 (0.562 to 0.954) | 0.610 (0.502 to 0.742) |
| Relative risk versus matching placebo† | — | 0.759 (0.548 to 1.052) | — | 0.834 (0.608 to 1.144) |
| P value versus matching placebo† | | 0.10 | | 0.26 |
| Change from baseline in $FEV_1$ (l) at Week 12‡ | N = 163 | N = 354 | N = 173 | N = 344 |
| LS mean (SE) change | 0.15 (0.03) | 0.23 (0.02) | 0.18 (0.03) | 0.22 (0.02) |
| LS mean difference versus matching placebo (95% CI)‡ | — | 0.08 (0.01 to 0.15) | — | 0.04 (−0.03 to 0.11) |
| P value versus matching placebo‡ | | 0.02 | | 0.25 |
| Baseline EOS <150 cells/μl | | | | |
| Annualized rate of severe exacerbations at Week 52† | N = 85 | N = 193 | N = 83 | N = 181 |
| Estimate (95% CI) | 0.511 (0.346 to 0.755) | 0.472 (0.358 to 0.623) | 0.642 (0.445 to 0.927) | 0.737 (0.575 to 0.946) |
| Relative risk versus matching placebo† | — | 0.925 (0.580 to 1.474) | — | 1.149 (0.747 to 1.767) |
| P value versus matching placebo† | | 0.74 | | 0.53 |
| Change from baseline in $FEV_1$ (l) at Week 12‡ | N = 83 | N = 185 | N = 83 | N = 176 |
| LS mean (SE) change | 0.13 (0.04) | 0.19 (0.03) | 0.11 (0.04) | 0.20 (0.03) |
| LS mean difference versus matching placebo (95% CI)‡ | — | 0.06 (−0.04 to 0.15) | — | 0.09 (−0.01 to 0.18) |
| P value versus matching placebo‡ | | 0.26 | | 0.08 |
| Baseline FeNO ≥50 ppb | | | | |
| Annualized rate of severe exacerbations at Week 52 | N = 71 | N = 119 | N = 75 | N = 124 |
| Estimate (95% CI) | 1.057 (0.722 to 1.547) | 0.326 (0.221 to 0.480) | 1.274 (0.901 to 1.801) | 0.388 (0.270 to 0.558) |
| Relative risk versus matching placebo† | — | 0.308 (0.183 to 0.519) | — | 0.305 (0.188 to 0.494) |
| P value versus matching placebo† | | <0.001 | | <0.001 |
| Change from baseline in $FEV_1$ (l) at Week 12 | N = 69 | N = 114 | N = 73 | N = 113 |
| LS mean (SE) change | 0.23 (0.05) | 0.53 (0.04) | 0.19 (0.05) | 0.59 (0.04) |
| LS mean difference versus matching placebo (95% CI)‡ | — | 0.30 (0.17 to 0.44) | — | 0.39 (0.26 to 0.52) |
| P value versus matching placebo‡ | | <0.001 | | <0.001 |
| Baseline FeNO ≥25 to 50 ppb | | | | |
| Annualized rate of severe exacerbations at Week 52 | N = 91 | N = 180 | N = 97 | N = 186 |
| Estimate (95% CI) | 0.925 (0.648 to 1.322) | 0.358 (0.258 to 0.495) | 1.045 (0.739 to 1.478) | 0.462 (0.343 to 0.622) |
| Relative risk versus matching placebo† | — | 0.386 (0.243 to 0.616) | — | 0.442 (0.282 to 0.693) |
| P value versus matching placebo† | | <0.001 | | <0.001 |
| Change from baseline in $FEV_1$ (l) at Week 12 | N = 88 | N = 174 | N = 94 | N = 182 |
| LS mean (SE) change | 0.21 (0.04) | 0.39 (0.03) | 0.23 (0.04) | 0.35 (0.03) |
| LS mean difference versus matching placebo (95% CI)‡ | — | 0.19 (0.09 to 0.28) | — | 0.12 (0.03 to 0.21) |
| P value versus matching placebo‡ | | <0.001 | | 0.01 |
| Baseline FeNO <25 ppb | | | | |
| Annualized rate of severe exacerbations at Week 52 | N = 149 | N = 325 | N = 144 | N = 317 |
| Estimate (95% CI) | 0.693 (0.525 to 0.916) | 0.521 (0.418 to 0.650) | 0.748 (0.565 to 0.992) | 0.593 (0.478 to 0.735) |
| Relative risk versus matching placebo† | — | 0.752 (0.541 to 1.046) | — | 0.792 (0.572 to 1.098) |
| P value versus matching placebo† | | 0.09 | | 0.16 |
| Change from baseline in $FEV_1$ (l) at Week 12 | N = 144 | N = 316 | N = 141 | N = 309 |
| LS mean (SE) change | 0.15 (0.03) | 0.20 (0.02) | 0.20 (0.03) | 0.23 (0.02) |
| LS mean difference versus matching placebo (95% CI)‡ | — | 0.05 (−0.02 to 0.12) | — | 0.03 (−0.04 to 0.10) |
| P value versus matching placebo‡ | | 0.14 | | 0.39 |

*CI denotes confidence interval, EOS eosinophils, FeNO fractional exhaled nitric oxide, $FEV_1$ forced expiratory volume in 1 second, LS least square, NA not applicable, ppb parts per billion, q2w every 2 weeks, q4w every 4 weeks, and SE standard error.
†Derived using a negative binomial model with the total number of events starting from randomization up to Visit 18 or last contact date as the response variable; the four treatment groups, age, region (pooled country), baseline eosinophil strata, baseline ICS dose level, and number of severe exacerbations in the year prior to the study as covariates; and log-transformed standardized observation duration as an offset variable.
‡Week 12 changes from baseline were derived using an MMRM approach, with change from baseline in pre-bronchodilator $FEV_1$ values at Week 12 as the response variable, and treatment, age, sex, baseline height, region (pooled country), baseline eosinophil strata, baseline ICS dose level, visit, treatment-by-visit interaction, baseline pre-bronchodilator $FEV_1$ value, and baseline-by-visit interaction as covariates.

TABLE 12

Summary of Additional Secondary Endpoints.

| Endpoint | Randomized treatment group | | | |
|---|---|---|---|---|
| | Placebo (N = 317) | Dupilumab 200 mg q2w (N = 631) | Placebo (N = 321) | Dupilumab 300 mg q2w (N = 633) |
| *Change from baseline in AQLQ (S) global score at Week 24* | | | | |
| LS mean (SE) change | 0.94 (0.06) | 1.14 (0.04) | 1.00 (0.06) | 1.15 (0.04) |
| LS mean difference versus matching placebo (95% CI)† | — | 0.20 (0.06 to 0.34) | — | 0.15 (0.01 to 0.28) |
| P value versus matching placebo† | | 0.004 | | 0.03 |
| *Change from baseline in AQLQ (S) global score at Week 52* | | | | |
| LS mean (SE) change | 0.99 (0.06) | 1.28 (0.04) | 1.03 (0.06) | 1.29 (0.04) |
| LS mean difference versus matching placebo (95% CI)† | — | 0.29 (0.15, 0.44) | — | 0.26 (0.12, 0.40) |
| P value versus matching placebo† | | <0.001 | | <0.001 |
| *Change from baseline in AQLQ (S) global score at Week 24 in patients with ≥300 eosinophils/μL* | | | | |
| LS mean (SE) change | 0.96 (0.09) | 1.37 (0.06) | 0.98 (0.09) | 1.32 (0.06) |
| LS mean difference versus matching placebo (95% CI)† | — | 0.41 (0.20 to 0.62) | — | 0.34 (0.13 to 0.54) |
| P value versus matching placebo† | | <0.001 | | 0.001 |
| *Change from baseline in ACQ-5 score at Week 2* | | | | |
| LS mean (SE) change | −0.56 (0.05) | −0.89 (0.04) | −0.61 (0.05) | −0.92 (0.04) |
| LS mean difference versus matching placebo (95% CI)‡ | — | −0.34 (−0.46, −0.22) | — | −0.31 (−0.42, −0.19) |
| P value versus matching placebo‡ | | <0.001 | | <0.001 |
| *Change from baseline in ACQ-5 score at Week 24* | | | | |
| LS mean (SE) change | −1.10 (0.06) | −1.44 (0.04) | −1.21 (0.06) | −1.40 (0.04) |
| LS mean difference versus matching placebo (95% CI)‡ | — | −0.35 (−0.48 to −0.21) | — | −0.19 (−0.32 to −0.05) |
| P value versus matching placebo‡ | | <0.001 | | 0.007 |
| *Change from baseline in ACQ-5 score at Week 52* | | | | |
| LS mean (SE) change | −1.15 (0.06) | −1.54 (0.04) | −1.30 (0.06) | −1.52 (0.04) |
| LS mean difference versus matching placebo (95% CI)‡ | — | −0.39 (−0.53, −0.25) | — | −0.22 (−0.36, −0.08) |
| P value versus matching placebo‡ | | <0.001 | | 0.002 |
| *Change from baseline in AM symptom score at Week 24* | | | | |
| LS mean (SE) change | −0.33 (0.03) | −0.52 (0.02) | −0.37 (0.03) | −0.49 (0.02) |
| LS mean difference versus matching placebo (95% CI)§ | — | −0.19 (−0.27 to −0.11) | — | −0.12 (−0.20 to −0.04) |
| P value versus matching placebo§ | | <0.001 | | 0.004 |
| *Change from baseline in AM symptom score at Week 52* | | | | |
| LS mean (SE) change | −0.40 (0.04) | −0.55 (0.03) | −0.43 (0.04) | −0.58 (0.03) |
| LS mean difference versus matching placebo (95% CI)§ | — | −0.15 (−0.24 to −0.06) | — | −0.16 (−0.24 to −0.07) |
| P value versus matching placebo§ | | <0.001 | | <0.001 |
| *Change from baseline in PM symptom score at Week 24* | | | | |
| LS mean (SE) change | −0.33 (0.04) | −0.53 (0.03) | −0.36 (0.04) | −0.51 (0.03) |
| LS mean difference versus matching placebo (95% CI)§ | — | −0.20 (−0.28 to −0.11) | — | −0.15 (−0.24 to −0.06) |
| P value versus matching placebo§ | | <0.001 | | <0.001 |
| *Change from baseline in PM symptom score at Week 52* | | | | |
| LS mean (SE) change | −0.39 (0.04) | −0.57 (0.03) | −0.42 (0.04) | −0.57 (0.03) |
| LS mean difference versus matching placebo (95% CI)§ | — | −0.18 (−0.28 to −0.09) | — | −0.14 (−0.24 to −0.05) |
| P value versus matching placebo§ | | <0.001 | | 0.003 |
| *Change from baseline in AM PEF (L/min) at Week 24* | | | | |
| LS mean (SE) change | 6.15 (3.49) | 28.19 (2.51) | 15.61 (3.47) | 25.01 (2.50) |
| LS mean difference versus matching placebo (95% CI)¶ | — | 22.04 (13.70 to 30.38) | — | 9.40 (1.11 to 17.68) |
| P value versus matching placebo¶ | | <0.001 | | 0.03 |
| *Change from baseline in AM PEF (l/min) at Week 52* | | | | |
| LS mean (SE) change | 2.35 (3.94) | 28.97 (2.82) | 12.69 (3.91) | 26.00 (2.82) |
| LS mean difference versus matching placebo (95% CI)¶ | — | 26.62 (17.20 to 36.04) | — | 13.31 (3.94 to 22.67) |
| P value versus matching placebo¶ | | <0.001 | | 0.005 |

TABLE 12-continued

Summary of Additional Secondary Endpoints.

| Endpoint | Placebo (N = 317) | Dupilumab 200 mg q2w (N = 631) | Placebo (N = 321) | Dupilumab 300 mg q2w (N = 633) |
|---|---|---|---|---|
| Change from baseline in PM PEF (l/min) at Week 24 | | | | |
| LS mean (SE) change | −2.86 (3.52) | 19.62 (2.53) | 8.14 (3.51) | 16.53 (2.52) |
| LS mean difference versus matching placebo (95% CI)¶ | | 22.48 (14.08 to 30.89) | | 8.39 (0.03 to 16.74) |
| P value versus matching placebo¶ | | <0.001 | | 0.049 |
| Change from baseline in PM PEF (l/min) at Week 52 | | | | |
| LS mean (SE) change | −6.01 (3.96) | 17.50 (2.84) | 4.44 (3.95) | 15.34 (2.84) |
| LS mean difference versus matching placebo (95% CI)¶ | | 23.51 (14.04 to 32.99) | | 10.90 (1.47 to 20.32) |
| P value versus matching placebo¶ | | <0.001 | | 0.024 |

| | Placebo 1.14 ml and 2 ml q2w combined (N = 638) | Dupilumab 200 mg and 300 mg q2w combined (N = 1264) |
|---|---|---|
| Annualized rate of severe exacerbation events requiring hospitalization or ER visit | | |
| Estimate (95% CI) | 0.065 (0.047 to 0.090) | 0.035 (0.025 to 0.048) |
| Relative risk versus matching placebo# | | 0.532 (0.347 to 0.816) |
| P value versus matching placebo# | | 0.004 |

*ACQ-5 denotes the Asthma Control Questionnaire 5-item version, AQLQ Asthma Quality of Life Questionnaire, CI confidence interval, ER emergency room, LS least square, PEF peak expiratory flow, q2w every 2 weeks, q4w every 4 weeks, and SE standard error.
†Derived from MMRM model with change from baseline in AQLQ global score up to Week 24 or 52 as the response variable, and the four treatment groups, age, region (pooled country), baseline eosinophil strata, baseline ICS dose level, visit, treatment by-visit interaction, baseline AQLQ global score and baseline-by-visit interaction as covariates.
‡Derived from an MMRM model with change from baseline in ACQ-5 up to Week 24 or 52 as the response variable, and the four treatment groups, age, region (pooled country), baseline eosinophil strata, baseline ICS dose level, visit, treatment by-visit interaction, baseline ACQ-5, and baseline-by-visit interaction as covariates.
§Derived from MMRM model with change from baseline in AM/PM symptom score (periodical average) up to week 52 as the response variable, and treatment, age, region (pooled country), baseline eosinophil strata, baseline ICS dose level, visit, treatment-by-visit interaction, baseline AM/PM symptom score, and baseline-by-visit interaction as covariates.
¶Derived from MMRM model with change from baseline in AM/PM PEF values (periodical average) up to week 52 as the response variable, and treatment, age, sex, baseline height, region (pooled country), baseline eosinophil strata, baseline ICS dose level, visit, treatment-by-visit interaction, baseline AM/PM PEF value, and baseline-by-visit interaction as covariates.
Derived using a negative binomial model with the total number of events starting from randomization up to Visit 18 or last contact date as the response variable; the two pooled treatment groups, age, region (pooled country), baseline eosinophil strata, baseline ICS dose level, and number of severe exacerbations in the year prior to the study as covariates; and log-transformed standardized observation duration as an offset variable.

TABLE 13

Summary of Change from Baseline in Type 2 Biomarker Levels.

| | Placebo (N = 317) | Dupilumab 200 mg q2w (N = 631) | Placebo (N = 321) | Dupilumab 300 mg q2w (N = 633) |
|---|---|---|---|---|
| Fractional exhaled nitric oxide | | | | |
| Mean baseline (SD) - ppb | 34.5 (28.7) | 34.4 (34.9) | 38.4 (38.0) | 34.0 (29.8) |
| Median (min to max) baseline - ppb | 26.0 (3 to 197) | 23.0 (3 to 387) | 27.0 (5 to 351) | 24.0 (4 to 202) |
| Change from baseline to Week 12 | | | | |
| Mean change (SD) - ppb | −2.4 (21.1) | −15.1 (31.4) | −3.6 (29.6) | −15.8 (25.2) |
| Mean change (SD) - % | 8.641 (68.047) | −21.954 (49.522) | 5.794 (63.044) | −27.254 (46.861) |
| Median (min to max) change - ppb | −1.0 (−81 to 78) | −6.0 (−371 to 69) | −1.0 (−309 to 69) | −7.0 (−177 to 62) |
| Median (min to max) change - % | −6.782 (−83.93 to 500.00) | −29.289 (−95.87 to 360.00) | −5.814 (−91.96 to 450.00) | −34.615 (−93.16 to 266.67) |
| Change from baseline to Week 24 | | | | |
| Mean change (SD) - ppb | −2.9 (21.3) | −16.6 (32.8) | −4.6 (30.2) | −16.6 (25.9) |
| Mean change (SD) - % | 9.774 (70.868) | −24.710 (49.373) | 4.383 (72.603) | −28.165 (50.465) |
| Median (min to max) change - ppb | −1.0 (−96 to 122) | −7.0 (−373 to 42) | −2.0 (−306 to 96) | −8.0 (−171 to 29) |
| Median (min to max) change - % | −6.667 (−87.50 to 583.33) | −33.333 (−97.16 to 420.00) | −10.526 (−91.07 to 620.00) | −38.462 (−92.26 to 580.00) |
| Change from baseline to Week 52 | | | | |
| Mean change (SD) - ppb | −2.1 (20.7) | −16.5 (27.3) | −5.2 (36.0) | −16.5 (27.0) |
| Mean change (SD) - % | 5.494 (58.379) | −28.705 (47.319) | 1.561 (61.831) | −26.450 (57.383) |
| Median (min to max) change - ppb | −1.0 (−76 to 103) | −8.0 (−188 to 46) | −2.0 (−307 to 218) | −8.0 (−177 to 54) |
| Median (min to max) change - % | −5.882 (−82.35 to 381.48) | −37.931 (−96.41 to 383.33) | −10.000 (−91.37 to 380.00) | −37.500 (−93.44 to 600.00) |

TABLE 13-continued

Summary of Change from Baseline in Type 2 Biomarker Levels.

| | Randomized treatment group | | | |
|---|---|---|---|---|
| | Placebo (N = 317) | Dupilumab 200 mg q2w (N = 631) | Placebo (N = 321) | Dupilumab 300 mg q2w (N = 633) |
| | Total IgE (IU/ml) | | | |
| Mean baseline (SD) - IU/ml | 394.2 (626.2) | 460.6 (816.6) | 448.5 (796.7) | 415.0 (701.4) |
| Median (min to max) baseline - IU/ml | 174.5 (1 to 5000) | 154.0 (1 to 5000) | 178.5 (3 to 5000) | 174.0 (1 to 5000) |
| Change from baseline to Week 12 | | | | |
| Mean change (SD) - IU/ml | 11.6 (306.6) | −161.9 (327.3) | −4.5 (174.1) | −143.9 (304.3) |
| Mean change (SD) in IU/ml - % | 24.088 (349.934) | −18.998 (207.581) | 3.062 (33.718) | −10.317 (488.825) |
| Median (min to max) change - IU/ml | −1.0 (−1044 to 4545) | −53.0 (−2612 to 687) | −1.0 (−791 to 1337) | −57.0 (−4974 to 1384) |
| Median (min to max) change - % | −1.875 (−55.18 to 6060.00) | −35.356 (−94.85 to 3816.67) | −0.327 (−53.95 to 266.67) | −36.364 (−99.48 to 11600.00) |
| Change from baseline to Week 24 | | | | |
| Mean change (SD) - IU/ml | 13.9 (304.3) | −246.6 (462.5) | 33.9 (372.8) | −217.0 (369.1) |
| Mean change (SD) in IU/ml - % | 28.049 (306.538) | −44.719 (98.770) | 28.770 (380.881) | −47.871 (65.897) |
| Median (min to max) change - IU/ml | −1.0 (−1654 to 3851) | −85.0 (−4007 to 571) | −1.0 (−931 to 3478) | −88.0 (−4241 to 871) |
| Median (min to max) change - % | −2.020 (−70.83 to 5134.67) | −53.280 (−98.97 to 1841.94) | −0.697 (−65.31 to 6485.71) | −53.913 (−99.18 to 1060.00) |
| Change from baseline to Week 52 | | | | |
| Mean change (SD) - IU/ml | 2.2 (433.3) | −318.1 (582.3) | −3.9 (323.2) | −303.4 (521.7) |
| Mean change (SD) in IU/ml - % | 32.774 (436.822) | −61.817 (67.319) | 8.203 (64.731) | −59.547 (160.018) |
| Median (min to max) change - IU/ml | −3.0 (−1704 to 4925) | −110.0 (−4637 to 573) | −3.0 (−1000 to 3246) | −119.0 (−4994 to 509) |
| Median (min to max) change - % | −3.271 (−68.51 to 6566.67) | −69.427 (−96.91 to 1202.70) | −4.444 (−80.12 to 652.94) | −70.258 (−99.88 to 3360.00) |
| | Blood eosinophils (cells/μl) | | | |
| Mean baseline (SD) - cells/μl | 370 (338) | 349 (345) | 391 (419) | 351 (369) |
| Median (min to max) baseline - cells/μl | 270 (0-2200) | 250 (0-3610) | 265 (0-3580) | 250 (0-4330) |
| Change from baseline to Week 12 | | | | |
| Mean change (SD) - cells/μl | −12.66 (269.52) | 118.31 (539.03) | −43.3 (350.43) | 88.88 (532.6) |
| Mean change (SD) - % | 46.375 (172.116) | 78.610 (403.288) | 34.649 (181.064) | 93.299 (576.646) |
| Median (min to max) change - cells/μl | 5 (−1610 to 1630) | 10 (−1790 to 5350) | −10 (−2220 to 1180) | 0 (−2970 to 6660) |
| Median (min to max) change - % | 0.000 (−100.00 to 1400.00) | 2.986 (−97.67 to 6900.00) | −3.704 (−100.00 to 1700.00) | 0.000 (−100.00 to 10100.00) |
| Change from baseline to Week 24 | | | | |
| Mean change (SD) - cells/μl | −23.556 (335.679) | 86.52 (622.63) | −32.049 (376.45) | 49.657 (494.575) |
| Mean change (SD) - % | 39.519 (156.576) | 62.538 (250.177) | 49.673 (252.040) | 68.958 (367.619) |
| Median (min to max) change - cells/μl | 0 (−1290 to 2630) | 0 (−2170 to 10200) | 0.000 (−2970 to 1390) | 0 (−3080 to 5350) |
| Median (min to max) change - % | 0.000 (−100.00 to 1200.00) | 0.000 (−100.00 to 2850.00) | 0.000 (−100.00 to 2300.00) | 0.000 (−100.00 to 5800.00) |
| Change from baseline to Week 52 | | | | |
| Mean change (SD) - cells/μl | −2.78 (313.82) | 23.849 (399.395) | −47.88 (344.83) | −2.26 (425.596) |
| Mean change (SD) - % | 115.548 (876.073) | 28.472 (150.256) | 33.603 (206.264) | 43.764 (301.609) |
| Median (min to max) change - cells/μl | 0 (−1670 to 1540) | −20 (−1690 to 3170) | −30 (−2330 to 1740) | −25 (−3670 to 3420) |
| Median (min to max) change - % | 0.000 (−99.26 to 12800.00) | −9.091 (−100.00 to 1900.00) | −11.438 (−100.00 to 2400.00) | −14.583 (−100.00 to 4300.00) |
| | Thymus and activation-regulated chemokine (TARC; pg/mL) | | | |
| Mean baseline (SD) - pg/mL | 377.8 (289.0) | 393.8 (457.4) | 398.0 (344.2) | 364.7 (295.4) |
| Median baseline (min to max) - pg/mL | 296 (33 to 1970) | 314.5 (16 to 8600) | 300 (34 to 3210) | 295 (16 to 3170) |
| Change from baseline to Week 12 | | | | |
| Mean change (SD) - pg/mL | −12.6 (199.2) | −153.6 (392.3) | 29.9 (472.7) | −139.9 (226.8) |
| Mean change (SD) - % | 9.537 (57.893) | −26.434 (40.121) | 14.583 (77.359) | −24.414 (86.001) |
| Median change (min to max) - pg/mL | −1 (−1554 to 800) | −96.5 (−7560 to 835) | −7.1 (−617 to 7850) | −96.4 (−2011 to 1674) |
| Median change (min to max) - % | −0.645 (−95.36 to 427.81) | −32.883 (−90.71 to 236.97) | −3.815 (−77.37 to 827.81) | −34.559 (−91.79 to 1747.6) |

TABLE 13-continued

Summary of Change from Baseline in Type 2 Biomarker Levels.

| | Randomized treatment group | | | |
|---|---|---|---|---|
| | Placebo (N = 317) | Dupilumab 200 mg q2w (N = 631) | Placebo (N = 321) | Dupilumab 300 mg q2w (N = 633) |
| Change from baseline to Week 24 | | | | |
| Mean change (SD) - pg/mL | 0.6 (279.0) | −160.5 (427.0) | 118.0 (2206.6) | −135.8 (215.8) |
| Mean change (SD) - % | 12.279 (75.287) | −26.666 (46.770) | 16.714 (115.621) | −26.925 (38.823) |
| Median change (min to max) - pg/mL | −10.0 (−1525 to 2820) | −103.5 (−7629 to 2327) | −0.0 (−910 to 37250) | −93.0 (−2005 to 590) |
| Median change (min to max) - % | −3.175 (−83.53 to 580.58) | −34.988 (−94.24 to 313.19) | 0.000 (−79.92 to 1354.55) | −34.251 (−92.12 to 211.47) |
| Change from baseline to Week 52 | | | | |
| Mean change (SD) - pg/mL | −11.4 (197.9) | −161.4 (450.9) | 138.3 (2169.6) | −125.2 (219.5) |
| Mean change (SD) - % | 11.384 (69.774) | −27.018 (42.836) | 26.028 (148.647) | −23.379 (50.305) |
| Median change (min to max) - pg/mL | −5.0 (−1456 to 1090) | −101.0 (−8187 to 885) | 8.0 (−669 to 33650) | −90.0 (−2196 to 590) |
| Median change (min to max) - % | −2.419 (−86.99 to 519.34) | −33.544 (−97.86 to 233.64) | 2.226 (−70.99 to 1725.64) | −34.483 (−91.24 to 586.71) |
| Periostin (ng/mL) | | | | |
| Mean baseline (SD) - ng/mL | 79.83 (36.60) | 79.85 (39.12) | 80.94 (40.73) | 78.42 (37.94) |
| Median baseline (min to max) - ng/mL | 72.1 (27.8 to 244.9) | 70.6 (20.5 to 368.2) | 71 (25.1 to 312.8) | 69.7 (19.2 to 298.5) |
| Change from baseline to Week 12 | | | | |
| Mean change (SD) - ng/mL | −1.22 (23.46) | −16.52 (32.20) | −1.27 (26.71) | −15.54 (29.51) |
| Mean change (SD) - % | 2.118 (27.112) | −12.795 (29.683) | 1.911 (28.007) | −13.554 (26.622) |
| Median change (min to max) - ng/mL | −0.6 (−119.7 to 106.6) | −8.40 (−266.4 to 66.4) | −0.6 (−103.5 to 127.6) | −10.65 (−234.5 to 77.8) |
| Median change (min to max) - % | −1.211 (−48.88 to 121.94) | −13.483 (−75.76 to 296.59) | −1.068 (−92.47 to 141.78) | −15.350 (−78.56 to 105.03) |
| Change from baseline to Week 52 | | | | |
| Mean change (SD) - ng/mL | −4.79 (22.23) | −18.83 (34.79) | −5.24 (27.29) | −19.49 (30.37) |
| Mean change (SD) - % | −2.004 (25.992) | −15.065 (31.303) | −2.538 (29.531) | −18.187 (24.427) |
| Median change (min to max) - ng/mL | −3.90 (−108.4 to 75.7) | −11.40 (−260 to 70.4) | −4.20 (−110.3 to 189.5) | −12.65 (−202.4 to 38.2) |
| Median change (min to max) - % | −5.410 (−70.89 to 134.18) | −17.213 (−77.16 to 343.41) | −6.988 (−70.84 to 236.28) | −19.719 (−72.28 to 75.11) |
| Eotaxin-3 (pg/mL) | | | | |
| Mean baseline (SD) - pg/mL | 52.172 (86.619) | 78.202 (339.495) | 50.892 (57.855) | 69.516 (481.528) |
| Median baseline (min to max) - pg/mL | 36.5 (1.95 to 1180) | 39.2 (1.95 to 6430) | 37.45 (1.95 to 723) | 38.3 (1.95 to 12000) |
| Change from baseline to Week 12 | | | | |
| Mean change (SD) - pg/mL | −3.157 (27.405) | −35.661 (137.286) | −1.795 (30.136) | −39.233 (355.197) |
| Mean change (SD) - % | 20.179 (145.501) | −14.212 (137.332) | 30.046 (260.896) | −25.550 (107.262) |
| Median change (min to max) - pg/mL | −0.2 (−164 to 114.8) | −14.650 (−2110 to 245.3) | 0 (−233 to 119.6) | −14.000 (−8750 to 33) |
| Median change (min to max) - % | −0.719 (−95.19 to 1571.73) | −39.587 (−98.78 to 1443.59) | 0 (−96.89 to 3858.97) | −40.977 (−98.73 to 1264.1) |
| Change from baseline to Week 24 | | | | |
| Mean change (SD) - pg/mL | −1.483 (34.127) | −31.796 (153.247) | −6.335 (35.606) | −44.278 (448.676) |
| Mean change (SD) - % | 33.047 (191.426) | −17.149 (136.065) | 15.413 (139.984) | −24.072 (108.415) |
| Median change (min to max) - pg/mL | −0.700 (−235.00 to 270.00) | −16.900 (−2872.00 to 1650.00) | −2.500 (−315.20 to 200.60) | −13.600 (−10690.00 to 113.40) |
| Median change (min to max) - % | −3.101 (−96.88 to 1889.74) | −42.700 (−98.78 to 1458.97) | −7.734 (−96.88 to 1315.38) | −40.326 (−98.61 to 1587.18) |
| Change from baseline to Week 52 | | | | |
| Mean change (SD) - pg/mL | −1.341 (52.531) | 62.496 (2227.767) | −1.178 (42.275) | −50.095 (533.671) |
| Mean change (SD) - % | 27.331 (132.523) | −3.527 (210.111) | 52.327 (304.987) | −23.606 (113.851) |
| Median change (min to max) - pg/mL | 0.000 (−528.00 to 337.30) | −12.900 (−3178.00 to 48070.00) | −0.850 (−312.10 to 205.90) | −14.100 (−11374.00 to 222.50) |
| Median change (min to max) - % | 0.000 (−94.07 to 1094.87) | −35.157 (−99.58 to 3294.87) | −2.729 (−95.14 to 3156.41) | −39.962 (−97.19 to 1780.00) |

*min to max denotes minimum to maximum, ppb parts per billion, q2w every two weeks, and SD standard deviation.

TABLE 14

Summary of Interaction Test For Efficacy.

| | Dupilumab 200 mg q2w vs matching placebo P Value | Dupilumab 300 mg q2w vs matching placebo P Value | Overall P Value |
|---|---|---|---|
| Annualized rate of severe exacerbation during 52-week treatment period* | | | |
| Blood Eosinophil (cells/µL) | <0.001 | <0.001 | <0.001 |
| FeNO (ppb) | 0.0076 | <0.001 | <0.001 |
| Periostin (ng/mL) | 0.1667 | 0.1347 | 0.1046 |
| ECP (ng/mL) | 0.0766 | 0.1302 | 0.079 |
| Total IgE (IU/mL) | 0.4161 | 0.2755 | 0.3036 |
| TARC (pg/mL) | 0.9688 | 0.5591 | 0.7689 |
| Eotaxin-3 (pg/mL) | 0.8099 | 0.1845 | 0.4494 |
| Pre-bronchodilator $FEV_1$ at Week 12† | | | |
| Blood Eosinophil (cells/µL) | 0.0361 | <0.001 | <0.001 |
| FeNO (ppb) | <0.001 | <0.001 | <0.001 |
| Periostin (ng/mL) | 0.0154 | 0.0195 | <0.001 |
| ECP (ng/mL) | 0.3076 | 0.0049 | 0.0102 |
| Total IgE (IU/mL) | 0.0270 | 0.0483 | 0.0245 |
| TARC (pg/mL) | 0.6540 | 0.3062 | 0.3759 |
| Eotaxin-3 (pg/mL) | 0.0421 | 0.0134 | 0.0151 |

*P-values of testing treatment-by-biomarker interaction effects based on un-penalized negative binomial regression spline models in the ITT population.
†P-values of testing treatment-by-biomarker interaction effects based on un-penalized regression spline models in the ITT population.

Discussion

Dupilumab significantly reduced annualized severe exacerbation rates in the ITT population, with greater treatment effects observed with increasing baseline levels of blood eosinophils and FeNO. Dupilumab also significantly decreased the rate of the most severe asthma exacerbations, those requiring hospitalization or emergency room visits. Assessment of $FEV_1$ and asthma control over time showed that efficacy of dupilumab was rapid, with significant differences versus placebo evident as early as the first evaluation at week 2 and maintained throughout the 52-week treatment period for both dose regimens. Significant and clinically meaningful improvements in $FEV_1$ of 0.32 to 0.34 L were observed at week 12 irrespective of baseline blood eosinophil count, with even larger increases of 0.43 to 0.47 L in patients with baseline blood ≥300 eosinophils/µL.

Furthermore, post-bronchodilator $FEV_1$ slope analysis indicated that compared with the loss of lung function observed in placebo patients, no loss was observed in dupilumab-treated patients suggesting a potential effect of dupilumab on airway remodeling. The slope analysis showed that placebo patients lost on average about 40 mL annually, which is consistent with data from other asthma cohorts. Furthermore, as IL-4Rα is expressed on smooth muscle cells, it is possible that there is a direct bronchodilator effect of the drug, in addition to the anti-Type 2 inflammatory effects.

The consistent and profound improvement seen with dupilutnab is likely attributable to its unique mechanism of action. With the increasing recent focus of the asthma community on exacerbations, driven by payer concerns of cost-effectiveness, emphasis has shifted away from the significant morbidity and quality of life issues associated with the substantial loss of lung function seen in moderate-to-severe asthma patients. Despite current therapies, these moderate-to-severe asthma patients are destined to continue to lose further lung function and decline with time. Thus, the possibility that a new treatment can provide substantial restoration of clinically meaningful levels of lung function, and perhaps even stave off future deterioration, could provide enormous benefit to these patients.

The results of this study confirm that interleukin-4 and interleukin-13 are key proximal drivers of Type 2 inflammation in asthma. Dupilumab is the first biologic to significantly reduce FeNO levels, in addition to other systemic Type 2 biomarkers such as IgE, confirming its biological activity on airway inflammation. Without intending to be bound by scientific theory, the unique mechanism of action of dupilumab, with dual blockade of interleukin-4 and interleukin-13 signaling, may explain why dupilumab shows significant treatment effect in a broader patient population and unprecedented effect on improvement in lung function, suggesting a potential direct bronchodilator effect in addition to its anti-inflammatory effect it is noteworthy that this study shows the most prominent association of benefit to baseline levels of blood eosinophils compared to the other two pivotal studies with dupilumab. Although there is no clear explanation why the association was more prominent in this study, blood eosinophils may be an insufficient measure of Type 2 inflammation, indicating that other biomarkers of type 2 inflammation such as FeNO may be important. Nevertheless, in general across all three studies, dupilumab seems to address a broader asthma population than those defined only by either elevated blood eosinophils or IgE levels, which is required for other approved biologics.

Dupilumab activity has been demonstrated against several atopic/allergic conditions, which are often co-morbid in asthma patients. In this study, over 80% of the patients suffered from a co-morbid atopic or allergic condition, including atopic dermatitis (about 10% of the population), nasal polyposis (about 20% of the population), and allergic rhinitis (over 65% of the population). The high rate of co-morbid atopic/allergic conditions suggests that these patients suffer from systemic over-activity of the Type 2 inflammatory axis, and thus treatment of asthma with dupilumab could simultaneously help alleviate these associated conditions.

Dupilumab was generally well tolerated and had an acceptable safety profile. With the exception of injection site reactions, incidence of TEAEs was similar across treatment groups. Consistent with the mechanism of action, and similar to what was observed in atopic dermatitis trials, dupilumab-treated patients showed a greater mean transient increase from baseline in blood eosinophil counts compared with placebo. Per study protocol, all cases of eosinophil counts >3,000 cells/µL on treatment were to be reported as AEs in this study. Most of the observed elevations in eosinophil counts were laboratory findings without clinical consequences or associated AEs. The increase in blood eosinophil counts is consistent with the hypothesis that dupilumab blocks interleukin-4 and interleukin-13 function in eosinophil survival, activation and recruitment to tissues, but not regress from bone marrow which is influenced by IL-5. As a result, initial treatment with dupilumab may result in transient increase in circulating blood eosinophil counts. No treatment-related conjunctivitis AEs were observed between dupilumab and placebo groups, in contrast to dupilumab atopic dermatitis studies.

In conclusion, in the largest study to date of dupilumab in patients with uncontrolled moderate-to-severe asthma, it is here demonstrated that dual blockade of interleukin-4 and interleukin-13 with dupilumab effectively treats a broad asthma population, providing significant reduction in the rate of severe exacerbations, rapid and sustained improvement in lung function and asthma control, and symptom relief. The most robust results were observed in patients with elevated Type 2 immune characteristics, including eosinophil counts and FeNO. Dupilumab is the only biologic to demonstrate efficacy in multiple studies of moderate-to-severe asthma patients, independent of baseline Type 2 biomarker levels. Dupilumab was generally well tolerated and had an acceptable safety profile. These data support the use of dupilumab as effective add-on therapy for this population of asthma patients with a high unmet need.

Example 3. QUEST Phase III Trial
Study-Dupilumab Reduces Severe Exacerbation Rate and Improves Lung Function in Adolescent Patients with Uncontrolled, Moderate-to-Severe Asthma The prevalence of asthma in children and adolescents has increased over the past 30 years (Asher (2014) *Int. J. Tuberc. Lung Dis.*). In 2011, approximately 11.4% of adolescents (age 12-17 years) in the USA reported currently having asthma (Bloom (2011) *Vital and Health Statistics Series*).

The rate of morbidity due to asthma is as high (or often higher) in adolescents as in younger children, however, adolescents are less likely to seek medical help (Couriel (2003) *J. Paediatric Resp. Rev.*). Many adolescents underestimate the severity of their asthma and overestimate their response to bronchodilators (Rhee (2008) *J. Asthma*; Andersson (2013) *Pediatrics*). Asthma profoundly influences adolescents' physical, psychological and social health and adversely affects their health-related quality of life (Cui (2016) *J. Pediatrics*).

This study assessed the efficacy and safety of dupilumab by subgroups of adolescents (age 12-17 years) and adults (age ≥18 years) with uncontrolled, moderate-to-severe asthma. Endpoints assessed during the 52-week treatment period were the annualized rate of severe exacerbations, and change from baseline in pre-bronchodilator $FEV_1$ (L). Baseline demographics and clinical characteristics are shown at FIG. 12.

Inclusion criteria: Age ≥12 years with physician-diagnosed uncontrolled asthma for ≥12 months (Global Initiative for Asthma (GINA) 2014); On treatment with medium-to-high dose ICS (inhaled corticosteroids) plus up to 2 additional controllers; Pre-bronchodilator $FEV_1$ (forced expiratory volume in 1 second) ≤80% predicted normal (adults) and ≤90% (adolescents) at screening and baseline; Bronchodilator reversibility ≥12% and 200 mL; ACQ-5 (5-item asthma control questionnaire) score ≥1.5 at screening and baseline; ≥1 exacerbation during the previous year; No minimum requirement for baseline blood eosinophil count or any other type 2 biomarker.

Exclusion criteria: Chronic obstructive pulmonary disease or other lung diseases that might impair lung function; Severe asthma exacerbation within 1 month of the enrollment visit or during screening period; Current smoker, smoker who stopped within 6 months before screening, or with a smoking history of >10 pack-years; Comorbid disease that might interfere with the evaluation of the study drug.

Statistical Analysis: Efficacy analyses were performed on the ITT population, defined as all randomized patients by allocated treatment whether or not treatment was received.

The annualized rate of severe asthma exacerbations during the 52-week treatment period was analyzed using a negative binomial regression model. Change from baseline in $FEV_1$ at various time points during the 52-week treatment period was analyzed using a mixed-effects model with repeated measures.

The primary endpoints, severe asthma exacerbation rates and $FEV_1$, were also analyzed in a subgroup of patients defined by age (<18 years and >18 years). The safety population included all patients who received ≥1 dose or part of a dose of the investigational treatment, analyzed according to the treatment received.

Figure 13A:
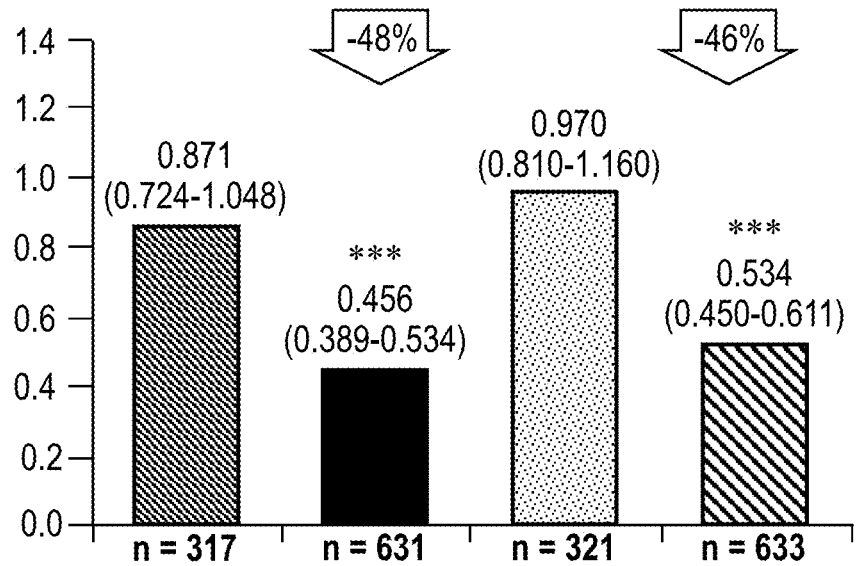
FIG. 13A-FIG. 13B graphically depict a reduction in severe exacerbations and improved $FEV_1$ in the overall intent-to-treat (ITT) population. Light grey circles, 1.14 mL placebo; dark grey circles, 2 mL placebo; triangles, 200 mg q2w dupilumab; Xs, 300 mg q2w dupilumab. ***P <0.001 vs. placebo. CI, confidence interval; LS, least squares; SE, standard error; arrow, primary endpoint.
Figure 13B:
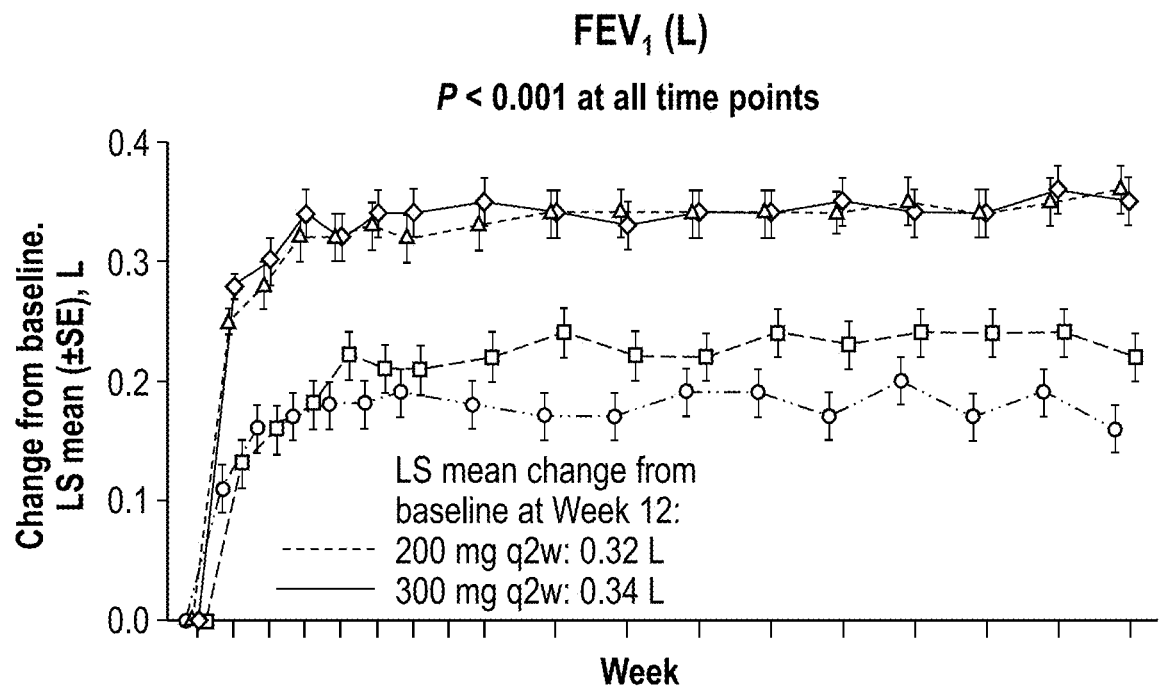
Figure 14A:
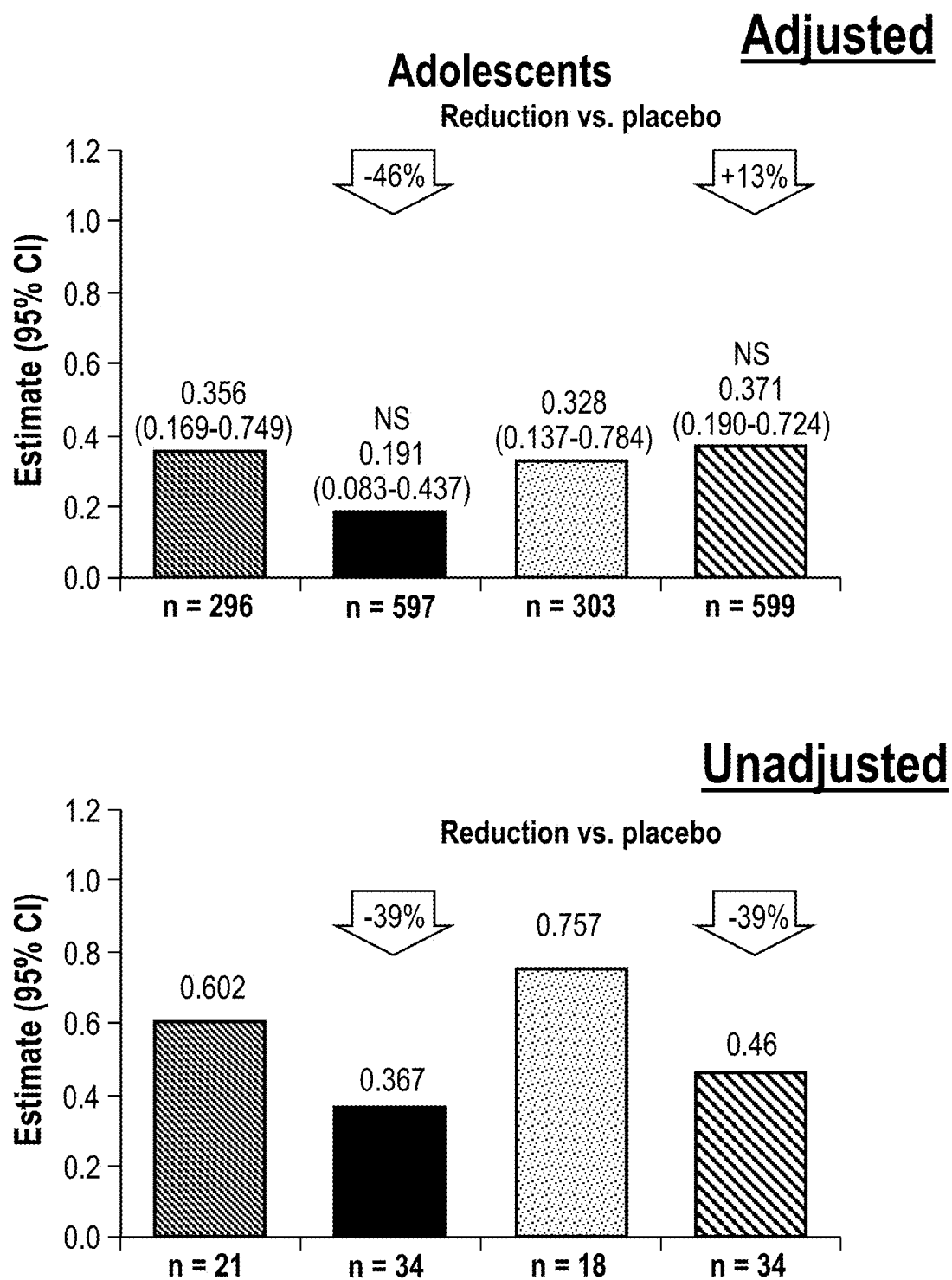

Dupilumab reduced severe exacerbations and improved $FEV_1$ in the overall ITT population (FIG. 13A and FIG. 13B), reduced severe exacerbation rates in adolescents and adults (FIG. 14A and FIG. 14B), and improved $FEV_1$ at weeks 12 (FIG. 15A) and 52 (FIG. 15B), as well as throughout the 52-week treatment period (FIG. 16A and FIG. 16B) in adolescents and adults.

Figures 18A, 18B:
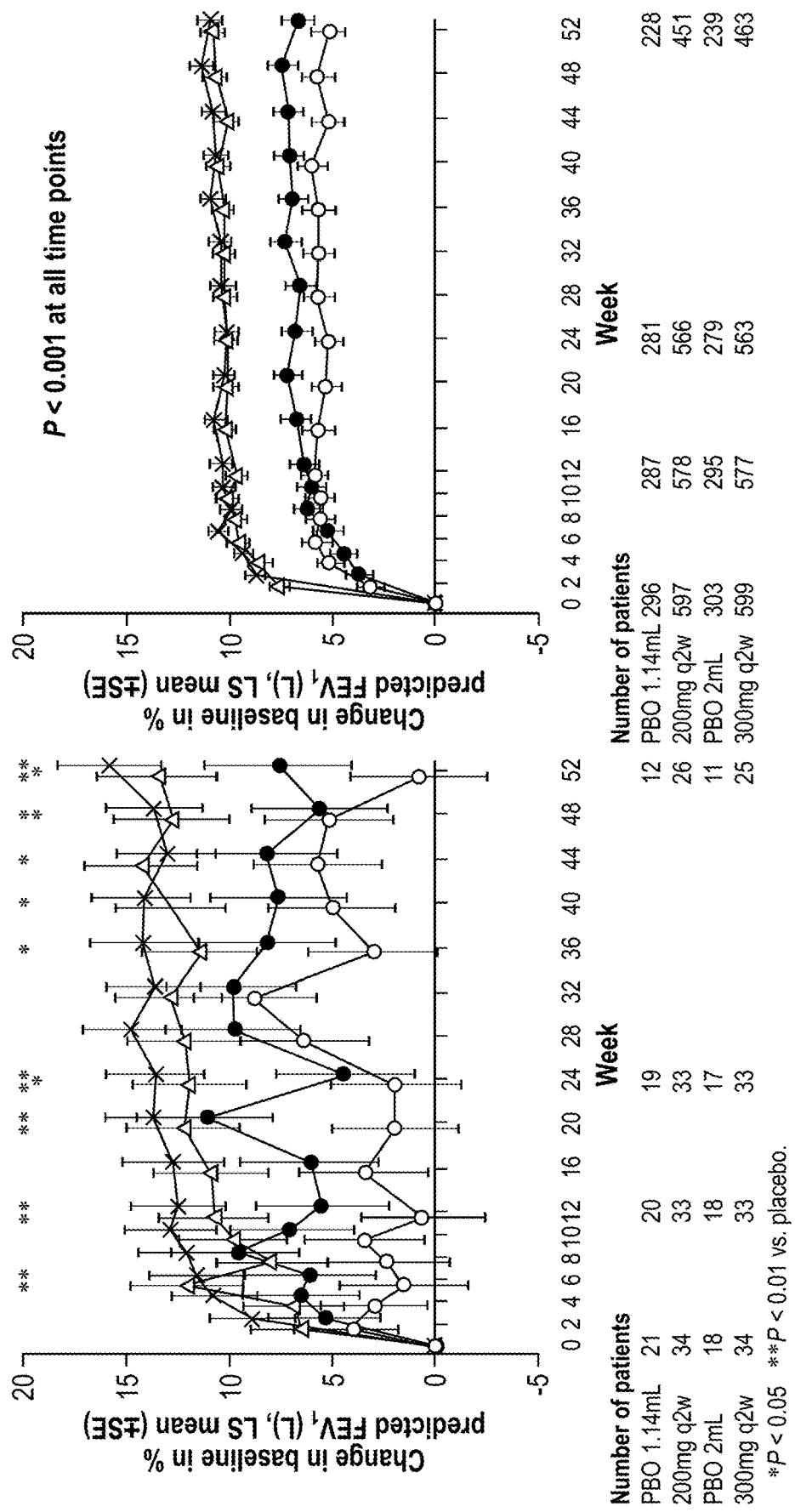
FIG. 18A-FIG. 18B graphically depicts an improvement in percent predicted $FEV_1$ during the 52-week treatment period in adolescents and adults. Light grey circles, 1.14 mL placebo; dark grey circles, 2 mL placebo; triangles, 200 mg q2w dupilumab; Xs, 300 mg q2w dupilumab. *P<0.05, **P<0.01 vs. placebo.
Figures 19A, 19B:
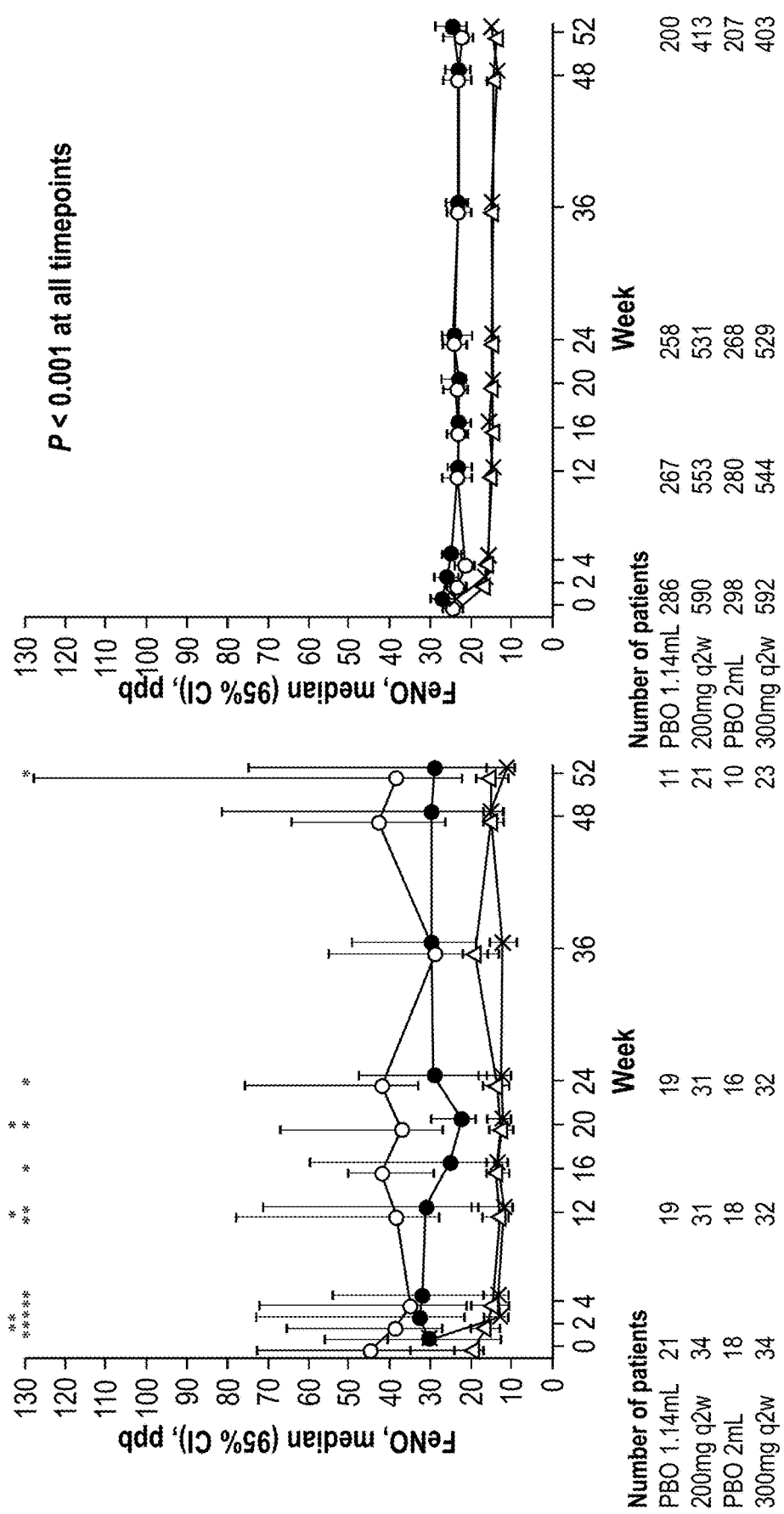
FIG. 19A-FIG. 19B graphically depict FeNO levels during the 52-week treatment period in adolescents and adults. Light grey circles, 1.14 mL placebo; dark grey circles, 2 mL placebo; triangles, 200 mg q2w dupilumab; Xs, 300 mg q2w dupilumab. *P<0.05, P<0.01, *P<0.001 vs. placebo.
Figures 20A, 20B:
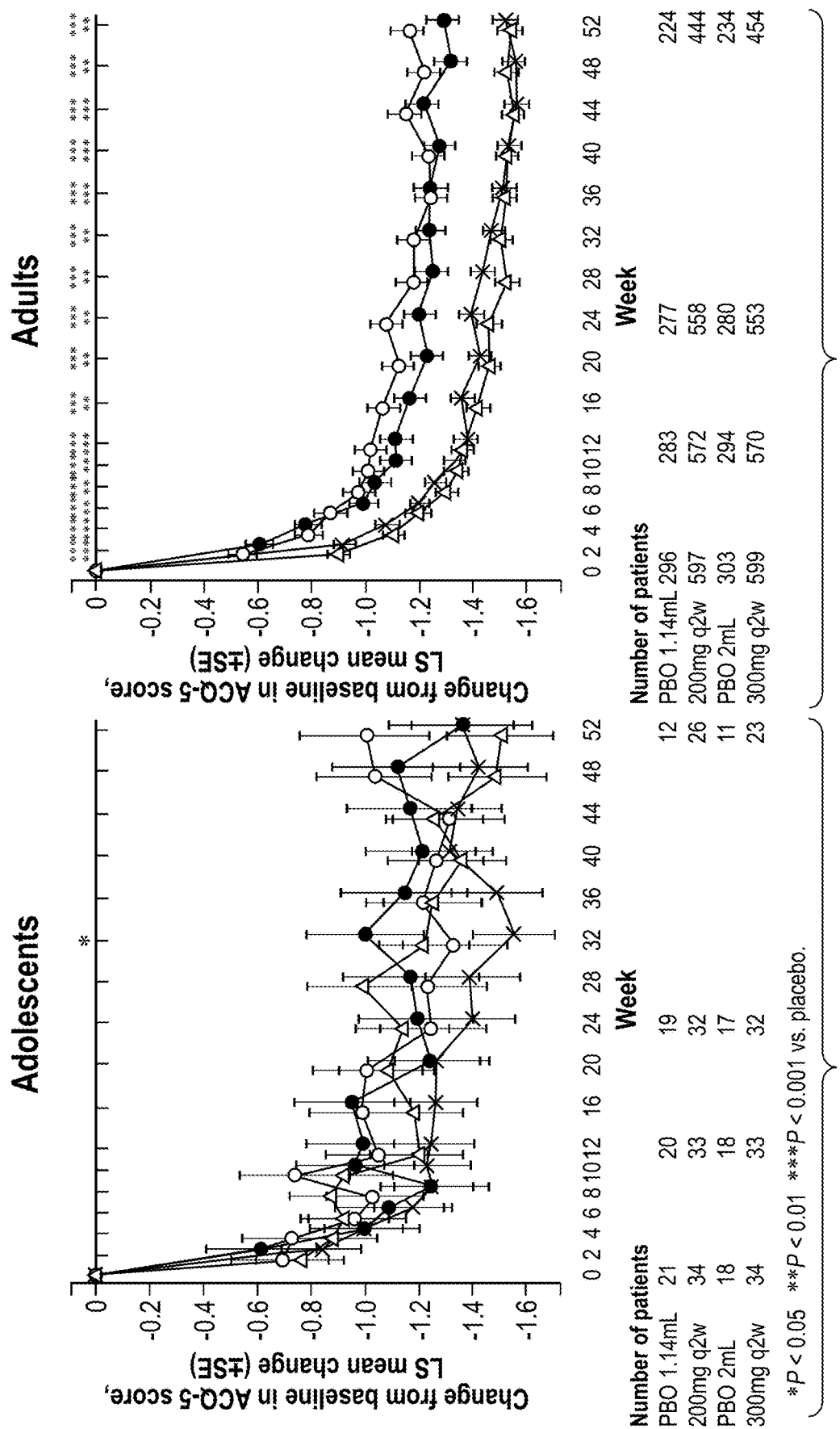
FIG. 20A-FIG. 20B graphically depict ACQ-5 scores during the 52-week treatment period in adolescents and adults. Light grey circles, 1.14 mL placebo; dark grey circles, 2 mL placebo; triangles, 200 mg q2w dupilumab; Xs, 300 mg q2w dupilumab. *P<0.05, P<0.01, *P<0.001 vs. placebo.
Figures 21A, 21B:
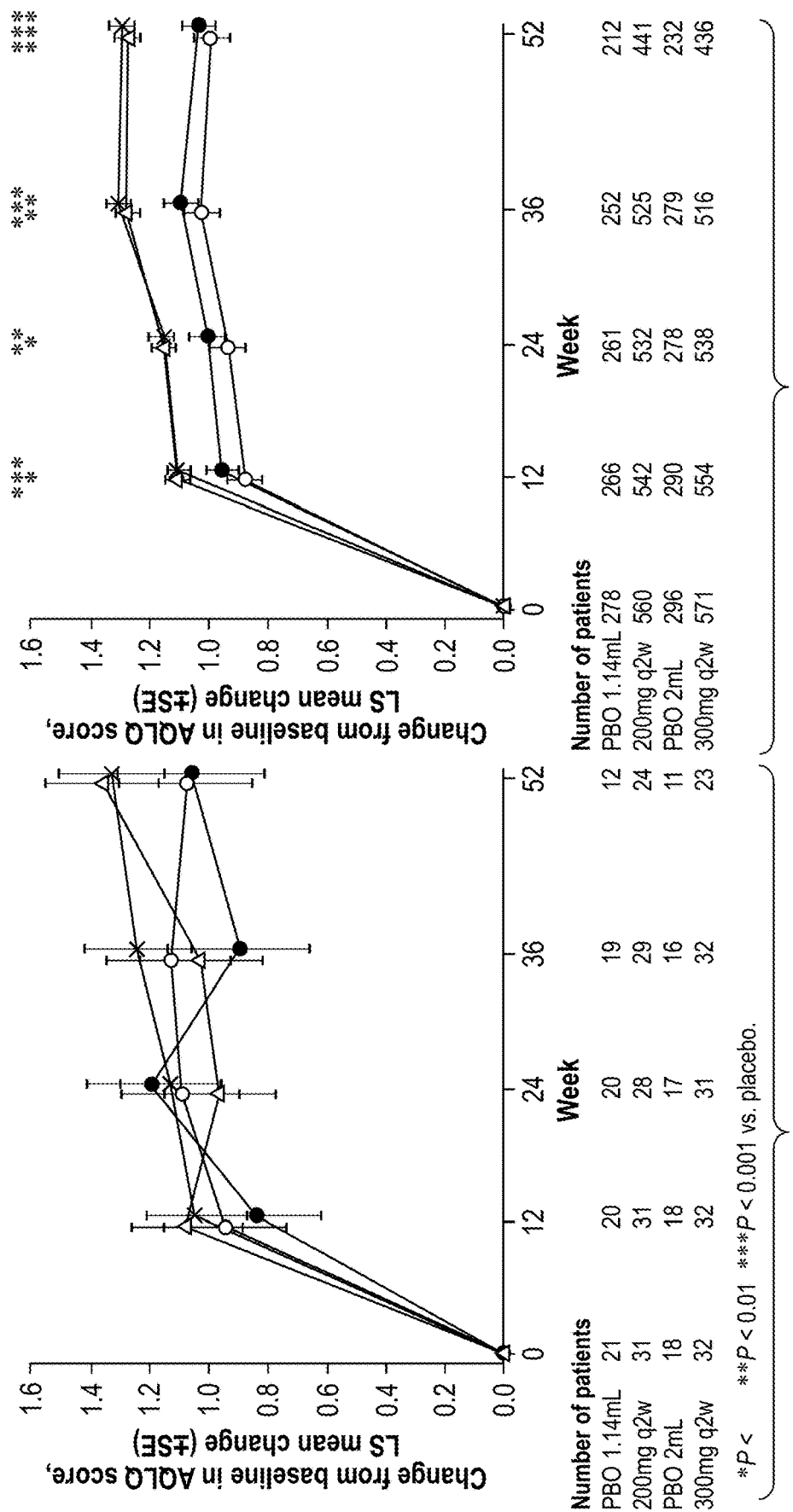
FIG. 21A-FIG. 21B graphically depict AQLQ scores during the 52-week treatment period in adolescents and adults. Light grey circles, 1.14 mL placebo; dark grey circles, 2 mL placebo; triangles, 200 mg q2w dupilumab; Xs, 300 mg q2w dupilumab. *P<0.05, P<0.01, *P<0.001 vs. placebo.

Dupilumab improved percent predicted $FEV_1$ during the 52-week treatment period in adolescents and adults (FIG. 18A and FIG. 18B). FeNO levels (FIG. 19A and FIG. 19B), ACQ-5 scores (FIG. 20A and FIG. 20B), and AQLQ scores (FIG. 21A and FIG. 21B) were assessed.

Adolescents comprised 107/1,902 enrolled patients (34 in dupilumab groups, 21/18 in matched-placebo groups); 35.5% were female, mean baseline FEV1 was 2.33 L, mean % predicted FEV1 70.45%, mean number of severe exacerbations in the previous year 1.91. Adolescents receiving placebo experienced fewer severe exacerbations (0.36/0.33) than adults (0.89/1.00). In adolescents, dupilumab 200 mg reduced annualized exacerbation rates by 46.4% while dupilumab 300 mg had no treatment effect vs. placebo (without intending to be bound by scientific theory, this was possibly due to small sample size and unbalanced number of prior events (mean 1.53 vs 2.22, respectively)). Unadjusted exacerbation rates were 0.46 (dupilumab 300 mg) and 0.76 (placebo). Significant improvements in change from baseline in FEV1 (L) vs placebo were seen in adolescents (dupilumab 200 mg: least-squares mean 0.36 [95% CI 0.12-0.61]; 300 mg: 0.27 [0.02-0.52]) (P<0.05) and were numerically greater vs adults (200 and 300 mg: 0.12 [0.07-0.18]).

The adverse event profile was comparable between subgroups (FIG. 17, FIG. 22, FIG. 23 and FIG. 24). The most common treatment-emergent adverse events (TEAEs) occurring more frequently in the dupilumab group combined were: Adolescents–respiratory tract infection viral (placebo, 2 [5.1%]; dupilumab, 7 [10.3%]); Adults—injection site erythema (placebo, 34 [5.7%]; dupilumab, 168 [14.1%]). Eosinophilia was only observed in the adult population.

Dupilumab significantly reduced annualized rates of severe exacerbation and improved lung function in adults with uncontrolled, moderate-to-severe asthma. Improvement in $FEV_1$ was rapid and sustained throughout the 52-week treatment period. Dupilumab also significantly improved lung function in adolescents with uncontrolled moderate-to-severe asthma, with numerical reductions observed for severe exacerbations As in adults, adolescents' improvement in $FEV_1$ was rapid and sustained throughout the 52-week treatment period. The magnitude of improvement in $FEV_1$ was greater in adolescents. Dupilumab was generally well tolerated.

Example 4. QUEST Phase III Trial
Study-Dupilumab Improves Health-Related
Rhinoconjunctivitis Quality of Life, Improves Lung
Function and Reduces Severe Exacerbation Rate in
Patients with Moderate-to-Severe Asthma Health-Related Quality of Life in Patients with Comorbid Allergic Rhinitis Allergic rhinitis (AR), a common type 2 comorbidity in asthma patients, contributes to increased overall disease burden. This analysis of the phase 3 LIBERTY ASTHMA QUEST study (NCT02414854) in uncontrolled, moderate-to-severe asthma patients assessed dupilumab's effect on the standardized rhinoconjunctivitis quality of life questionnaire [RQLQ(S)+12] in patients with self-reported comorbid AR.

Asthma patients, ≥12 years, uncontrolled with medium-to-high-dose ICS plus ≤2 additional controllers received add-on dupilumab 200/300 mg or matched placebo every 2 weeks (q2w) for 52 weeks. Patients with self-reported medical history of AR (63.5%; n/N=1.207/1,902) completed the validated RQLQ(S)+12 at weeks 12 and 52. A clinical AR diagnosis was not recorded.

Overall RQLQ(S)+12 score (baseline mean [SD] 1.90 [1.12]-2.01[1.16]) was significantly improved with dupilumab 200/300 mg q2w vs. placebo at week 52 (least squares mean difference [95% CI]-0.42[-0.61, -0.24]/-0.39[-0.56, -0.21]; P<0.0001). Dupilumab 200/300 mg significantly (P<0.001) improved activities (0.44 [0.68, 0.21]/0.39 [0.61, 0.16]), sleep (0.47 [0.69, 0.25]/0.38 [0.59, 0.17]), and eye symptoms (0.37 [0.58, 0.16]/0.39 [0.59, 0.19]) domain scores from baseline to week 52 vs placebo; and by week 12 for dupilumab 300 mg (0.23 [0.42, 0.04], 0.26 [0.45, 0.07], 0.26 [0.45, 0.08] respectively; P<0.05). Nasal symptoms domain scores significantly improved with dupilumab 200/300 mg vs. placebo by week 12 (0.36 [0.56, 0.16]/0.32 [0.51, 0.13]; P<0.001) and week 52 (0.61 [0.84, 0.39]/0.55 [0.76, 0.33]; P<0.0001). The most common adverse event, with higher frequency in dupilumab vs, placebo, was injection-site reactions (15%/18% vs. 5%/10%).

Dupilumab significantly improved rhinoconjunctivitis-specific health-related quality of life in patients with uncontrolled, moderate-to-severe asthma and comorbid AR, and was generally well tolerated.

Population: patients with comorbid AR. Endpoints/Visit: LS mean change from baseline during the 52-week treatment period for RQLQ domains (nasal symptoms, eye symptoms, activities, sleep); safety (ITT). Treatment arms: Dupilumab 200 mg and 300 mg q2w and matched placebo.

Improved Lung Function and Reduced Severe Exacerbation in Patients with or without Comorbid Allergic Rhinitis A post hoc analysis of the phase 3 LIBERTY ASTHMA QUEST study (NCT02414854) in asthma patients (≥12 years, uncontrolled with medium-to-high-dose ICS plus ≤2 additional controllers) with a self-reported medical history of comorbid AR (63.5%; n/N=1,207/1,902) or without comorbid AR assessed the effect of add-on dupilumab 200 mg or 300 mg or matched placebo every 2 weeks (q2w) on the annualized rate of severe exacerbations and forced expiratory volume in 1 second ($FEV_1$). A clinical diagnosis of AR was not recorded.

Baseline characteristics of patients with and without AR were generally similar. The annualized rate of severe exacerbations was reduced vs placebo with dupilumab 200 mg q2w (relative risk with AR:0.606 [95% CI, 0.451-0.814]; P=0.0009; without AR:0.406 [95% CI, 0.273-0.605]; P<0.0001) with similar results for 300 mg q2w. $FEV_1$ was improved at week 12 with dupilumab 200 mg q2w (LS mean difference vs. placebo with AR:0.14L [95% CI, 0.07-0.21]; P<0.0001; without AR:0.13L [95% CI, 0.05-0.22]; P=0.0023) and sustained to week 52 (both with and without AR: P<0.0001), with similar results at week 52 for 300 mg q2w. The most common adverse event in dupilumab-treated (vs. placebo) groups was injection-site reactions (200 mg/300 mg vs. matched-placebos: 15%/18% vs. 5%/10%).

Dupilumab significantly improved $FEV_1$ and reduced annual severe exacerbation rates in this difficult-to-control asthma population with comorbid AR and also in patients without concomitant AR.

Population: Patients with and without comorbid AR (AR defined according to CSR). Endpoints: LS mean change from baseline in FEV1 at weeks 12 and 52; severe exacerbations during the 52-week treatment period. Safety: ITT.

Example 5. QUEST Phase III Trial
Study-Dupilumab Suppresses Type 2 Biomarkers in
Asthma Patients with and without Comorbid
Chronic Rhinosinusitis with Nasal Polyposis
(CRS+NP) or Chronic Rhinosinusitis without Nasal
Polyposis (CRS-NP) in Patients with
Moderate-to-Severe Asthma In the phase 3 LIBERTY ASTHMA QUEST study (NCT02414854), dupilumab 200/300 mg every 2 weeks versus matched placebo suppressed type 2 biomarkers in patients with uncontrolled, moderate-to-severe asthma and improved health-related quality of life, assessed by SNOT-22, in the difficult-to-treat subgroup with comorbid chronic rhinosinusitis with nasal polyposis (CRS+NP) or (CRSwNP) and comorbid chronic rhinosinusitis without nasal polyposis (CRS-NP). This post hoc analysis assessed dupilumab's effect on type 2 biomarkers in this subgroup.

Baseline/change from baseline over time were assessed for fractional exhaled nitric oxide (FeNO), total IgE, and eotaxin-3. CRS with or without NP was self-reported by 20.1% (n/N=382/1,897) patients.

Baseline FeNO and eotaxin-3 values were numerically higher in patients with CRS-NP or CRS+NP than in those without. Biomarker suppression was evident in all dupilumab-treated patients by week 12. At week 52, significant biomarker suppression was observed in patients with and without CRS-NP or CRS+NP, as shown by median percentage changes from baseline (dupilumab 200/300 mg vs. matched placebo), with CRS-NP or CRS+NP: FeNO 46.2/37.7 vs. 5.5/6.4, IgE 74.8/76.8 vs. 0.0/2.0, eotaxin-3 47.7/50.9 vs. 1.5/5.4 (all P≤0.0001); without CRS-NP or CRS+NP: FeNO 31.0/35.9 vs. 5.9/10.1, IgE 67.3/67.7 vs. 3.3/6.6, eotaxin-3 31.8/37.2 vs. 0.0/0.8 (all P<0.0001). The most common adverse event, with higher frequency in dupilumab vs placebo, was injection-site reactions (15%/18% vs. 5%/10N.

Dupilumab suppressed local and systemic type-2 biomarkers in patients with and without CRS+/−NP.

Population: patients with and without comorbid CRS or NP. Endpoints: percent change from baseline serum total IgE, plasma eotaxin-3, and FeNO over the 52-week treatment period. Safety: ITT. Treatment arms: dupilumab 200 and 300 mg q2w and matched placebo.

Example 6. QUEST Phase III Trial
Study-Dupilumab Reduces Severe Exacerbations
and Improves Lung Function in Late-Onset,
Uncontrolled, Moderate-to-Severe Asthma Patients In the phase 3 LIBERTY ASTHMA QUEST study (NCT02414854), this post-hoc analysis assessed the efficacy of dupilumab in patients with late onset of asthma (age >40 years) and baseline post-bronchodilator FEN/1/forced vital capacity [FVC] ratio <0.7, (which suggests fixed airway obstruction), or ≥0.7.

Annualized rate of severe exacerbations during the 52-week treatment period was assessed using negative binomial regression models. Change from baseline in pre- and post-bronchodilator FEV1 (L) and pre-bronchodilator FEV1/FVC ratio at weeks 12 and 52 were analyzed using mixed-effect models with repeated measures.

Dupilumab 200 mg and 300 mg q2w vs. placebo significantly reduced the annualized rate of severe exacerbations in patients with late-onset asthma and fixed airway obstruction (68.8% and 75.7%, respectively, both P<0.0001) and in patients without fixed airway obstruction (55.1% and 50.7%, respectively, both P<0.05) (FIG. 27). At week 12, pre- and post-bronchodilator FEV1 and FEV1/FVC ratio improved in dupilumab-treated patients with late-onset asthma and fixed airway obstruction (P<0.05 vs placebo, either or both doses). Similar improvements were observed at week 52 (dupilumab 200 mg q2w P<0.05 for pre- and post-bronchodilator FEV1; dupilumab 300 mg q2w pre-bronchodilator FEV1. P=0.09, post-bronchodilator FEV1 P=0.06). Late-onset asthma patients without fixed airway obstruction, had more modest improvements vs. placebo in pre-bronchodilator FEV1 at weeks 12 and 52 than did those with fixed airway obstruction P≥0.05). The most frequent adverse event in dupilumab-treated groups vs. matched-placebo was injection-site reactions (15%/18% vs. 5%/10%).

In patients with late-onset asthma with or without fixed airway obstruction, dupilumab significantly reduced severe exacerbation rates. Furthermore, lung function improvements were observed at weeks 12 and 52 in patients with late-onset asthma and fixed airway obstruction, who typically experience worse asthma outcomes than do those without fixed airway obstruction.

Population: ITT population with age of onset asthma >40 years and post-BD FEV1/FVC <0.7; ITT population with age of onset asthma >40 years and post-BD FEV1/FVC≥0.7.

Endpoints/Visit (data for inclusion in abstract: severe exacerbations during the 52-week treatment period; LS mean change from baseline in pre-BD FEV1 (L) at weeks 12 and 52; LS mean change from baseline in post BD FEV1 (L) at weeks 12 and 52; LS mean change from baseline in FEV1/FVC ratio at weeks 12 and 52; safety.

Treatment arms: Dupilumab 200 mg q2w, dupilumab 300 mg q2w and matched-placebo groups.

What is claimed is:

1. A method for treating a subject having severe uncontrolled asthma comprising:
   administering to the subject a loading dose of an antibody or an antigen-binding fragment thereof that specifically binds to interleukin-4 receptor (IL-4R); and
   administering to the subject a plurality of maintenance doses of the antibody or the antigen-binding fragment thereof,
   wherein the plurality of maintenance doses is administered during a treatment phase comprising an induction phase, an oral corticosteroid (OCS) reduction phase, and an OCS maintenance phase, and
   wherein the antibody or antigen-binding fragment thereof comprises three heavy chain complementary determining region (CDR) sequences comprising SEQ ID NOs: 3, 4, and 5, respectively, and three light chain CDR sequences comprising SEQ ID NOs: 6, 7, and 8, respectively.

2. The method of claim 1, wherein a maintenance dose of antibody or antigen-binding fragment thereof is administered once every other week (q2w).

3. The method of claim 1, wherein the OCS reduction phase is about 16 weeks in length.

4. The method of claim 1, wherein the subject has a blood eosinophil count of less than about 150 cells/µl, greater than or equal to about 150 cells/µl, or greater than about 300 cells/µl.

5. The method of claim 1, wherein the antibody or antigen-binding fragment thereof comprises a heavy chain variable region (HCVR) comprising the amino acid sequence of SEQ ID NO: 1, and a light chain variable region (LCVR) comprising the amino acid sequence of SEQ ID NO: 2.

6. The method of claim 1, wherein the loading dose is about 600 mg of the antibody or the antigen-binding fragment thereof and each maintenance dose is about 300 mg of the antibody or the antigen-binding fragment thereof.

7. The method of claim 1, wherein the maintenance doses are about 200 mg every other week (q2w), about 300 mg q2w, about 500 mg every fourth week (q4w), or about 750 mg q4w.

8. The method of claim 1, wherein the subject has a blood eosinophil count of less than about 150 cells/µl greater than or equal to about 150 cells/µl or greater than about 300 cells/µl.

9. The method of claim 6, wherein the OCS use is reduced to less than 5 mg per day at week 24 following administration of the loading dose, the OCS use is reduced by at least 75%, or the OCS use is reduced by at least 90%.

10. The method of claim 1, wherein a first maintenance dose of antibody or antigen-binding fragment thereof is administered two weeks after the loading dose of antibody or antigen-binding fragment thereof.

11. The method of claim 6, wherein health related quality of life is improved.

12. The method of claim 1, wherein the subject is an adult, the subject is an adolescent, or the subject is 12 years of age or older.

13. The method of claim 1, wherein each maintenance dose of the antibody or antigen-binding fragment thereof is administered every fourth week (q4w).

14. The method of claim 1, wherein the maintenance doses are each about 500 mg or about 750 mg of the antibody or the antigen-binding fragment thereof.

15. The method of claim 1, wherein the maintenance doses of antibody or antigen-binding fragment thereof are administered for at least 24 weeks.

16. The method of claim 1, wherein the subject uses 50%, 75%, 90% or less OCS in the maintenance phase compared to the induction phase, wherein OCS use by the subject is reduced to about 5 mg/day or less in the maintenance phase or wherein OCS use is eliminated in the maintenance phase.

17. The method of claim 1, wherein OCS use by the subject is optimized prior to treatment with the antibody or antigen-binding fragment thereof.

18. The method of claim 1, wherein the OCS is prednisone or prednisolone.

19. The method of claim 1, wherein the subject experiences a reduction in annualized severe asthma exacerbations.

20. The method of claim 1, wherein the subject experiences an improvement in lung function as measured by forced expiratory volume ($FEV_1$) or by forced expiratory flow at 25-75% of the pulmonary volume (FEF25-75).

21. The method of claim 1, wherein the subject has an FeNO level of greater than or equal to 25 ppb, between about 25 ppb and about 50 ppb, or greater than or equal to about 50 ppb.

22. The method of claim 1, wherein the subject exhibits at least a 10% or a 25% reduction in a biomarker selected from the group consisting of FeNO, eotaxin-3, total IgE, periostin and thymus and activation regulated chemokine (TARC) at week 4, week 12 or week 24 following administration of the loading dose.

23. The method of claim 1, wherein the maintenance doses are administered for at least 24 weeks.

24. The method of claim 1, wherein dependency on OCS use is substantially eliminated after a period of time following administration of the loading dose, optionally wherein the period of time is after 40 weeks, 45 weeks, 50 weeks, 52 weeks or greater.

25. A method for treating a subject having severe uncontrolled asthma comprising:
   administering to the subject a loading dose of about 600 mg of an antibody or an antigen-binding fragment thereof that specifically binds to interleukin-4 receptor (IL-4R); and
   administering to the subject a plurality of maintenance doses of the antibody or the antigen-binding fragment thereof, wherein each maintenance dose is about 300 mg of the antibody or antigen-binding fragment thereof,
   wherein the plurality of maintenance doses is administered during a treatment phase comprising an induction phase, an oral corticosteroid (OCS) reduction phase, and a maintenance phase, and
   wherein the antibody or antigen-binding fragment thereof comprises the heavy and light chain CDR sequences from the HCVR/LCVR sequence pair comprising SEQ ID NOs: 1 and 2.

26. The method of claim 25, wherein a maintenance dose of antibody or antigen-binding fragment thereof is administered once every other week (q2w).

27. The method of claim 25, wherein the maintenance doses of antibody or antigen-binding fragment thereof are administered for at least 24 weeks.

28. The method of claim 25, wherein the subject uses 50%, 75%, 90% or less OCS in the maintenance phase compared to the induction phase, wherein OCS use by the subject is reduced to about 5 mg/day or less in the maintenance phase or wherein OCS use is eliminated in the maintenance phase.

29. The method of claim 25, wherein the OCS is prednisone or prednisolone.

30. The method of claim 25, wherein the subject experiences a reduction in annualized severe asthma exacerbations.

31. A method of reducing or eliminating oral corticosteroid (OCS) use in a subject suffering from steroid dependent severe asthma, the method comprising:
   administering to the subject a loading dose of an antibody or an antigen-binding fragment thereof that specifically binds to interleukin-4 receptor (IL-4R); and
   administering to the subject a plurality of maintenance doses of the antibody or the antigen-binding fragment thereof,
   wherein a reduction of at least 50% in OCS use is achieved at week 24 following administration of the loading dose, and
   wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively.

32. The method of claim 31, wherein the OCS is prednisone or prednisolone.

33. The method of claim 31, wherein the antibody or antigen-binding fragment thereof comprises heavy and light chain CDR sequences from the HCVR/LCVR sequence pair comprising SEQ ID NOs: 1 and 2.

34. A method for treating a subject having severe uncontrolled asthma comprising:
   administering to the subject an initial dose of an antibody or an antigen-binding fragment thereof that specifically binds to interleukin-4 receptor (IL-4R); and
   administering to the subject a plurality of secondary doses of the antibody or the antigen-binding fragment thereof,
   wherein the plurality of secondary doses are administered during a treatment phase comprising an induction phase, an oral corticosteroid (OCS) reduction phase, and an OCS maintenance phase, and
   wherein the antibody or antigen-binding fragment thereof comprises three heavy chain complementary determining region (CDR) sequences comprising SEQ ID NOs: 3, 4, and 5, respectively, and three light chain CDR sequences comprising SEQ ID NOs: 6, 7, and 8, respectively.

35. The method of claim 34, wherein the OCS is prednisone or prednisolone.

36. The method of claim 34, wherein the antibody or antigen-binding fragment thereof comprises the heavy and light chain CDR sequences from the HCVR/LCVR sequence pair comprising SEQ ID NOs: 1 and 2.

37. The method of claim 1, wherein the antibody or antigen-binding fragment thereof is administered by a prefilled needle and syringe, a prefilled autoinjector delivery device or a prefilled pen delivery device.

38. The method of claim 25, wherein the antibody or antigen-binding fragment thereof is administered by a prefilled needle and syringe, a prefilled autoinjector delivery device or a prefilled pen delivery device.

39. The method of claim 31, wherein the antibody or antigen-binding fragment thereof is administered by a prefilled needle and syringe, a prefilled autoinjector delivery device or a prefilled pen delivery device.

40. The method of claim 34, wherein the antibody or antigen-binding fragment thereof is administered by a prefilled needle and syringe, a prefilled autoinjector delivery device or a prefilled pen delivery device.

* * * * *

UNITED STATES PATENT AND TRADEMARK OFFICE
CERTIFICATE OF CORRECTION

PATENT NO. : 11,034,768 B2
APPLICATION NO. : 16/173848
DATED : June 15, 2021
INVENTOR(S) : Amin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 150 days.

Signed and Sealed this
Thirty-first Day of January, 2023

*Katherine Kelly Vidal*

Katherine Kelly Vidal
*Director of the United States Patent and Trademark Office*